(12) United States Patent
Wu

(10) Patent No.: US 8,729,081 B2
(45) Date of Patent: May 20, 2014

(54) COMPOSITIONS AND METHODS FOR TREATING ALCOHOL USE DISORDERS, PAIN AND OTHER DISEASES

(75) Inventor: Jay Jie-Qiang Wu, Fremont, CA (US)

(73) Assignee: VM Discovery Inc., Fremont, CA (US)

( * ) Notice: Subject to any disclaimer, the term of this patent is extended or adjusted under 35 U.S.C. 154(b) by 296 days.

(21) Appl. No.: 13/123,399

(22) PCT Filed: Oct. 12, 2009

(86) PCT No.: PCT/US2009/060367
§ 371 (c)(1),
(2), (4) Date: Aug. 3, 2011

(87) PCT Pub. No.: WO2010/042925
PCT Pub. Date: Apr. 15, 2010

(65) Prior Publication Data
US 2011/0301149 A1 Dec. 8, 2011

Related U.S. Application Data

(60) Provisional application No. 61/104,672, filed on Oct. 10, 2008.

(51) Int. Cl.
*C07D 413/12* (2006.01)
*C07D 498/04* (2006.01)
*C07D 471/04* (2006.01)
*A61K 31/538* (2006.01)
*A61K 31/498* (2006.01)
*A61K 31/4375* (2006.01)

(52) U.S. Cl.
USPC ........... 514/249; 514/312; 514/300; 514/316; 514/326; 514/253.1; 514/278; 514/254.02; 546/153; 546/187; 546/209; 546/122; 544/354; 544/350; 544/364; 544/369; 540/599; 540/597

(58) Field of Classification Search
USPC .......... 546/153, 187, 209, 122; 544/354, 350, 544/364, 369; 540/599, 597; 514/249, 312, 514/300, 316, 326, 253.1, 278, 254.2, 514/254.02
See application file for complete search history.

(56) References Cited

U.S. PATENT DOCUMENTS

| | | | |
|---|---|---|---|
| 4,206,117 A | 6/1980 | Philipsborn et al. | |
| 2005/0288282 A1 | 12/2005 | Delorme et al. | |
| 2009/0053192 A1* | 2/2009 | Millan et al. | 424/94.6 |
| 2009/0163545 A1* | 6/2009 | Goldfarb | 514/312 |

FOREIGN PATENT DOCUMENTS

| | | |
|---|---|---|
| EP | 1 394 154 | 3/2004 |
| EP | 1 541 564 | 6/2005 |
| EP | 1 897 872 | 3/2008 |
| EP | 1 911 738 | 4/2008 |
| WO | WO 03/008411 | 1/2003 |
| WO | WO 03/055851 | 7/2003 |
| WO | WO 03/059884 | 7/2003 |
| WO | WO 2005/039549 | 5/2005 |
| WO | WO 2005/082367 | 9/2005 |
| WO | WO 2005/097786 | 10/2005 |
| WO | WO 2006/103045 | 10/2006 |
| WO | WO 2007/006546 | 1/2007 |
| WO | WO 2007/107758 | 9/2007 |
| WO | WO 2008/006043 | 1/2008 |
| WO | WO 2008/038841 | 4/2008 |
| WO | WO 2008/053861 | 5/2008 |
| WO | WO 2008/053863 | 5/2008 |
| WO | WO 2008/117982 | 10/2008 |
| WO | WO 2009/042294 | 4/2009 |
| WO | WO 2010/042925 | 4/2010 |

OTHER PUBLICATIONS

International Search Report for International Application No. PCT/US2009/060367, mailed on May 25, 2010.
Written Opinion for International Application No. PCT/US2009/060367, mailed on May 25, 2010.
International Preliminary Report on Patentability for International Application No. PCT/US2009/060367, mailed on May 25, 2010.
Supplementary European Search Report for EP Application No. EP 09 82 0030, dated Apr. 11, 2012.
Database Registry [Online] Chemical Abstracts Service, Columbus, Ohio, US (Aug. 10, 2006) XP002672241, Database Accession No. 902619-02-7.
Database Registry [Online] Chemical Abstracts Service, Columbus, Ohio, US (Aug. 16, 2006) XP002672242, Database Accession No. 901716-44-7.
Database Registry [Online] Chemical Abstracts Service, Columbus, Ohio, US (Aug. 22, 2008) XP002672243, Database Accession No. 1016358-28-3.
Database Registry [Online] Chemical Abstracts Service, Columbus, Ohio, US (Sep. 19, 2008) XP002672244, Database Accession No. 1050553-20-2.
Database Registry [Online] Chemical Abstracts Service, Columbus, Ohio, US (Oct. 12, 2007) XP002672245, Database Accession No. 950436-85-8.

\* cited by examiner

*Primary Examiner* — Kahsay Habte
(74) *Attorney, Agent, or Firm* — Cooley LLP

(57) ABSTRACT

The present invention provides compounds which antagonize epsilon protein kinase C (PKCε). These compounds have a structural formula (Ia), (Ic) or (II). The present invention also provides pharmaceutical compositions containing these compounds and methods of treating various diseases, conditions, and/or symptoms by using these compounds.

26 Claims, 2 Drawing Sheets

COMPOSITIONS AND METHODS FOR TREATING ALCOHOL USE DISORDERS, PAIN AND OTHER DISEASES

CROSS-REFERENCE TO RELATED APPLICATION

This application is a U.S. National Stage application of International Application No. PCT/US2009/060367, filed on Oct. 12, 2009, which claims priority to U.S. Provisional Application No. 61/104,672, filed on Oct. 10, 2008 and entitled "COMPOSITIONS AND METHODS FOR TREATING ALCOHOL USE DISORDERS, PAIN AND OTHER DISEASES", the content of which is herein incorporated by reference in its entirety for all purposes.

STATEMENT AS TO RIGHTS TO INVENTIONS MADE UNDER FEDERALLY SPONSORED RESEARCH AND DEVELOPMENT

This invention was made partly with the U.S. Federal Government support under grant no. R44AA014843. The U.S. Federal Government may have certain rights in the invention.

FIELD OF THE INVENTION

The present invention generally relates to compounds which specifically bind or antagonize epsilon isozyme of the protein kinase C (PKCε), and the pharmaceutical compositions containing those compounds, and the therapeutic use of those compounds.

BACKGROUND OF THE INVENTION

Alcohol abuse and alcoholism are significant public health issues faced by many countries. In the United States alone, alcohol use disorders affect about 14 million people, costing approximately $184 billion a year due to lost wages, legal costs, and medical costs resulting from associated injuries and liver, cardiac, neoplastic, or infectious diseases. Treatment generally consists of pharmacological interventions to manage detoxification, and psychosocial therapies aimed at rehabilitation and reducing alcohol-associated problems. While some treatments are effective in reducing alcohol consumption, it is estimated that 40-70% of patients return to excessive drinking within a year after treatment (*Addiction* (1996) 91:1773-1796). Advances in neuroscience have excited interest in developing pharmaceuticals to dampen craving for alcohol and provide more effective treatment. So far, only three drugs have been approved for treatment in the United States: Disulfuram, naltrexone and acamprosate. Disulfuram is an irreversible inhibitor of aldehyde dehydrogenase and reinforces a patient's desire to avoid alcohol because when alcohol is consumed, levels of acetaldehyde increase, resulting in nausea, hypotension and flushing. Disulfuram is useful for the short-term treatment of highly motivated and compliant patients, but there is no evidence that it is effective in long-term therapy and it carries a risk of significant liver, cardiac, and nervous system toxicity if taken with alcohol. Naltrexone is a non-selective opioid receptor antagonist that decreases the euphoric and reinforcing effects of alcohol and reduces relapse to drinking, especially when combined with psychotherapy. Although most studies have shown it to be beneficial (*Addiction* (2001) 96:1565-1573 and references therein), others have not (*N Eng J Med* (2001) 345:1734-1739 and references therein). Its clinical usefulness appears limited as naltrexone can cause fatigue, sedation, nausea, and abdominal pain in a significant number of patients, its beneficial effects tend to diminish over time, and compliance is variable. Acamprosate can reduce the frequency of drinking and is indicated for maintenance of abstinence (*Am J Health Syst Pharm* (2004) 61:2272-2279 and references therein). Its mechanism of action is not well understood, though it may mainly act to inhibit NMDA and mGluR5 receptors. Although generally well tolerated, it can cause diarrhea in up to 20% of patients, and it also can cause rash, dizziness, and loss of libido. For both naltrexone and acamprosate compliance is generally low, with only about half of patients completing treatment with either drug. Clearly, there is a need to develop more effective compounds, and several new ones are currently being studied, including the 5HT3 receptor antagonist ondansetron and the anticonvulsant topiramate (*Am J Health Syst Pharm* (2004) 61:2380-2388 and refs therein).

A large body of preclinical data has accumulated through studies of mice deficient in PKCε and animals treated with a peptide inhibitor of PKCε, supporting therapeutic use of PKCε inhibitors to treat alcohol abuse and alcoholism (Hodge et al., *Nat. Neurosci.*, 1999, 2, 997-1002). Using PKCε null mice, it has been shown that PKCε regulates alcohol consumption, dependence and reward. Restoration of neuronal PKCε by means of tetracycline-regulated transgenic expression elevates alcohol intake to levels observed in wild type mice, indicating that reduced alcohol consumption in PKCε null mice is due to loss of PKCε in adult neurons (Choi et al., *J. Neurosci.*, 2002, 22, 9905-9911). PKCε null mice also show reduced operant self-administration of alcohol and reduced relapse drinking following alcohol deprivation (Olive et al., *Eur. J. Neurosci.*, 2000, 12, 4131-4140). These findings are associated with less severe alcohol withdrawal seizures (Olive et al., *Neuroscience*, 2001, 103, 171-179) and markedly reduced dopamine release in the nucleus accumbens following ethanol injection (Olive et al., *Eur. J. Neurosci.*, 2000, 12, 4131-4140). These results suggest that the positive rewarding and reinforcing properties of alcohol, as well as the negative effects of alcohol withdrawal could be reduced by PKCε inhibition.

Other studies provide a strong case for therapeutic use of PKCε inhibitors to reduce pain associated with alcoholic polyneuropathy and inflammatory and neuropathic pain. Another study (Dina et al., *J. Neurosci.*, 2000, 20, 8614-8619) analyzed the role of PKCε in alcohol-induced pain using a rat model of alcohol-induced hyperalgesia and found that the hyperalgesia was acutely attenuated by non-selective PKC inhibitors and by a selective peptide inhibitor of PKCε, εV1-2, injected intradermally at the site of nociceptive testing. Another study (Aley et al., *J. Neurosci.*, 2000, 20, 4680-4685) identified a PKCε-mediated mechanism for chronic inflammatory pain. In this case, a nonselective inhibitor of several PKC isozymes and a selective PKCε inhibitor antagonized the prolonged hyperalgesic response in the carrageenan injected rat hindpaw equally.

In addition, evidence indicates that PKCε inhibitors could be useful for the treatment of anxiety, which is commonly associated with alcoholism and may contribute to excessive drinking. Other studies (Hodge et al., *Nat. Neurosci.*, 1999, 2, 997-1002; Hodge et al., *J. Clin. Invest.*, 2002, 110, 1003-1010) examined $GABA_A$ receptor function in PKCε null mice and found that these mice are supersensitive to the acute hypnotic effects of barbiturates, benzodiazepines, ethanol and neurosteroids.

A large amount of evidence from preclinical studies and patient tumor analysis has indicated that PKCε is a transforming oncogene and played a critical role in tumor cell proliferation, motility, invasion and drug resistance (Gorin & Pan,

*Molecular Cancer*, 2009, 8, 9). In vitro, overexpression of PKCε has been demonstrated to increase proliferation, motility, and invasion of fibroblasts or immortalized epithelial cells. In addition, xenograft and transgenic animal models have clearly shown that overexpression of PKCε is tumorigenic resulting in metastatic disease. PKCε has been found to be overexpressed in tumor-derived cell lines and histopathological tumor specimens from various organ sites. Activation of PKCε causes up-regulation of inhibitors of apoptosis proteins (IAPs) and MDR1 (multidrug-resistant protein), resulting in anti-apoptosis and chemotherapy resistance (Bourguignon et al., *J. Biol. Chem.*, 2009, 284, 26533-26546). Thus, PKCε inhibitors could be therapeutically useful in treating a variety of cancer including breast, head and neck, prostate and lung cancer either used alone or in combination with standard cancer therapy.

In another study of type 2 diabetes (Schmitz-Peiffer et al., *Cell Metabolism*, 2007, 6, 320-328), a role for PKCε in 13 cell dysfunction was established. Deletion of PKCε augmented insulin secretion and prevented glucose intolerance in fat-fed mice. Importantly, a PKCε-inhibitory peptide improved insulin availability and glucose tolerance in diabetic mice. In another study (Samuel et al., *J. Clin. Invest.*, 2007, 117, 739-745), PKCε, but not other isoforms of PKC, was activated in the high-fat fed rats resulting in hepatic steatosis and hepatic insulin resistance. Knocking down PKCε expression by treating the rats with an antisense oligonucleotide against PKCε protected rats from fat-induced hepatic insulin resistance. Therefore, PKCε inhibitors of this invention could be beneficial treating type 2 or type 1 diabete in humans.

In another study (Kaiser et al., *Arch. Biochem. Biophys.*, 2009, 482, 104-11), PKCε was shown to contribute to hepatic steatosis in experimental ethanol-induced and non-alcoholic fatty liver disease using PKCε knockout mice and in wild-type nice that received an anti-sense oligonucleotide to knockdown PKCε expression. The data suggest that activation of PKCε exacerbates hepatic lipid accumulation by inducing insulin resistance. Thus, inhibition of PKCε with the inhibitors of this invention could prevent and/or treat liver diseases.

It was also demonstrated that PKCε is a target to control inflammation and immune-mediated disorders (Aksoy et al., *Intern. J. Biochem. Cell Biol.*, 2004, 36, 183-188). Controlling the kinase activity of PKCε might represent an efficient strategy to prevent or treat certain inflammatory disorders of microbial origin. Furthermore, pharmacological inhibition of PKCε suppressed chronic inflammation in murine cardiac transplantation model (Koyanagi et al., *J. Mol. Cell. Cardio.*, 2007, 43, 517-522). It is possible that the PKCε inhibitors of this invention could be used therapeutically for prevention and treatment of various inflammatory conditions associated with e.g. microbial infection and organ transplantation.

Above mentioned studies provide a strong case for development of PKCε inhibitors to treat diseases or disorders or conditions mentioned above. Given the large number of people who may be helped by such a drug, and given the high cost of these diseases, the benefits to society could be enormous if an effective PKCε inhibitor can be developed.

PKC is a family of serine-threonine kinases with important roles in cell growth, differentiation, ion channel and receptor regulation, gene expression, tumor promotion and apoptosis. The mammalian PKC family contains at least 9 genes grouped into 3 classes: conventional (α, β, γ), novel (δ, ε, η/L, θ), and atypical (ξ, ι/λ) PKC isozymes. PKC inhibitors have been considered attractive as therapeutic agents. A relatively selective inhibitor of PKCβ, LY333531, has undergone a clinical study for the treatment of diabetic retinopathy. The use of PKC inhibitors has been suggested for clinical applications ranging from the treatment of psoriasis to cancer (*Expert Opin Investig Drugs* (2001) 10:2117-2140 and refs therein). Knowledge of specific roles attributable to individual PKC isozymes has been hampered by the lack of isozyme-selective drugs—there are currently no selective small organic molecule inhibitors of PKCε and the search for selective drugs has been difficult because of several methodological limitations (*Biochemical Journal* (2003) 371:199-204 and refs therein).

Thus, there is still a strong need for compounds that act as epsilon isozyme-selective inhibitors of the protein PKC.

SUMMARY OF THE INVENTION

In one aspect, the present invention provides a compound having structural Formula (Ia) or (Ic):

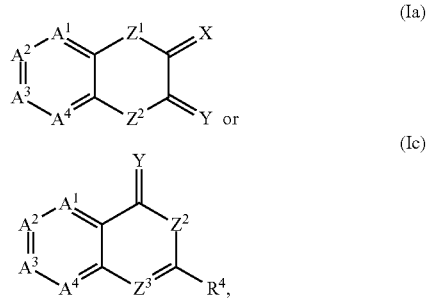

or a salt, solvate, or physiologically functional derivative thereof,
wherein:
X and Y are independently $CR^1R^5$, $NR^1$, O or S, provided that at least one of X and Y is $CR^1R^5$ or $NR^1$;
$Z^1$ and $Z^2$ are independently $CHR^2$, $NR^2$, O, or S;
$Z^3$ is $CR^6$ or N;
$A^1$, $A^2$, $A^3$, and $A^4$ are independently $CR^3$ or N;
each $R^1$, $R^2$, $R^3$, $R^4$, and $R^5$ is independently hydrogen, halogen, acyl, substituted acyl, alkoxycarbonyl, substituted alkoxycarbonyl, aryloxycarbonyl, substituted aryloxycarbonyl, —C(O)$NR^7R^8$, alkyl, substituted alkyl, aryl, substituted aryl, arylalkyl, substituted arylalkyl, cycloheteroalkyl, substituted cycloheteroalkyl, heteroaryl, substituted heteroaryl, heteroarylalkyl, substituted heteroarylalkyl, heteroalkyl, or substituted heteroalkyl;
$R^7$ and $R^8$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl, or alternatively, $R^7$ and $R^8$, taken together with the nitrogen atom to which they are attached, form a 4-, 5-, 6-, or 7-membered cycloheteroalkyl ring;
with the following provisos:
(a) at least one of $Z^1$ and $Z^2$ is $CHR^2$ or $NR^2$;
(b) at least one of $A^1$, $A^2$, $A^3$, and $A^4$ is $CR^3$;
(c) at least one of $R^1$, $R^2$, $R^3$ and $R^5$ is not hydrogen;
(d) when $R^1$ and $R^5$ are independently hydrogen, aryl or substituted aryl; $R^2$ is hydrogen, arylalkyl or substituted arylalkyl; then $R^3$ is not aryl, substituted aryl, heteroaryl, or substituted heteroaryl;
(e) when $R^3$ is —C(O)$NR^5R^6$; $R^2$ is hydrogen or substituted arylalkyl; and at least one of $R^1$ and $R^5$ is not halogen, acyl, substituted acyl, alkoxycarbonyl, substituted alkoxycarbonyl, alkyl, or substituted alkyl; and (f) when R³ is —C(O)NR⁵R⁶; R⁵ is hydrogen; R⁶ is substituted alkyl, arylalkyl, substituted arylalkyl, heteroaryl, heteroalkyl or substituted aryl; R² is hydrogen or substituted arylalkyl; then at least one R¹ is not halogen, acyl, substituted acyl, alkoxycarbonyl, substituted alkoxycarbonyl, alkyl, or substituted alkyl.

In another aspect, the present invention provides a compound having structural formula (II):

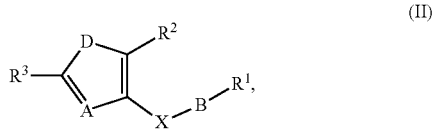

(II)

or a salt, solvate, or physiologically functional derivative thereof,
wherein:
A is N or CH;
B is a 5-, 6-, or 7-membered cycloalkyl, substituted cycloalkyl, cycloheteroalkyl, substituted cycloheteroalkyl, aryl, substituted aryl, heteroaryl, or substituted heteroaryl ring;
D is NR⁴, S, or O;
R¹, R², R³, and R⁴ are independently hydrogen, halogen, acyl, substituted acyl, alkoxycarbonyl, substituted alkoxycarbonyl, aryloxycarbonyl, substituted aryloxycarbonyl, —C(O)NR⁵R⁶, alkyl, substituted alkyl, aryl, substituted aryl, arylalkyl, substituted arylalkyl, cycloheteroalkyl, substituted cycloheteroalkyl, heteroaryl, substituted heteroaryl, heteroarylalkyl, substituted heteroarylalkyl, heteroalkyl, or substituted heteroalkyl;
R⁵ and R⁶ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl, or alternatively, R⁵ and R⁶, taken together with the nitrogen atom to which they are attached, form a 4-, 5-, 6-, or 7-membered cycloheteroalkyl ring; and
X is —CH₂—, —CH₂—O—, —CH₂—S—, —O— or —S—.

In another aspect, the present invention provides a pharmaceutical composition comprising one or more compounds of the present invention having structural formula (Ia), (Ic), (Ii), or (II), or a salt, solvate, or physiologically functional derivative thereof, and a pharmaceutically acceptable vehicle.

In still another aspect, the present invention provides a method of treating a disease or condition associated with irregular activity of PKCε in a patient, comprising administering to the patient a therapeutically effective amount of one or more compounds of the present invention having structural formula (Ia), (Ic), (Ii) or (II), or a salt, solvate, or physiologically functional derivative thereof.

DETAILED DESCRIPTION OF THE INVENTION

Figure 1:
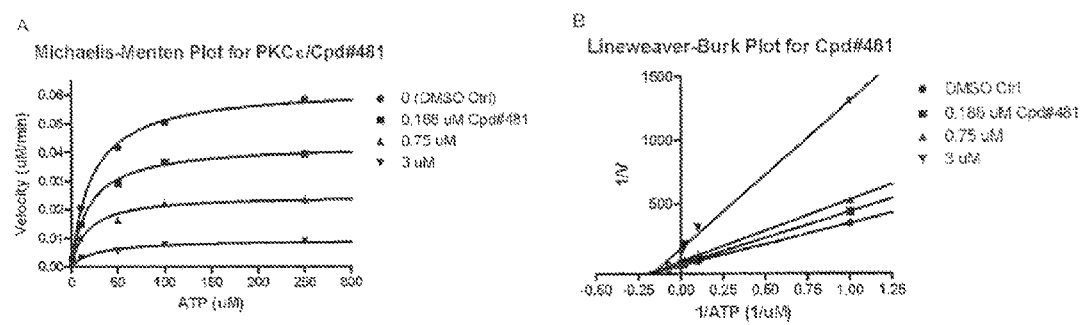
FIG. 1. Kinetic analysis showed that a compound of the present invention (#481) inhibits PKCε non-competitively with ATP. (A) Initial velocity (Vi) plotted against ATP concentration at various concentrations of the compound plus vehicle control. (B) Lineweaver-Burk double reciprocal plot showing differences in $V_{max}$ but not in $k_m$ for the 4 conditions.
Figure 2:
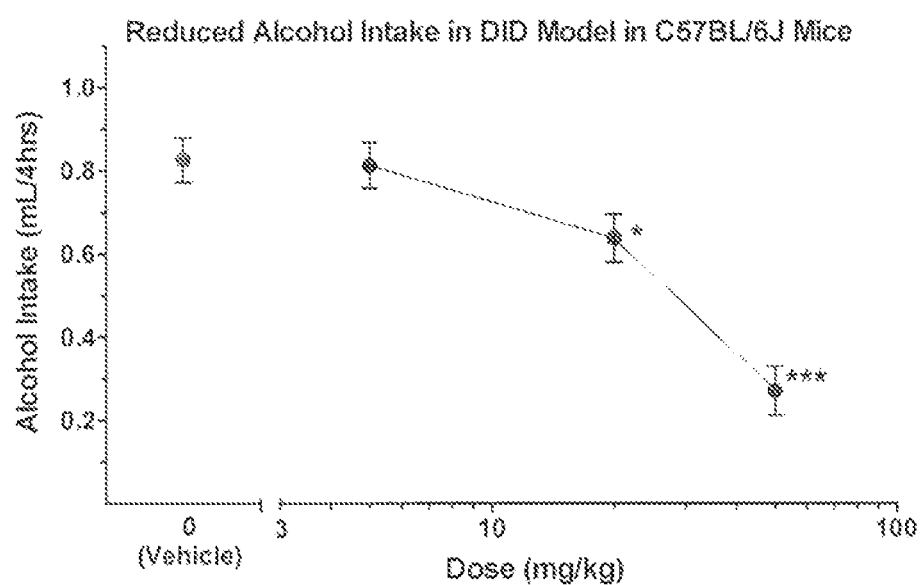
FIG. 2. A compound of the present invention (#901) significantly reduced oral intake of alcohol (20% ethanol) in C57BL/6J mice under the 4-hr drinking in the dark (DID) protocol ($F(3,66)=29.65$, $p<0.0001$, one-way ANOVA repeated measurement followed by Dunnet's post-hoc test). The data are presented as mean±SEM. *$p<0.05$, ***$p<0.001$ as compared with the vehicle control.

There are no reported small organic molecule inhibitors of PKCε kinase that specifically bind to the PKCε and inhibit PKCε non-competitively with respect to ATP. The term of "allosteric inhibitor" of a protein kinase generally refer to a protein kinase inhibitor binding at the protein's allosteric site (i.e., a site other than the protein's active site or ATP-binding site) and hence inhibiting protein activity non-competitively with respect to ATP. Allosteric inhibitors are an emerging class of small organic molecule therapeutic agents that may be able to offer patients better outcomes than with traditional small organic molecule therapies. The present invention relates to novel small organic molecules that inhibit PKCε non-competitively with respect to ATP. There are many advantages to a ATP-non-competitive PKCε inhibitor. This potential stems from its ability to offer greater selectivity and better modulatory control at disease mediating proteins or targets. Allosteric inhibitors hind to regulatory sites distinct from the active site on the protein, resulting in conformational changes that may profoundly influence protein function.

For one, these inhibitors would not compete with ATP. A serine/threonine protein kinase, such as PKCε, catalyzes the transfer of a phosphate group from a molecule of ATP to a serine/threonine residue located on a protein substrate. The inhibitors of kinases so far known in the art are usually competitive with either ATP or the substrate of the kinase, or both simultaneously. Since the concentration of ATP in a cell is normally very high (millimolar), compounds that are competitive with ATP may show diminished efficacy and duration of action since it would be difficult for such compounds to reach the concentrations within the cell that are necessary to displace the ATP from its binding site for the extended time needed to achieve therapeutic use effectively. Allosteric inhibitors do not compete with endogenous ligands, e.g. ATP or substrate, and therefore can exert their influence even if an endogenous ligand is bound to another site on the same target at the same time. Allosteric inhibitors may offer a less disruptive way to influence the functioning of biological systems. Since they bind on a distinct site, it is possible to combine allosteric modulators with orthosteric drugs to achieve better therapeutic use. Compounds which inhibit kinases in an reversible manner and are non-competitive with ATP or protein substrate are mostly sought after for therapeutic development. Since orthosteric modulators need to compete with natural ligands, they require higher doses, raising safety issues. Allosteric modulators do not compete with natural ligands and may be effective at lower, safer doses.

The compound of the present invention, or a salt, prodrug or softdrug, salt of prodrug or softdrug, solvate or hydrate, or physiologically functional derivative thereof, or a pharmaceutical composition containing the compound of the present invention, or a salt, prodrug or softdrug, salt of prodrug or softdrug, solvate or hydrate, or physiologically functional derivative thereof and one or more pharmaceutically acceptable vehicle, is administered a therapeutically effective amount of a compound of the present invention to said patient, preferably a human, suffering from a disease, disorder, symptom or condition selected from the group consisting of: acute pain, chronic pain, inflammatory pain, neuropathic pain, diabetic neuropathy, alcoholic polyneuropathy, canceror chemotherapy-induced pain, a generalized pain disorder, tonic pain, persistent pain, postoperative pain, chemical-induced pain, drug-induced pain, migraine, anxiety, skeletal muscle spasms, convulsive seizures, alcohol abuse and alcoholism associated diseases, insomnia, pain associated with alcohol-induced hyperalgesia, type 1 and type 2 diabetes, diabetic complications, hepatic steatosis or liver cirrhosis, bipolar disorder, mania, epilepsy, sleeping disorder, burn, posttraumatic stress disorder, cardiac disorder, smoking, inflammation and immune-mediated disorders (including microbial infection and organ transplantation), insomnia, postoperative pain, cancer (including breast, head and neck, prostate and lung cancer), maladaptive substance use, substance dependence, alcohol use or abuse, substance use or abuse, drug use or abuse, drug-related effect and a combination thereof for medical treatment purpose A compound of the present invention inhibits PKCε at less than one micromolar concentration and acts reversibly and noncompetitively with ATP and substrate, indicating that it binds at an allosteric site of the enzyme. The compounds of the present invention exhibited high specificity to PKCε when compared with related kinases, including other isozymes of PKC family, the highly related PKCθ. This specificity may be related to actions at an allosteric site that is quite unique to PKCε.

DEFINITIONS

Terms used in the claims and specification are defined as set forth below unless otherwise specified.

The term "compound(s) of the present invention", or "the present compound(s)" refers to one or more compounds encompassed by the structural formulae and/or any subgeneric formulae disclosed herein and includes any specific compounds within these generic formula whose structure is disclosed herein. Compounds of the invention may contain one or more chiral centers and/or double bonds and therefore, may exist as stereoisomers, such as double-bond isomers (i.e., geometric isomers), the racemic mixtures, enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. The compounds of the invention may also exist in several tautomeric forms. Accordingly, the chemical structures depicted herein encompass all possible tautomeric forms of the illustrated compounds. Compounds also include isotopically labeled compounds where one or more atoms have an atomic mass different from the atomic mass conventionally found in nature. Examples of isotopes that may be incorporated into the compounds include, but are not limited to, $^2$H, $^3$H, $^{13}$C, $^{14}$C, $^{15}$N, $^{17}$O, $^{18}$O, etc. Compounds may exist in unsolvated forms as well as solvated forms, including hydrated forms and as N-oxides. In general, the salt, hydrated, solvated, ester, prodrug, softdrug, salt of prodrug or softdrug, and N-oxide forms, as well as metabolite(s) or physiologically functional derivative(s) of the compound of the present invention are within the scope of the present invention. Certain compounds of the present invention may exist in multiple crystalline forms or an amorphous form. In general, all physical forms are equivalent for the uses contemplated by the present invention and are intended to be within the scope of the present invention. In some embodiments, compounds of the present invention also include compounds where one or more carbon atoms have been replaced by one or more boron atoms.

The term "physiologically functional derivative(s)" used herein refers to any physiologically tolerated derivative of a compound of the present invention, for example, an ester or prodrug, which, upon administration to a mammal, e.g., a human, are transformed directly or indirectly to a compound of formula (Ia), (Ic), (Ii), (II), or an active metabolite thereof. Physiologically functional derivatives include prodrugs of the compounds of the present invention. Examples of prodrug are described in H. Okada et al., *Chem. Pharm. Bull.* 1994, 42, 57-61. Such prodrugs can be metabolized in vivo to a compound of the invention. These prodrugs may themselves be active or not.

"Alkyl" by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl). Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl(isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans (E or Z) conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent, refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In some embodiments, the alkyldiyl group is ($C_1$-$C_{20}$) alkyldiyl, more preferably, ($C_1$-$C_{10}$) alkyldiyl, most preferably, ($C_1$-$C_6$) alkyldiyl.

"Alkyleno" by itself or as part of another substituent, refers to a straight-chain alkyldiyl group having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, ethano, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used.

"Acyl" by itself or as part of another substituent refers to a radical —C(O)$R^{200}$, where $R^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Amino" by itself or as part of another substituent refers to a radical —NR$^a$R$^b$, where R$^a$ and R$^b$ are independently hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein, or alternatively R$^a$ and R$^b$, taken together with the atoms to which they are bonded, form a cycloheteroalkyl ring. Representative examples include, but are not limited to —NH$_2$, —NHCH$_3$, —N(CH$_3$)$_2$, —NH-phenyl, —NH—CH$_2$-phenyl, pyrrolidine, and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octacene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 10 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or sp$^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Aryloxy," by itself or as part of another substituent, refers to a radical of the formula —O—$R^{201}$, where $R^{201}$ is aryl, substituted aryl, arylalkyl, or substituted arylalkyl.

"Aryloxycarbonyl," by itself or as part of another substituent, refers to a radical of the formula —C(O)—O—$R^{201}$, where $R^{201}$ is aryl, substituted aryl, arylalkyl, or substituted arylalkyl.

"Cycloalkyl" or "carbocyclyl" by itself or as part of another substituent, refers to a saturated or unsaturated cyclic alkyl radical, as defined herein. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In some embodiments, a cycloalkyl group comprises from 3 to 10 ring atoms ($C_3$-$C_{10}$ cycloalkyl). In other embodiments, a cycloalkyl group comprises from 3 to 7 ring atoms ($C_3$-$C_7$ cycloalkyl).

"Cycloheteroalkyl" or "heterocyclyl" by itself or as part of another substituent, refers to a saturated or unsaturated cyclic alkyl radical in which one or more carbon atoms (and optionally any associated hydrogen atoms) are independently replaced with the same or different heteroatom. Typical heteroatoms to replace the carbon atom(s) include, but are not limited to, B, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, borolane, dioxaborolane, and the like. In some embodiments, the cycloheteroalkyl group comprises from 3 to 10 ring atoms (3-10 membered cycloheteroalkyl). In other embodiments, the cycloalkyl group comprise from 5 to 7 ring atoms (5-7 membered cycloheteroalkyl).

A cycloheteroalkyl group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteroalkyl group may be attached to the remainder of the molecule via a ring carbon atom or a ring heteroatom.

"Heteroalkyl, Heteroalkanyl, Heteroalkenyl, Heteroalkanyl, Heteroalkyldiyl and Heteroalkyleno" by themselves or as part of another substituent, refer to alkyl, alkenyl, alkenyl, alkynyl, alkyldiyl and alkyleno groups, respectively, in which one or more of the carbon atoms (and any associated hydrogen atoms) are each independently replaced with the same or different heteroatomic groups. Typical heteroatomic groups which can be included in these groups include, but are not limited to, —O—, —S—, —O—O—, —S—S—, —O—S—, —$NR^{203}R^{204}$—, =N—N=, —N=N—, —N=N—$NR^{205}R^{206}$, —$PR^{207}$—, —P(O)$_2$—, POR$^{208}$—, —O—P(O)$_2$—, —SO—, —SO$_2$—, —SnR$^{209}$ R$^{210}$—, —BR$^{211}$R$^{212}$, BOR$^{213}$OR$^{214}$ and the like, where R$^{203}$, R$^{204}$, R$^{205}$, R$^{206}$, R$^{207}$, R$^{208}$, R$^{209}$, R$^{210}$, R$^{211}$, R$^{212}$, R$^{213}$ and R$^{214}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, furopyridine, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is ($C_1$-$C_3$) alkyl and the heteroaryl moiety is a 5-10 membered heteroaryl.

"Heteroaryloxy," by itself or as part of another substituent, refers to a radical of the formula —O—R$^{201}$, where R$^{201}$ is heteroaryl, substituted heteroaryl, heteroarylalkyl, or substituted heteroarylalkyl.

"Heteroaryloxycarbonyl," by itself or as part of another substituent, refers to a radical of the formula —C(O)—O—R$^{201}$, where R$^{201}$ is heteroaryl, substituted heteroaryl, heteroarylalkyl, or substituted heteroarylalkyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octacene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, B, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, Oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthcne and the like.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute, i.e., a compound of the present invention), or an aggregate that consists of a solute ion or molecule (the compound of the present invention) with one or more solvent molecules. When the solvent contains water, the solvate my be hydrate.

"Prodrug or softdrug" refers to a precursor of a pharmaceutically active compound wherein the precursor itself may or may not be pharmaceutically active but, upon administration, will be converted, either metabolically or otherwise, into the pharmaceutically active compound or drug of interest. For example, prodrug or softdrug is an ester or an ether form of a pharmaceutically active compound. Several prodrugs have been prepared and disclosed for a variety of pharmaceuticals. See, for example, Bundgaard, H. and Moss, J., J. Pharm. Sci. 78: 122-126 (1989). Thus, one of ordinary skill in the art knows how to prepare these precursors, prodrugs or softdrugs with commonly employed techniques of organic synthesis.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(s)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, substituted alkyl, arylalkyl, alkyldiyl, substituted alkyldiyl, aryl, substituted aryl, arylalkyl, substituted arylalkyl, heteroalkyl, substituted heteroalkyl, heteroalkyldiyl, substituted heteroalkyldiyl, heteroaryl, substituted heteroaryl, heteroarylalkyl substituted heteroarylalkyl; each $R^b$ is independently hydrogen or $R^a$; and each $R^c$ is independently $R^b$ or alternatively, the two $R^c$s are taken together with the nitrogen atom to which they are bonded form a cycloheteroalkyl ring which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Patient" or "subject" includes, but is not limited to animals such as, for example, mammals. Preferably, the patient is a human.

The term "associated with", when used in reference to a disease, condition, symptom, or disorder (generally or specifically), means a disease, condition, symptom, or disorder that are connected to one or more factors, such as irregular activity of PKCε. The connection can be a causal relationship or non-causal relationship.

"Treating", "treat" or "treatment" of any disease or disorder refers, in some embodiments, to ameliorating, mitigating or preventing the disease, condition, symptom or disorder (i.e., arresting or reducing the development of the disease or at least one of the clinical symptoms thereof). In other embodiments "treating", "treat" or "treatment" refers to ameliorating or mitigating at least one physical parameter, which may not be discernible by the patient. In yet other embodiments, "treating", "treat" or "treatment" refers to inhibiting the disease, condition, symptom or disorder, either physically, (e.g., stabilization of a discernible symptom), physiologically, (e.g., stabilization of a physical parameter) or both. In yet other embodiments, "treating", "treat" or "treatment" refers to delaying the onset of the disease or disorder. "Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

The phrases "effective amount" and "amount sufficient to" refer to amounts of a biologically active agent that produce an intended biological activity.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

"Vehicle" refers to a diluent, adjuvant, excipient or carrier with which a compound is administered.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

The terms "protein" and "polypeptide" are used interchangeably herein to refer a polymer of amino acids, and unless otherwise limited, include atypical amino acids that can function in a similar manner to naturally occurring amino acids.

The term "receptor" refers to a molecule or complex of molecules, typically (although not necessarily) a protein(s), that is specifically bound by one or more particular ligands. The receptor is said to be a receptor for such ligand(s). Ligand-receptor binding, in many instances, induces one or more biological responses.

A "modulator" of a polypeptide is either an inhibitor or an enhancer of an action or function of the polypeptide. Similarly, a "modulator" of a signaling pathway is an inhibitor or enhancer of at least one function mediated by the signaling pathway. Aspects of modulators are defined below with respect to polypeptides; however, those of skill in the art readily appreciate that these definitions also apply to signaling pathways.

A "non-selective" modulator of a polypeptide (e.g., PKCε) is an agent that modulates other members of the same family of polypeptides (e.g., other PKCs) at the concentrations typically employed for modulation of the particular polypeptide.

A "selective" modulator of a polypeptide significantly modulates the particular polypeptide at a concentration at which other members of the same family of polypeptides are not significantly modulated.

A modulator "acts directly on" a polypeptide when the modulator exerts its action by interacting directly with the polypeptide.

A modulator "acts indirectly on" a polypeptide when the modulator exerts its action by interacting with a molecule other than the polypeptide, which interaction results in modulation of an action or function of the polypeptide.

An "inhibitor" or "antagonist" of a polypeptide is an agent that reduces, by any mechanism, any action or function of the polypeptide, as compared to that observed in the absence (or presence of a smaller amount) of the agent. An inhibitor of a polypeptide can affect: (1) the expression, mRNA stability, protein trafficking, modification (e.g., phosphorylation), or degradation of a polypeptide, or (2) one or more of the normal action or functions of the polypeptide. An inhibitor of a polypeptide can be non-selective or selective. Preferred inhibitors (antagonists) are generally small molecules that act directly on, and are selective for, the target polypeptide.

A "reversible" inhibitor is one whose effects can be reversed (i.e., one that does not irreversibly inactivate the target polypeptide).

A "competitive" inhibitor of a polypeptide is one that competes for binding to the polypeptide with another component required for polypeptide function. For example, PKCε function requires the binding of ATP (adenosine triphosphate) and substrate. Accordingly, a competitive inhibitor of PKCε can act, for example, by binding at the ATP or substrate binding sites. This inhibition is generally reversible by increasing the concentration of ATP or substrate to the reaction mixture. Such an inhibitor is said to inhibit PKCε competitively with respect to ATP or substrate, respectively.

A "non-competitive" inhibitor of a polypeptide generally binds the polypeptide at a site other than the binding site of another component required for polypeptide function. This inhibition cannot be reversed by increasing the concentration of component(s) required for polypeptide function.

An "enhancer" or "activator" or "agonist" is an agent that increases, by any mechanism, any polypeptide action or function, as compared to that observed in the absence (or presence of a smaller amount) of the agent. An enhancer of a polypeptide can affect: (1) the expression, mRNA stability, protein trafficking, modification (e.g., phosphorylation), or degradation of a polypeptide, or (2) one or more of the normal actions or functions of the polypeptide. An enhancer of a polypeptide can be non-selective or selective. Preferred enhancers (agonists) are generally small molecules that act directly on, and are selective for, the target polypeptide.

As used herein, an "allosteric modulator" of an polypeptide, typically an enzyme or receptor, is a modulator that binds at a location other than the active site of the target polypeptide, altering activity by inducing an allosteric change in the shape of the target polypeptide.

The term "specific binding" is defined herein as the preferential binding of binding partners to another (e.g., two polypeptides, a polypeptide and nucleic acid molecule, or two nucleic acid molecules) at specific sites. The term "specifically bind(s)" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site(s)).

The term "in combination with", "co-administer" or "co-administering", when used in reference to administration of the present compound and other active agent(s), means that the present compound and other active agent(s) are administered to a patient in a coordinated fashion. For example, the present compound and other active agent(s) are administered in such a way that there is at least some chronological overlap in their physiological activity on the subject. Thus, a compound of the present invention can be administered simultaneously and/or sequentially with another agent. In sequential administration, there may even be some substantial delay (e.g., minutes or even hours or days) before administration of the second agent as long as the first administered agent is exerting some physiological effect on the organism when the second administered agent is administered or becomes active in the subject.

The term "reducing pain" or "reduce(s) pain" as used herein, refers to decreasing the level of pain a subject perceives relative to the level of pain the subject would have perceived were it not for the intervention. Where the subject is a person, the level of pain the person perceives can be assessed by asking him or her to describe the pain or compare it to other painful experiences. Alternatively, pain levels can be determined by measuring the subject's physical responses to the pain, such as the release of stress-related factors or the activity of pain-transducing nerves in the peripheral nervous system or the CNS. One can also determine pain levels by measuring the amount of a well-characterized analgesic required for a person to report that no pain is present or for a subject to stop exhibiting symptoms of pain. A reduction in pain can also be measured as an increase in the threshold at which a subject experiences a given stimulus as painful. In certain embodiments, a reduction in pain is achieved by decreasing "hyperalgesia," the heightened sensitivity to a noxious stimulus, and such inhibition can occur without impairing "nociception," the subject's normal sensitivity to a "noxious" stimulus. The pain is due to a condition selected from the group consisting of, but not limited to, causalgia, diabetes, collagen vascular disease, trigeminal neuralgia, spinal cord injury, brain stem injury, thalamic pain syndrome, complex regional pain syndrome type 1/reflex sympathetic dystrophy, Fabry's syndrome, small fiber neuropathy, cancer, cancer chemotherapy, chronic alcoholism, stroke, abscess, demyelinating disease, viral infection, anti-viral therapy, AIDS, AIDS therapy, burn, sunburn, arthritis, colitis, carditis, dermatitis, myositis, neuritis, mucositis, urethritis, cystitis, gastritis, pneumonitis, collagen vascular disease, trauma, surgery, amputation, toxin, chemotherapy, fibromyalgia, irritable bowel syndrome, migraine, anxiety, skeletal muscle spasms, convulsive seizures, epilepsy, a temporomandibular disorder or a combination thereof.

As used with reference to pain reduction, "a subject in need thereof" refers to an animal or person, preferably a person, expected to experience pain in the near future. Such animal or person may have an ongoing condition that is causing pain currently and is likely to continue to cause pain. Alternatively, the animal or person has been, is, or will be enduring a procedure or event that usually has painful consequences. Chronic painful conditions such as diabetic neuropathic hyperalgesia and collagen vascular diseases are examples of the first type; dental work, particularly that accompanied by inflammation or nerve damage, and toxin exposure (including exposure to chemotherapeutic agents) are examples of the latter type.

"Inflammatory pain" refers to pain arising from inflammation. Inflammatory pain often manifests as increased sensitivity to mechanical stimuli (mechanical hyperalgesia or tenderness). For examples, inflammatory pain is due to a condition selected from the group consisting of: burn, sunburn, arthritis, colitis, carditis, dermatitis, myositis, neuritis, mucositis, urethritis, cystitis, gastritis, pneumonitis, and collagen vascular disease.

"Neuropathic pain" refers to pain arising from conditions or events that result from damage to or dysfunction of the peripherial or central nervous system. "Neuropathy" refers to a disease process resulting in damage to nerves. "Causalgia" denotes a state of chronic pain following nerve injury. "Allodynia" refers to a condition in which a person experiences pain in response to a normally nonpainful stimulus, such as a gentle touch. For examples, neuropathic pain is or is due to a condition or event selected from the group consisting of: postherpetic neuralgia, root avulsions, painful traumatic mononeuropathy, painful polyneuropathy (particularly due to diabetes), central pain syndromes (potentially caused by virtually any lesion at any level of the nervous system), postsurgical pain syndromes (eg, postmastectomy syndrome, post-thoracotomy syndrome, phantom pain (pain felt in the region of an amputated body part)), complex regional pain syndrome (reflex sympathetic dystrophy and causalgia), collagen vascular disease, trigeminal neuralgia, spinal cord injury, brain stem injury, thalamic pain syndrome, Fabry's syndrome, small fiber neuropathy, cancer, cancer chemotherapy, alcoholism, chronic alcohol use or abuse, stroke, abscess, demyelinating disease, viral infection, anti-viral therapy, AIDS, AIDS therapy, tissue injury, dysesthesia (eg, burning, tingling), mononeuropathies (eg, carpal tunnel syndrome, radiculopathy), plexopathies (typically caused by nerve compression, as by a neuroma, tumor, or herniated disk), and polyneuropathies (typically caused by various metabolic neuropathies). Neuropathic pain is due to an agent selected from the group consisting of: trauma, surgery, amputation, toxin, and chemotherapy.

As used herein, the term "generalized pain disorder" refers to a group of idiopathic pain syndromes (e.g., fibromyalgia, irritable bowel syndrome, and temporomandibular disorders), for which the pathogenic mechanism is currently unknown or unclear or with controversial explanations, characterized by diffuse or generalized pain, and for which a diagnosis of inflammation or neuropathy as the direct cause of pain is excluded.

An "analgesic agent" refers to a molecule or combination of molecules that causes a reduction in pain.

A "neuroleptic" refers to a class of tranquilizing drugs, used to treat psychotic conditions, that modulate neurotransmitter activity in the central nervous system and can act by modulating acetylcholine, dopamine, norepinephrine, serotonin, or γ-aminobutyric acid (GABA) transmission.

The term "neurosteroid" refers to a class of steroids, the natural forms of which are produced by cells of the central or peripheral nervous systems, independently of the steroidogenic activity of the endocrine glands. Neurosteroids are derived from cholesterol, and examples of neurosteroids include $3\alpha$, $5\alpha$-tetrahydroprogesterone, $3\alpha,5\beta$-tetrahydroprogesterone, and $3\alpha,5\alpha$-tetrahydrodeoxycorticosterone. For examples, ganaxalone and alphaxalone.

The difference between "acute" and "chronic" pain is one of timing: acute pain is experienced soon (e.g., generally within about 48 hours, more typically within about 24 hours, and most typically within about 12 hours) after the occurrence of the event (such as inflammation or nerve injury) that led to such pain. By contrast, there is a significant time lag between the experience of chronic pain and the occurrence of the event that led to such pain. Such time lag is generally at least about 48 hours after such event, more typically at least about 96 hours after such event, and most typically at least about one week after such event. The chronic pain usually lasts for days, weeks, months or even years.

The term "maladaptive substance use" refers to the use of any substance that results in adverse consequences for the user that outweigh any benefits derived from the substance. Substances that are used in a maladaptive manner are generally consumed or administered (usually self-administered) to the body, by any route of administration, to produce an effect on the body that the user generally experiences as pleasurable. The substance can be a single substance (cocaine, for example) or a type of substance (e.g., food, in general). The adverse consequences can include, for example, adverse effects on health, the ability to care for oneself, the ability to form and maintain human relationships, and/or the ability to work. The adverse consequences are generally significant enough that the user would like to control, reduce, or end substance use or, alternatively, the user's family members and/or friends would like to see the user control, reduce, or end substance use. Maladaptive substance use can include uncontrollable craving for the substance; substance dependence, including psychological and/or physical dependence; and maladaptive substance use; as well as any of the individual symptoms of substance dependence and/or abuse listed below.

A "symptom of maladaptive substance use" includes any symptom arising from maladaptive substance use. Thus, a symptom of maladaptive substance use arises from the previous, and/or ongoing, use of a substance. Examples include, but are not limited to, elevated drug reward, incentive salience for the drug, drug craving, drug preference, drug seeking, and drug consumption, as compared to that in a normal population (i.e., one that is not using the substance in a maladaptive manner), as well as any of the individual symptoms of substance dependence and/or abuse listed below.

"Substance dependence" includes a maladaptive pattern of substance use, leading to clinically significant impairment or distress, as manifested by three (or more) of the following symptoms, occurring at any time in the same 12-month period: (1) Tolerance, as defined by either of the following: (a) a need for markedly increased amounts of the substance to achieve intoxication or desired effect, or (b) markedly diminished effect with continued use of the same amount of the substance; (2) Withdrawal, as manifested by either of the following: (a) the characteristic withdrawal syndrome for the substance, or (b) the same (or closely related) substance is taken to relieve or avoid withdrawal symptoms; (3) The substance is often taken in larger amounts or over a longer period than was intended; (4) There is a persistent desire or unsuccessful efforts to cut down or control substance use; (5) A great deal of time is spent in activities necessary to obtain the substance (e.g., visiting multiple doctors or driving long distances), use the substance (e.g., chain-smoking), or recover from its effects; (6) Important social, occupational, or recreational activities are given up or reduced because of substance use; and (7) The substance use is continued despite knowledge of having a persistent or recurrent physical or psychological problem that is likely to have been caused or exacerbated by the substance (e.g., current cocaine use despite recognition of cocaine-induced depression, or continued drinking despite recognition that an ulcer was made worse by alcohol consumption). (See *American Psychiatric Association, Diagnostic Criteria for DSM-IV*, Washington D.C., APA, 1994.) "Substance dependence" includes a maladaptive pattern of substance use, leading to clinically significant impairment or distress, as manifested by three (or more) of the following symptoms, occurring at any time in the same 12-month period: (1) Tolerance, as defined by either of the following: (a) a need for markedly increased amounts of the substance to achieve intoxication or desired effect, or (b) markedly diminished effect with continued use of the same amount of the substance; (2) Withdrawal, as manifested by either of the following: (a) the characteristic withdrawal syndrome for the substance, or (b) the same (or closely related) substance is taken to relieve or avoid withdrawal symptoms; (3) The substance is often taken in larger amounts or over a longer period than was intended; (4) There is a persistent desire or unsuccessful efforts to cut down or control substance use; (5) A great deal of time is spent in activities necessary to obtain the substance (e.g., visiting multiple doctors or driving long distances), use the substance (e.g., chain-smoking), or recover from its effects; (6) Important social, occupational, or recreational activities are given up or reduced because of substance use; and (7) The substance use is continued despite knowledge of having a persistent or recurrent physical or psychological problem that is likely to have been caused or exacerbated by the substance (e.g., current cocaine use despite recognition of cocaine-induced depression, or continued drinking despite recognition that an ulcer was made worse by alcohol consumption). (See *American Psychiatric Association, Diagnostic Criteria for DSM-IV*, Washington D.C., APA, 1994.)

A person is "dependent upon a substance" if such person is determined by a licensed physician or other appropriate accredited medical personnel to meet the criteria for substance dependence with respect to such substance.

"Substance abuse" includes a maladaptive pattern of substance use leading to clinically significant impairment or distress, as manifested by one (or more) of the following, occurring within a 12-month period: (1) recurrent substance use resulting in a failure to fulfill major role obligations at work, school, or home (e.g., repeated absences or poor work performance related to substance use; substance-related absences, suspensions, or expulsions from school; neglect of children or household); (2) recurrent substance use in situations in which it is physically hazardous (e.g., driving an automobile or operating a machine when impaired by substance use); (3) recurrent substance-related legal problems (e.g., arrests for substance-related disorderly conduct); and (4) continued substance use despite having persistent or recurrent social or interpersonal problems caused or exacerbated by the effects of the substance (e.g., arguments with spouse about consequences of intoxication, physical fights). (See *American Psychiatric Association, Diagnostic Criteria for DSM-IV*, Washington D.C., APA, 1994.)

The terms drug reward, incentive salience for the drug, drug craving, drug preference, drug seeking, and drug consumption refer to "drugs" because these concepts have generally been used in the drug dependence/abuse context. However, it should be understood that these terms, as used herein, also encompass reward, incentive salience, craving, preference, seeking and consumption of any substance that is used in a maladaptive manner.

The term "drug reward" refers to the tendency of a drug or substance to cause pleasurable effects that induce a subject to alter their behavior to obtain more of the drug or substance.

The phrase "incentive salience for the drug" refers to a particular form of motivation to consume a previously experienced drug or substance that results from a hypersensitive neural state thought to be mediated by dopaminergic systems.

The term "drug craving" refers to the desire to experience the effects of a previously experienced drug or substance or to ameliorate the negative symptoms of drug or substance withdrawal by taking more of a previously experienced drug or substance.

The term "drug preference" refers to the tendency to consume a drug or substance that produces pleasurable effects, a opposed than a control substance that does not produce such effects (drug preference for alcohol can be tested, for example, by allowing an animal access to two bottles, one containing an alcohol solution, and one containing water and comparing the amount of each the animal consumes).

The term "drug seeking" refers to behavior aimed at obtaining a drug or substance, even in the face of negative health and social consequences. Drug seeking is often uncontrollable and compulsive.

"Drug consumption" refers to the amount of drug or substance consumed by a subject over a selected period of time.

A "drug of abuse" includes any substance, the excessive consumption or administration of which can result in a diagnosis of substance dependence or abuse as defined herein or as defined by the current DSM Criteria promulgated by the American Psychiatric Association or equivalent criteria. Drugs of abuse include, without limitation, an opioid, a psychostimulant, a cannabinoid, an empathogen, a dissociative drug, and ethanol. Thus, for example, heroin, cocaine, methamphetamines, *cannabis*, 3-4 methylenedioxy-methamphetamine (MDMA), barbiturates, phencyclidine (PCP), ketamine, and ethanol are all drugs of abuse, as defined herein.

The phrase "a drug-related effect" refers to an in vivo effect that occurs in response to a drug. Exemplary effects include stimulant, sedative, hypnotic, and ataxic effects.

A "sedative effect" refers to a decrease in activity and/or excitement in a subject.

A "hypnotic effect" includes an increase in drowsiness and/or a facilitation of the onset and/or maintenance of sleep.

An "ataxic effect" refers to a decrease in motor coordination.

An agent is said to "mitigate" a symptom of maladaptive substance use or a drug-related effect if the agent inhibits (i.e., reduces or prevents) the symptom or effect.

A "benzodiazepine" is referred to a agent selected from the group consisting of: alprazolam, chlordiazepoxide, chlordiazepoxide hydrochloride, chlormezanone, clobazam, clonazepam, clorazepate dipotassium, diazepam, droperidol, estazolam, fentanyl citrate, flurazepam hydrochloride, halazepam, lorazepam, midazolam hydrochloride, oxazepam, prazepam, quazepam, temazepam, and triazolam.

A "barbiturate" referred to a agent selected from the group consisting of: amobarbital, amobarbital sodium, aprobarbital, butabarbital sodium, hexobarbital sodium, mephobarbital, metharbital, methohexital sodium, pentobarbital, pentobarbital sodium, phenobarbital, phenobarbital sodium, secobarbital, secobarbital sodium, talbutal, thiamylal sodium, and thiopental sodium.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The term "cancer" refers to or describes the physiological condition in mammals that is typically characterized by unregulated cell growth. Examples of cancer include, for example, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multi forme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), and chronic lymphocytic leukemia (CML).

It is to be understood that this invention is not limited to particular methods, reagents, compounds, compositions, or biological systems, which can, of course, vary. It is also to be understood that the terminology used herein is for the purpose of describing particular aspects only, and is not intended to be limiting. As used in this specification and the appended claims, the singular forms "a", "an", and "the" include plural referents unless the content clearly dictates otherwise. Thus, for example, reference to "a compound" includes a combination of two or more compounds or molecules, and the like.

Compounds

In one aspect, the present invention provides compounds having structural formula (Ia) or (Ic):

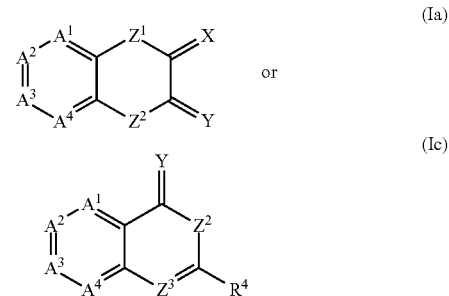

or a salt, solvate, or physiologically functional derivative thereof, wherein:
X and Y are independently $CR^1R^5$, $NR^1$, O or S:
$Z^1$ and $Z^2$ are independently $CHR^2$, $NR^2$, O, or S;
$Z^3$ is $CR^6$ or N;
$A^1$, $A^2$, $A^3$, and $A^4$ are independently $CR^3$ or N;
$R^1$, $R^2$, $R^3$, $R^4$, $R^5$ and $R^6$ are independently hydrogen, halogen, acyl, substituted acyl, alkoxycarbonyl, substituted alkoxycarbonyl, aryloxycarbonyl, substituted aryloxycarbonyl, —C(O)$NR^7R^8$, alkyl, substituted alkyl, cycloheteroalkyl, substituted cycloheteroalkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl;

$R^7$ and $R^8$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl, or alternatively, $R^7$ and $R^8$, taken together with the nitrogen atom to which they are attached, form a 4-; 5-, 6-, or 7-membered cycloheteroalkyl ring;

with the following provisos:
(a) at least one of $Z^1$ and $Z^2$ is $CHR^2$ or $NR^2$;
(b) at least one of $A^1$, $A^2$, $A^3$, and $A^4$ is $CR^3$;
(c) at least one of $R^1$, $R^2$, $R^3$ and $R^5$ is not hydrogen; and
(d) when $R^1$ and $R^5$ are independently hydrogen, aryl or substituted aryl; $R^2$ is hydrogen, arylalkyl or substituted arylalkyl; then $R^3$ is not aryl, substituted aryl, heteroaryl, or substituted heteroaryl.
(e) when $R^3$ is —C(O)$NR^7R^8$; $R^2$ is hydrogen or substituted arylalkyl; then at least one of $R^1$ and $R^5$ is not halogen, acyl, substituted acyl, alkoxycarbonyl, substituted alkoxycarbonyl, alkyl, or substituted alkyl.
(f) when $R^3$ is —C(O)$NR^7R^8$; $R^7$ is hydrogen; $R^8$ is substituted alkyl, arylalkyl, substituted arylalkyl, heteroaryl, heteroalkyl or substituted aryl; $R^2$ is hydrogen or substituted arylalkyl; then at least one $R^1$ is not halogen, acyl, substituted acyl, alkoxycarbonyl, substituted alkoxycarbonyl, alkyl, or substituted alkyl.

In one embodiment of formula (Ia) or (Ic), $Z^2$ is $NR^2$ and Y is O or.

In one embodiment of formula (Ia) or (Ic), $Z^2$ is $NR^2$, Y is O or S, X is $CR^1R^5$, and $Z^1$ is O or S.

In one embodiment of formula (Ia), $R^5$ is hydrogen, alkyl or substituted alkyl, and $R^1$ is benzyl or substituted benzyl. In one embodiment of formula (Ia), the compound has structural formula (Ih):

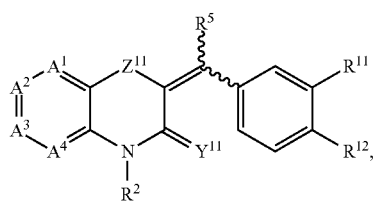

(Ih)

wherein, $A^1$, $A^2$, $A^3$, and $A^4$ are the same as defined above in formula (Ia);

$Z^{11}$ and $Y^{11}$ are independently O or S;

$R^2$, $R^{11}$ and $R^{12}$ are independently hydrogen, halogen, acyl, substituted acyl, alkoxycarbonyl, substituted alkoxycarbonyl, —C(O)$NR^7R^8$, alkyl, substituted alkyl, cycloheteroalkyl, substituted cycloheteroalkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl, or alternatively, $R^{11}$ and $R^{12}$, taken together with atoms to which they are attached, form a 4-, 5-, 6-, or 7-membered cycloalkyl or cycloheteroalkyl ring. It is understood by one skilled in the art that the wiggled bond has E or Z configuration.

In one embodiment of formula (Ih), $R^{12}$ is —C(O)$NR^7R^8$.

In one embodiment of formula (Ih), $A^1$, $A^2$, $A^3$, and $A^4$ are $CR^3$. In one embodiment of formula (Ih), $A^1$, $A^2$, $A^3$, and $A^4$ are CH.

In some embodiments, the compound having a structural formula (Ia), (Ic) or (Ih) is selected from the group consisting of (Table 1.1-1.3):

TABLE 1.1

(301)

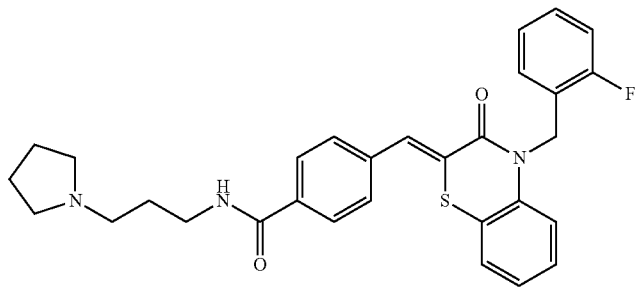 [SMILES: O=C(NCCCN1CCCC1)c1ccc(/C=C2\Sc3ccccc3N(Cc3ccccc3F)C2=O)cc1]

(303)

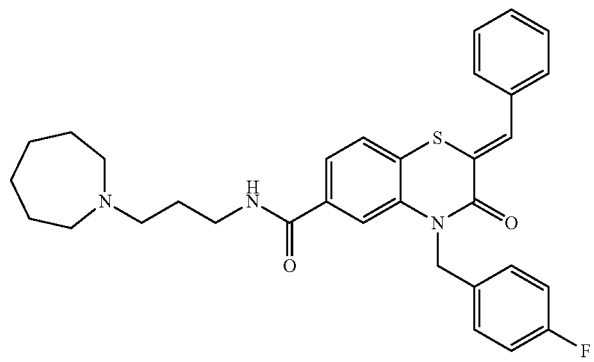 [SMILES: O=C(NCCCN1CCCCCC1)c1ccc2c(c1)N(Cc1ccc(F)cc1)C(=O)/C(=C/c1ccccc1)S2]

TABLE 1.1-continued
(305)
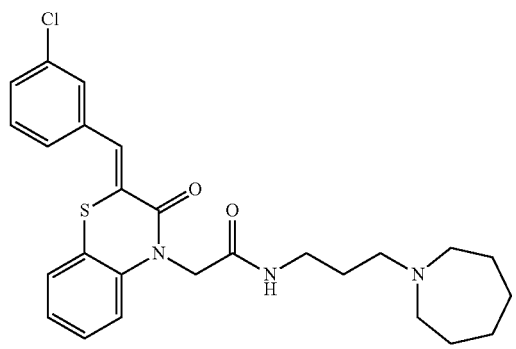 [SMILES: O=C(CN1C(=O)/C(=C/c2cccc(Cl)c2)Sc2ccccc21)NCCCN1CCCCCC1]
(307)
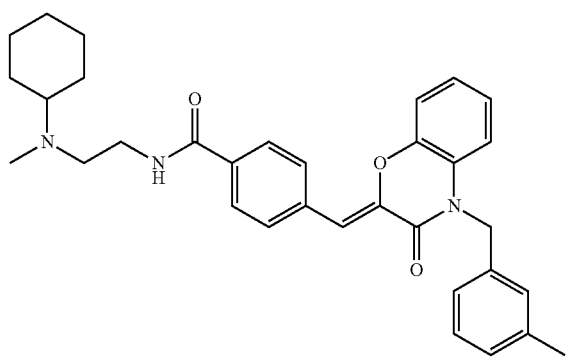
(309)
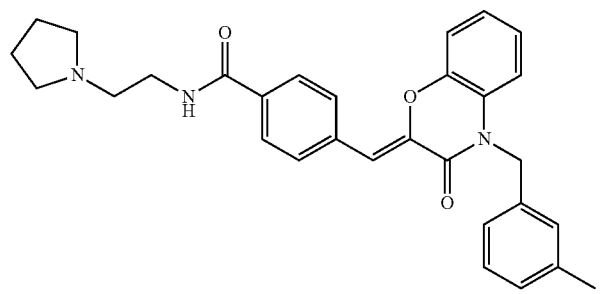 [SMILES: Cc1cccc(CN2C(=O)/C(=C/c3ccc(C(=O)NCCN4CCCC4)cc3)Oc3ccccc32)c1]
(311)
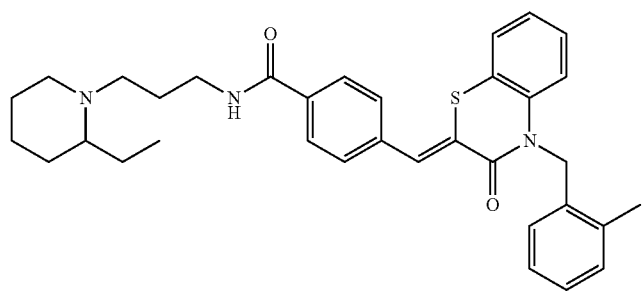 [SMILES: CCC1CCCCN1CCCNC(=O)c1ccc(/C=C2\Sc3ccccc3N(Cc3ccccc3C)C2=O)cc1]

TABLE 1.1-continued
(313)
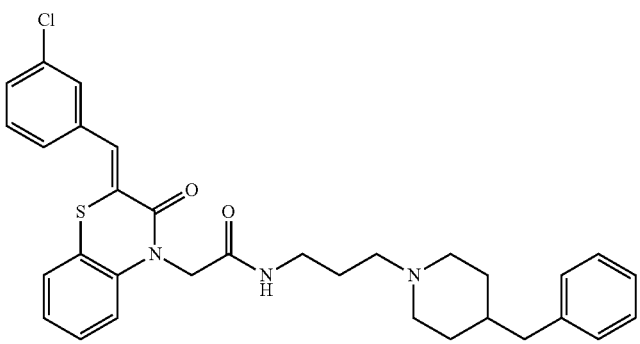 [SMILES: O=C(CN1C(=O)/C(=C/c2cccc(Cl)c2)Sc2ccccc21)NCCCN1CCC(Cc2ccccc2)CC1]
(315)
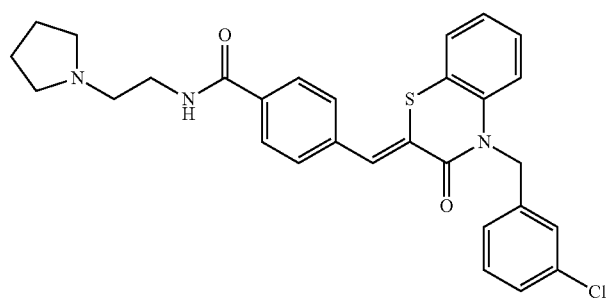 [SMILES: O=C(NCCN1CCCC1)c1ccc(/C=C2\Sc3ccccc3N(Cc3cccc(Cl)c3)C2=O)cc1]
(317)
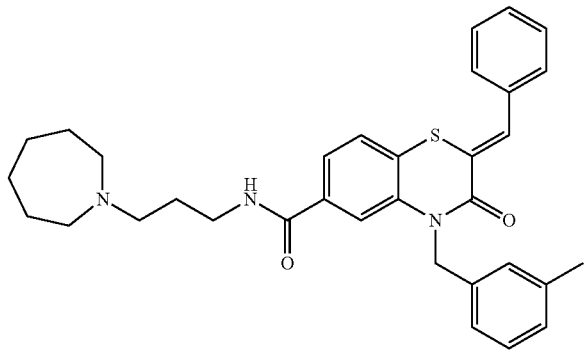 [SMILES: Cc1cccc(CN2C(=O)/C(=C/c3ccccc3)Sc3ccc(C(=O)NCCCN4CCCCCC4)cc32)c1]
(319)
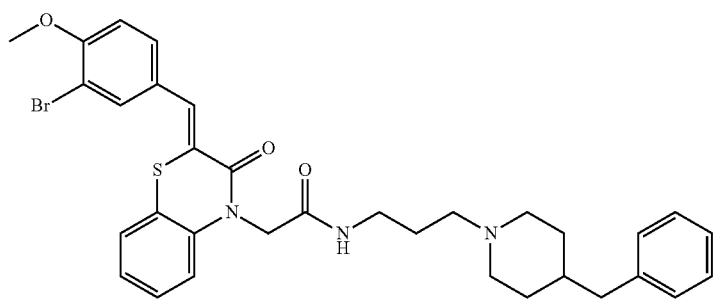 [SMILES: COc1ccc(/C=C2\Sc3ccccc3N(CC(=O)NCCCN3CCC(Cc4ccccc4)CC3)C2=O)cc1Br]

TABLE 1.1-continued
(321)
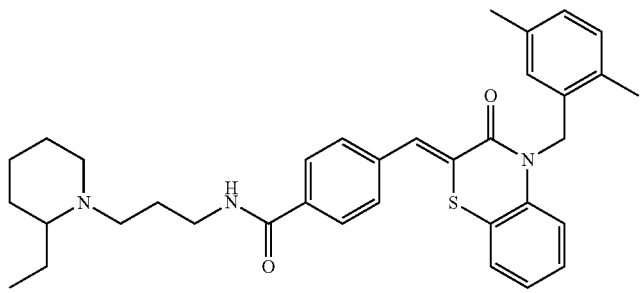 [SMILES: CCC1CCCCN1CCCNC(=O)c1ccc(/C=C2\Sc3ccccc3N(Cc3cc(C)ccc3C)C2=O)cc1]
(323)
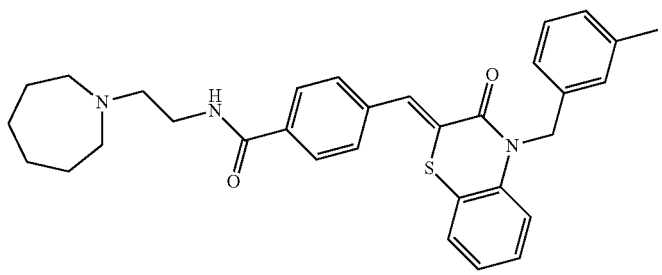 [SMILES: Cc1cccc(CN2C(=O)/C(=C/c3ccc(C(=O)NCCN4CCCCCC4)cc3)Sc3ccccc32)c1]
(325)
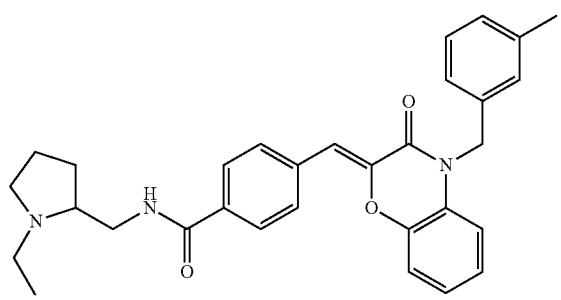 [SMILES: CCN1CCCC1CNC(=O)c1ccc(/C=C2\Oc3ccccc3N(Cc3cccc(C)c3)C2=O)cc1]
(327)
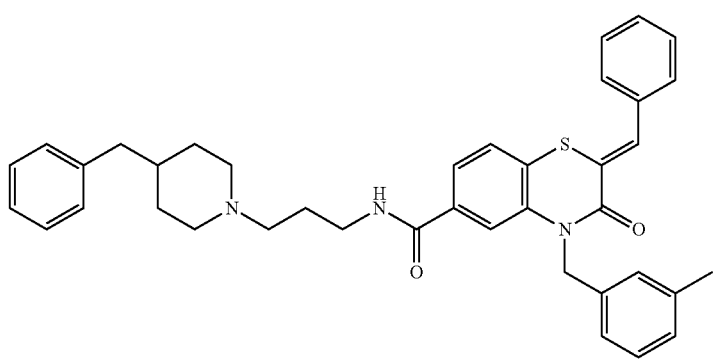 [SMILES: Cc1cccc(CN2C(=O)/C(=C/c3ccccc3)Sc3ccc(C(=O)NCCCN4CCC(Cc5ccccc5)CC4)cc32)c1]
(329)
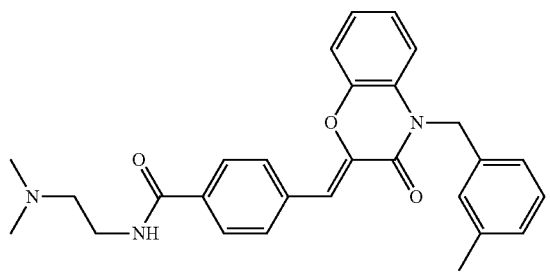 [SMILES: Cc1cccc(CN2C(=O)/C(=C/c3ccc(C(=O)NCCN(C)C)cc3)Oc3ccccc32)c1]

TABLE 1.1-continued
(331)
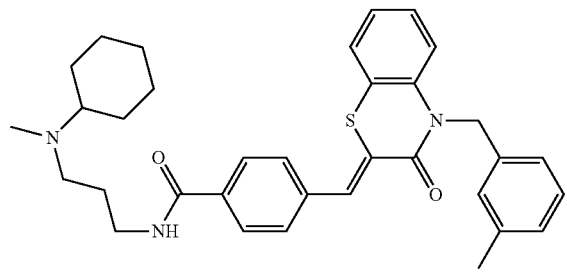 [SMILES: Cc1cccc(CN2C(=O)/C(=C/c3ccc(C(=O)NCCCN(C)C4CCCCC4)cc3)Sc3ccccc32)c1]
(333)
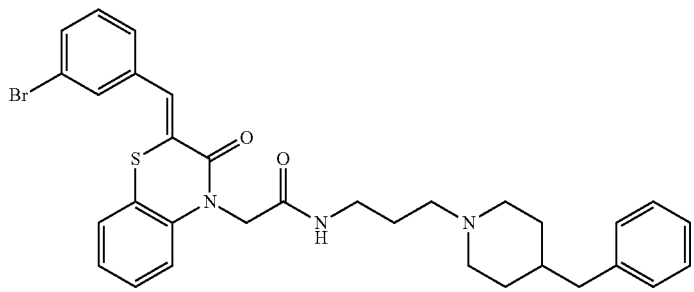 [SMILES: O=C(CN1C(=O)/C(=C/c2cccc(Br)c2)Sc2ccccc21)NCCCN1CCC(Cc2ccccc2)CC1]
(335)
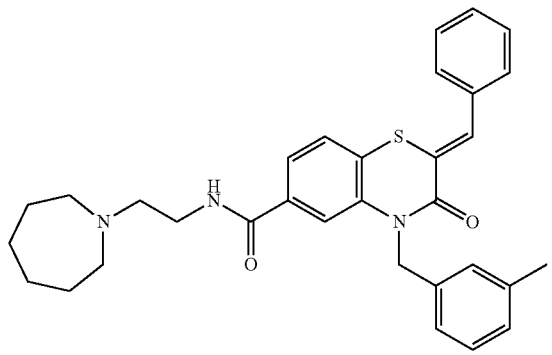 [SMILES: Cc1cccc(CN2C(=O)/C(=C/c3ccccc3)Sc3ccc(C(=O)NCCN4CCCCCC4)cc32)c1]
(337)
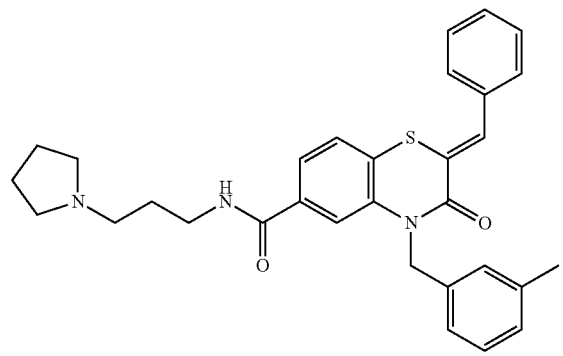 [SMILES: Cc1cccc(CN2C(=O)/C(=C/c3ccccc3)Sc3ccc(C(=O)NCCCN4CCCC4)cc32)c1]

TABLE 1.1-continued
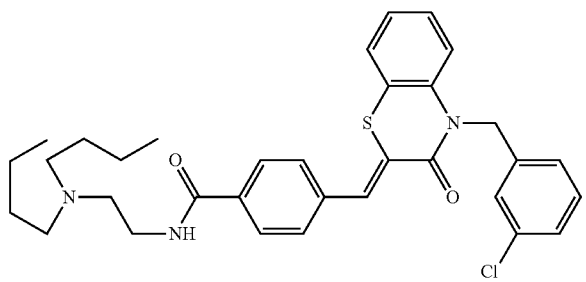 [SMILES: CCCCN(CCCC)CCNC(=O)c1ccc(/C=C2\Sc3ccccc3N(Cc3cccc(Cl)c3)C2=O)cc1]
(339)
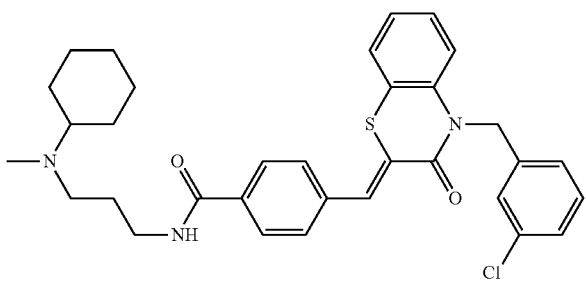 [SMILES: CN(CCCNC(=O)c1ccc(/C=C2\Sc3ccccc3N(Cc3cccc(Cl)c3)C2=O)cc1)C1CCCCC1]
(341)
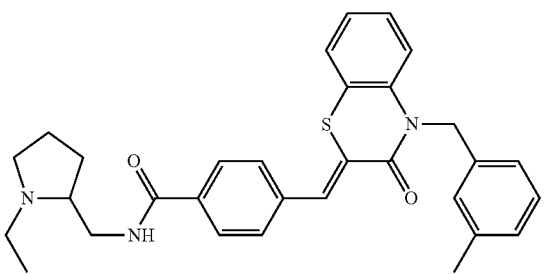 [SMILES: CCN1CCCC1CNC(=O)c1ccc(/C=C2\Sc3ccccc3N(Cc3cccc(C)c3)C2=O)cc1]
(343)
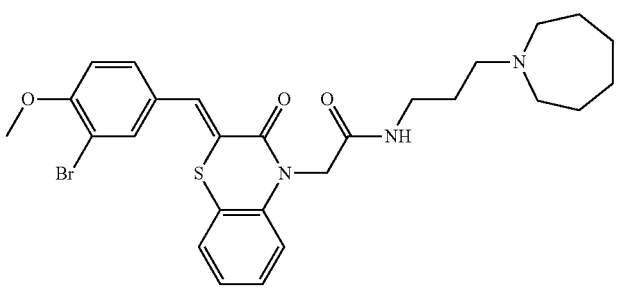 [SMILES: COc1ccc(/C=C2\Sc3ccccc3N(CC(=O)NCCCN3CCCCCC3)C2=O)cc1Br]
(345)
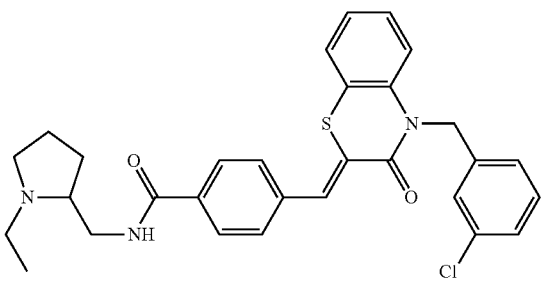 [SMILES: CCN1CCCC1CNC(=O)c1ccc(/C=C2\Sc3ccccc3N(Cc3cccc(Cl)c3)C2=O)cc1]
(347)

TABLE 1.1-continued
(349)
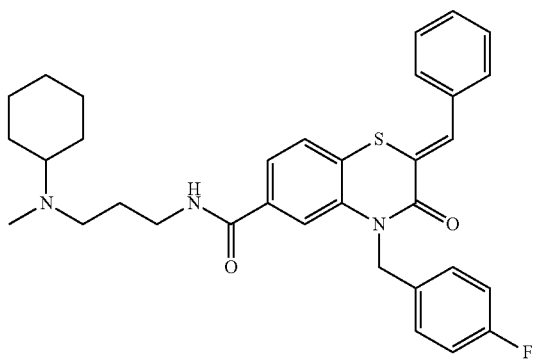 [SMILES: CN(CCCNC(=O)c1ccc2c(c1)N(Cc1ccc(F)cc1)C(=O)/C(=C/c1ccccc1)S2)C1CCCCC1]
(351)
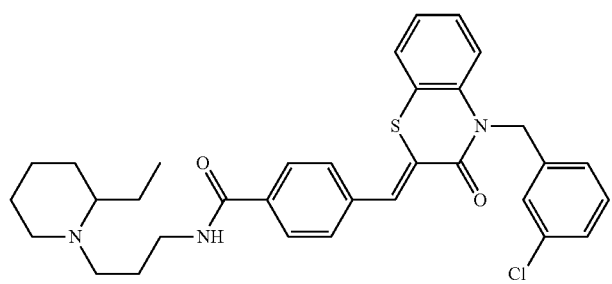 [SMILES: CCC1CCCCN1CCCNC(=O)c1ccc(/C=C2\Sc3ccccc3N(Cc3cccc(Cl)c3)C2=O)cc1]
(353)
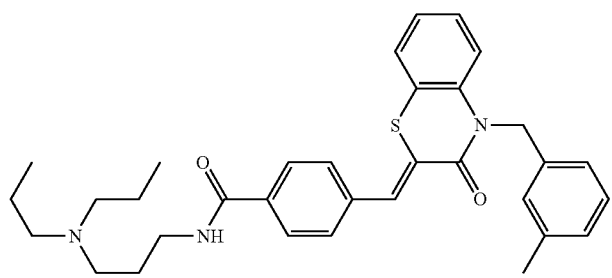 [SMILES: CCCN(CCC)CCCNC(=O)c1ccc(/C=C2\Sc3ccccc3N(Cc3cccc(C)c3)C2=O)cc1]
(355)
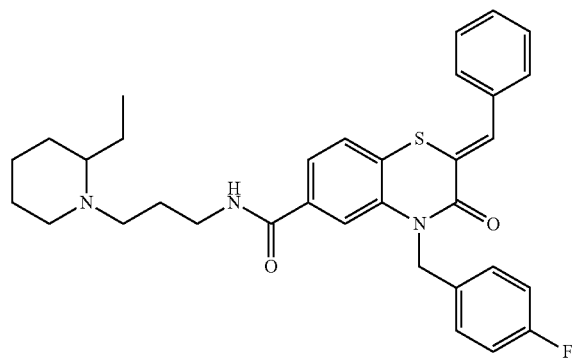 [SMILES: CCC1CCCCN1CCCNC(=O)c1ccc2c(c1)N(Cc1ccc(F)cc1)C(=O)/C(=C/c1ccccc1)S2]

TABLE 1.1-continued
(357)
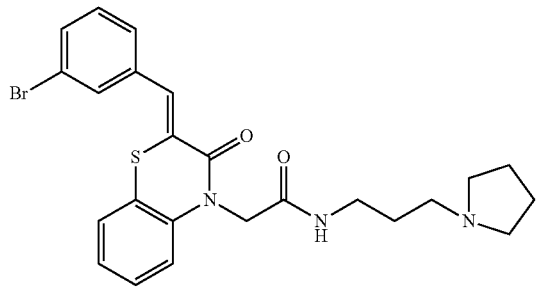 [SMILES: O=C(CN1C(=O)/C(=C/c2cccc(Br)c2)Sc2ccccc21)NCCCN1CCCC1]
(359)
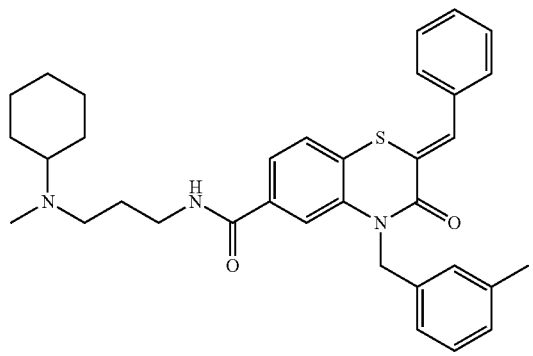
(361)
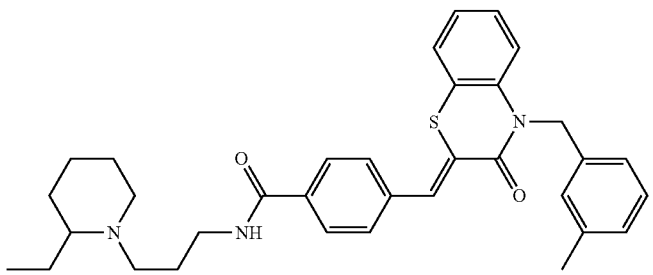 [SMILES: CCC1CCCCN1CCCNC(=O)c1ccc(/C=C2\Sc3ccccc3N(Cc3cccc(C)c3)C2=O)cc1]
(363)
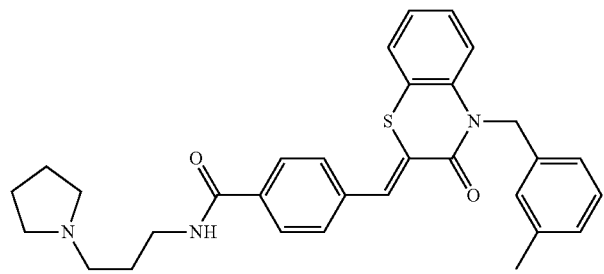 [SMILES: Cc1cccc(CN2C(=O)/C(=C/c3ccc(C(=O)NCCCN4CCCC4)cc3)Sc3ccccc32)c1]
(365)
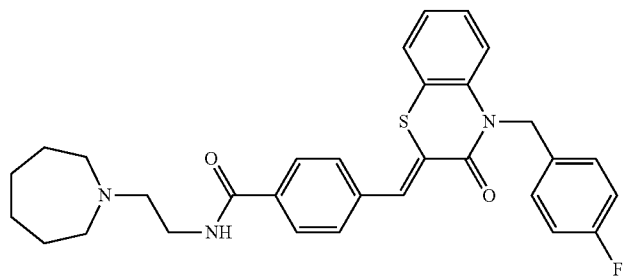 [SMILES: O=C(NCCN1CCCCCC1)c1ccc(/C=C2\Sc3ccccc3N(Cc3ccc(F)cc3)C2=O)cc1]

TABLE 1.1-continued
(367)
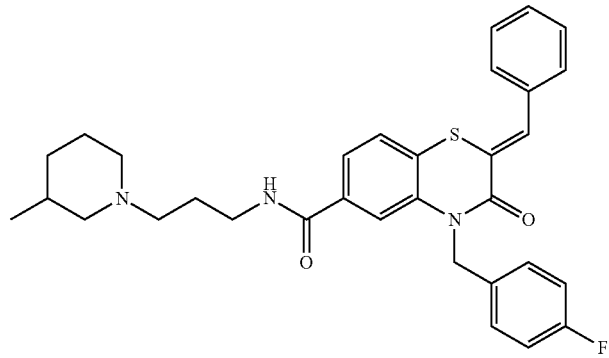 [SMILES: CC1CCCN(CCCNC(=O)c2ccc3c(c2)N(Cc2ccc(F)cc2)C(=O)/C(=C/c2ccccc2)S3)C1]
(369)
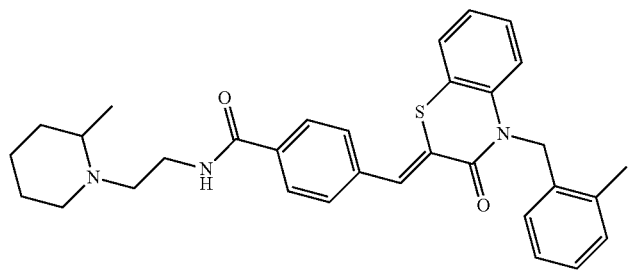 [SMILES: Cc1ccccc1CN1C(=O)/C(=C/c2ccc(C(=O)NCCN3CCCCC3C)cc2)Sc2ccccc21]
(371)
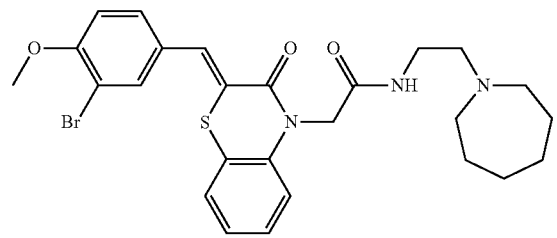 [SMILES: COc1ccc(/C=C2\Sc3ccccc3N(CC(=O)NCCN3CCCCCC3)C2=O)cc1Br]
(375)
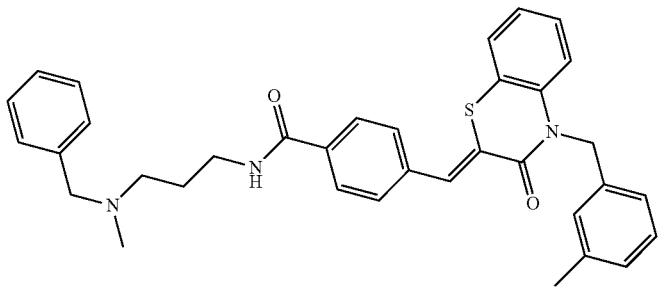 [SMILES: Cc1cccc(CN2C(=O)/C(=C/c3ccc(C(=O)NCCCN(C)Cc4ccccc4)cc3)Sc3ccccc32)c1]
(377)
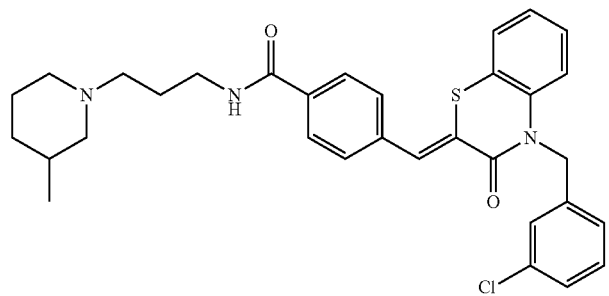 [SMILES: CC1CCCN(CCCNC(=O)c2ccc(/C=C3\Sc4ccccc4N(Cc4cccc(Cl)c4)C3=O)cc2)C1]

TABLE 1.1-continued
(379)
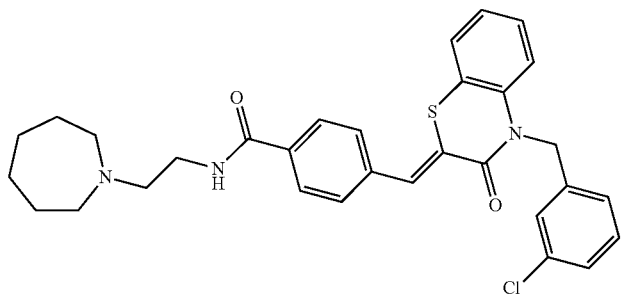 [SMILES: O=C(NCCN1CCCCCC1)c1ccc(/C=C2\Sc3ccccc3N(Cc3cccc(Cl)c3)C2=O)cc1]
(381)
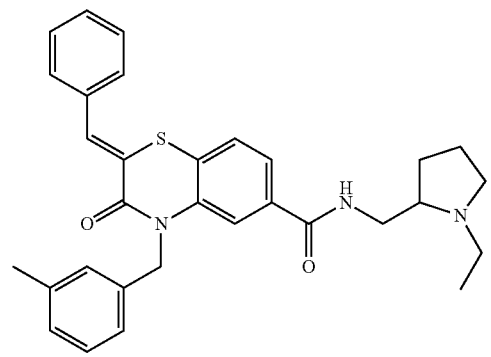 [SMILES: CCN1CCCC1CNC(=O)c1ccc2c(c1)N(Cc1cccc(C)c1)C(=O)/C(=C/c1ccccc1)S2]
(383)
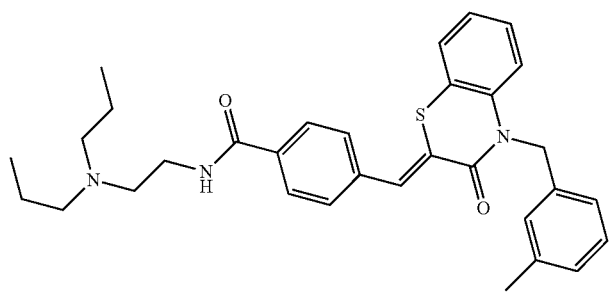 [SMILES: CCCN(CCC)CCNC(=O)c1ccc(/C=C2\Sc3ccccc3N(Cc3cccc(C)c3)C2=O)cc1]
(385)
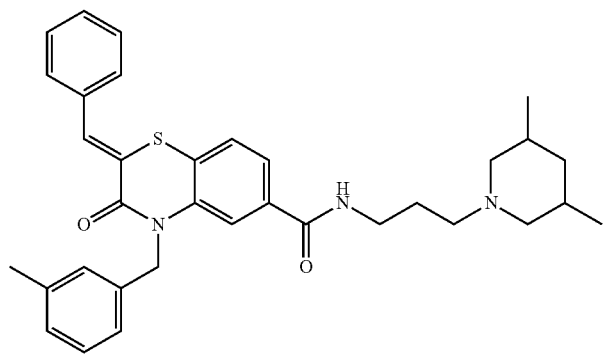

TABLE 1.1-continued
(387)
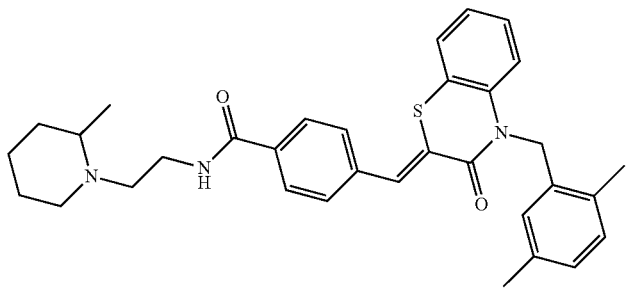 [SMILES: Cc1ccc(C)c(CN2C(=O)/C(=C/c3ccc(C(=O)NCCN4CCCCC4C)cc3)Sc3ccccc32)c1]
(389)
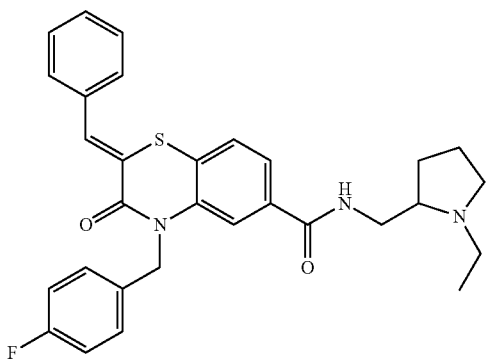 [SMILES: CCN1CCCC1CNC(=O)c1ccc2c(c1)N(Cc1ccc(F)cc1)C(=O)/C(=C/c1ccccc1)S2]
(391)
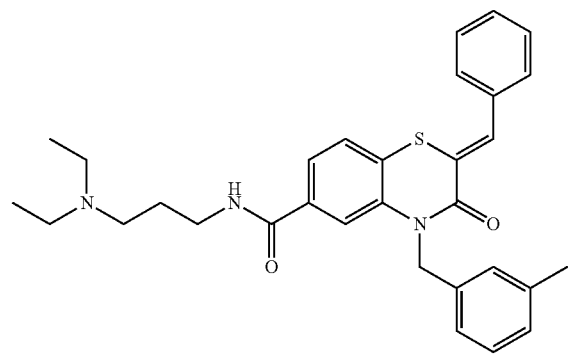 [SMILES: CCN(CC)CCCNC(=O)c1ccc2c(c1)N(Cc1cccc(C)c1)C(=O)/C(=C/c1ccccc1)S2]
(393)
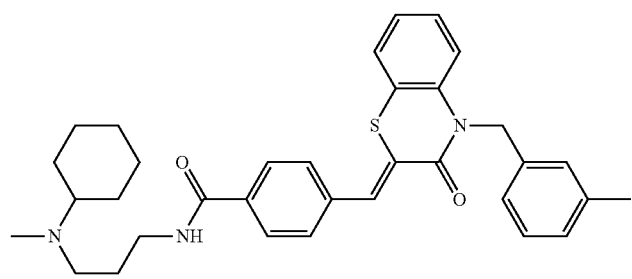

TABLE 1.1-continued
(395)
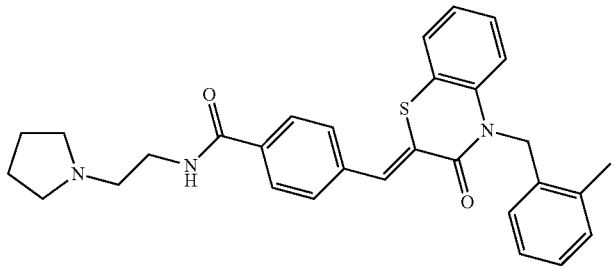 [SMILES: Cc1ccccc1CN1C(=O)/C(=C/c2ccc(C(=O)NCCN3CCCC3)cc2)Sc2ccccc21]
(397)
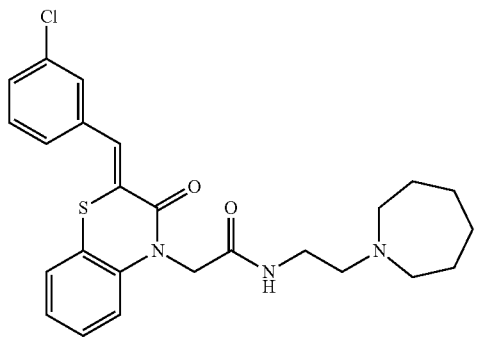 [SMILES: O=C(CN1C(=O)/C(=C/c2cccc(Cl)c2)Sc2ccccc21)NCCN1CCCCCC1]
(399)
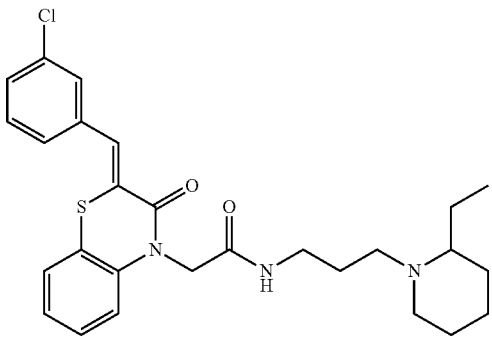 [SMILES: CCC1CCCCN1CCCNC(=O)CN1C(=O)/C(=C/c2cccc(Cl)c2)Sc2ccccc21]
(201)
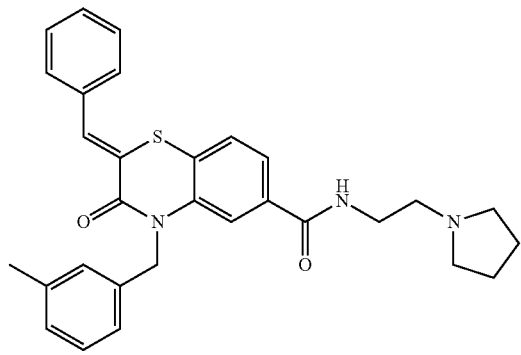 [SMILES: Cc1cccc(CN2C(=O)/C(=C/c3ccccc3)Sc3ccc(C(=O)NCCN4CCCC4)cc32)c1]
(203)
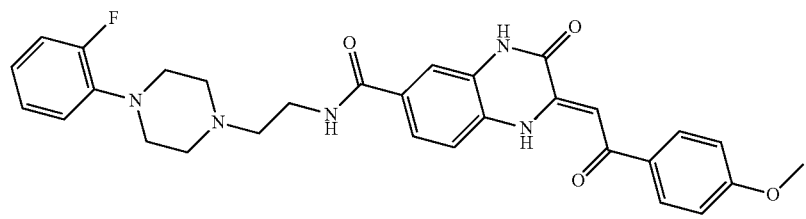 [SMILES: COc1ccc(C(=O)/C=C2\Nc3ccc(C(=O)NCCN4CCN(c5ccccc5F)CC4)cc3NC2=O)cc1]

TABLE 1.1-continued
(205)
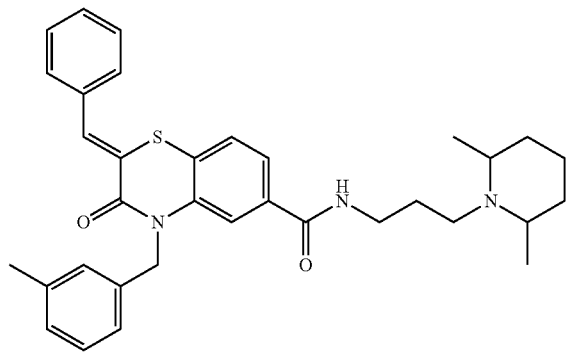 [SMILES: Cc1cccc(CN2C(=O)/C(=C/c3ccccc3)Sc3ccc(C(=O)NCCCN4C(C)CCCC4C)cc32)c1]
(207)
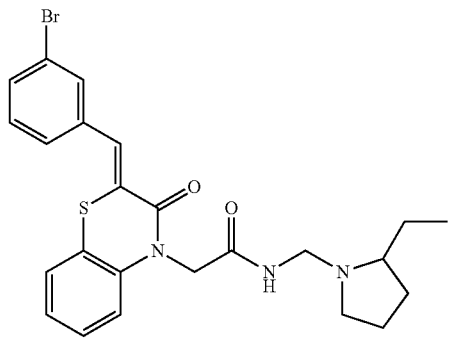 [SMILES: CCC1CCCN1CNC(=O)CN1C(=O)/C(=C/c2cccc(Br)c2)Sc2ccccc21]
(209)
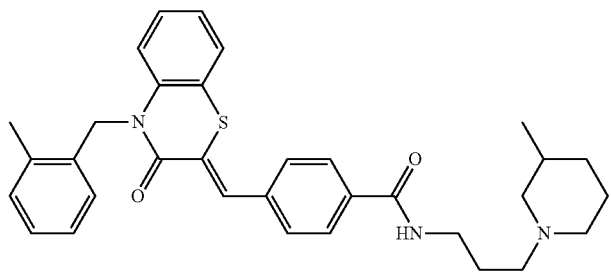 [SMILES: Cc1ccccc1CN1C(=O)/C(=C/c2ccc(C(=O)NCCCN3CCCC(C)C3)cc2)Sc2ccccc21]
(211)
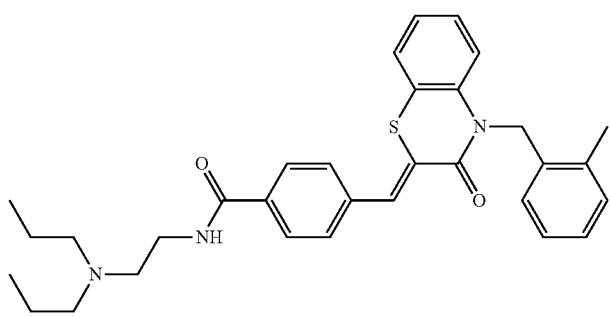 [SMILES: CCCN(CCC)CCNC(=O)c1ccc(/C=C2\Sc3ccccc3N(Cc3ccccc3C)C2=O)cc1]

TABLE 1.1-continued (213)

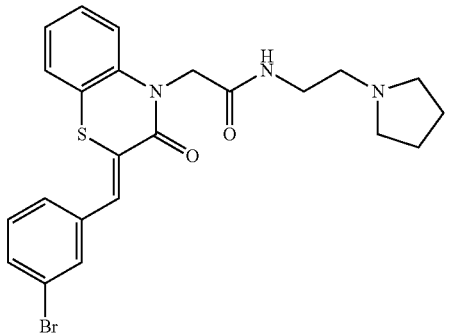 [SMILES: O=C(CN1C(=O)/C(=C/c2cccc(Br)c2)Sc2ccccc21)NCCN1CCCC1]

or a salt, prodrug or softdrug, salt of prodrug or softdrug, solvate or hydrate, or physiologically functional derivative thereof.

Compounds listed in Table 1.1 may also be represented by their chemical names as follows:

| ID | IUPAC Name |
|---|---|
| 301 | 4-{(Z/E)-[4-(2-fluorobenzyl)-3-oxo-3,4-dihydro-2H-1,4-benzothiazin-2-ylidene]methyl}-N-(3-pyrrolidin-1-ylpropyl)benzamide |
| 303 | (2Z/2E)-N-(3-azepan-1-ylpropyl)-4-(4-fluorobenzyl)-3-oxo-2-(phenylmethylidene)-3,4-dihydro-2H-1,4-benzothiazine-6-carboxamide |
| 305 | N-(3-azepan-1-ylpropyl)-2-{(2Z/2E)-2-[(3-chlorophenyl)methylidene]-3-oxo-2,3-dihydro-4H-1,4-benzothiazin-4-yl}acetamide |
| 307 | N-{2-[cyclohexyl(methyl)amino]ethyl}-4-{(Z/E)-[4-(3-methylbenzyl)-3-oxo-3,4-dihydro-2H-1,4-benzoxazin-2-ylidene]methyl}benzamide |
| 309 | 4-{(Z/E)-[4-(3-methylbenzyl)-3-oxo-3,4-dihydro-2H-1,4-benzoxazin-2-ylidene]methyl}-N-(2-pyrrolidin-1-ylethyl)benzamide |
| 311 | N-[3-(2-ethylpiperidin-1-yl)propyl]-4-{(Z/E)-[4-(2-methylbenzyl)-3-oxo-3,4-dihydro-2H-1,4-benzothiazin-2-ylidene]methyl}benzamide |
| 313 | N-[3-(4-benzylpiperidin-1-yl)propyl]-2-{(2Z/2E)-2-[(3-chlorophenyl)methylidene]-3-oxo-2,3-dihydro-4H-1,4-benzothiazin-4-yl}acetamide |
| 315 | 4-{(Z/E)-[4-(3-chlorobenzyl)-3-oxo-3,4-dihydro-2H-1,4-benzothiazin-2-ylidene]methyl}-N-(2-pyrrolidin-1-ylethyl)benzamide |
| 317 | (2Z/2E)-N-(3-azepan-1-ylpropyl)-4-(3-methylbenzyl)-3-oxo-2-(phenylmethylidene)-3,4-dihydro-2H-1,4-benzothiazine-6-carboxamide |
| 319 | N-[3-(4-benzylpiperidin-1-yl)propyl]-2-{(2Z/2E)-2-[(3-bromo-4-methoxyphenyl)methylidene]-3-oxo-2,3-dihydro-4H-1,4-benzothiazin-4-yl}acetamide |
| 321 | 4-{(Z/E)-[4-(2,5-dimethylbenzyl)-3-oxo-3,4-dihydro-2H-1,4-benzothiazin-2-ylidene]methyl}-N-[3-(2-ethylpiperidin-1-yl)propyl]benzamide |
| 323 | N-(2-azepan-1-ylethyl)-4-{(Z/E)-[4-(3-methylbenzyl)-3-oxo-3,4-dihydro-2H-1,4-benzothiazin-2-ylidene]methyl}benzamide |
| 325 | N-[(1-ethylpyrrolidin-2-yl)methyl]-4-{(Z/E)-[4-(3-methylbenzyl)-3-oxo-3,4-dihydro-2H-1,4-benzoxazin-2-ylidene]methyl}benzamide |
| 327 | (2Z/2E)-N-[3-(4-benzylpiperidin-1-yl)propyl]-4-(3-methylbenzyl)-3-oxo-2-(phenylmethylidene)-3,4-dihydro-2H-1,4-benzothiazine-6-carboxamide |
| 329 | N-[2-(dimethylamino)ethyl]-4-{(Z/E)-[4-(3-methylbenzyl)-3-oxo-3,4-dihydro-2H-1,4-benzoxazin-2-ylidene]methyl}benzamide |
| 331 | N-{3-[cyclohexyl(methyl)amino]propyl}-4-{(Z/E)-[4-(2-methylbenzyl)-3-oxo-3,4-dihydro-2H-1,4-benzothiazin-2-ylidene]methyl}benzamide |
| 333 | N-[3-(4-benzylpiperidin-1-yl)propyl]-2-{(2Z/2E)-2-[(3-bromophenyl)methylidene]-3-oxo-2,3-dihydro-4H-1,4-benzothiazin-4-yl}acetamide |
| 335 | (2Z/2E)-N-(2-azepan-1-ylethyl)-4-(3-methylbenzyl)-3-oxo-2-(phenylmethylidene)-3,4-dihydro-2H-1,4-benzothiazine-6-carboxamide |
| 337 | (2Z/2E)-4-(3-methylbenzyl)-3-oxo-2-(phenylmethylidene)-N-(3-pyrrolidin-1-ylpropyl)-3,4-dihydro-2H-1,4-benzothiazine-6-carboxamide |
| 339 | 4-{(Z/E)-[4-(3-chlorobenzyl)-3-oxo-3,4-dihydro-2H-1,4-benzothiazin-2-ylidene]methyl}-N-[2-(dibutylamino)ethyl]benzamide |
| 341 | 4-{(Z/E)-[4-(3-chlorobenzyl)-3-oxo-3,4-dihydro-2H-1,4-benzothiazin-2-ylidene]methyl}-N-{3-[cyclohexyl(methyl)amino]propyl}benzamide |
| 343 | N-[(1-ethylpyrrolidin-2-yl)methyl]-4-{(Z/E)-[4-(3-methylbenzyl)-3-oxo-3,4-dihydro-2H-1,4-benzothiazin-2-ylidene]methyl}benzamide |
| 345 | N-(3-azepan-1-ylpropyl)-2-{(2Z/2E)-2-[(3-bromo-4-methoxyphenyl)methylidene]-3-oxo-2,3-dihydro-4H-1,4-benzothiazin-4-yl}acetamide |
| 347 | 4-{(Z/E)-[4-(3-chlorobenzyl)-3-oxo-3,4-dihydro-2H-1,4-benzothiazin-2-ylidene]methyl}-N-[(1-ethylpyrrolidin-2-yl)methyl]benzamide |

-continued

| ID | IUPAC Name |
|---|---|
| 349 | (2Z/2E)-N-{3-[cyclohexyl(methyl)amino]propyl}-4-(4-fluorobenzyl)-3-oxo-2-(phenylmethylidene)-3,4-dihydro-2H-1,4-benzothiazine-6-carboxamide |
| 351 | 4-{(Z/E)-[4-(3-chlorobenzyl)-3-oxo-3,4-dihydro-2H-1,4-benzothiazin-2-ylidene]methyl}-N-[3-(2-ethylpiperidin-1-yl)propyl]benzamide |
| 353 | N-[3-(dipropylamino)propyl]-4-{(Z/E)-[4-(3-methylbenzyl)-3-oxo-3,4-dihydro-2H-1,4-benzothiazin-2-ylidene]methyl}benzamide |
| 355 | (2Z/2E)-N-[3-(2-ethylpiperidin-1-yl)propyl]-4-(4-fluorobenzyl)-3-oxo-2-(phenylmethylidene)-3,4-dihydro-2H-1,4-benzothiazine-6-carboxamide |
| 357 | 2-{(2Z/2E)-2-[(3-bromophenyl)methylidene]-3-oxo-2,3-dihydro-4H-1,4-benzothiazin-4-yl}-N-(3-pyrrolidin-1-ylpropyl)acetamide |
| 359 | (2Z/2E)-N-{3-[cyclohexyl(methyl)amino]propyl}-4-(3-methylbenzyl)-3-oxo-2-(phenylmethylidene)-3,4-dihydro-2H-1,4-benzothiazine-6-carboxamide |
| 361 | N-[3-(2-ethylpiperidin-1-yl)propyl]-4-{(Z/E)-[4-(3-methylbenzyl)-3-oxo-3,4-dihydro-2H-1,4-benzothiazin-2-ylidene]methyl}benzamide |
| 363 | 4-{(Z/E)-[4-(3-methylbenzyl)-3-oxo-3,4-dihydro-2H-1,4-benzothiazin-2-ylidene]methyl}-N-(3-pyrrolidin-1-ylpropyl)benzamide |
| 365 | (2Z/2E)-N-(2-azepan-1-ylethyl)-4-(4-fluorobenzyl)-3-oxo-2-(phenylmethylidene)-3,4-dihydro-2H-1,4-benzothiazine-6-carboxamide |
| 367 | (2Z/2E)-4-(4-fluorobenzyl)-N-[3-(3-methylpiperidin-1-yl)propyl]-3-oxo-2-(phenylmethylidene)-3,4-dihydro-2H-1,4-benzothiazine-6-carboxamide |
| 369 | 4-{(Z/E)-[4-(2-methylbenzyl)-3-oxo-3,4-dihydro-2H-1,4-benzothiazin-2-ylidene]methyl}-N-[2-(2-methylpiperidin-1-yl)ethyl]benzamide |
| 371 | N-(2-azepan-1-ylethyl)-2-{(2Z/2E)-2-[(3-bromo-4-methoxyphenyl)methylidene]-3-oxo-2,3-dihydro-4H-1,4-benzothiazin-4-yl}acetamide |
| 375 | N-{3-[benzyl(methyl)amino]propyl}-4-{(Z/E)-[4-(3-methylbenzyl)-3-oxo-3,4-dihydro-2H-1,4-benzothiazin-2-ylidene]methyl}benzamide |
| 377 | 4-{(Z/E)-[4-(3-chlorobenzyl)-3-oxo-3,4-dihydro-2H-1,4-benzothiazin-2-ylidene]methyl}-N-[3-(3-methylpiperidin-1-yl)propyl]benzamide |
| 379 | N-(2-azepan-1-ylethyl)-4-{(Z/E)-[4-(3-chlorobenzyl)-3-oxo-3,4-dihydro-2H-1,4-benzothiazin-2-ylidene]methyl}benzamide |
| 381 | (2Z/2E)-N-[(1-ethylpyrrolidin-2-yl)methyl]-4-(3-methylbenzyl)-3-oxo-2-(phenylmethylidene)-3,4-dihydro-2H-1,4-benzothiazine-6-carboxamide |
| 383 | N-[2-(dipropylamino)ethyl]-4-{(Z/E)-[4-(3-methylbenzyl)-3-oxo-3,4-dihydro-2H-1,4-benzothiazin-2-ylidene]methyl}benzamide |
| 385 | (2Z/2E)-N-[3-(3,5-dimethylpiperidin-1-yl)propyl]-4-(3-methylbenzyl)-3-oxo-2-(phenylmethylidene)-3,4-dihydro-2H-1,4-benzothiazine-6-carboxamide |
| 387 | 4-{(Z/E)-[4-(2,5-dimethylbenzyl)-3-oxo-3,4-dihydro-2H-1,4-benzothiazin-2-ylidene]methyl}-N-[2-(2-methylpiperidin-1-yl)ethyl]benzamide |
| 389 | (2Z/2E)-N-[(1-ethylpyrrolidin-2-yl)methyl]-4-(4-fluorobenzyl)-3-oxo-2-(phenylmethylidene)-3,4-dihydro-2H-1,4-benzothiazine-6-carboxamide |
| 391 | (2Z/2E)-N-[3-(diethylamino)propyl]-4-(3-methylbenzyl)-3-oxo-2-(phenylmethylidene)-3,4-dihydro-2H-1,4-benzothiazine-6-carboxamide |
| 393 | N-{3-[cyclohexyl(methyl)amino]propyl}-4-{(Z/E)-[4-(3-methylbenzyl)-3-oxo-3,4-dihydro-2H-1,4-benzothiazin-2-ylidene]methyl}benzamide |
| 395 | 4-{(Z/E)-[4-(2-methylbenzyl)-3-oxo-3,4-dihydro-2H-1,4-benzothiazin-2-ylidene]methyl}-N-(2-pyrrolidin-1-ylethyl)benzamide |
| 397 | N-(2-azepan-1-ylethyl)-2-{(2Z/2E)-2-[(3-chlorophenyl)methylidene]-3-oxo-2,3-dihydro-4H-1,4-benzothiazin-4-yl}acetamide |
| 399 | 2-{(2Z/2E)-2-[(3-chlorophenyl)methylidene]-3-oxo-2,3-dihydro-4H-1,4-benzothiazin-4-yl}-N-[3-(2-ethylpiperidin-1-yl)propyl]acetamide |
| 201 | (2Z/2E)-4-(3-methylbenzyl)-3-oxo-2-(phenylmethylidene)-N-(2-pyrrolidin-1-ylethyl)-3,4-dihydro-2H-1,4-benzothiazine-6-carboxamide |
| 203 | (2Z/2E)-N-{2-[4-(2-fluorophenyl)piperazin-1-yl]ethyl}-2-[2-(4-methoxyphenyl)-2-oxoethylidene]-3-oxo-1,2,3,4-tetrahydroquinoxaline-6-carboxamide |
| 205 | (2Z/2E)-N-[3-(2,6-dimethylpiperidin-1-yl)propyl]-4-(3-methylbenzyl)-3-oxo-2-(phenylmethylidene)-3,4-dihydro-2H-1,4-benzothiazine-6-carboxamide |
| 207 | 2-{(2Z/2E)-2-[(3-bromophenyl)methylidene]-3-oxo-2,3-dihydro-4H-1,4-benzothiazin-4-yl}-N-[(1-ethylpyrrolidin-2-yl)methyl]acetamide |
| 209 | 4-{(Z/E)-[4-(2-methylbenzyl)-3-oxo-3,4-dihydro-2H-1,4-benzothiazin-2-ylidene]methyl}-N-[3-(3-methylpiperidin-1-yl)propyl]benzamide |
| 211 | N-[2-(dipropylamino)ethyl]-4-{(Z/E)-[4-(2-methylbenzyl)-3-oxo-3,4-dihydro-2H-1,4-benzothiazin-2-ylidene]methyl}benzamide |
| 213 | 2-{(2Z/2E)-2-[(3-bromophenyl)methylidene]-3-oxo-2,3-dihydro-4H-1,4-benzothiazin-4-yl}-N-(2-pyrrolidin-1-ylethyl)acetamide. |

TABLE 1.2
(421)
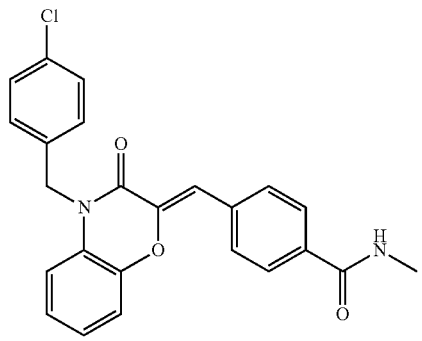 [SMILES: CNC(=O)c1ccc(/C=C2\Oc3ccccc3N(Cc3ccc(Cl)cc3)C2=O)cc1]
(423)
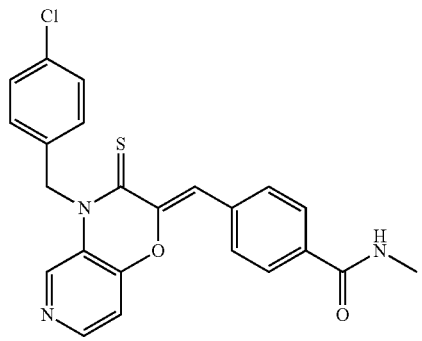
(425)
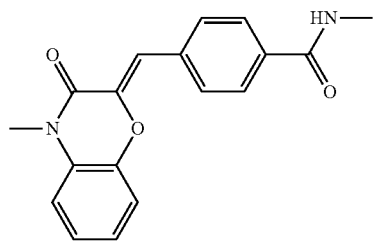
(427)
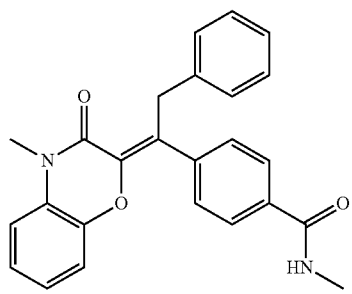 [SMILES: CNC(=O)c1ccc(/C(Cc2ccccc2)=C2\Oc3ccccc3N(C)C2=O)cc1]

TABLE 1.2-continued
(429)
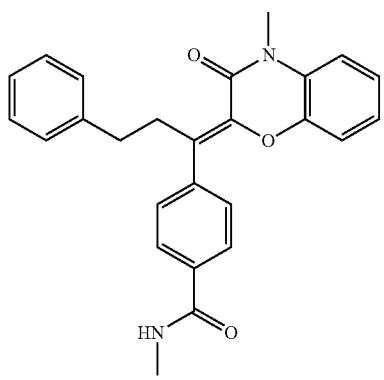 [SMILES: CNC(=O)c1ccc(/C(CCc2ccccc2)=C2\Oc3ccccc3N(C)C2=O)cc1]
(431)
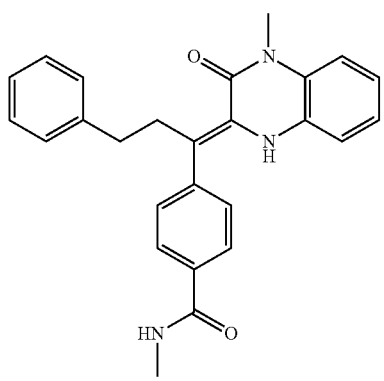 [SMILES: CNC(=O)c1ccc(/C(CCc2ccccc2)=C2\Nc3ccccc3N(C)C2=O)cc1]
(433)
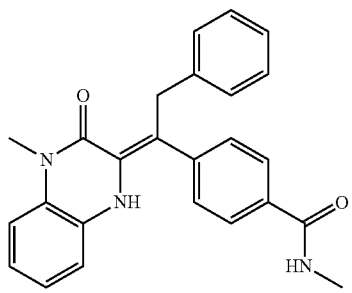
(435)
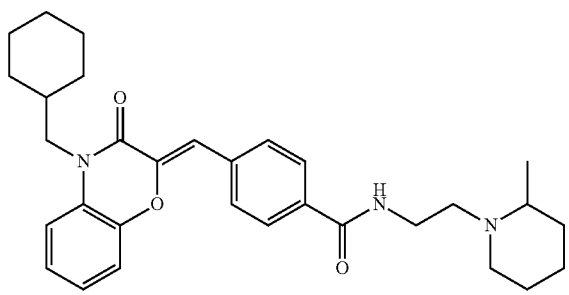 [SMILES: CC1CCCCN1CCNC(=O)c1ccc(/C=C2\Oc3ccccc3N(CC3CCCCC3)C2=O)cc1]

TABLE 1.2-continued
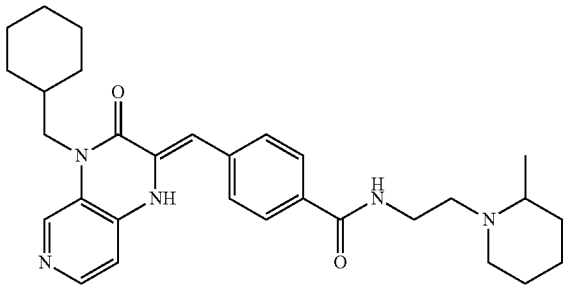 [SMILES: CC1CCCCN1CCNC(=O)c1ccc(/C=C2\Nc3ccncc3N(CC3CCCCC3)C2=O)cc1]
(437)
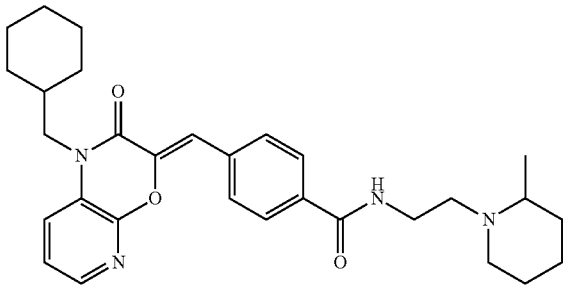
(439)
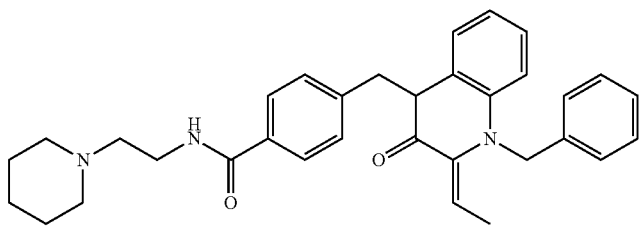
(441)
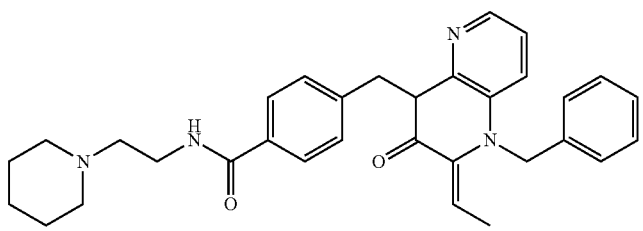
(443)
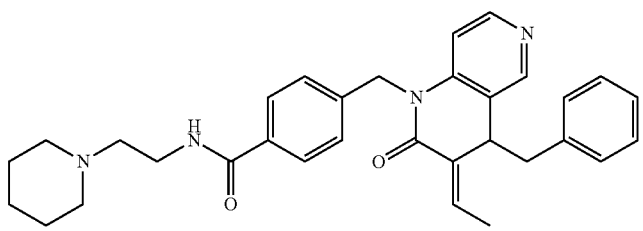 [SMILES: C/C=C1/C(=O)C(Cc2ccc(C(=O)NCCN3CCCCC3)cc2)c2ccccc2N1Cc1ccccc1]
(445)
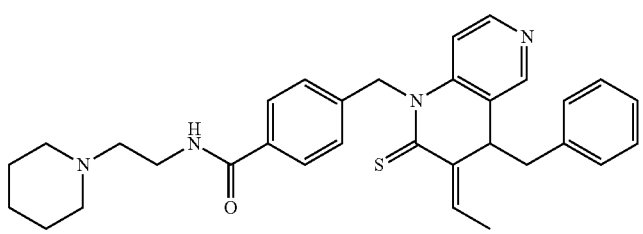 [SMILES: C/C=C1/C(=S)N(Cc2ccc(C(=O)NCCN3CCCCC3)cc2)c2ccncc2C1Cc1ccccc1]
(447)

TABLE 1.2-continued
(449)
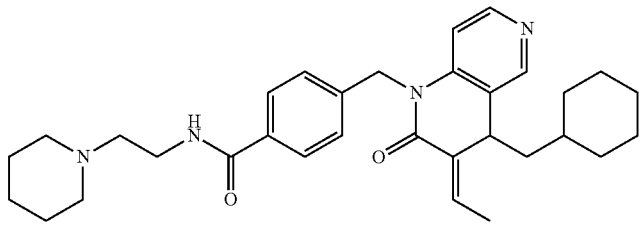 [SMILES: C/C=C1/C(=O)N(Cc2ccc(C(=O)NCCN3CCCCC3)cc2)c2ccncc2C1CC1CCCCC1]
(451)
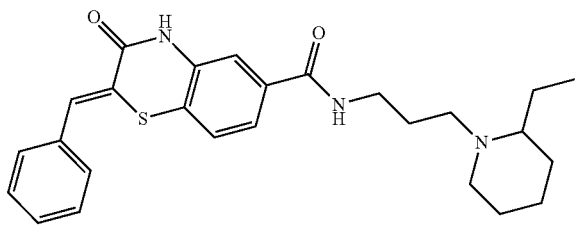 [SMILES: CCC1CCCCN1CCCNC(=O)c1ccc2c(c1)NC(=O)/C(=C/c1ccccc1)S2]
(453)
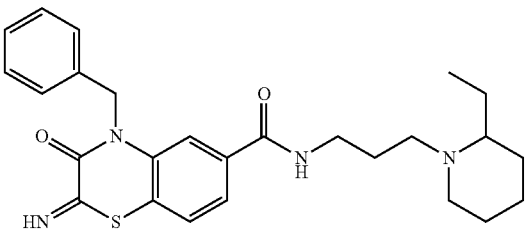
(455)
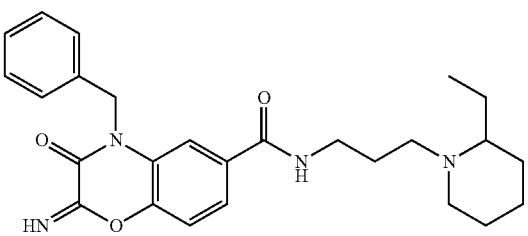 [SMILES: CCC1CCCCN1CCCNC(=O)c1ccc2sc(=N)c(=O)n(Cc3ccccc3)c2c1]
(457)
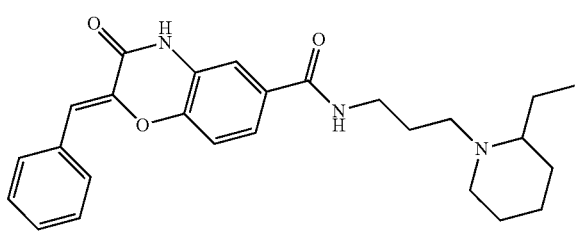 [SMILES: CCC1CCCCN1CCCNC(=O)c1ccc2c(c1)NC(=O)/C(=C/c1ccccc1)O2]
(459)
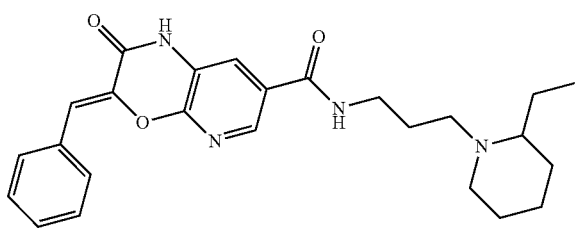

TABLE 1.2-continued
(461)
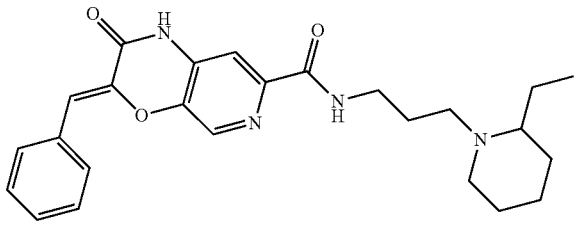 [SMILES: CCC1CCCCN1CCCNC(=O)c1cc2c(cn1)O/C(=C\c1ccccc1)C(=O)N2]
(463)
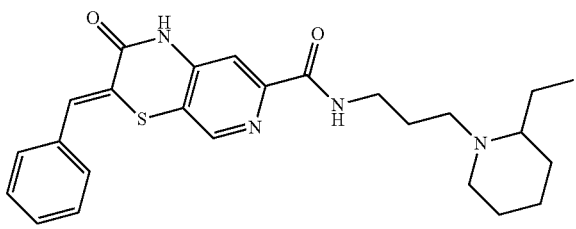 [SMILES: CCC1CCCCN1CCCNC(=O)c1cc2c(cn1)S/C(=C\c1ccccc1)C(=O)N2]
(465)
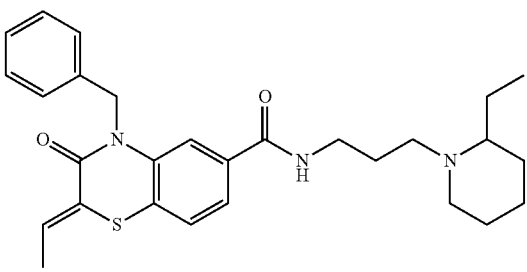 [SMILES: C/C=C1\Sc2ccc(C(=O)NCCCN3CCCCC3CC)cc2N(Cc2ccccc2)C1=O]
(467)
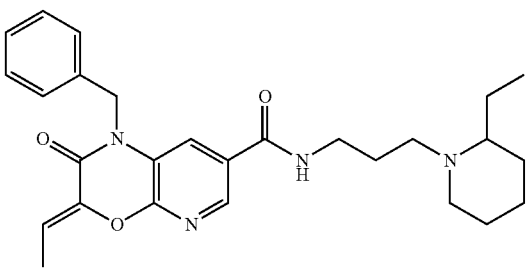 [SMILES: C/C=C1\Oc2ncc(C(=O)NCCCN3CCCCC3CC)cc2N(Cc2ccccc2)C1=O]
(469)
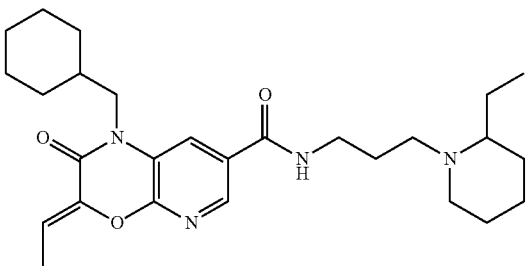 [SMILES: C/C=C1\Oc2ncc(C(=O)NCCCN3CCCCC3CC)cc2N(CC2CCCCC2)C1=O]

TABLE 1.2-continued
(471)
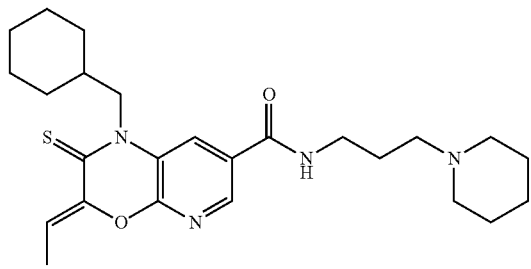 [SMILES: C/C=C1\Oc2ncc(C(=O)NCCCN3CCCCC3)cc2N(CC2CCCCC2)C1=S]
(473)
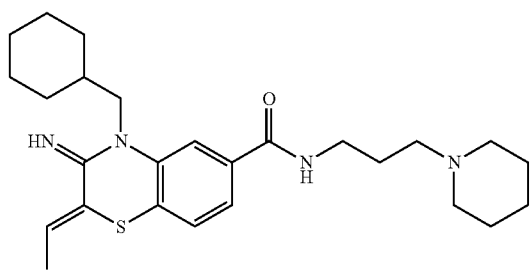 [SMILES: C/C=C1\Sc2ccc(C(=O)NCCCN3CCCCC3)cc2N(CC2CCCCC2)C1=N]
(475)
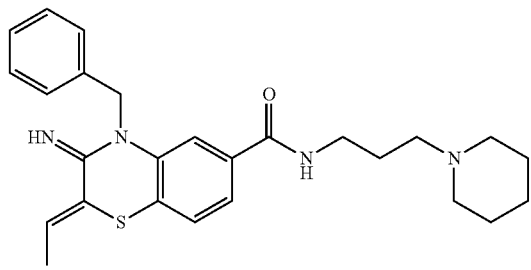 [SMILES: C/C=C1\Sc2ccc(C(=O)NCCCN3CCCCC3)cc2N(Cc2ccccc2)C1=N]
(477)
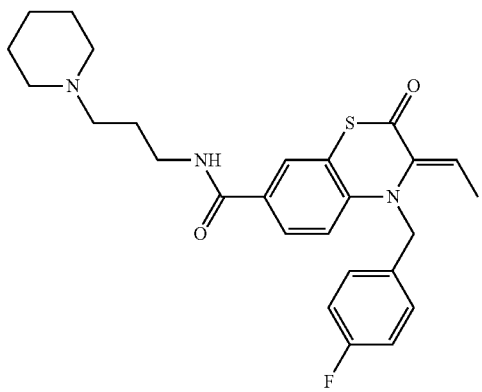 [SMILES: C/C=C1/C(=S)Oc2cc(C(=O)NCCCN3CCCCC3)ccc2N1Cc1ccc(F)cc1]

TABLE 1.2-continued
(479)
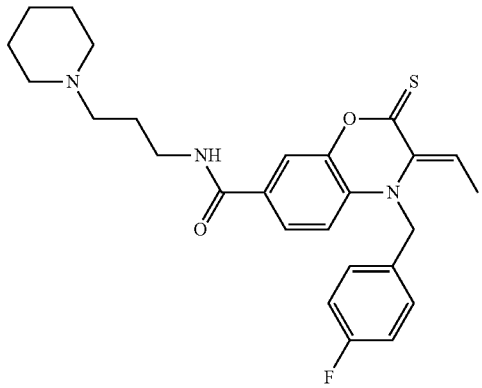
(481)
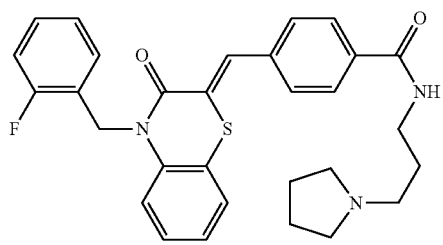 [SMILES: O=C(NCCCN1CCCC1)c1ccc(/C=C2\Sc3ccccc3N(Cc3ccccc3F)C2=O)cc1]
(483)
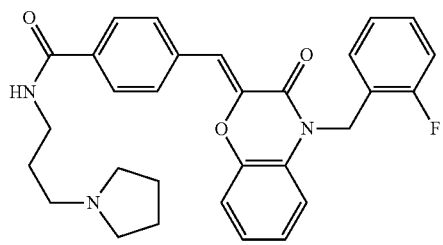 [SMILES: O=C(NCCCN1CCCC1)c1ccc(/C=C2\Oc3ccccc3N(Cc3ccccc3F)C2=O)cc1]
(485)
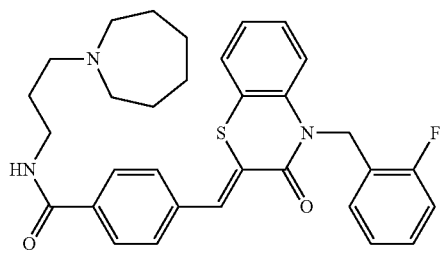 [SMILES: O=C(NCCCN1CCCCCC1)c1ccc(/C=C2\Sc3ccccc3N(Cc3ccccc3F)C2=O)cc1]
(801)
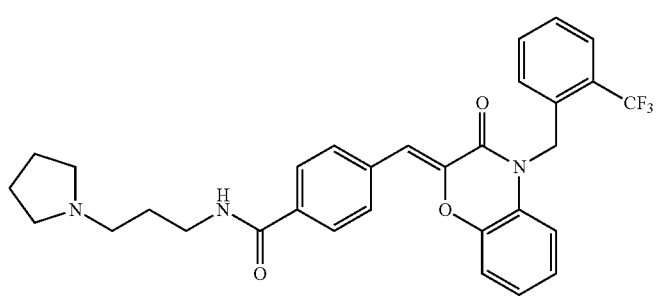 [SMILES: O=C(NCCCN1CCCC1)c1ccc(/C=C2\Oc3ccccc3N(Cc3ccccc3C(F)(F)F)C2=O)cc1]

TABLE 1.2-continued
(803)
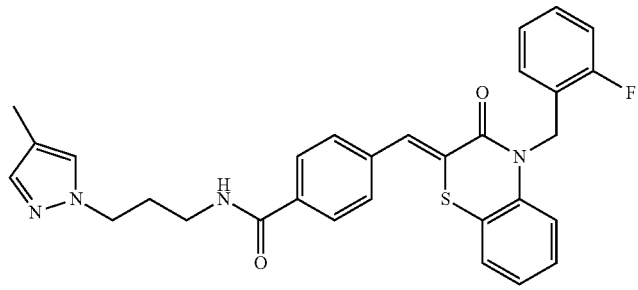 [SMILES: Cc1cnn(CCCNC(=O)c2ccc(/C=C3\Sc4ccccc4N(Cc4ccccc4F)C3=O)cc2)c1]
(805)
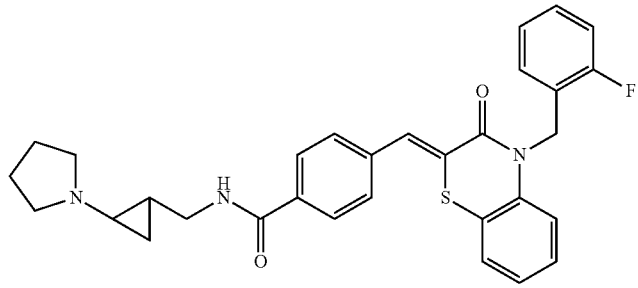 [SMILES: O=C(NCC1CC1N1CCCC1)c1ccc(/C=C2\Sc3ccccc3N(Cc3ccccc3F)C2=O)cc1]
(807)
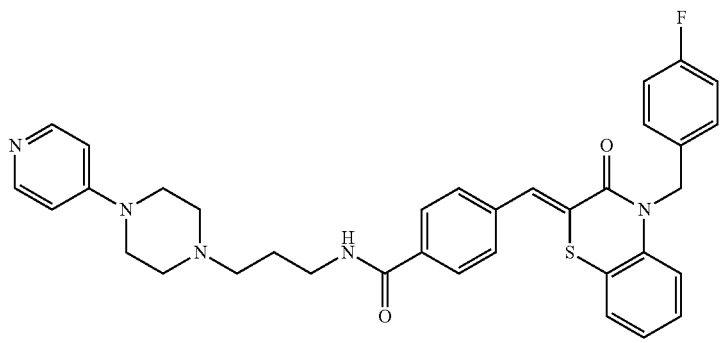 [SMILES: O=C(NCCCN1CCN(c2ccncc2)CC1)c1ccc(/C=C2\Sc3ccccc3N(Cc3ccc(F)cc3)C2=O)cc1]
(809)
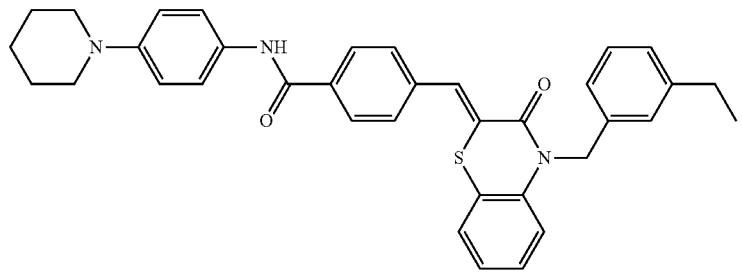 [SMILES: CCc1cccc(CN2C(=O)/C(=C/c3ccc(C(=O)Nc4ccc(N5CCCCC5)cc4)cc3)Sc3ccccc32)c1]
(811)
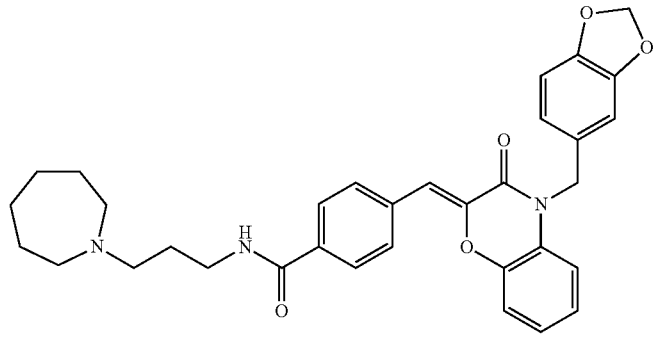 [SMILES: O=C(NCCCN1CCCCCC1)c1ccc(/C=C2\Oc3ccccc3N(Cc3ccc4c(c3)OCO4)C2=O)cc1]

TABLE 1.2-continued
(813)
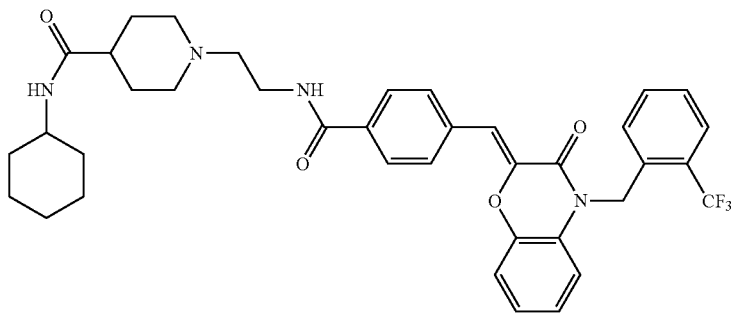 [SMILES: O=C(NCCN1CCC(C(=O)NC2CCCCC2)CC1)c1ccc(/C=C2\Oc3ccccc3N(Cc3ccccc3C(F)(F)F)C2=O)cc1]
(815)
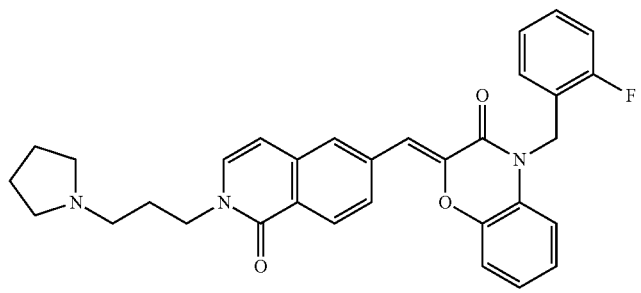 [SMILES: O=C1/C(=C/c2ccc3c(=O)n(CCCN4CCCC4)ccc3c2)Oc2ccccc2N1Cc1ccccc1F]
(817)
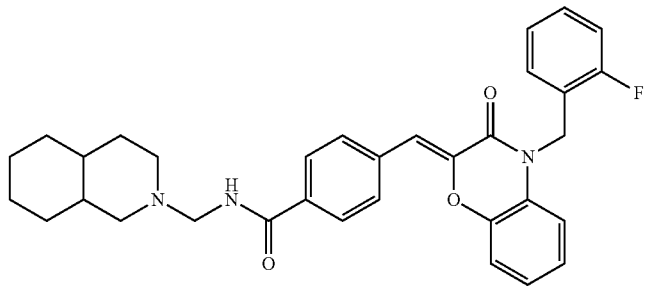 [SMILES: O=C(NCN1CCC2CCCCC2C1)c1ccc(/C=C2\Oc3ccccc3N(Cc3ccccc3F)C2=O)cc1]
(819)
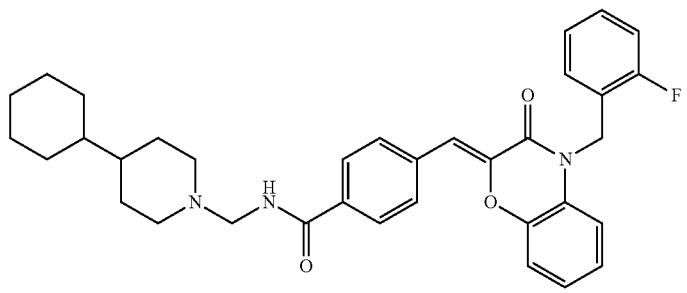 [SMILES: O=C(NCN1CCC(C2CCCCC2)CC1)c1ccc(/C=C2\Oc3ccccc3N(Cc3ccccc3F)C2=O)cc1]

TABLE 1.2-continued
(821)
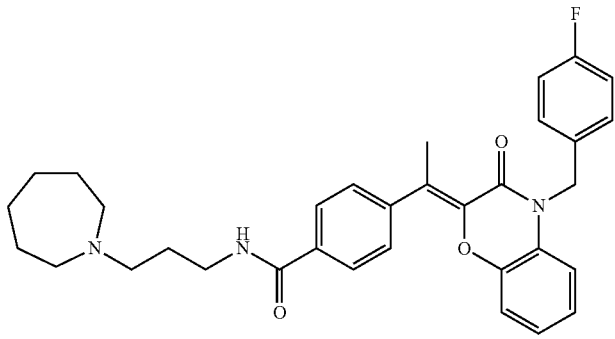 [SMILES: C/C(=C1/Oc2ccccc2N(Cc2ccc(F)cc2)C1=O)c1ccc(C(=O)NCCCN2CCCCCC2)cc1]
(823)
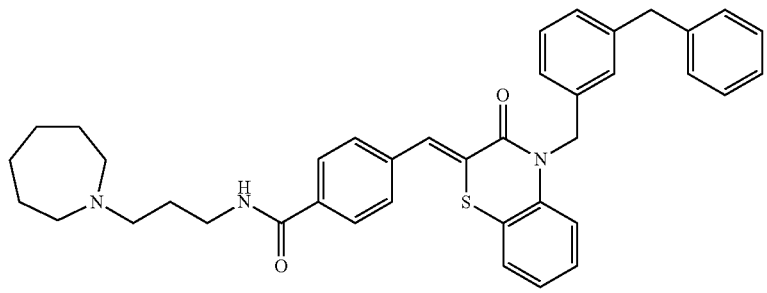 [SMILES: O=C(NCCCN1CCCCCC1)c1ccc(/C=C2\Sc3ccccc3N(Cc3cccc(Cc4ccccc4)c3)C2=O)cc1]
(825)
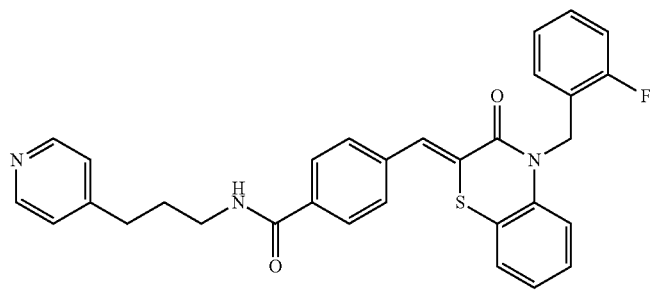 [SMILES: O=C(NCCCc1ccncc1)c1ccc(/C=C2\Sc3ccccc3N(Cc3ccccc3F)C2=O)cc1]
(827)
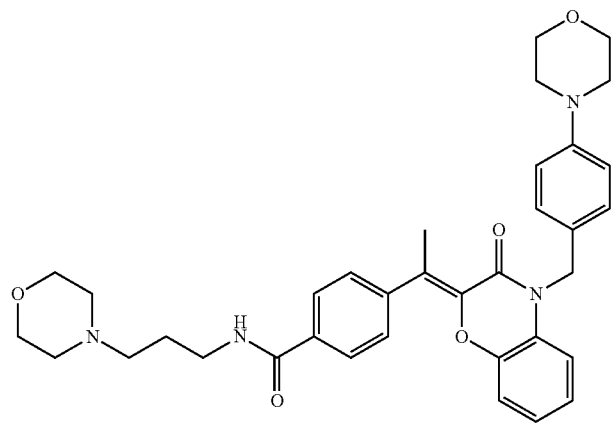 [SMILES: C/C(=C1/Oc2ccccc2N(Cc2ccc(N3CCOCC3)cc2)C1=O)c1ccc(C(=O)NCCCN2CCOCC2)cc1]

TABLE 1.2-continued
(829)
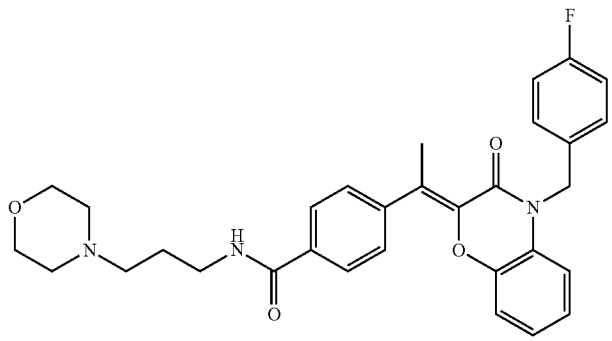 [SMILES: C/C(=C1/Oc2ccccc2N(Cc2ccc(F)cc2)C1=O)c1ccc(C(=O)NCCCN2CCOCC2)cc1]
(831)
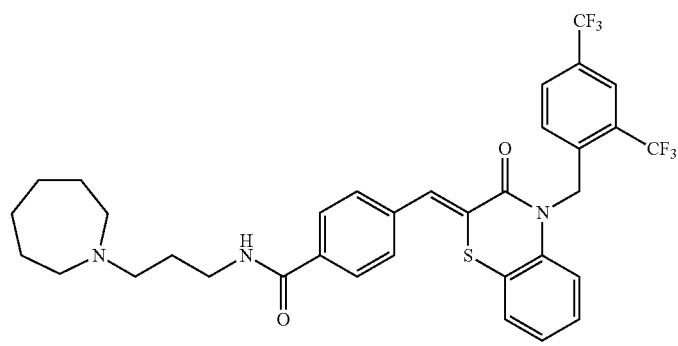 [SMILES: O=C(NCCCN1CCCCCC1)c1ccc(/C=C2\Sc3ccccc3N(Cc3ccc(C(F)(F)F)cc3C(F)(F)F)C2=O)cc1]
(835)
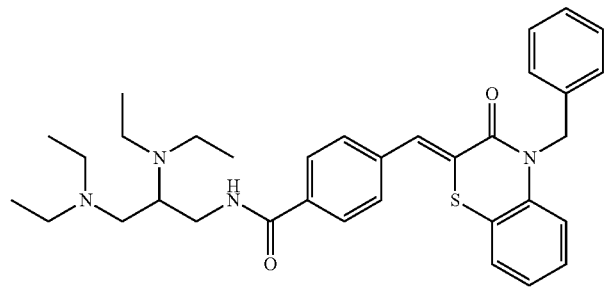 [SMILES: CCN(CC)CC(CNC(=O)c1ccc(/C=C2\Sc3ccccc3N(Cc3ccccc3)C2=O)cc1)N(CC)CC]
(837)
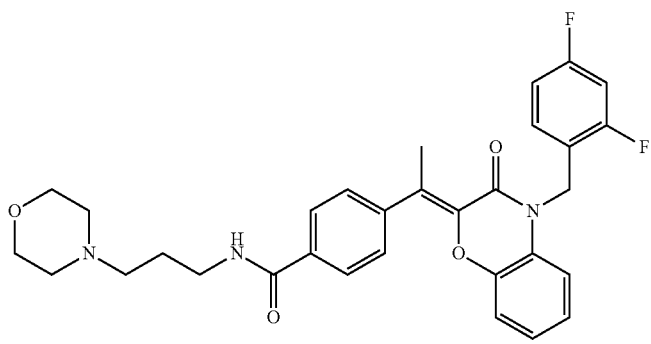 [SMILES: C/C(=C1/Oc2ccccc2N(Cc2ccc(F)cc2F)C1=O)c1ccc(C(=O)NCCCN2CCOCC2)cc1]

TABLE 1.2-continued

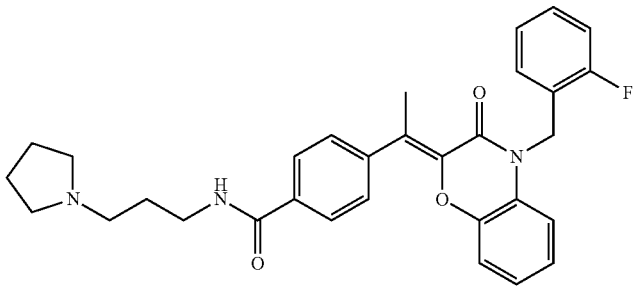 [SMILES: C/C(=C1/Oc2ccccc2N(Cc2ccccc2F)C1=O)c1ccc(C(=O)NCCCN2CCCC2)cc1]
(839)

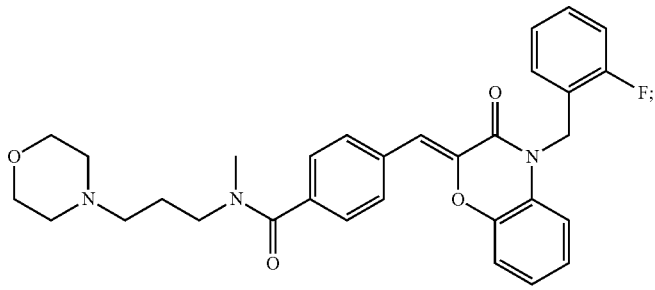 [SMILES: CN(CCCN1CCOCC1)C(=O)c1ccc(/C=C2\Oc3ccccc3N(Cc3ccccc3F)C2=O)cc1]
(841)

or a salt, solvate, or physiologically functional derivative thereof.

Compounds listed in Table 1.2 may also be represented by their chemical names as follows:

| ID | IUPAC Name |
|---|---|
| 421 | 4-{(Z/E)-[4-(4-chlorobenzyl)-3-oxo-3,4-dihydro-2H-1,4-benzoxazin-2-ylidene]methyl}-N-methylbenzamide |
| 423 | 4-{(Z/E)-[4-(4-chlorobenzyl)-3-thioxo-3,4-dihydro-2H-pyrido[4,3-b][1,4]oxazin-2-ylidene]methyl}-N-methylbenzamide |
| 425 | N-methyl-4-[(Z/E)-(4-methyl-3-oxo-3,4-dihydro-2H-1,4-benzoxazin-2-ylidene)methyl]benzamide |
| 427 | N-methyl-4-[(1Z/1E)-1-(4-methyl-3-oxo-3,4-dihydro-2H-1,4-benzoxazin-2-ylidene)-2-phenylethyl]benzamide |
| 429 | N-methyl-4-[(1Z/1E)-1-(4-methyl-3-oxo-3,4-dihydro-2H-1,4-benzoxazin-2-ylidene)-3-phenylpropyl]benzamide |
| 431 | N-methyl-4-[(1Z/1E)-1-(4-methyl-3-oxo-3,4-dihydroquinoxalin-2(1H)-ylidene)-3-phenylpropyl]benzamide |
| 433 | N-methyl-4-[(1Z/1E)-1-(4-methyl-3-oxo-3,4-dihydroquinoxalin-2(1H)-ylidene)-2-phenylethyl]benzamide |
| 435 | 4-{(Z/E)-[4-(cyclohexylmethyl)-3-oxo-3,4-dihydro-2H-1,4-benzoxazin-2-ylidenel]methyl}-N-[2-(2-methylpiperidin-1-yl)ethyl]benzamide |
| 437 | 4-{(Z/E)-[4-(cyclohexylmethyl)-3-oxo-3,4-dihydropyrido[3,4-b]pyrazin-2(1H)-ylidene]methyl}-N-[2-(2-methylpiperidin-1-yl)ethyl]benzamide |
| 439 | 4-{(Z/E)-[1-(cyclohexylmethyl)-2-thioxo-1,2-dihydro-3H-pyrido[2,3-b][1,4]oxazin-3-ylidene]methyl}-N-[2-(2-methylpiperidin-1-yl)ethyl]benzamide |
| 441 | 4-{[(2Z/2E)-1-benzyl-2-ethylidene-3-oxo-1,2,3,4-tetrahydroquinolin-4-yl]methyl}-N-[2-(piperidin-1-yl)ethyl]benzamide |
| 443 | 4-{[(2Z/2E)-1-benzyl-2-ethylidene-3-oxo-1,2,3,4-tetrahydro-1,5-naphthyridin-4-yl]methyl}-N-[2-(piperidin-1-yl)ethyl]benzamid |
| 445 | 4-{[(6E/6Z)-5-benzyl-6-ethylidene-7-oxo-5,6,7,8-tetrahydroquinolin-8-yl]methyl}-N-[2-(piperidin-1-yl)ethyl]benzamide |
| 447 | 4-{[(6E/6Z)-5-benzyl-6-ethylidene-7-thioxo-5,6,7,8-tetrahydroquinolin-8-yl]methyl}-N-[2-(piperidin-1-yl)ethyl]benzamide |
| 449 | 4-{[(3E/3Z)-4-(cyclohexylmethyl)-3-ethylidene-2-oxo-3,4-dihydroquinolin-1(2H)-yl]methyl}-N-[2-(piperidin-1-yl)ethyl]benzamide |
| 451 | (2Z/2E)-2-benzylidene-N-[3-(2-ethylpiperidin-1-yl)propyl]-3-oxo-3,4-dihydro-2H-1,4-benzothiazine-6-carboxamide |
| 453 | 4-benzyl-N-[3-(2-ethylpiperidin-1-yl)propyl]-2-imino-3-oxo-3,4-dihydro-2H-1,4-benzothiazine-6-carboxamide |
| 455 | 4-benzyl-N-[3-(2-ethylpiperidin-1-yl)propyl]-2-imino-3-oxo-3,4-dihydro-2H-1,4-benzoxazine-6-carboxamide |

| ID | IUPAC Name |
|---|---|
| 457 | (2Z/2E)-2-benzylidene-N-[3-(2-ethylpiperidin-1-yl)propyl]-3-oxo-3,4-dihydro-2H-1,4-benzoxazine-6-carboxamide |
| 459 | (3Z/3E)-3-benzylidene-N-[3-(2-ethylpiperidin-1-yl)propyl]-2-oxo-2,3-dihydro-1H-pyrido[2,3-b][1,4]oxazine-7-carboxamide |
| 461 | (3Z/3E)-3-benzylidene-N-[3-(2-ethylpiperidin-1-yl)propyl]-2-oxo-2,3-dihydro-1H-pyrido[3,4-b][1,4]oxazine-7-carboxamide |
| 463 | (3Z/3E)-3-benzylidene-N-[3-(2-ethylpiperidin-1-yl)propyl]-2-oxo-2,3-dihydro-1H-pyrido[3,4-b][1,4]thiazine-7-carboxamide |
| 465 | (2Z/2E)-4-benzyl-2-ethylidene-N-[3-(2-ethylpiperidin-1-yl)propyl]-3-oxo-3,4-dihydro-2H-1,4-benzothiazine-6-carboxamide |
| 467 | (3Z/3E)-1-benzyl-3-ethylidene-N-[3-(2-ethylpiperidin-1-yl)propyl]-2-oxo-2,3-dihydro-1H-pyrido[2,3-b][1,4]oxazine-7-carboxamide |
| 469 | (3Z/3E)-1-(cyclohexylmethyl)-3-ethylidene-N-[3-(2-ethylpiperidin-1-yl)propyl]-2-oxo-2,3-dihydro-1H-pyrido[2,3-b][1,4]oxazine-7-carboxamide |
| 471 | (3Z/3E)-1-(cyclohexylmethyl)-3-ethylidene-N-[3-(piperidin-1-yl)propyl]-2-thioxo-2,3-dihydro-1H-pyrido[2,3-b][1,4]oxazine-7-carboxamide |
| 473 | (2Z/2E)-4-(cyclohexylmethyl)-2-ethylidene-3-imino-N-[3-(piperidin-1-yl)propyl]-3,4-dihydro-2H-1,4-benzothiazine-6-carboxamide |
| 475 | (2Z/2E)-4-benzyl-2-ethylidene-3-imino-N-[3-(piperidin-1-yl)propyl]-3,4-dihydro-2H-1,4-benzothiazine-6-carboxamide |
| 477 | (3Z/3E)-3-ethylidene-4-(4-fluorobenzyl)-2-oxo-N-[3-(piperidin-1-yl)propyl]-3,4-dihydro-2H-1,4-benzothiazine-7-carboxamide |
| 479 | (3Z/3E)-3-ethylidene-4-(4-fluorobenzyl)-N-[3-(piperidin-1-yl)propyl]-2-thioxo-3,4-dihydro-2H-1,4-benzoxazine-7-carboxamide |
| 481 | 4-{(Z/E)-[4-(2-fluorobenzyl)-3-oxo-3,4-dihydro-2H-1,4-benzothiazin-2-ylidene]methyl}-N-[3-(pyrrolidin-1-yl)propyl]benzamide |
| 483 | 4-{(Z/E)-[4-(2-fluorobenzyl)-3-oxo-3,4-dihydro-2H-1,4-benzoxazin-2-ylidene]methyl}-N-[3-(pyrrolidin-1-yl)propyl]benzamide hydrate |
| 485 | N-[3-(azepan-1-yl)propyl]-4-{(Z/E)-[4-(2-fluorobenzyl)-3-oxo-3,4-dihydro-2H-1,4-benzothiazin-2-ylidene]methyl}benzamide |
| 801 | 4-[(Z/E)-{3-oxo-4-[2-(trifluoromethyl)benzyl]-3,4-dihydro-2H-1,4-benzoxazin-2-ylidene}methyl]-N-[3-(pyrrolidin-1-yl)propyl]benzamide |
| 803 | 4-{(Z/E)-[4-(2-fluorobenzyl)-3-oxo-3,4-dihydro-2H-1,4-benzothiazin-2-ylidene]methyl}-N-[3-(4-methyl-1H-pyrazol-1-yl)propyl]benzamide |
| 805 | 4-{(Z/E)-[4-(2-fluorobenzyl)-3-oxo-3,4-dihydro-2H-1,4-benzothiazin-2-ylidene]methyl}-N-{[2-(pyrrolidin-1-yl)cyclopropyl]methyl}benzamide |
| 807 | 4-{(Z/E)-[4-(4-fluorobenzyl)-3-oxo-3,4-dihydro-2H-1,4-benzothiazin-2-ylidene]methyl}-N-{3-[4-(pyridin-4-yl)piperazin-1-yl]propyl}benzamide |
| 809 | 4-{(Z/E)-[4-(3-ethylbenzyl)-3-oxo-3,4-dihydro-2H-1,4-benzothiazin-2-ylidene]methyl}-N-[4-(piperidin-1-yl)phenyl]benzamide |
| 811 | N-[3-(azepan-1-yl)propyl]-4-{(Z/E)-[4-(1,3-benzodioxol-5-ylmethyl)-3-oxo-3,4-dihydro-2H-1,4-benzoxazin-2-ylidene]methyl}benzamide |
| 813 | N-cyclohexyl-1-{2-[({4-[(Z/E)-{3-oxo-4-[2-(trifluoromethyl)benzyl]-3,4-dihydro-2H-1,4-benzoxazin-2-ylidene}methyl]phenyl}carbonyl)amino]ethyl}piperidine-4-carboxamide |
| 815 | (2Z/2E)-4-(2-fluorobenzyl)-2-({1-oxo-2-[3-(pyrrolidin-1-yl)propyl]-1,2-dihydroisoquinolin-6-yl}methylidene)-2H-1,4-benzoxazin-3(4H)-one |
| 817 | 4-{(Z/E)-[4-(2-fluorobenzyl)-3-oxo-3,4-dihydro-2H-1,4-benzoxazin-2-ylidene]methyl}-N-(octahydroisoquinolin-2(1H)-ylmethyl)benzamide |
| 819 | N-[(4-cyclohexylpiperidin-1-yl)methyl]-4-{(Z/E)-[4-(2-fluorobenzyl)-3-oxo-3,4-dihydro-2H-1,4-benzoxazin-2-ylidene]methyl}benzamide |
| 821 | N-[3-(azepan-1-yl)propyl]-4-{(1Z/1E)-1-[4-(4-fluorobenzyl)-3-oxo-3,4-dihydro-2H-1,4-benzoxazin-2-ylidene]ethyl}benzamide |
| 823 | N-[3-(azepan-1-yl)propyl]-4-{(Z/E)-[4-(3-benzylbenzyl)-3-oxo-3,4-dihydro-2H-1,4-benzothiazin-2-ylidene]methyl}benzamide |
| 825 | 4-{(Z/E)-[4-(2-fluorobenzyl)-3-oxo-3,4-dihydro-2H-1,4-benzothiazin-2-ylidene]methyl}-N-[3-(pyridin-4-yl)propyl]benzamide |
| 827 | 4-[(1Z/1E)-1-{4-[4-(morpholin-4-yl)benzyl]-3-oxo-3,4-dihydro-2H-1,4-benzoxazin-2-ylidene}ethyl]-N-[3-(morpholin-4-yl)propyl]benzamide |
| 829 | N-4-{(1Z/1E)-1-[4-(4-fluorobenzyl)-3-oxo-3,4-dihydro-2H-1,4-benzoxazin-2-ylidene]ethyl}-N-[3-(morpholin-4-yl)propyl]benzamide |
| 831 | N-[3-(azepan-1-yl)propyl]-4-[(Z/E)-{4-[2,4-bis(trifluoromethyl)benzyl]-3-oxo-3,4-dihydro-2H-1,4-benzothiazin-2-ylidene}methyl]benzamide |
| 835 | 4-[(Z/E)-(4-benzyl-3-oxo-3,4-dihydro-2H-1,4-benzothiazin-2-ylidene)methyl]-N-[2,3-bis(diethylamino)propyl]benzamide |
| 837 | 4-{(1Z/1E)-1-[4-(2,4-difluorobenzyl)-3-oxo-3,4-dihydro-2H-1,4-benzoxazin-2-ylidene]ethyl}-N-[3-(morpholin-4-yl)propyl]benzamide |
| 839 | 4-{(1Z/1E)-1-[4-(2-fluorobenzyl)-3-oxo-3,4-dihydro-2H-1,4-benzoxazin-2-ylidene]ethyl}-N-[3-(pyrrolidin-1-yl)propyl]benzamide |
| 841 | 4-{(Z/E)-[4-(2-fluorobenzyl)-3-oxo-3,4-dihydro-2H-1,4-benzoxazin-2-ylidene]methyl}-N-methyl-N-[3-(morpholin-4-yl)propyl]benzamide; | or a salt, solvate, or physiologically functional derivative thereof.

In one embodiment of formula (Ic), $Z^2$ is $NR^2$, Y is O or S, and $R^4$ is —$OR^{13}$, —$SR^{13}$, $NHR^{13}$;

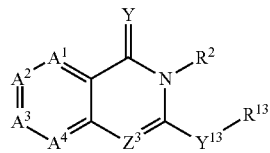

(Ii)

wherein $Y^{13}$ is O, S or NH; and $R^{13}$ is hydrogen, alkyl, substituted alkyl, cycloheteroalkyl, substituted cycloheteroalkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl.

In some embodiments, the compound having a structural formula (II) is selected from the group consisting of Table 1.3.

TABLE 1.3

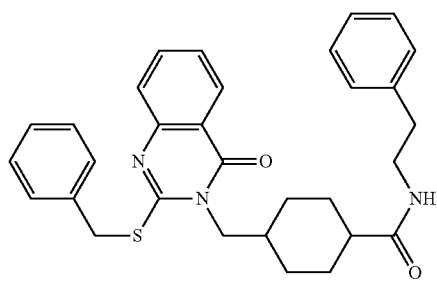 [SMILES: O=C(NCCc1ccccc1)C1CCC(Cn2c(SCc3ccccc3)nc3ccccc3c2=O)CC1]
(401)

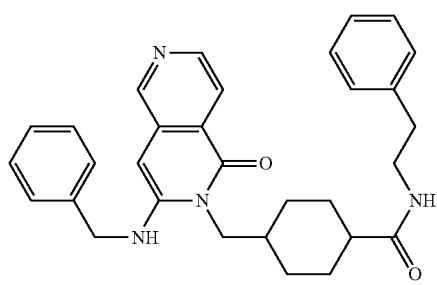 [SMILES: O=C(NCCc1ccccc1)C1CCC(Cn2c(NCc3ccccc3)cc3cnccc3c2=O)CC1]
(403)

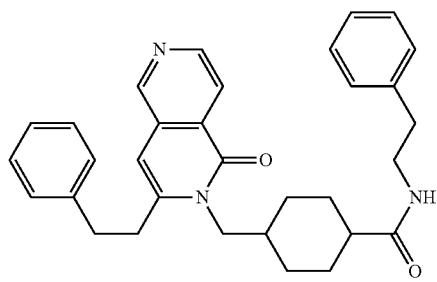 [SMILES: O=C(NCCc1ccccc1)C1CCC(Cn2c(CCc3ccccc3)cc3cnccc3c2=O)CC1]
(405)

TABLE 1.3-continued

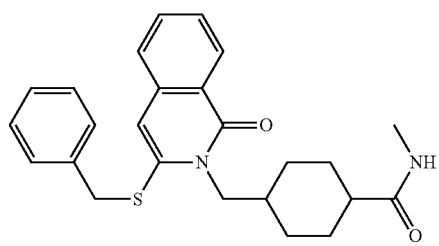 [SMILES: CNC(=O)C1CCC(Cn2c(SCc3ccccc3)cc3ccccc3c2=O)CC1]
(407)

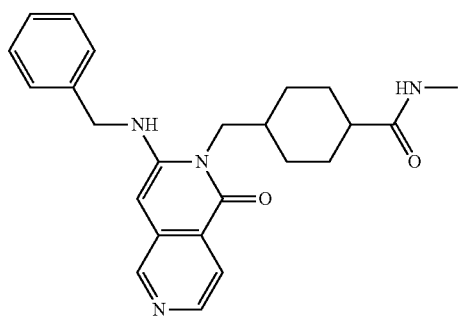 [SMILES: CNC(=O)C1CCC(Cn2c(NCc3ccccc3)cc3cnccc3c2=O)CC1]
(409)

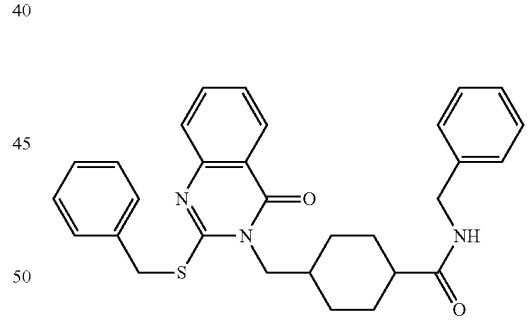
(411)

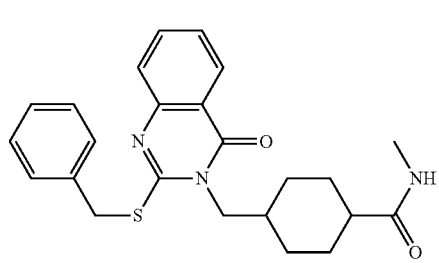
(413)

(415)

TABLE 1.3-continued

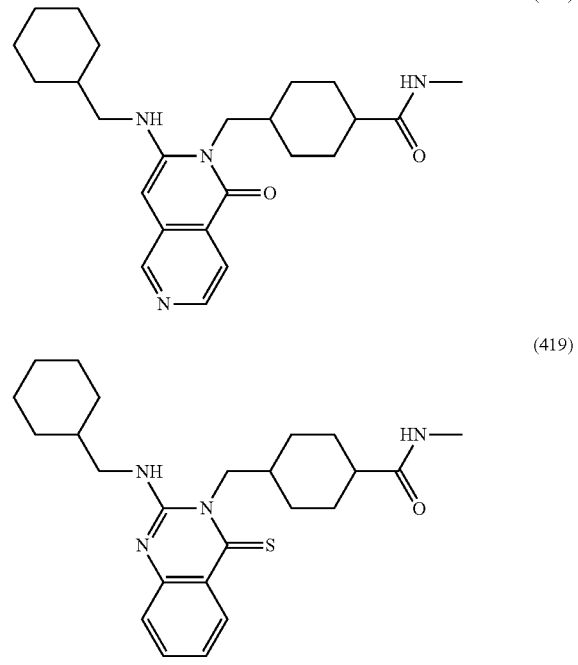

(417)

(419)

or a salt, solvate, or physiologically functional derivative thereof.

Compounds listed in Table 1.3 may also be represented by their chemical names as follows:

| ID | IUPAC Name |
|---|---|
| 401 | 4-{[2-(benzylsulfanyl)-4-oxoquinazolin-3(4H)-yl]methyl}-N-(2-phenylethyl)cyclohexanecarboxamide |
| 403 | 4-{[3-(benzylamino)-1-oxo-2,6-naphthyridin-2(1H)-yl]methyl}-N-(2-phenylethyl)cyclohexanecarboxamide |
| 405 | 4-{[1-oxo-3-(2-phenylethyl)-2,6-naphthyridin-2(1H)-yl]methyl}-N-(2-phenylethyl)cyclohexanecarboxamide |
| 407 | 4-{[3-(benzylsulfanyl)-1-oxoisoquinolin-2(1H)-yl]methyl}-N-methylcyclohexanecarboxamide |
| 409 | N-methyl-4-{[1-oxo-3-(2-phenylethyl)isoquinolin-2(1H)-yl]methyl}cyclohexanecarboxamide |
| 411 | 4-{[3-(benzylamino)-1-oxo-2,6-naphthyridin-2(1H)-yl]methyl}-N-methylcyclohexanecarboxamide |
| 413 | N-benzyl-4-{[2-(benzylsulfanyl)-4-oxoquinazolin-3(4H)-yl]methyl}cyclohexanecarboxamide |
| 415 | 4-{[2-(benzylsulfanyl)-4-oxoquinazolin-3(4H)-yl]methyl}-N-methylcyclohexanecarboxamide |
| 417 | 4-({3-[(cyclohexylmethyl)amino]-1-oxo-2,6-naphthyridin-2(1H)-yl}methyl)-N-methylcyclohexanecarboxamide |
| 419 | 4-({2-[(cyclohexylmethyl)amino]-4-thioxoquinazolin-3(4H)-yl}methyl)-N-methylcyclohexanecarboxamide. |

In one aspect, the present invention provides a compound of the present invention having a structural formula (II),

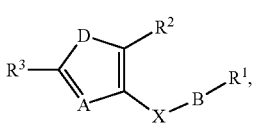

(II)

or a salt, solvate, or physiologically functional derivative thereof, wherein:

A is N or CH;

B is a 5-, 6-, or 7-membered cycloalkyl, substituted cycloalkyl, cycloheteroalkyl, substituted cycloheteroalkyl, aryl, substituted aryl, heteroaryl, or substituted heteroaryl ring;

D is $NR^4$, S, or O;

$R^1$, $R^2$, $R^3$, and $R^4$ are independently hydrogen, halogen, acyl, substituted acyl, alkoxycarbonyl, substituted alkoxycarbonyl, aryloxycarbonyl, substituted aryloxycarbonyl, —C(O)$NR^5R^6$, alkyl, substituted alkyl, cycloheteroalkyl, substituted cycloheteroalkyl, aryl, substituted aryl, arylalkyl, substituted arylalkyl, heteroaryl, substituted heteroaryl, heteroaryl alkyl, substituted heteroarylalkyl, heteroalkyl, or substituted heteroalkyl;

$R^5$ and $R^6$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl, or alternatively, $R^5$ and $R^6$, taken together with the nitrogen atom to which they are attached, form a 4-, 5-, 6-, or 7-membered cycloheteroalkyl ring;

X is —$CH_2$—, —$CH_2$—O—, —$CH_2$—S—, —O— or —S—.

In one embodiment, the compound having a structural formula (II) does not include the compounds listed above, while in another embodiment, the compound having a structural formula (II) includes the compounds listed above.

In one embodiment of formula (II), A is N; and D is O.

In one embodiment of formula (II), A is N, D is O, and $R^3$ is benzyl or substituted benzyl.

In one embodiment of formula (II), the B ring is a cycloheteroalkyl or a substituted cycloheteroalkyl ring. In one embodiment of formula (II), the compound has structural formula (IIa),

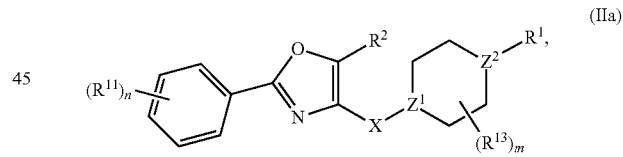

(IIa)

wherein:

$R^1$, $R^2$ and X have same definitions as in formula (II);

$Z^1$ and $Z^2$ are independently $CR^{12}$ and N;

$R^{11}$ and $R^{13}$ independently represent one or multiple substituents. $R^{11}$ and $R^{13}$ are independently selected from hydrogen, halogen, acyl, substituted acyl, alkoxycarbonyl, substituted alkoxycarbonyl, aryloxycarbonyl, substituted aryloxycarbonyl, —C(O)$NR^5R^6$, alkyl, substituted alkyl, cycloheteroalkyl, substituted cycloheteroalkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl; and $R^{12}$ is selected from hydrogen, alkyl, substituted alkyl.

In one embodiment of formula (IIa), $R^1$ is —C(O)$NHR^5$, wherein the preferred amine, i.e., —$NHR^5$, is derived from a group consisted of, but not limited to:

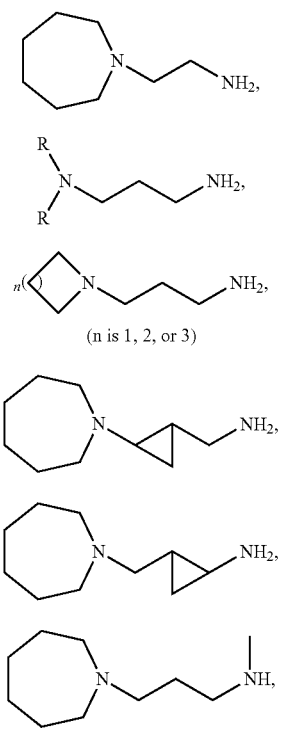
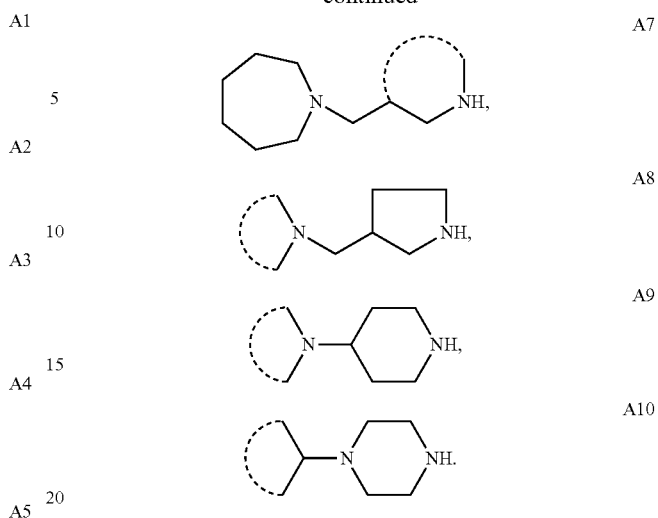
wherein each of the ring with dotted line (in A7, A8, A9 or A10) represents a 5-, 6-, or 7-membered cycloalkyl, substituted cycloalkyl, heterocycloalkyl, substituted heterocycloalkyl, aryl, substituted aryl, heteroaryl, or substituted heteroaryl ring.
In some embodiments, the compound having a structural formula (II) or (IIa) is selected from the group consisting of Table 2.1:
TABLE 2.1
(501)
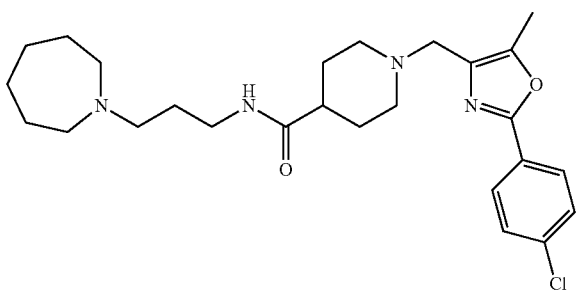 [SMILES: Cc1oc(-c2ccc(Cl)cc2)nc1CN1CCC(C(=O)NCCCN2CCCCCC2)CC1]
(503)
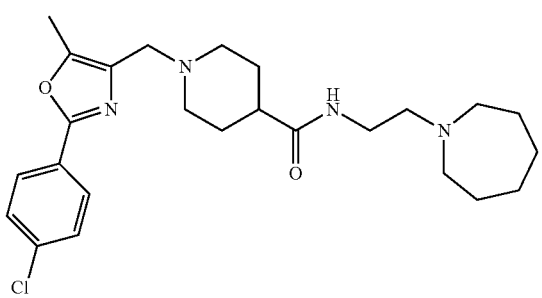 [SMILES: Cc1oc(-c2ccc(Cl)cc2)nc1CN1CCC(C(=O)NCCN2CCCCCC2)CC1]

TABLE 2.1-continued
(505)
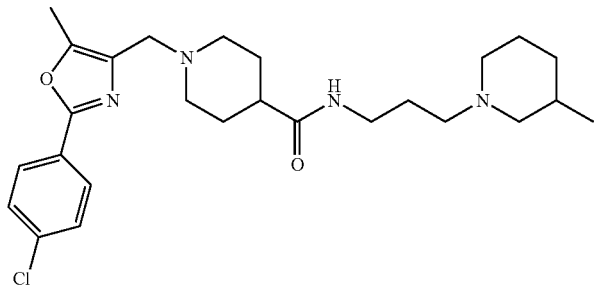 [SMILES: Cc1oc(-c2ccc(Cl)cc2)nc1CN1CCC(C(=O)NCCCN2CCCC(C)C2)CC1]
(507)
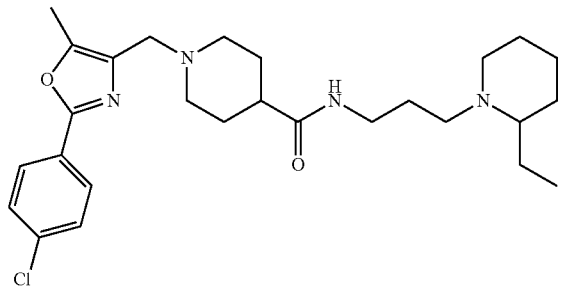 [SMILES: CCC1CCCCN1CCCNC(=O)C1CCN(Cc2nc(-c3ccc(Cl)cc3)oc2C)CC1]
(509)
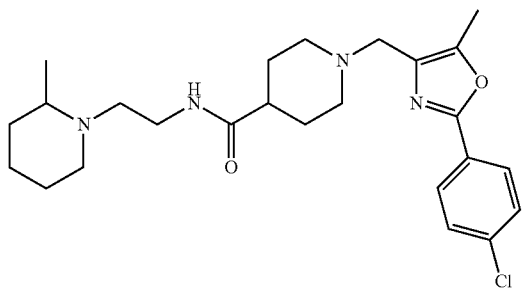 [SMILES: Cc1oc(-c2ccc(Cl)cc2)nc1CN1CCC(C(=O)NCCN2CCCCC2C)CC1]
(511)
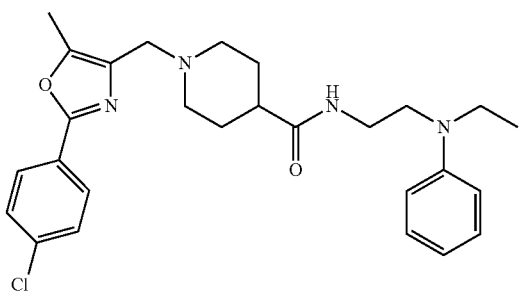 [SMILES: CCN(CCNC(=O)C1CCN(Cc2nc(-c3ccc(Cl)cc3)oc2C)CC1)c1ccccc1]
(513)
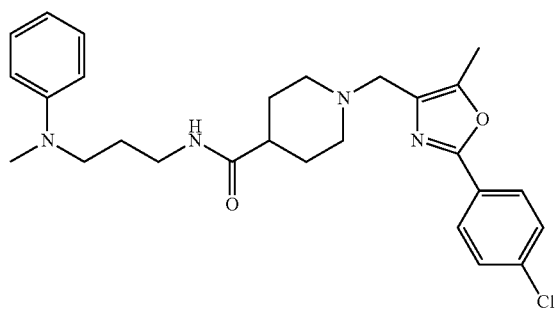 [SMILES: Cc1oc(-c2ccc(Cl)cc2)nc1CN1CCC(C(=O)NCCCN(C)c2ccccc2)CC1]

TABLE 2.1-continued
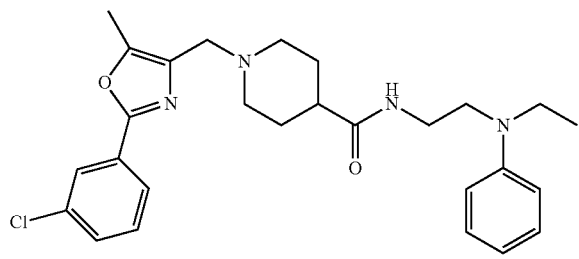 [SMILES: CCN(CCNC(=O)C1CCN(Cc2nc(-c3cccc(Cl)c3)oc2C)CC1)c1ccccc1]
(515)
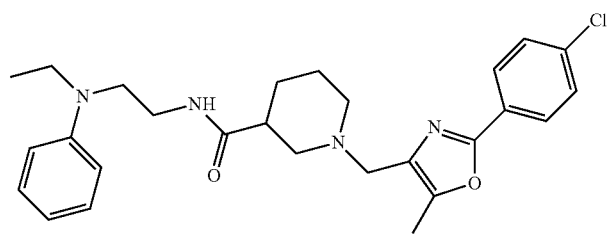 [SMILES: CCN(CCNC(=O)C1CCCN(Cc2nc(-c3ccc(Cl)cc3)oc2C)C1)c1ccccc1]
(517)
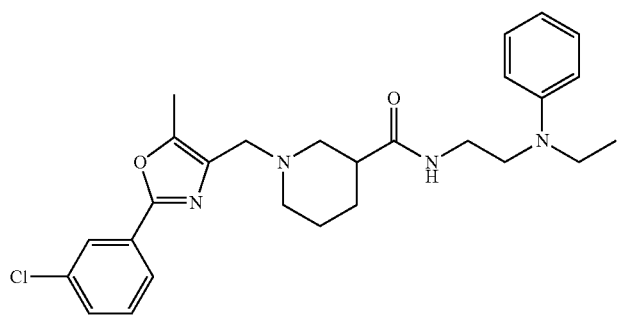 [SMILES: CCN(CCNC(=O)C1CCCN(Cc2nc(-c3cccc(Cl)c3)oc2C)C1)c1ccccc1]
(519)
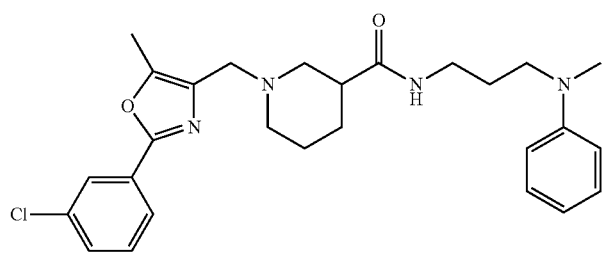 [SMILES: Cc1oc(-c2cccc(Cl)c2)nc1CN1CCCC(C(=O)NCCCN(C)c2ccccc2)C1]
(521)
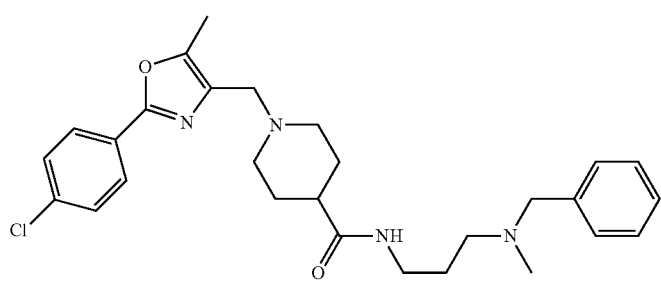 [SMILES: Cc1oc(-c2ccc(Cl)cc2)nc1CN1CCC(C(=O)NCCCN(C)Cc2ccccc2)CC1]
(525)

TABLE 2.1-continued
(527)
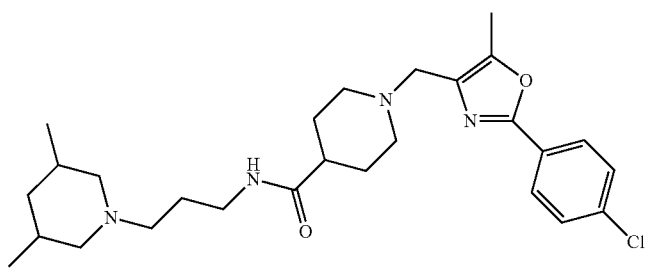 [SMILES: Cc1oc(-c2ccc(Cl)cc2)nc1CN1CCC(C(=O)NCCCN2CC(C)CC(C)C2)CC1]
(529)
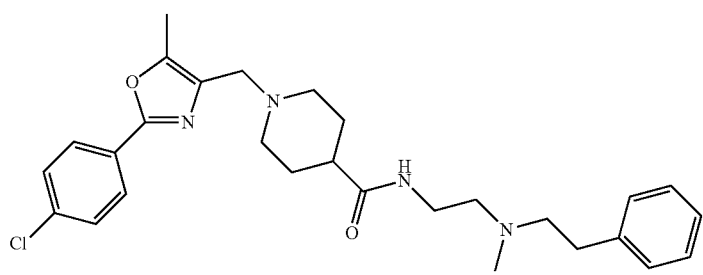 [SMILES: Cc1oc(-c2ccc(Cl)cc2)nc1CN1CCC(C(=O)NCCN(C)CCc2ccccc2)CC1]
(531)
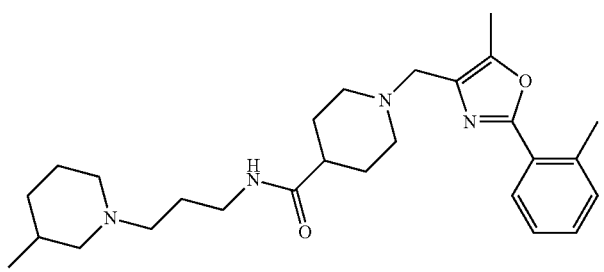
(533)
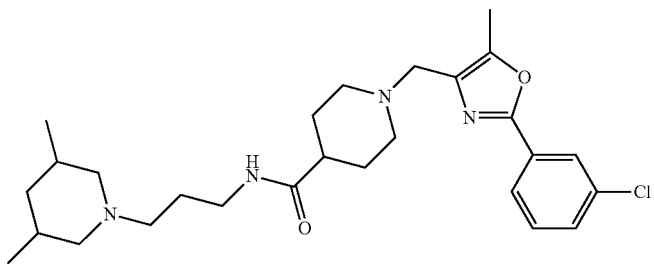 [SMILES: Cc1oc(-c2cccc(Cl)c2)nc1CN1CCC(C(=O)NCCCN2CC(C)CC(C)C2)CC1]
(535)
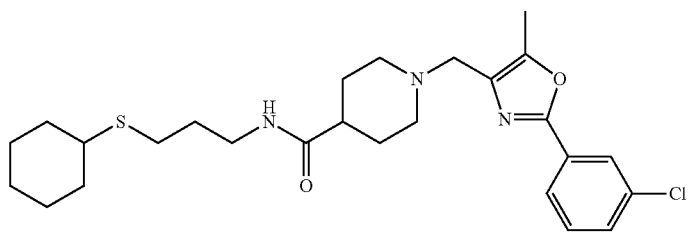 [SMILES: Cc1oc(-c2cccc(Cl)c2)nc1CN1CCC(C(=O)NCCCSC2CCCCC2)CC1]

TABLE 2.1-continued
(537)
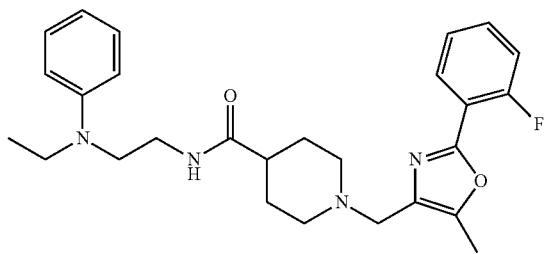 [SMILES: CCN(CCNC(=O)C1CCN(Cc2nc(-c3ccccc3F)oc2C)CC1)c1ccccc1]
(539)
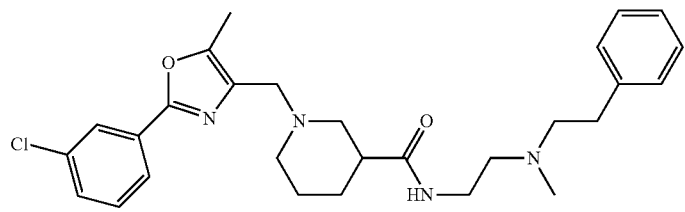 [SMILES: Cc1oc(-c2cccc(Cl)c2)nc1CN1CCCC(C(=O)NCCN(C)CCc2ccccc2)C1]
(541)
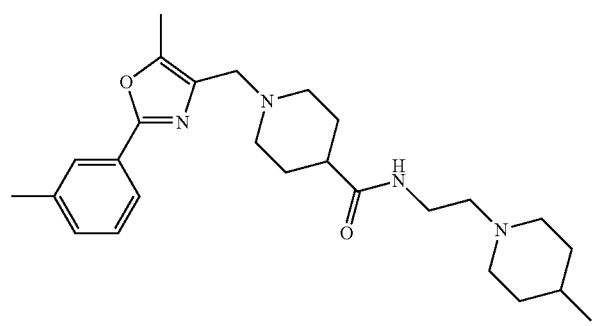
(545)
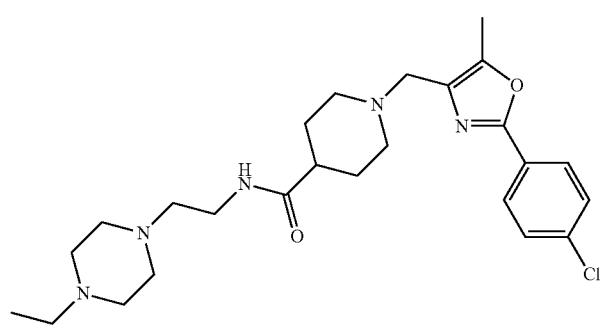 [SMILES: CCN1CCN(CCNC(=O)C2CCN(Cc3nc(-c4ccc(Cl)cc4)oc3C)CC2)CC1]
(547)
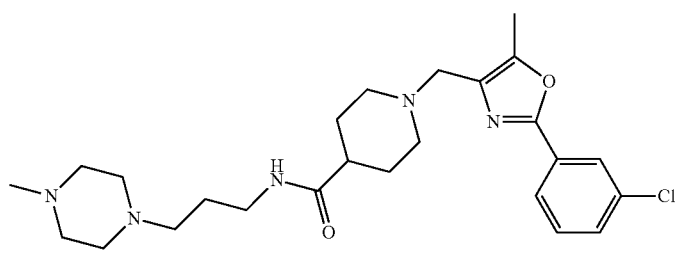 [SMILES: Cc1oc(-c2cccc(Cl)c2)nc1CN1CCC(C(=O)NCCCN2CCN(C)CC2)CC1]

TABLE 2.1-continued
(549)
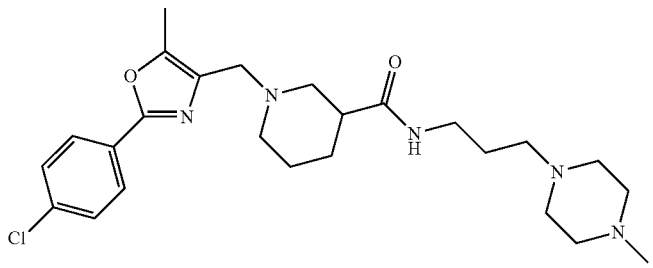 [SMILES: Cc1oc(-c2ccc(Cl)cc2)nc1CN1CCCC(C(=O)NCCCN2CCN(C)CC2)C1]
(551)
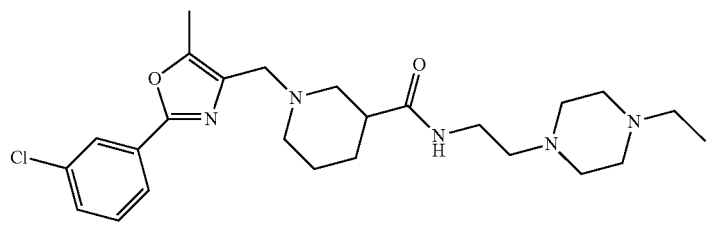 [SMILES: CCN1CCN(CCNC(=O)C2CCCN(Cc3nc(-c4cccc(Cl)c4)oc3C)C2)CC1]
(553)
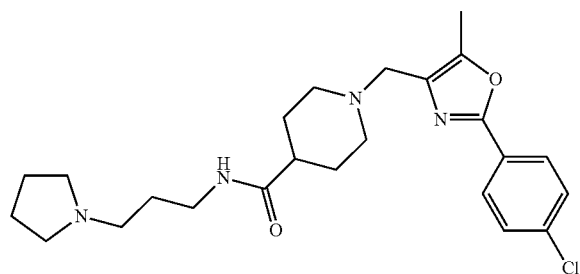 [SMILES: Cc1oc(-c2ccc(Cl)cc2)nc1CN1CCC(C(=O)NCCCN2CCCC2)CC1]
(555)
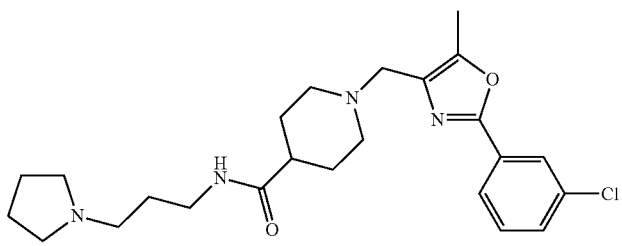 [SMILES: Cc1oc(-c2cccc(Cl)c2)nc1CN1CCC(C(=O)NCCCN2CCCC2)CC1]
(557)
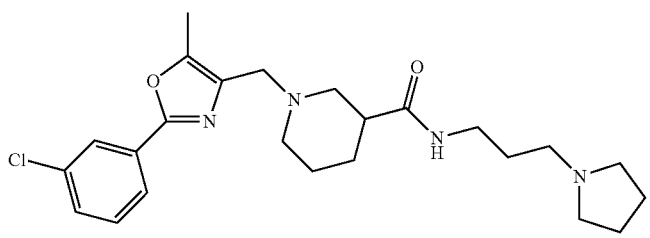 [SMILES: Cc1oc(-c2cccc(Cl)c2)nc1CN1CCCC(C(=O)NCCCN2CCCC2)C1]
(559)
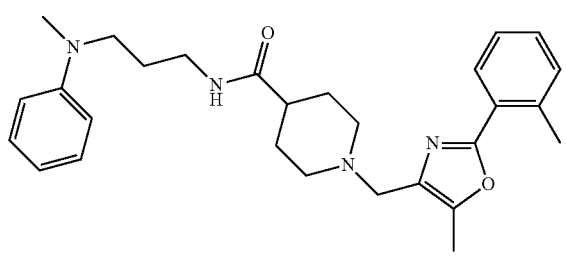 [SMILES: Cc1ccccc1-c1nc(CN2CCC(C(=O)NCCCN(C)c3ccccc3)CC2)c(C)o1]

US 8,729,081 B2
95 96
TABLE 2.1-continued
(561)
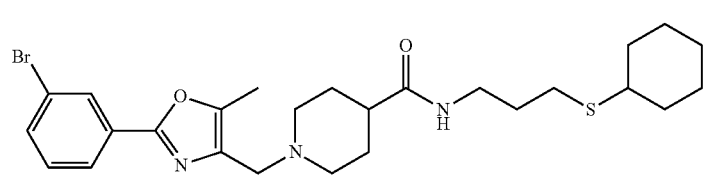 [SMILES: Cc1oc(-c2cccc(Br)c2)nc1CN1CCC(C(=O)NCCCSC2CCCCC2)CC1]
(567)
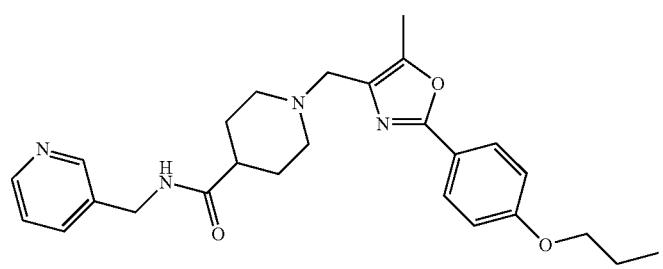 [SMILES: CCCOc1ccc(-c2nc(CN3CCC(C(=O)NCc4cccnc4)CC3)c(C)o2)cc1]
(575)
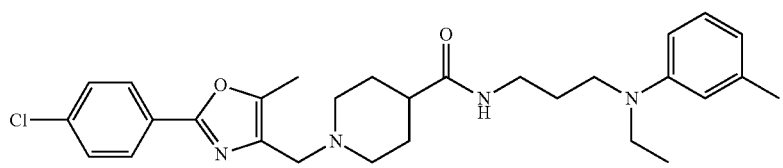 [SMILES: CCN(CCCNC(=O)C1CCN(Cc2nc(-c3ccc(Cl)cc3)oc2C)CC1)c1cccc(C)c1]
(577)
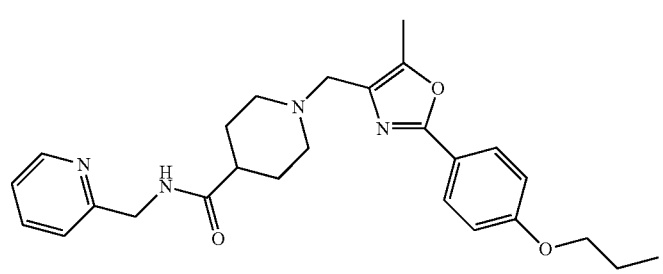 [SMILES: CCCOc1ccc(-c2nc(CN3CCC(C(=O)NCc4ccccn4)CC3)c(C)o2)cc1]
(579)
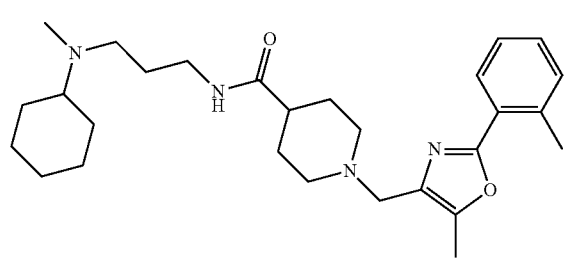 [SMILES: Cc1ccccc1-c1nc(CN2CCC(C(=O)NCCCN(C)C3CCCCC3)CC2)c(C)o1]
(581)
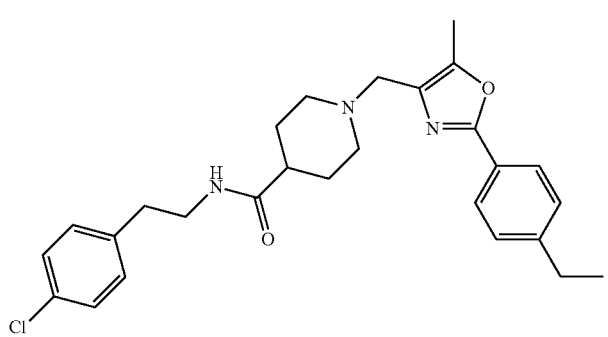 [SMILES: CCc1ccc(-c2nc(CN3CCC(C(=O)NCCc4ccc(Cl)cc4)CC3)c(C)o2)cc1]

TABLE 2.1-continued
(583)
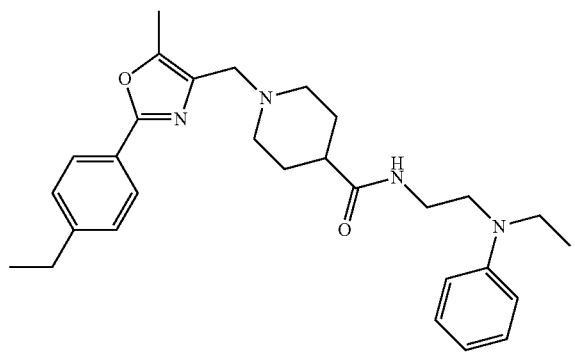 [SMILES: CCc1ccc(-c2nc(CN3CCC(C(=O)NCCN(CC)c4ccccc4)CC3)c(C)o2)cc1]
(585)
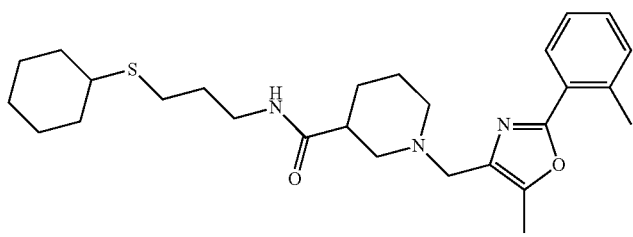 [SMILES: Cc1ccccc1-c1nc(CN2CCCC(C(=O)NCCCSC3CCCCC3)C2)c(C)o1]
(587)
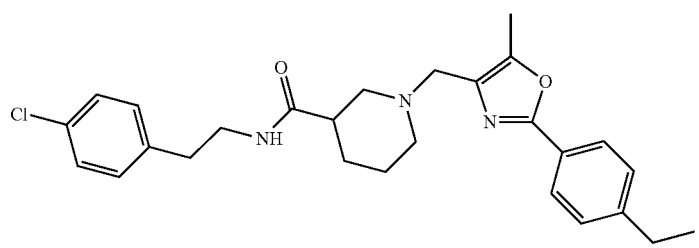 [SMILES: CCc1ccc(-c2nc(CN3CCCC(C(=O)NCCc4ccc(Cl)cc4)C3)c(C)o2)cc1]
(589)
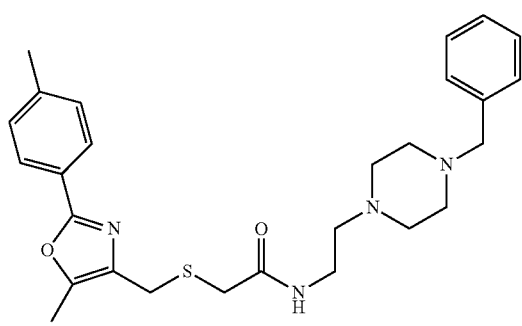 [SMILES: Cc1ccc(-c2nc(CSCC(=O)NCCN3CCN(Cc4ccccc4)CC3)c(C)o2)cc1]
(595)
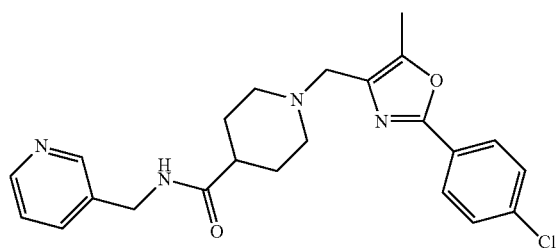 [SMILES: Cc1oc(-c2ccc(Cl)cc2)nc1CN1CCC(C(=O)NCc2cccnc2)CC1]

TABLE 2.1-continued
(597)
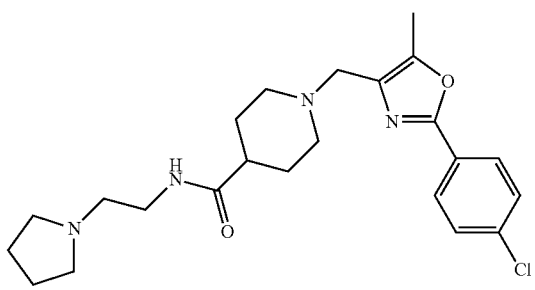 [SMILES: Cc1oc(-c2ccc(Cl)cc2)nc1CN1CCC(C(=O)NCCN2CCCC2)CC1]
(599)
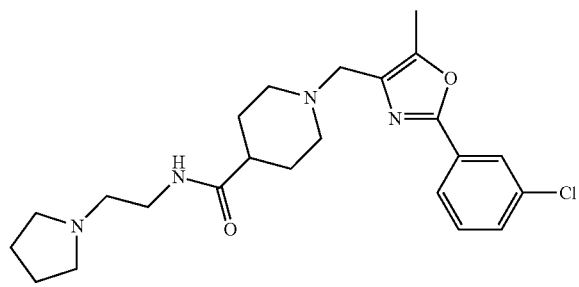 [SMILES: Cc1oc(-c2cccc(Cl)c2)nc1CN1CCC(C(=O)NCCN2CCCC2)CC1]
(901)
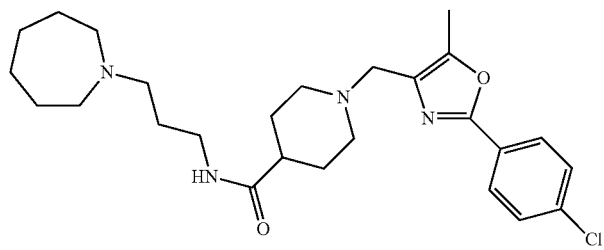 [SMILES: Cc1oc(-c2ccc(Cl)cc2)nc1CN1CCC(C(=O)NCCCN2CCCCCC2)CC1]
(903)
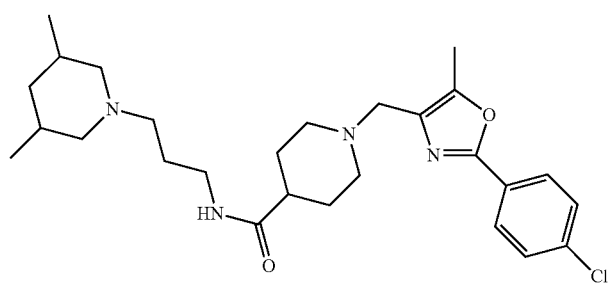 [SMILES: Cc1oc(-c2ccc(Cl)cc2)nc1CN1CCC(C(=O)NCCCN2CC(C)CC(C)C2)CC1]
(905)
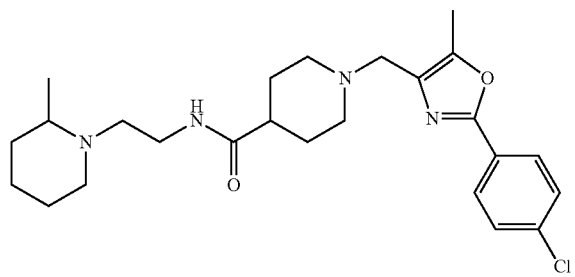 [SMILES: Cc1oc(-c2ccc(Cl)cc2)nc1CN1CCC(C(=O)NCCN2CCCCC2C)CC1]

TABLE 2.1-continued
(907)
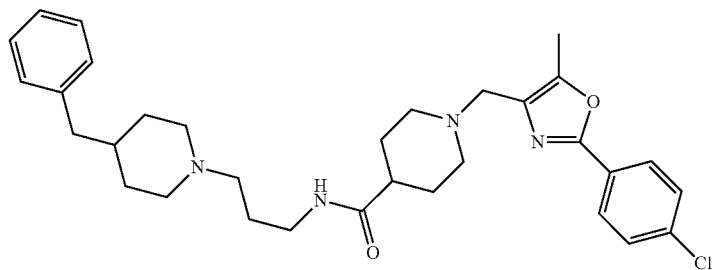 [SMILES: Cc1oc(-c2ccc(Cl)cc2)nc1CN1CCC(C(=O)NCCCN2CCC(Cc3ccccc3)CC2)CC1]
(909)
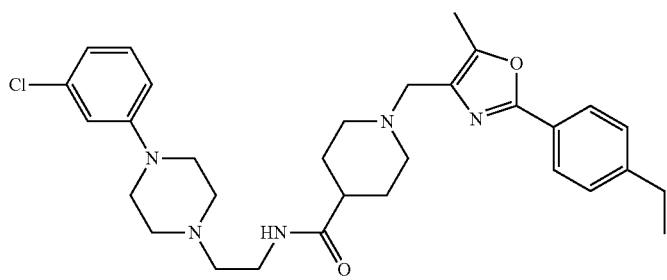 [SMILES: CCc1ccc(-c2nc(CN3CCC(C(=O)NCCN4CCN(c5cccc(Cl)c5)CC4)CC3)c(C)o2)cc1]
(911)
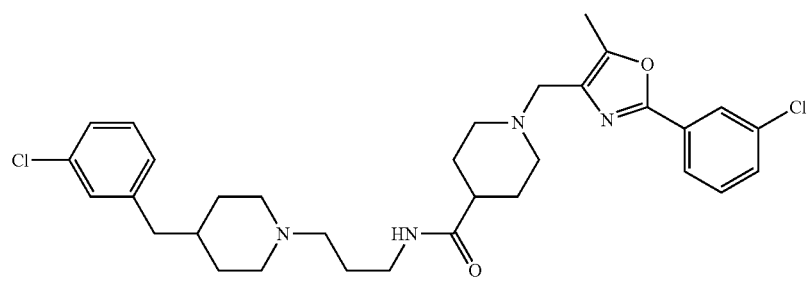 [SMILES: Cc1oc(-c2cccc(Cl)c2)nc1CN1CCC(C(=O)NCCCN2CCC(Cc3cccc(Cl)c3)CC2)CC1]
(913)
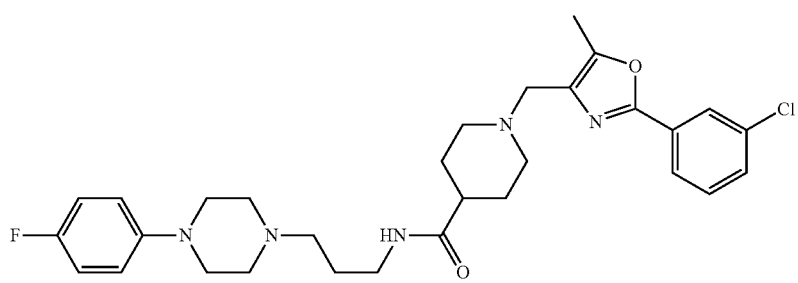 [SMILES: Cc1oc(-c2cccc(Cl)c2)nc1CN1CCC(C(=O)NCCCN2CCN(c3ccc(F)cc3)CC2)CC1]
(915)
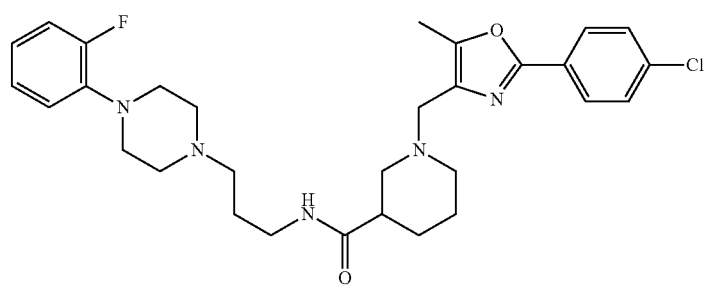 [SMILES: Cc1oc(-c2ccc(Cl)cc2)nc1CN1CCCC(C(=O)NCCCN2CCN(c3ccccc3F)CC2)C1]

TABLE 2.1-continued
(919)
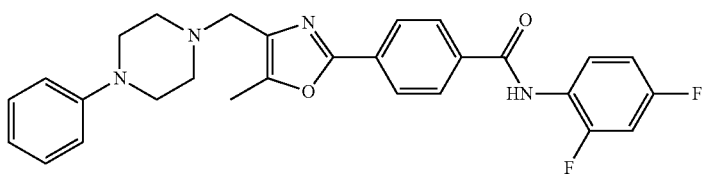 [SMILES: Cc1oc(-c2ccc(C(=O)Nc3ccc(F)cc3F)cc2)nc1CN1CCN(c2ccccc2)CC1]
(929)
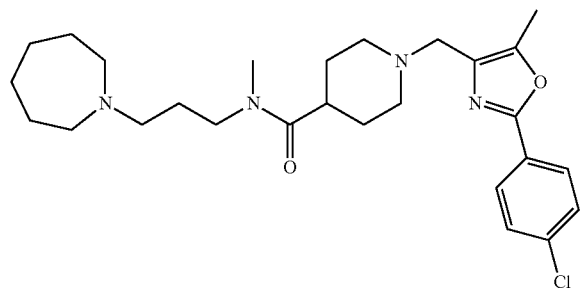 [SMILES: Cc1oc(-c2ccc(Cl)cc2)nc1CN1CCC(C(=O)N(C)CCCN2CCCCCC2)CC1]
(931)
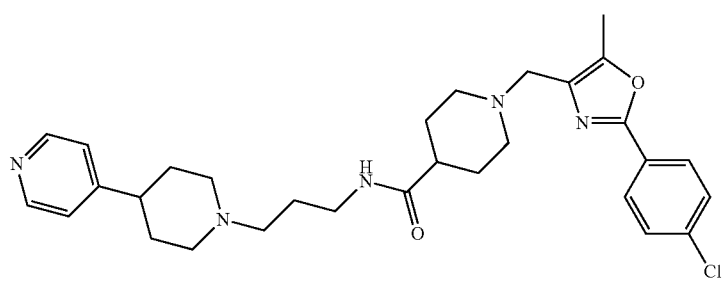 [SMILES: Cc1oc(-c2ccc(Cl)cc2)nc1CN1CCC(C(=O)NCCCN2CCC(c3ccncc3)CC2)CC1]
(933)
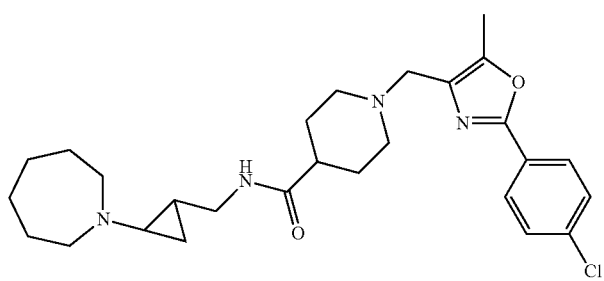 [SMILES: Cc1oc(-c2ccc(Cl)cc2)nc1CN1CCC(C(=O)NCC2CC2N2CCCCCC2)CC1]
(935)
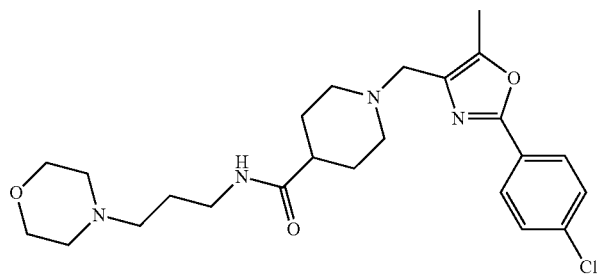 [SMILES: Cc1oc(-c2ccc(Cl)cc2)nc1CN1CCC(C(=O)NCCCN2CCOCC2)CC1]

TABLE 2.1-continued
(937)
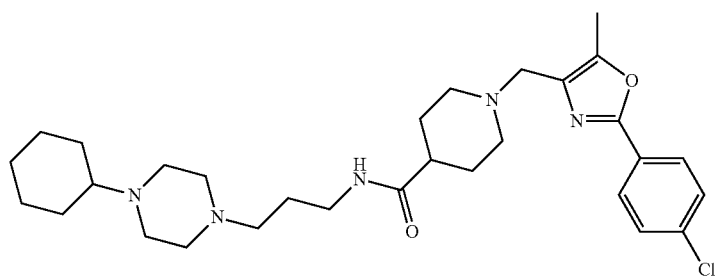 [SMILES: Cc1oc(-c2ccc(Cl)cc2)nc1CN1CCC(C(=O)NCCCN2CCN(C3CCCCC3)CC2)CC1]
(939)
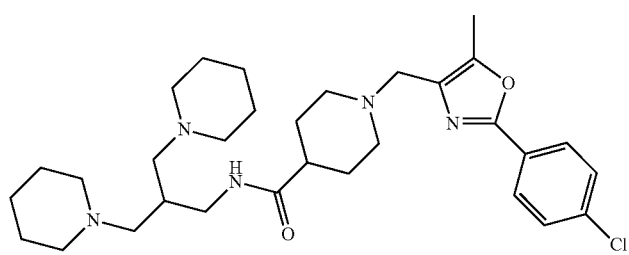 [SMILES: Cc1oc(-c2ccc(Cl)cc2)nc1CN1CCC(C(=O)NCC(CN2CCCCC2)CN2CCCCC2)CC1]
(941)
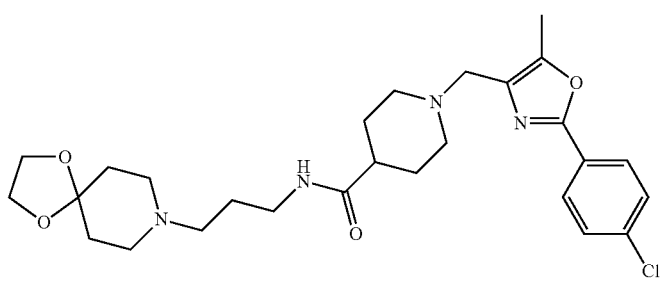 [SMILES: Cc1oc(-c2ccc(Cl)cc2)nc1CN1CCC(C(=O)NCCCN2CCC3(CC2)OCCO3)CC1]
(943)
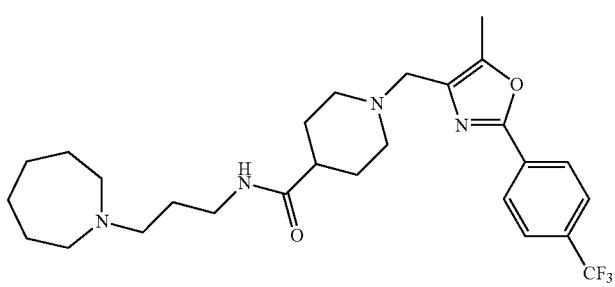 [SMILES: Cc1oc(-c2ccc(C(F)(F)F)cc2)nc1CN1CCC(C(=O)NCCCN2CCCCCC2)CC1]
(945)
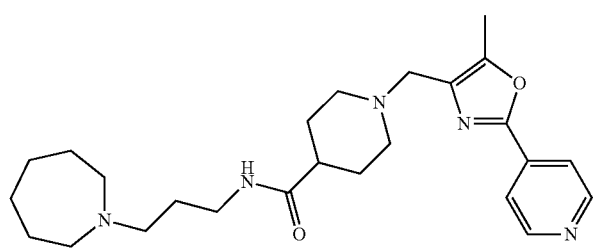 [SMILES: Cc1oc(-c2ccncc2)nc1CN1CCC(C(=O)NCCCN2CCCCCC2)CC1]

TABLE 2.1-continued
(947)
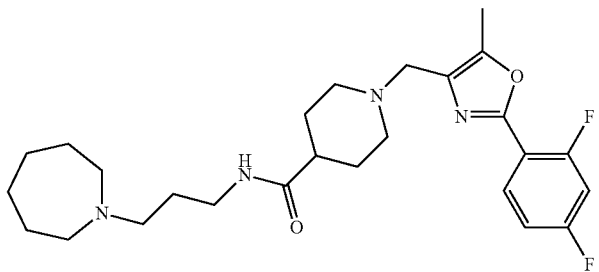 [SMILES: Cc1oc(-c2ccc(F)cc2F)nc1CN1CCC(C(=O)NCCCN2CCCCCC2)CC1]
(949)
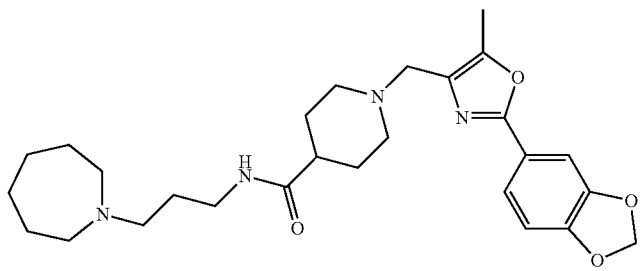 [SMILES: Cc1oc(-c2ccc3c(c2)OCO3)nc1CN1CCC(C(=O)NCCCN2CCCCCC2)CC1]
(951)
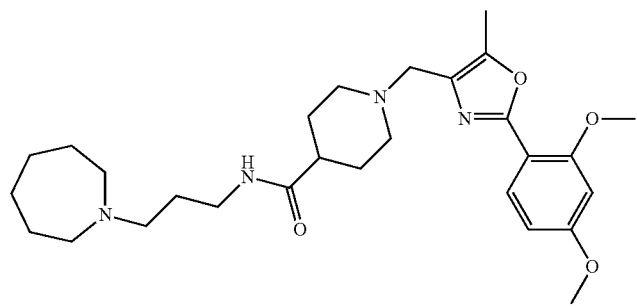 [SMILES: COc1ccc(-c2nc(CN3CCC(C(=O)NCCCN4CCCCCC4)CC3)c(C)o2)c(OC)c1]
(953)
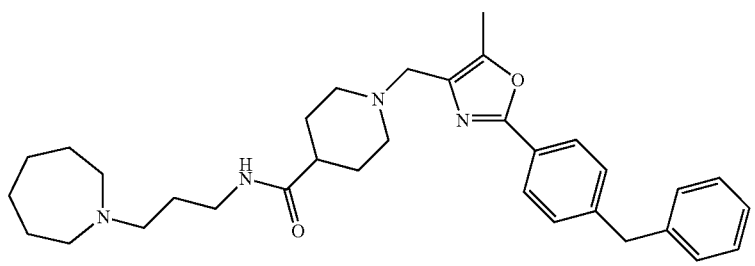 [SMILES: Cc1oc(-c2ccc(Cc3ccccc3)cc2)nc1CN1CCC(C(=O)NCCCN2CCCCCC2)CC1]
(955)
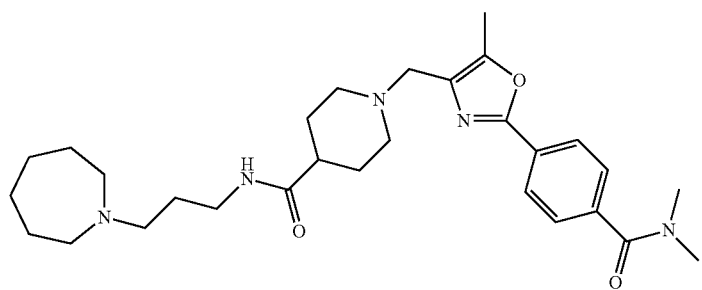 [SMILES: Cc1oc(-c2ccc(C(=O)N(C)C)cc2)nc1CN1CCC(C(=O)NCCCN2CCCCCC2)CC1]

TABLE 2.1-continued
(957)
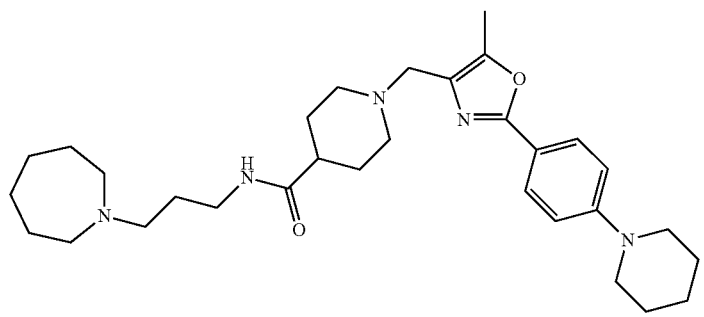 [SMILES: Cc1oc(-c2ccc(N3CCCCC3)cc2)nc1CN1CCC(C(=O)NCCCN2CCCCCC2)CC1]
(959)
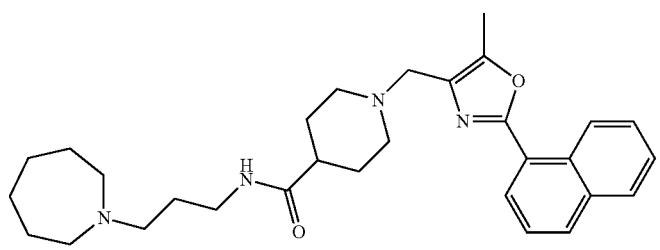 [SMILES: Cc1oc(-c2cccc3ccccc23)nc1CN1CCC(C(=O)NCCCN2CCCCCC2)CC1]
(961)
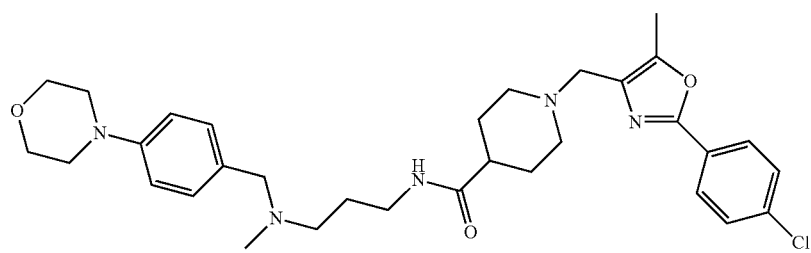 [SMILES: Cc1oc(-c2ccc(Cl)cc2)nc1CN1CCC(C(=O)NCCCN(C)Cc2ccc(N3CCOCC3)cc2)CC1]
(963)
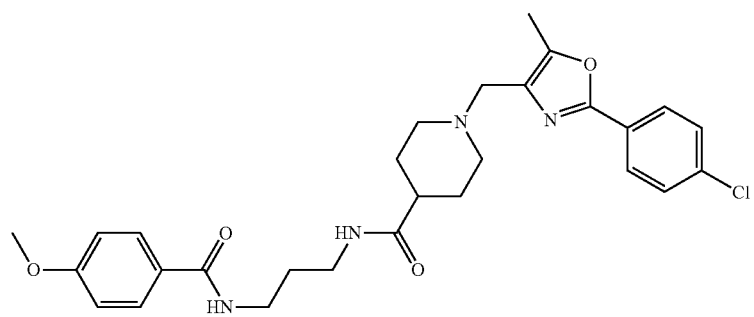 [SMILES: COc1ccc(C(=O)NCCCNC(=O)C2CCN(Cc3nc(-c4ccc(Cl)cc4)oc3C)CC2)cc1]
(965)
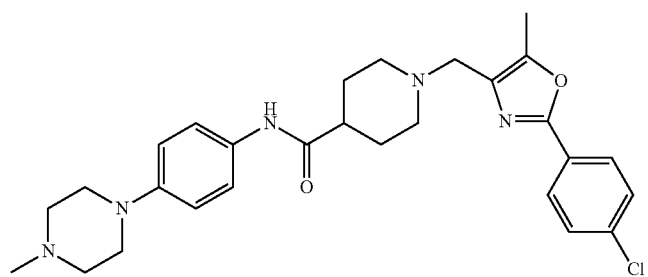 [SMILES: Cc1oc(-c2ccc(Cl)cc2)nc1CN1CCC(C(=O)Nc2ccc(N3CCN(C)CC3)cc2)CC1]

TABLE 2.1-continued (967)

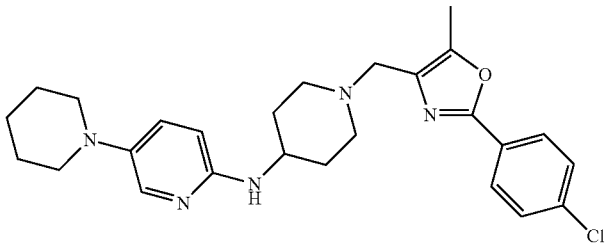 [SMILES: Cc1oc(-c2ccc(Cl)cc2)nc1CN1CCC(Nc2ccc(N3CCCCC3)cn2)CC1]

(969)

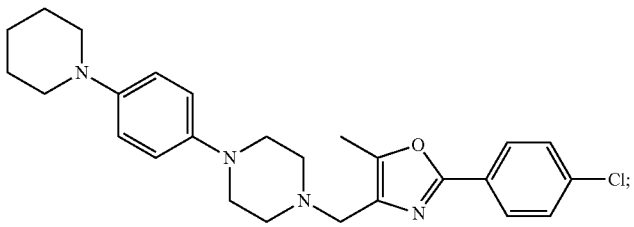 [SMILES: Cc1oc(-c2ccc(Cl)cc2)nc1CN1CCN(c2ccc(N3CCCCC3)cc2)CC1]

or a salt, solvate, or physiologically functional derivative thereof.

Compounds listed in Table 2.1 may also be represented by their chemical names as follows:

| ID | IUPAC Name |
|---|---|
| 501 | N-(3-azepan-1-ylpropyl)-1-{[2-(4-chlorophenyl)-5-methyl-1,3-oxazol-4-yl]methyl}piperidine-4-carboxamide |
| 503 | N-(2-azepan-1-ylethyl)-1-{[2-(4-chlorophenyl)-5-methyl-1,3-oxazol-4-yl]methyl}piperidine-4-carboxamide |
| 505 | 1-{[2-(4-chlorophenyl)-5-methyl-1,3-oxazol-4-yl]methyl}-N-[3-(3-methylpiperidin-1-yl)propyl]piperidine-4-carboxamide |
| 507 | 1-{[2-(4-chlorophenyl)-5-methyl-1,3-oxazol-4-yl]methyl}-N-[3-(2-ethylpiperidin-1-yl)propyl]piperidine-4-carboxamide |
| 509 | 1-{[2-(4-chlorophenyl)-5-methyl-1,3-oxazol-4-yl]methyl}-N-[2-(2-methylpiperidin-1-yl)ethyl]piperidine-4-carboxamide |
| 511 | 1-{[2-(4-chlorophenyl)-5-methyl-1,3-oxazol-4-yl]methyl}-N-{2-[ethyl(phenyl)amino]ethyl}piperidine-4-carboxamide |
| 513 | 1-{[2-(4-chlorophenyl)-5-methyl-1,3-oxazol-4-yl]methyl}-N-{3-[methyl(phenyl)amino]propyl}piperidine-4-carboxamide |
| 515 | 1-{[2-(3-chlorophenyl)-5-methyl-1,3-oxazol-4-yl]methyl}-N-{2-[ethyl(phenyl)amino]ethyl}piperidine-4-carboxamide |
| 517 | 1-{[2-(4-chlorophenyl)-5-methyl-1,3-oxazol-4-yl]methyl}-N-{2-[ethyl(phenyl)amino]ethyl}piperidine-3-carboxamide |
| 519 | 1-{[2-(3-chlorophenyl)-5-methyl-1,3-oxazol-4-yl]methyl}-N-{2-[ethyl(phenyl)amino]ethyl}piperidine-3-carboxamide |
| 521 | 1-{[2-(3-chlorophenyl)-5-methyl-1,3-oxazol-4-yl]methyl}-N-{3-[methyl(phenyl)amino]propyl}piperidine-3-carboxamide |
| 525 | N-{3-[benzyl(methyl)amino]propyl}-1-{[2-(4-chlorophenyl)-5-methyl-1,3-oxazol-4-yl]methyl}piperidine-4-carboxamide |
| 527 | 1-{[2-(4-chlorophenyl)-5-methyl-1,3-oxazol-4-yl]methyl}-N-[3-(3,5-dimethylpiperidin-1-yl)propyl]piperidine-4-carboxamide |
| 529 | 1-{[2-(4-chlorophenyl)-5-methyl-1,3-oxazol-4-yl]methyl}-N-{2-[methyl(2-phenylethyl)amino]ethyl}piperidine-4-carboxamide |
| 531 | 1-{[5-methyl-2-(2-methylphenyl)-1,3-oxazol-4-yl]methyl}-N-[3-(3-methylpiperidin-1-yl)propyl]piperidine-4-carboxamide |
| 533 | 1-{[2-(3-chlorophenyl)-5-methyl-1,3-oxazol-4-yl]methyl}-N-[3-(3,5-dimethylpiperidin-1-yl)propyl]piperidine-4-carboxamide |
| 535 | 1-{[2-(3-chlorophenyl)-5-methyl-1,3-oxazol-4-yl]methyl}-N-[3-(cyclohexylsulfanyl)propyl]piperidine-4-carboxamide |
| 537 | N-{2-[ethyl(phenyl)amino]ethyl}-1-{[2-(2-fluorophenyl)-5-methyl-1,3-oxazol-4-yl]methyl}piperidine-4-carboxamide |
| 539 | 1-{[2-(3-chlorophenyl)-5-methyl-1,3-oxazol-4-yl]methyl}-N-{2-[methyl(2-phenylethyl)amino]ethyl}piperidine-3-carboxamide |
| 541 | 1-{[5-methyl-2-(3-methylphenyl)-1,3-oxazol-4-yl]methyl}-N-[2-(4-methylpiperidin-1-yl)ethyl]piperidine-4-carboxamide |
| 545 | 1-{[2-(4-chlorophenyl)-5-methyl-1,3-oxazol-4-yl]methyl}-N-[2-(4-ethylpiperazin-1-yl)ethyl]piperidine-4-carboxamide |

-continued

| ID | IUPAC Name |
|---|---|
| 547 | 1-{[2-(3-chlorophenyl)-5-methyl-1,3-oxazol-4-yl]methyl}-N-[3-(4-methylpiperazin-1-yl)propyl]piperidine-4-carboxamide |
| 549 | 1-{[2-(4-chlorophenyl)-5-methyl-1,3-oxazol-4-yl]methyl}-N-[3-(4-methylpiperazin-1-yl)propyl]piperidine-3-carboxamide |
| 551 | 1-{[2-(3-chlorophenyl)-5-methyl-1,3-oxazol-4-yl]methyl}-N-[2-(4-ethylpiperazin-1-yl)ethyl]piperidine-3-carboxamide |
| 553 | 1-{[2-(4-chlorophenyl)-5-methyl-1,3-oxazol-4-yl]methyl}-N-(3-pyrrolidin-1-ylpropyl)piperidine-4-carboxamide |
| 555 | 1-{[2-(3-chlorophenyl)-5-methyl-1,3-oxazol-4-yl]methyl}-N-(3-pyrrolidin-1-ylpropyl)piperidine-4-carboxamide |
| 557 | 1-{[2-(3-chlorophenyl)-5-methyl-1,3-oxazol-4-yl]methyl}-N-(3-pyrrolidin-1-ylpropyl)piperidine-3-carboxamide |
| 559 | 1-{[5-methyl-2-(2-methylphenyl)-1,3-oxazol-4-yl]methyl}-N-{3-[methyl(phenyl)amino]propyl}piperidine-4-carboxamide |
| 561 | 1-{[2-(3-bromophenyl)-5-methyl-1,3-oxazol-4-yl]methyl}-N-[3-(cyclohexylsulfanyl)propyl]piperidine-4-carboxamide |
| 567 | 1-{[5-methyl-2-(4-propoxyphenyl)-1,3-oxazol-4-yl]methyl}-N-(pyridin-3-ylmethyl)piperidine-4-carboxamide |
| 575 | 1-{[2-(4-chlorophenyl)-5-methyl-1,3-oxazol-4-yl]methyl}-N-{3-[ethyl(3-methylphenyl)amino]propyl}piperidine-4-carboxamide |
| 577 | 1-{[5-methyl-2-(4-propoxyphenyl)-1,3-oxazol-4-yl]methyl}-N-(pyridin-2-ylmethyl)piperidine-4-carboxamide |
| 579 | N-{3-[cyclohexyl(methyl)amino]propyl}-1-{[5-methyl-2-(2-methylphenyl)-1,3-oxazol-4-yl]methyl}piperidine-4-carboxamide |
| 581 | N-[2-(4-chlorophenyl)ethyl]-1-{[2-(4-ethylphenyl)-5-methyl-1,3-oxazol-4-yl]methyl}piperidine-4-carboxamide |
| 583 | N-{2-[ethyl(phenyl)amino]ethyl}-1-{[2-(4-ethylphenyl)-5-methyl-1,3-oxazol-4-yl]methyl}piperidine-4-carboxamide |
| 585 | N-[3-(cyclohexylsulfanyl)propyl]-1-{[5-methyl-2-(2-methylphenyl)-1,3-oxazol-4-yl]methyl}piperidine-3-carboxamide |
| 587 | N-[2-(4-chlorophenyl)ethyl]-1-{[2-(4-ethylphenyl)-5-methyl-1,3-oxazol-4-yl]methyl}piperidine-3-carboxamide |
| 589 | N-[2-(4-benzylpiperazin-1-yl)ethyl]-2-({[5-methyl-2-(4-methylphenyl)-1,3-oxazol-4-yl]methyl}sulfanyl)acetamide |
| 595 | 1-{[2-(4-chlorophenyl)-5-methyl-1,3-oxazol-4-yl]methyl}-N-(pyridin-3-ylmethyl)piperidine-4-carboxamide |
| 597 | 1-{[2-(4-chlorophenyl)-5-methyl-1,3-oxazol-4-yl]methyl}-N-(2-pyrrolidin-1-ylethyl)piperidine-4-carboxamide |
| 599 | 1-{[2-(3-chlorophenyl)-5-methyl-1,3-oxazol-4-yl]methyl}-N-(2-pyrrolidin-1-ylethyl)piperidine-4-carboxamide. |
| 901 | N-[3-(azepan-1-yl)propyl]-1-{[2-(4-chlorophenyl)-5-methyl-1,3-oxazol-4-yl]methyl}piperidine-4-carboxamide |
| 903 | 1-{[2-(4-chlorophenyl)-5-methyl-1,3-oxazol-4-yl]methyl}-N-[3-(3,5-dimethylpiperidin-1-yl)propyl]piperidine-4-carboxamide |
| 905 | 1-{[2-(4-chlorophenyl)-5-methyl-1,3-oxazol-4-yl]methyl}-N-[2-(2-methylpiperidin-1-yl)ethyl]piperidine-4-carboxamide |
| 907 | N-[3-(4-benzylpiperidin-1-yl)propyl]-1-{[2-(4-chlorophenyl)-5-methyl-1,3-oxazol-4-yl]methyl}piperidine-4-carboxamide |
| 909 | N-{2-[4-(3-chlorophenyl)piperazin-1-yl]ethyl}-1-{[2-(4-ethylphenyl)-5-methyl-1,3-oxazol-4-yl]methyl}piperidine-4-carboxamide |
| 911 | N-{3-[4-(3-chlorobenzyl)piperidin-1-yl]propyl}-1-{[2-(3-chlorophenyl)-5-methyl-1,3-oxazol-4-yl]methyl}piperidine-4-carboxamide |
| 913 | 1-{[2-(3-chlorophenyl)-5-methyl-1,3-oxazol-4-yl]methyl}-N-{3-[4-(4-fluorophenyl)piperazin-1-yl]propyl}piperidine-4-carboxamide |
| 915 | 1-{[2-(4-chlorophenyl)-5-methyl-1,3-oxazol-4-yl]methyl}-N-{3-[4-(2-fluorophenyl)piperazin-1-yl]propyl}piperidine-3-carboxamide |
| 919 | N-(2,4-difluorophenyl)-4-{5-methyl-4-[(4-phenylpiperazin-1-yl)methyl]-1,3-oxazol-2-yl}benzamide |
| 929 | N-[3-(azepan-1-yl)propyl]-1-{[2-(4-chlorophenyl)-5-methyl-1,3-oxazol-4-yl]methyl}-N-methylpiperidine-4-carboxamide |
| 931 | 1-{[2-(4-chlorophenyl)-5-methyl-1,3-oxazol-4-yl]methyl}-N-{3-[4-(pyridin-4-yl)piperidin-1-yl]propyl}piperidine-4-carboxamide |
| 933 | N-{[2-(azepan-1-yl)cyclopropyl]methyl}-1-{[2-(4-chlorophenyl)-5-methyl-1,3-oxazol-4-yl]methyl}piperidine-4-carboxamide |
| 935 | 1-{[2-(4-chlorophenyl)-5-methyl-1,3-oxazol-4-yl]methyl}-N-[3-(morpholin-4-yl)propyl]piperidine-4-carboxamide |
| 937 | 1-{[2-(4-chlorophenyl)-5-methyl-1,3-oxazol-4-yl]methyl}-N-[3-(4-cyclohexylpiperazin-1-yl)propyl]piperidine-4-carboxamide |
| 939 | 1-{[2-(4-chlorophenyl)-5-methyl-1,3-oxazol-4-yl]methyl}-N-[3-(piperidin-1-yl)-2-(piperidin-1-ylmethyl)propyl]piperidine-4-carboxamide |
| 941 | 1-{[2-(4-chlorophenyl)-5-methyl-1,3-oxazol-4-yl]methyl}-N-[3-(1,4-dioxa-8-azaspiro[4.5]dec-8-yl)propyl]piperidine-4-carboxamide |
| 943 | N-[3-(azepan-1-yl)propyl]-1-({5-methyl-2-[4-(trifluoromethyl)phenyl]-1,3-oxazol-4-yl}methyl)piperidine-4-carboxamide |
| 945 | N-[3-(azepan-1-yl)propyl]-1-{[5-methyl-2-(pyridin-4-yl)-1,3-oxazol-4-yl]methyl}piperidine-4-carboxamide |
| 947 | N-[3-(azepan-1-yl)propyl]-1-{[2-(2,4-difluorophenyl)-5-methyl-1,3-oxazol-4-yl]methyl}piperidine-4-carboxamide |

-continued

| ID | IUPAC Name |
|---|---|
| 949 | N-[3-(azepan-1-yl)propyl]-1-{[2-(1,3-benzodioxol-5-yl)-5-methyl-1,3-oxazol-4-yl]methyl}piperidine-4-carboxamide |
| 951 | N-[3-(azepan-1-yl)propyl]-1-{[2-(2,4-dimethoxyphenyl)-5-methyl-1,3-oxazol-4-yl]methyl}piperidine-4-carboxamide |
| 953 | N-[3-(azepan-1-yl)propyl]-1-{[2-(4-benzylphenyl)-5-methyl-1,3-oxazol-4-yl]methyl}piperidine-4-carboxamide |
| 955 | N-[3-(azepan-1-yl)propyl]-1-({2-[4-(dimethylcarbamoyl)phenyl]-5-methyl-1,3-oxazol-4-yl}methyl)piperidine-4-carboxamide |
| 957 | N-[3-(azepan-1-yl)propyl]-1-({5-methyl-2-[4-(piperidin-1-yl)phenyl]-1,3-oxazol-4-yl}methyl)piperidine-4-carboxamide |
| 959 | N-[3-(azepan-1-yl)propyl]-1-{[5-methyl-2-(naphthalen-1-yl)-1,3-oxazol-4-yl]methyl}piperidine-4-carboxamide |
| 961 | 1-{[2-(4-chlorophenyl)-5-methyl-1,3-oxazol-4-yl]methyl}-N-(3-{methyl[4-(morpholin-4-yl)benzyl]amino}propyl)piperidine-4-carboxamide |
| 963 | 1-{[2-(4-chlorophenyl)-5-methyl-1,3-oxazol-4-yl]methyl}-N-(3-{[(4-methoxyphenyl)carbonyl]amino}propyl)piperidine-4-carboxamide |
| 965 | 1-{[2-(4-chlorophenyl)-5-methyl-1,3-oxazol-4-yl]methyl}-N-[4-(4-methylpiperazin-1-yl)phenyl]piperidine-4-carboxamide |
| 967 | N-(1-{[2-(4-chlorophenyl)-5-methyl-1,3-oxazol-4-yl]methyl}piperidin-4-yl)-5-(piperidin-1-yl)pyridin-2-amine |
| 969 | 1-{[2-(4-chlorophenyl)-5-methyl-1,3-oxazol-4-yl]methyl}-4-[4-(piperidin-1-yl)phenyl]piperazine. |

In one embodiment of formula (II), the B ring is an aryl, substituted aryl, heteroaryl or a substituted heteroaryl ring. In one embodiment of formula (II), the compound has structural formula (IIb),

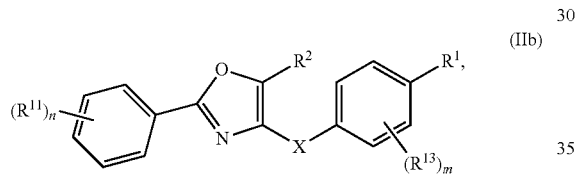

(IIb)

wherein:

$R^1$, $R^2$ and X have the same definitions as in formula (II); and $R^{11}$ and $R^{13}$ independently represent one or multiple substituents. $R^{11}$ and $R^{13}$ are independently selected from hydrogen, halogen, acyl, substituted acyl, alkoxycarbonyl, substituted alkoxycarbonyl, aryloxycarbonyl, substituted aryloxycarbonyl, —C(O)NR$^5$R$^6$, alkyl, substituted alkyl, cycloheteroalkyl, substituted cycloheteroalkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl.

In one embodiment of formula (IIb), $R^1$ is —C(O)NHR$^5$, wherein the preferred amine, i.e., —NHR$^5$, is derived from a group consisted of, but not limited to:

A1

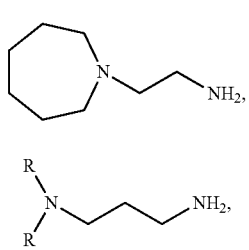

A2

A3

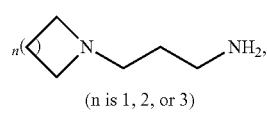

(n is 1, 2, or 3)

A4

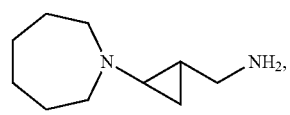

A5

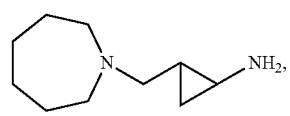

A5

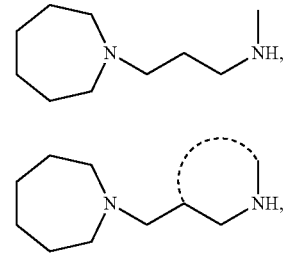

A7

A8

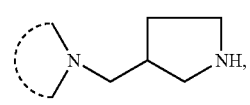

A9

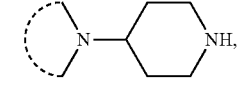

A10 wherein each of the ring with dotted line (in A7, A8, A9 or A10) represents a 5-, 6-, or 7-membered cycloalkyl, substi tuted cycloalkyl, heterocycloalkyl, substituted heterocycloalkyl, aryl, substituted aryl, heteroaryl, or substituted heteroaryl ring.
In some embodiments, the compound having a structural formula (II) or (Jib) is selected from the group consisting of Table 2.2.
TABLE 2.2
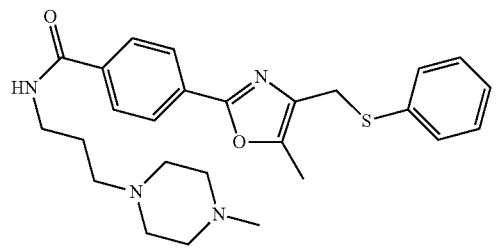 [SMILES: Cc1oc(-c2ccc(C(=O)NCCCN3CCN(C)CC3)cc2)nc1CSc1ccccc1]
(523)
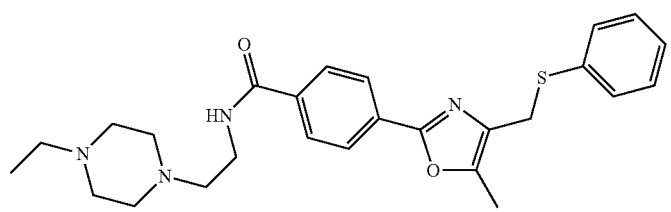 [SMILES: CCN1CCN(CCNC(=O)c2ccc(-c3nc(CSc4ccccc4)c(C)o3)cc2)CC1]
(543)
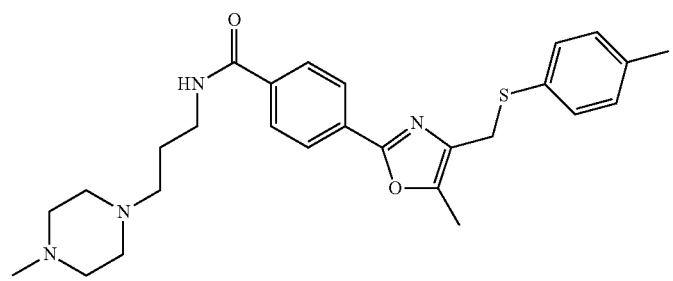
(563)
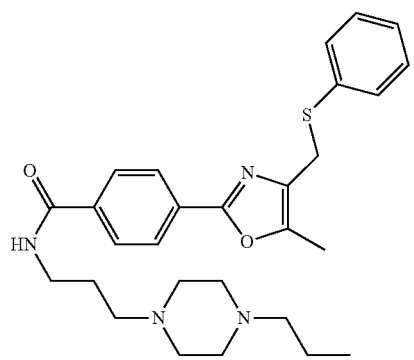 [SMILES: CCCN1CCN(CCCNC(=O)c2ccc(-c3nc(CSc4ccccc4)c(C)o3)cc2)CC1]
(565)
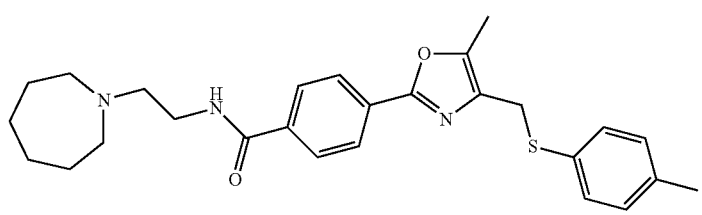 [SMILES: Cc1ccc(SCc2nc(-c3ccc(C(=O)NCCN4CCCCCC4)cc3)oc2C)cc1]
(569)

TABLE 2.2-continued
(571)
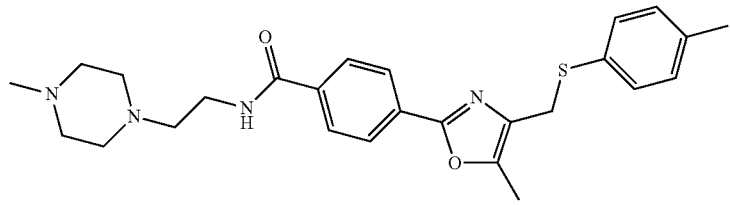
(573)
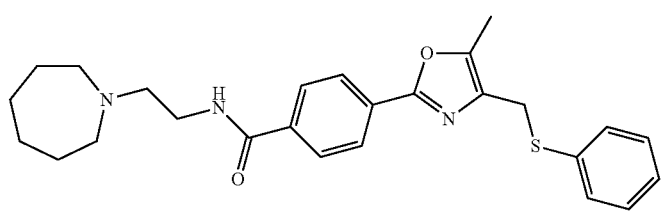 [SMILES: Cc1oc(-c2ccc(C(=O)NCCN3CCCCCC3)cc2)nc1CSc1ccccc1]
(591)
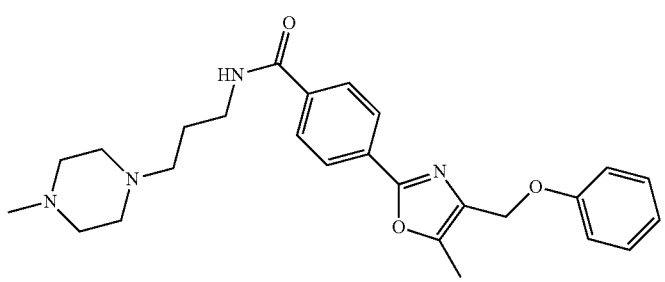 [SMILES: Cc1oc(-c2ccc(C(=O)NCCCN3CCN(C)CC3)cc2)nc1COc1ccccc1]
(593)
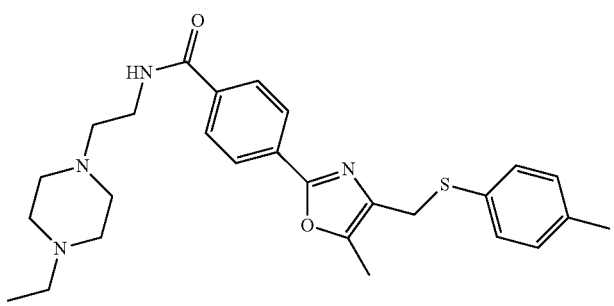 [SMILES: CCN1CCN(CCNC(=O)c2ccc(-c3nc(CSc4ccc(C)cc4)c(C)o3)cc2)CC1]
(917)
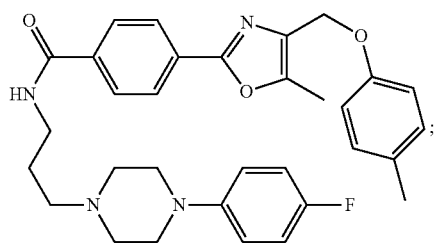 [SMILES: Cc1ccc(OCc2nc(-c3ccc(C(=O)NCCCN4CCN(c5ccc(F)cc5)CC4)cc3)oc2C)cc1]
or a salt, solvate, or physiologically functional derivative thereof.

Compounds listed in Table 2.2 may also be represented by their chemical names as follows

| ID | IUPAC Name |
|---|---|
| 543 | N-[2-(4-ethylpiperazin-1-yl)ethyl]-4-{5-methyl-4-[(phenylsulfanyl)methyl]-1,3-oxazol-2-yl}benzamide |
| 523 | 4-{5-methyl-4-[(phenylsulfanyl)methyl]-1,3-oxazol-2-yl}-N-[3-(4-methylpiperazin-1-yl)propyl]benzamide |
| 563 | 4-(5-methyl-4-{[(4-methylphenyl)sulfanyl]methyl}-1,3-oxazol-2-yl)-N-[3-(4-methylpiperazin-1-yl)propyl]benzamide |
| 565 | 4-{5-methyl-4-[(phenylsulfanyl)methyl]-1,3-oxazol-2-yl}-N-[3-(4-propylpiperazin-1-yl)propyl]benzamide |
| 569 | N-(2-azepan-1-ylethyl)-4-(5-methyl-4-{[(4-methylphenyl)sulfanyl]methyl}-1,3-oxazol-2-yl)benzamide |
| 571 | 4-(5-methyl-4-{[(4-methylphenyl)sulfanyl]methyl}-1,3-oxazol-2-yl)-N-[2-(4-methylpiperazin-1-yl)ethyl]benzamide |
| 573 | N-(2-azepan-1-ylethyl)-4-{5-methyl-4-[(phenylsulfanyl)methyl]-1,3-oxazol-2-yl}benzamide |
| 591 | 4-[5-methyl-4-(phenoxymethyl)-1,3-oxazol-2-yl]-N-[3-(4-methylpiperazin-1-yl)propyl]benzamide |
| 593 | N-[2-(4-ethylpiperazin-1-yl)ethyl]-4-(5-methyl-4-{[(4-methylphenyl)sulfanyl]methyl}-1,3-oxazol-2-yl)benzamide |
| 917 | N-{3-[4-(4-fluorophenyl)piperazin-1-yl]propyl}-4-{5-methyl-4-[(4-methylphenoxy)methyl]-1,3-oxazol-2-yl}benzamide. |

Synthesis of the Compounds

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; BuLi: butyllithium; Piv: pivaloyl; Ac: acetyl; THF: tetrahydrofuran; DMSO: dimethylsulfoxide; EDC: N-(3-Dimethylaminopropyl)-N'-ethylcarbodiimide; Boc: tert-butyloxy carbonyl; Et$_3$N: triethylamine; DCM: dichloromethane; DCE: dichloroethane; DME: dimethoxyethane; DBA: diethylamine; DAST: diethylaminosulfur trifluoride; EtMgBr: ethylamgnesium bromide; BSA: bovine serum albumin; TFA: trifluoracetic acid; DMF: N,N-dimethylformamide; SOCl$_2$: thionyl chloride; CDI: carbonyl diimidazole; rt: room temperature; HPLC: high performance liquid chromatography; TLC: thin-layer chromatography. The compounds described herein may be prepared in a variety of ways known to one skilled in the art.

Some of the compounds described herein can be obtained from commercial sources, such as Aldrich Chemical Co. (Milwaukee, Wis.), Sigma. Chemical Co. (St. Louis, Mo.), Maybridge (Cornwall, England), Asinex (Winston-Salem, N.C.), ChemBridge (San Diego, Calif.), ChemDiv (San Diego, Calif.), SPECS (Delft, The Netherlands), Timtec (Newark, Del.) or can be synthesized. The compounds described herein and other related compounds having different substituents identified by any of the methods described above can be synthesized using techniques and materials known to those of skill in the art, such as described, for example, in March, *ADVANCED ORGANIC CHEMISTRY* 4.sup.th Ed., (Wiley 1992); Carey and Sundberg, *ADVANCED ORGANIC CHEMISTRY* 3.sup.rd Ed., Vols. A and B (Plenum 1992), and Green and Wuts, *PROTECTIVE GROUPS IN ORGANIC SYNTHESIS* 2.sup.nd Ed. (Wiley 1991). Starting materials useful for preparing compounds described herein or intermediates thereof are commercially available or can be prepared by well-known synthetic methods (see, e.g., Harrison et al., "Compendium of Synthetic Organic Methods", Vols. 1-8 (John Wiley and Sons, 1971-1996); "*Beilstein Handbook of Organic Chemistry,*" Beilstein Institute of Organic Chemistry, Frankfurt, Germany; Feiser et al., "Reagents for Organic Synthesis," Volumes 1-21, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995). Other methods for synthesis of the compounds described herein and/or starting materials are either described in the art or will be readily apparent to the skilled artisan. Alternatives to the reagents and/or protecting groups may be found in the references provided above and in other compendiums well known to the skilled artisan. Guidance for selecting suitable protecting groups can be found, for example, in Greene & Wuts, "Protective Groups in Organic Synthesis," Wiley Interscience, 1999. Accordingly, the synthetic methods and strategy presented herein are illustrative rather than comprehensive.

The procedures described herein for synthesizing the present compounds may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS) can be used as well. Methods of protection and deprotection, purification and identification and quantification are well known in the chemical arts.

Scheme 1. General synthetic scheme of the compounds of the present invention having structural formula (Ih) or (Ia), wherein, $A^1$, $A^2$, $A^3$, $A^4$, $R^2$, $R^7$ and $R^8$ are the same as defined in formula (Ia), $Z^{11}$ and $Y^{11}$ are independently O or S: and

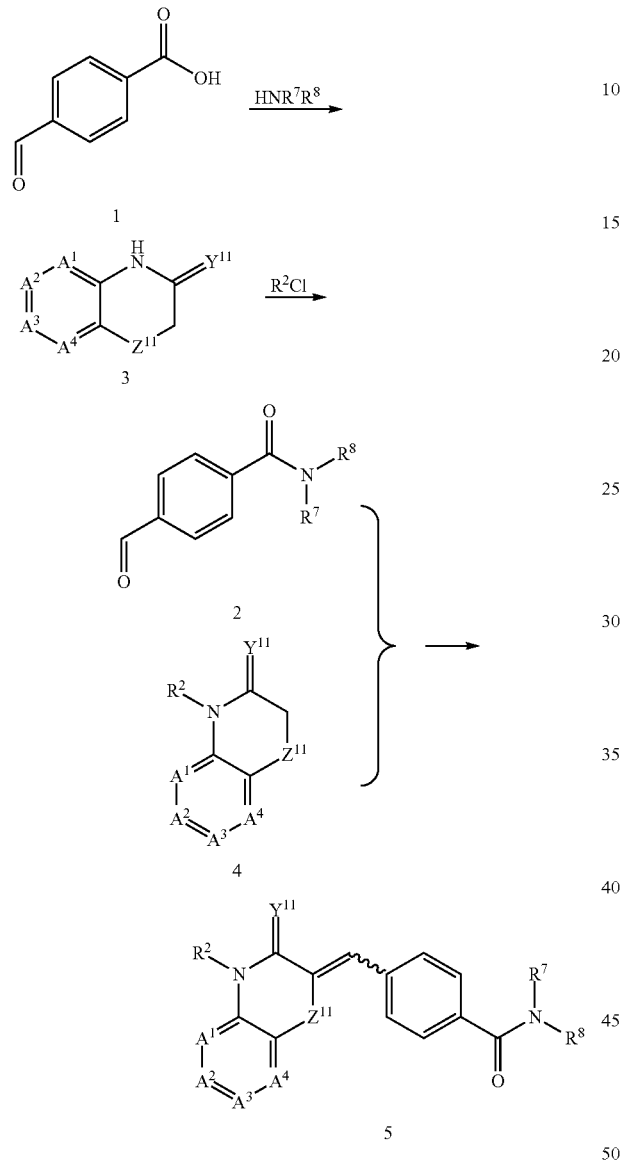

Scheme 2. General synthetic scheme of compounds of the present invention having formula (II), (IIa) or (IIb).

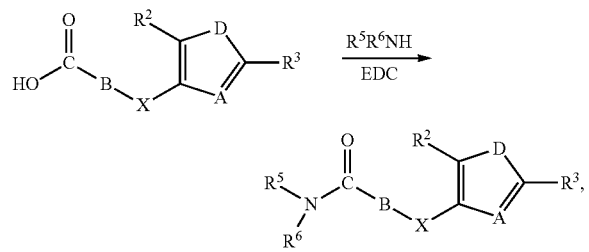

where the amine, i.e., $R^5R^6NH$, may be, but not limited to, selected from the group consisted of A1 to A10 as shown below:

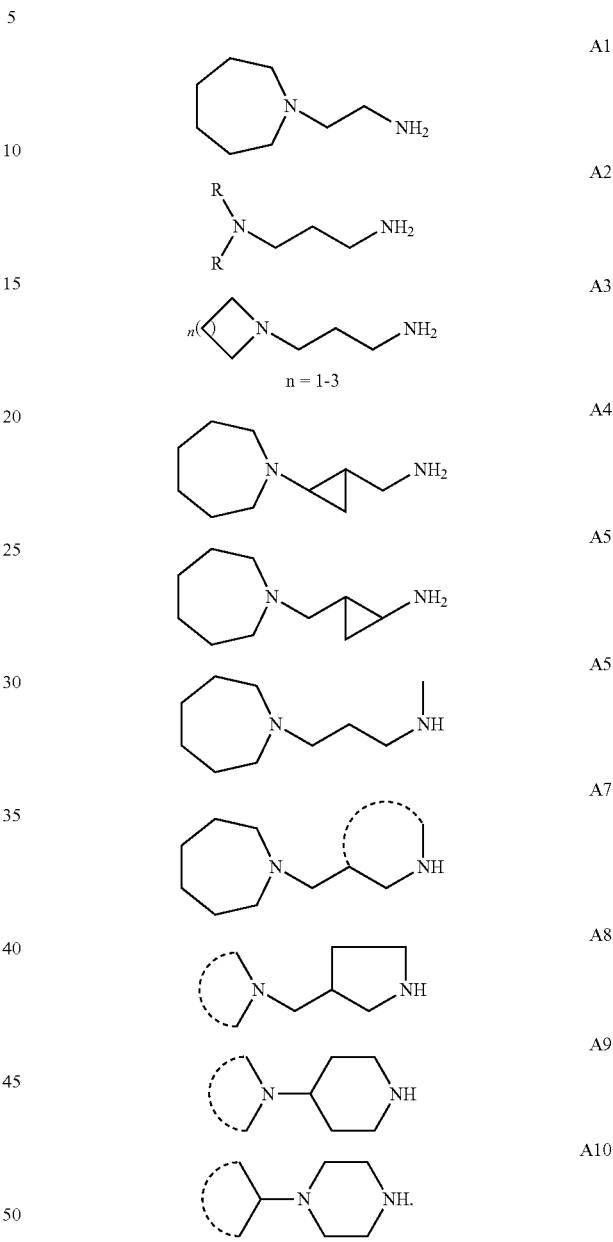

B ring or the dotted-ring in A7, A8, A9 and A10 is independently 5-, 6-, or 7-membered cycloalkyl, substituted cycloalkyl, cycloheteroalkyl, substituted cycloheteroalkyl, aryl, substituted aryl, heteroaryl, or substituted heteroaryl ring.

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the present invention. Various modifications of the invention in addition to those described herein will become apparent to those skilled in the art from the foregoing described and accompanying figures. Such modifications fall within the scope of the appended claims.

A. Synthesis Example 1

Compound 929: N-[3-(azepan-1-yl)propyl]-1-{[2-(4-chlorophenyl)-5-methyl-1,3-oxazol-4-yl]methyl}-N-methylpiperidine-4-carboxamide

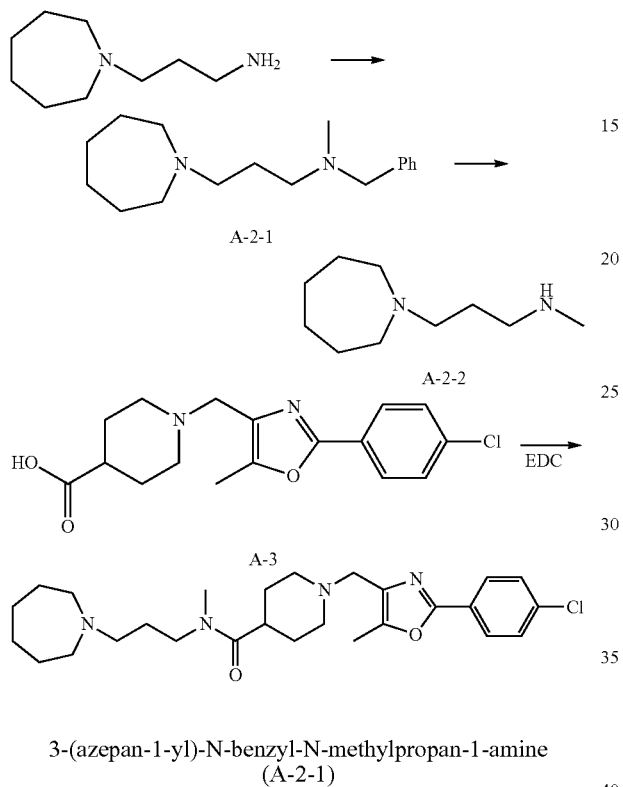

3-(azepan-1-yl)-N-benzyl-N-methylpropan-1-amine (A-2-1)

To a mixture of 3-(Azepan-1-yl)propan-1-amine (0.10 g, 0.64 mmole) in methylene chloride (5 mL) were added benzaldehyde (0.64 mmole) and NaBH(OAc)₃ (0.63 g, 3.0 mmol). The reaction solution was stirred at room temperature for 3 h. Then, paraformaldehyde (200 mg) was added to the reaction mixture and stirring was continued for 6 h. 2N aqueous NaOH (2 mL) was added to quench the reaction, followed by addition of methylene chloride (30 mL). The organic layer was separated, dried over anhydrous Na₂SO₄, and filtered. The filtrate was evaporated to supply 3-(azepan-1-yl)-N-benzyl-N-methylpropan-1-amine (151 mg).

3-(azepan-1-yl)-N-methylpropan-1-amine (A-2-2)

3-(Azepan-1-yl)-N-benzyl-N-methylpropan-1-amine (100 mg) was dissolved in MeOH (20 mL) and to the solution was added 10% Pd/C (50 mg). The reaction mixture was shook under 50 psi hydrogen atmosphere for 2 h. The catalyst was filtered over Cellite and washed with methanol. The filtrated was evaporated to give 3-(azepan-1-yl)-N-methylpropan-1-amine, used without further purification.

N-(3-(azepan-1-yl)propyl)-1-((2-(4-chlorophenyl)-5-methyloxazol-4-yl)methyl)-N-methylpiperidine-4-carboxamide To a solution of 1-((2-(4-chlorophenyl)-5-methyloxazol-4-yl)methyl)piperidine-4-carboxylic acid (A-3, 70 mg, 0.52 mmole), 3-(azepan-1-yl)-N-methylpropan-1-amine (20 mg) and DIPEA (0.05 mL) in DMF (2 mL) was added EDC (35 mg). The reaction solution was stirred at room temperature for 12 hours. The reaction was diluted with EtOAc (30 mL). The organic layer was washed with saturated sodium bicarbonate (10 mL), water (10 mL) and dried over anhydrous magnesium sulfate. After filtration and concentration, the residue was purified through chromatography (CH2Cl2:MeOH 10:1) to give N-(3-(azepan-1-yl)propyl)-1-((2-(4-chlorophenyl)-5-methyloxazol-4-yl)methyl)-N-methylpiperidine-4-carboxamide (42 mg, 82%). H¹NMR (300 MHz, CDCl₃), ppm: 7.97 (d, 2H), 7.48 (d, 2H), 3.80 (m, 1H), 3.63 (m, 2H), 3.45 (m, 2H), 3.31-3.14 (m, 7H), 2.75 (s, 3H), 2.44 (m, 4H), 2.01 (m, 2H), 1.85 (m, 10H), 1.30 (m, 2H), 1.26 (m, 2H). MS (ESI+) M/z: 487, 489 (M+H).

B. Synthesis Example 2

Compound 901: N-(3-(azepan-1-yl)propyl)-1-((2-(4-chlorophenyl)-5-methyloxazol-4-yl)methyl)piperidine-4-carboxamide

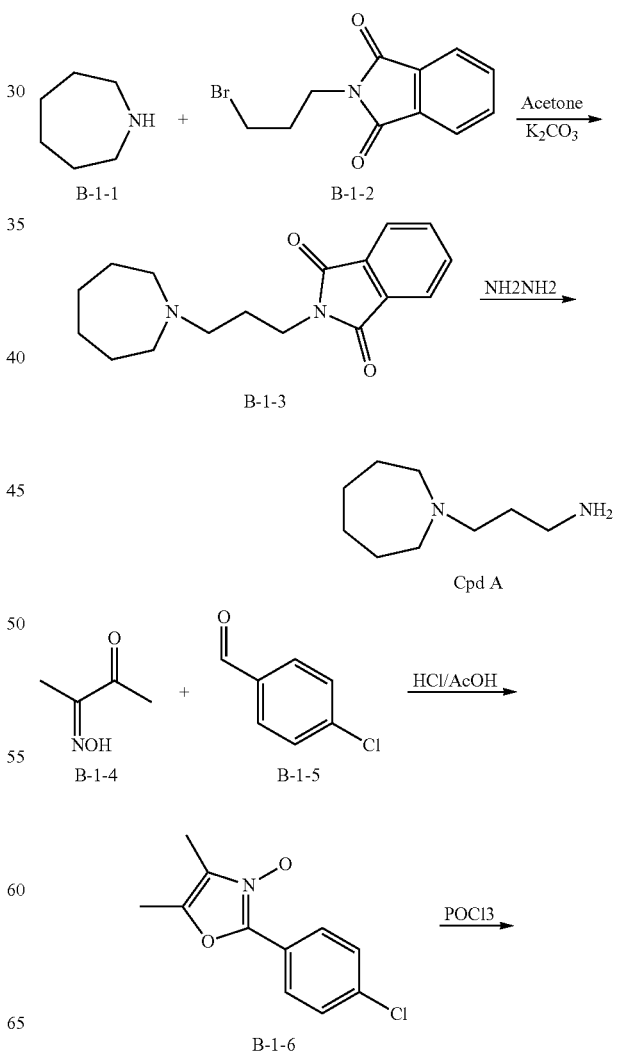

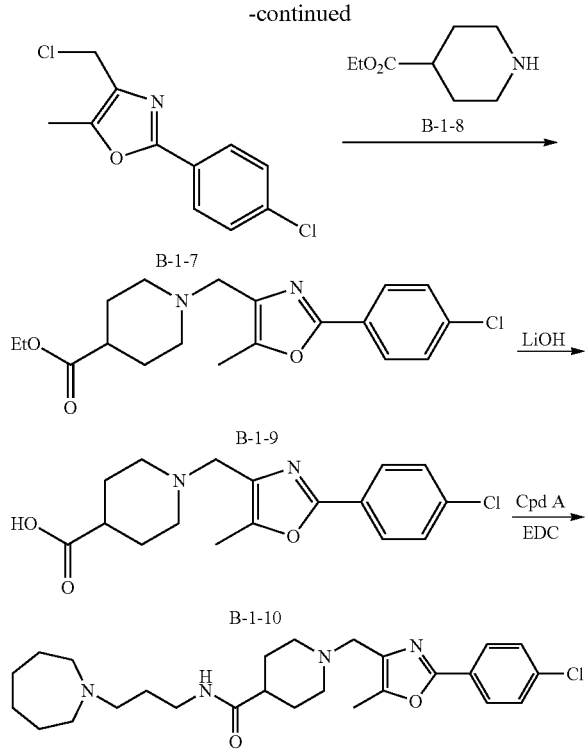

2-(3-(Azepan-1-yl)propyl)isoindoline-1,3-dione (B-1-3)

The mixture of Azepane (2.3 mL), 2-(3-bromopropyl)isoindoline-1,3-dione (5.4 g) and potassium carbonate (5.5 g) in acetone (50 mL) was stirred at room temperature overnight. The solid was filtered and the filtrate was concentrated to provide 2-(3-(azepan-1-yl)propyl)isoindoline-1,3-dione, used without purification.

3-(Azepan-1-yl)propan-1-amine (Cpd A)

To a solution of 2-(3-(azepan-1-yl)propyl)isoindoline-1,3-dione (3.5 g) in Ethanol (20 mL) was added hydrazine (0.58 mL). The reaction mixture was reflux for 13 h and then cooled down to room temperature. TFA (2.0 mL) was added, the resulted white solid was filtered and the solvent was evaporated to give 3-(azepan-1-yl)propan-1-amine, used without further purification.

Ethyl 1-((2-(4-chlorophenyl)-5-methyloxazol-4-yl)methyl)piperidine-4-carboxylate (B-1-9)

The mixture of 4-(chloromethyl)-2-(4-chlorophenyl)-5-methyloxazole (1.21 g, 5 mmole, commercially from Fluorochem) and ethyl piperidine-4-carboxylate (0.81 mL, 1.05 equiv.), $K_2CO_3$ (1.03 g, 1.5 equiv) in dioxane was stirred at 70° C. for 2 h. The reaction solution was cooled to room temperature and the solid was filtered off, rinsed with dichloromethane. The filtrate was concentrated and the residue was recrystallized from hexane to furnish Ethyl 1-((2-(4-chlorophenyl)-5-methyloxazol-4-yl)methyl)piperidine-4-carboxylate (1.65 g, 91%).

1-((2-(4-chlorophenyl)-5-methyloxazol-4-yl)methyl)piperidine-4-carboxylic acid (B-1-10)

Ethyl 1-((2-(4-chlorophenyl)-5-methyloxazol-4-yl)methyl)piperidine-4-carboxylate (1.0 g, 2.7 mmole) and LiOH (240 mg, 10 mmol) were mixed with MeOH (5 mL), THF (5 ml) and Water (2 mL). The mixture was stirred at 50 for 2 h. 4N HCl in dioxane (3 mL) was added the reaction solution was stirred at room temperature for another 1 h. The solvent was removed under vacuum to give 1-((2-(4-chlorophenyl)-5-methyloxazol-4-yl)methyl)piperidine-4-carboxylic acid as white solid, the crude product was used without purification.

N-(3-(azepan-1-yl)propyl)-1-((2-(4-chlorophenyl)-5-methyloxazol-4-yl)methyl)piperidine-4-carboxamide To a solution of 1-((2-(4-chlorophenyl)-5-methyloxazol-4-yl)methyl)piperidine-4-carboxylic acid (0.25 g, 0.75 mmole), 3-(Azepan-1-yl)propan-1-amine (0.33 g) and DIPEA (0.32 mL) in DMF (5 mL) was added EDC (0.153 g). The reaction solution was stirred at room temperature overnight. The solvent removed and EtOAc (100 mL) was added. The organic layer was washed with saturated sodium bicarbonate (50 mL), water (50 mL) and dried over anhydrous magnesium sulfate. After filtration, the residue after concentration of the filtrate was crystallized from EtOAc/Hexane to provide the N-(3-(azepan-1-yl)propyl)-1-((2-(4-chlorophenyl)-5-methyloxazol-4-yl)methyl)piperidine-4-carboxamide as white solid (0.30 g, 85%). $H^1$NMR (300 MHz, $CDCl_3$), ppm: 7.94 (d, 2H), 7.49 (m, 1H), 7.39 (d, 2H), 3.44 (s, 2H), 3.36 (m, 2H), 2.99 (d, 2H), 2.67 (m, 4H), 2.60 (t, 2H), 2.39 (s, 3H), 2.07 (m, 3H), 1.83 (m, 4H), 1.65 (m, 10H). MS (ESI+) M/z: 473, 475 (M+H).

C. Synthesis Example 3

Compound 481: 4-{(Z/E)-[4-(2-fluorobenzyl)-3-oxo-3,4-dihydro-2H-1,4-benzothiazin-2-ylidene]methyl}-N-(3-pyrrolidin-1-ylpropyl)benzamide 4-{(Z/E)-[4-(2-fluorobenzyl)-3-oxo-3,4-dihydro-2H-1,4-benzothiazin-2-ylidene]methyl}-N-(3-pyrrolidin-1-ylpropyl)benzamide can be similarly synthesized as in Examples 1 and 2, according to the scheme given below. The trans (Z) configuration with $H^1$NMR (300 MHz, $CD_3OD$), ppm: 7.94 (d, 2H), 7.89 (s, 1H), 7.77 (d, 2H), 7.36-7.25 (m, 2H), 7.16 (m, 2H), 7.12-7.02 (m, 4H), 5.44 (s, 2H), 3.52 (t, 2H), 3.30 (m, 4H), 3.14 (t, 2H), 2.15-1.98 (m, 6H). LCMS (ESI+) M/z: 516 (M+H).

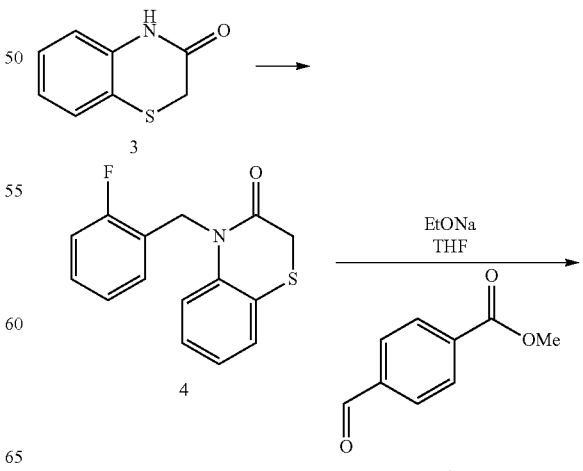

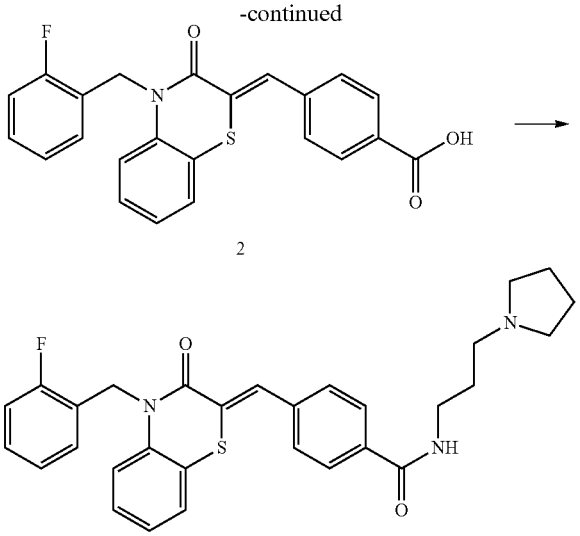

Characterization of Activity of PKCε Inhibitors

The utility of the compounds in accordance with the present invention as PKCε inhibitors antagonists may be readily determined without undue experimentation by methodology well known in the art, including many commercially available and validated bioassays. Examples are provided below.

In Vitro Assays for PKCε

There are many in vitro commercially available and validated bioassays (Ma, H., et al, *Expert Opin Drug Discov.* 2008 June; 3(6): 607-621 and references therein) which can be used to characterize the activities of compounds of the present invention against PKCε protein kinase. Compounds can be tested against the activity of recombinant PKCε. In a final reaction volume of 25 μL, PKCε (h) (0.4 nM, Human recombinant protein expressed in insect cells. Mw=83.7 kDa) is incubated with kinase buffer (20 mM HEPES-HCl, pH 7.5, 10 mM MgCl$_2$, 1 mM EGTA, 0.02% Brij35, 0.1 mM Na$_3$VO$_4$, 0.02 mg/ml BSA, 2 mM DTT, and 1% DMSO), 0.1 mg/mL phosphatidylserine, 10 μg/mL diacylglycerol, 20 μM S25-PKC peptide substrate (RFARKGSLRQKNV-OH, Mw=1561 Da), 10 mM MgAcetate and 10 μM [γ-33P-ATP] (specific activity approx. 500 cpm/pmol). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting Control samples are incubated without inhibitor to measure maximal activity or with the general kinase inhibitor Staurosporine (5 μM) to measure complete inhibition. For each compound the % inhibition can be calculated by the formula, or by curve fits: % Inhibition=(Max activity−Activity with compound)/(Max activity−Activity with Control)*100. Compounds with inhibitory activity are assayed using at least 5 concentrations (1 nM-300 μM). Concentrations are adjusted to generate a complete dose-response curve. Each sample is assayed in duplicate and each experiment is repeated three times. Results are fitted by non-linear regression analysis to a sigmoidal dose-response curve with variable slope to calculate Hill slope, log IC$_{50}$ and Imax values for each inhibitor, using the program Prism 5 (GraphPad Software, Inc., San Diego, Calif.).

The above in vitro assay can also be used to measure the initial velocity of the kinase reaction, varying the concentrations of ATP (1-60 μM) or S25 peptide substrate (1-500 nM). Values for k$_m$ and V$_{max}$ are calculated for drug- and vehicle-treated samples by linear regression analysis of double reciprocal Lineweaver Burke plots (see Examples). Samples are assayed in duplicate and experiments are repeated three times to calculate mean values for km and Vmax, which is compared for the two treatment conditions (vehicle or compound) by two-tailed, unpaired t-tests, and considered significantly different where P<0.05.

Kinase profiling was performed using HotSpot technology (Reaction Biology Corp. 11 Malvern, Pa., USA). This technology is a radioisotope-based P81 filter-binding assay. Compound of the present invention were dissolved in pure DMSO to make a 10 mM stock, then diluted in pure DMSO to make a serial dilution based on the IC$_{50}$ ranges. PKCε (h) (0.4 nM, human recombinant protein expressed in insect cells. Mw=83.7 kDa) and substrate (20 μM peptide substrate, [RFARKGSLRQKNV]) were diluted in the reaction buffer (20 mM HEPES-HCl, pH 7.5, 10 mM MgCl$_2$, 1 mM EGTA, 0.02% Brij35, 0.1 mM Na$_3$VO$_4$, 0.02 mg/ml BSA, 2 mM DTT, and 1% DMSO), and then 5 nL of compound was delivered into PKCε (h) and substrate mixture by acoustic technology using Echo 550 (LabCyte Inc., Sunnyvale, Calif.). The reaction was initiated by the addition of [γ-33P-ATP] into the reaction mixture (final concentration was 10 μM) and stopped after at least 40 min incubation at room temperature. The unreacted free 33P-ATP was washed away before detection.

The intrinsic PKCε antagonist activity of a compound which may be used in the present invention may be determined by these assays. In particular, the compounds of the aforementioned examples, including Tables 1.1, 1.2, 1.3, 2.1 and 2.2 had activity in antagonizing the PKCε in the aforementioned assays, generally with an IC$_{50}$ of less than 25 μM. Preferred compounds within the present invention had activity in antagonizing the PKCε in the aforementioned assays with an IC$_{50}$ of less than 1 μM. Such a result is indicative of the intrinsic activity of the compounds in use as antagonists of PKCε.

Examples of compounds of the present inventions having activity in antagonizing the PKCε in the aforementioned assays with an IC$_{50}$ value of in the range of 0.01 to 1 μM include (ID numbers): #481, #483, 4485, #597, #801, #817, #821, #825, #829, #837, #841, #901, #907, #929, #911, #935 and #949.

The compounds of the present invention have high selectivity in antagonizing the PKCε while they have little to no activity in inhibiting other members of PKC family and PKC-related protein kinases. For example, the IC$_{50}$ values of compound #481 are higher than 20 μM for the following kinases: PKCalpha, PKCbeta1, PKCbeta2, PKCdelta, PKCeta, PKCgamma, PKCiota, PKCmu, PKCtheta, PKCzeta, CDK1/cyclinB, cMET, FYN, MEK1, PDPK1, ROCK1, RSK1, TrkA, Akt1, CAMKIIa_alpha and PKA.

In Vivo Assays

Alcohol Intake in Drink-in-Dark (DID) model (Rhodes J S, et al, *Physiol Behav.* (2005) 84:53-63). Mice are acclimated in animal facility and housed three to four per cage in standard cages until 1 week prior to the start of an experiment when they are transferred to individual housing. Approximately 2 weeks prior to the start of an experiment, the mice are switched to a reverse light/dark schedule such that lights turned on at 2030 h and off at 0830 h. Food (Purina 5001™) is always provided ad libitum. Water is provided ad libitum except when ethanol is substituted for water for 4 h per day.

The animals are divided into 4 groups and given intraperitoneal (i.p.) injections of vehicle, and a test article (TA) at 5, 20 and 50 mg/kg body weight, respectively, starting 3 h after lights off in the animal rooms. Then the water bottles are replaced with 10 ml graduated cylinders fitted with sipper tubes containing 20% (v/v) ethanol in tap water. The ethanol cylinders remain in place for 4 h. The fluid levels are checked every 30 minutes for 4 h. After the 4-h period, the ethanol cylinders are replaced with water bottles. This procedure is repeated 3 times on days at least 2 days apart and each group of mice get a different injection of vehicle, and TA at 5, 20 or 50 mg/kg each time. Similarly, mice are administered with TA by oral gavage and ethanol or water intake is monitored for 4 h.

Rotarod Ataxia. This test measures motor incoordination (ataxia) induced by a test article (TA). The CNS-mediated sedative effects may also be assessed in this rotarod assay. Mice or rats are trained to remain on the rotarod at 14 rpm for 300 sec and each animal is retested for its ability to stay on the rotarod rotating at 14 rpm for 300 sec (baseline). The animal is then administered a single dose of TA, positive control or vehicle by oral gavage (or i.p. injection). Animals are placed back on the rotarod at 15, 30, 45, 60, 75 and 90 minutes after treatment. The latency to fall from the rotarod is recorded for each trial. Each animal is tested twice at each time point. The ataxia effect of the TA at each time point is estimated as follows: ataxia (%)=100×[1−{latency in TA treated animal}/{latency in vehicle group}]. Among all ataxia effects at various time points, the largest one also refers to sedative effect. Alternatively, this test measures incoordination induced by a moderately intoxicating dose of alcohol. After administered with TA, the animal is injected with 1.5 g/kg ethanol i.p. and placed back on the rotarod at 15, 30, 45, 60, 75 and 90 min post-injection. The latency to fall from the rotarod is recorded for each trial.

Loss of the righting reflex (LORR). This test measures the hypnotic response to alcohol or TA. LORR duration is measured by administering ethanol (20% v/v in 0.9% saline) i.p. at 4.0 g/kg. Mice is first injected i.p. with vehicle or with one dose of TA. After 20 min, mice are tested to see if they can still right themselves and if they are able, then 4.0 g/kg ethanol is injected. After ethanol injection, mice are placed on their backs. Loss of the righting reflex is defined as the animal being unable to right itself 3 times within a 30-sec period. The mouse is considered to have recovered the righting reflex when it can right itself 3 times within a 1-min time frame.

Elevated Plus Maze. This test measures anxiety-like behavior by exploiting the innate conflict in rodents between exploration of a novel area and aversion to open areas and height. Mice or rats are examined in a quiet room with normal lighting conditions. The plus maze is elevated 60 cm off the floor, constructed of wood coated with gloss enamel white paint with two open arms and two closed arms extending from a central platform. White tape is placed on the floor to provide traction. The animals are placed on the central platform facing an open arm and allowed to explore the maze for 5 min. They are tracked using Ethovision software (Noldus Information Technology, Leesburg, Va., USA). Animals receive an i.p. injection of vehicle or TA 30 min before testing. The number of open and closed arm entries and the time spent on each arm are determined to calculate the percentage of time spent on the open arms and the percentage of entries into the open arms. Entries into an arm are scored if all four paws of the mice enter the arm. Data for percentage of arm entries, percentage of time spent in the open arm, and the number of closed arm entries are compared for the drug- and vehicle-treated groups using one-way ANOVA with post-hoc Tukey tests. Differences between pairs of mean values are considered significant where $P<0.05$. An increase in the percentage of total time spent in the open arms or in the percentage of entries into the open arms is considered evidence for a decrease in anxiety-like behavior. The number of closed arm entries is examined to control for drug-induced changes in locomotor activity.

Locomotor Activity in Mice. In this series of experiments, the compound of the present invention can be tested to see if it is able to attenuate the locomotor stimulant response to ethanol either given acutely or chronically in female DBA/2J mice (Jackson Laboratory West, Palo Alto, Calif.). Locomotor activity is measured in automated Accuscan activity monitors (Accuscan Instruments Inc., Columbus, Ohio). Mice are housed in each of 2 monitors in a 40×40×30 cm (length×width×height) clear acrylic box during testing. Encompassing chambers provide external sound-attenuation clue to foam lining, and a fan further masks outside noise and provides ventilation. Chambers are illuminated with an 8 W fluorescent light bulb during testing. The activity monitors have 2 sets of 2, evenly spaced photocell beams and detectors located 2 cm above the chamber floor. Beam breaks from the movement of the mice are automatically recorded and translated by Accuscan software into total distance traveled (cm). *Acute Locomotor Activity Procedure*. Mice are moved in their home cages to the procedure room and left undisturbed to acclimate for 45 to 60 minutes prior to testing. Mice are weighed, injected with the pretreatment vehicle or VMD-101 (5, 20, 75 mg/kg, i.p.), and placed individually into holding cages. At the conclusion of the pretreatment interval (30 minutes), each subject is injected with saline or ethanol (2 g/kg, i.p.) and placed into the activity monitor (Holstein et al., *Alcohol Clin Exp Res*. (2009) 33:108-20). Activity is recorded for 30 minutes in 5-minute time bins. At the conclusion of testing, blood samples (50 µl) are collected from the periorbital sinus of ethanol treated mice for the determination of blood ethanol concentration (BEC) using an Analox Alcohol Analyzer (Analox Instruments, Lunenburg, Mass.). *Chronic Locomotor Activity Procedure*. The procedure is the same as acute procedure except the mice are chronically sensitized by daily i.p. injection of EtOH (2.5 g/kg) for 10 days and the test is performed on the $11^{th}$ day (Boehm et al., *Psychopharmacology* (Berl). (2008) 197:191-201).

Chronic Constriction Injury (CCI) Mono-Neuropathic Pain Model in Rats. The CCI model is one of the most commonly used mono-neuropathic pain model firstly described in details by Bennett and Xie (Bennett and Xie, (1988), Pain 33:87-107). It mimics important clinical chronic pain symptoms such as mechanical allodynia and thermal hyperalgesia. This model is established by loosely-ligating the sciatic nerve. In brief, under anesthesia with pentobarbital (40 mg/kg, i.p.), a 1.5-cm incision is made 0.5 cm below the pelvis, and the biceps femoris and the gluteous superficialis (right side) are separated. The left sciatic nerve is exposed and isolated at mid-thigh level by blunt dissection. This nerve is chronically constricted by placing 4 loose ligatures of 5-0 chromic catgut (Ethicon Inc., Somerville, N.J.) with 1-mm spacing being placed around the nerve. After the loose ligation, the skin incision will be closed with silk sutures after the hemostasis. The rats are allowed to recover and placed in a cage with soft bedding for at least 7 days before behavioral testing. Sham controls are subjected to the same surgical procedure except the nerve is not ligated. This procedure results in tactile allodynia in the left hindpaw. Rats are included in the study only if they do not exhibit motor dysfunction (e.g., paw dragging or dropping) and their paw withdrawal threshold (PWT) is below 4.0 g. On day 14 after surgery, each group of rats will be treated with TA at one of four doses, vehicle or positive controls by oral gavage (or i.p. injection), and PWT is determined by calibrated von Frey filaments at various time points: pre-dose, 0.5, 1, 1.5, 2, 3, 4 h post-dose.

von Frey Test for Mechanical (Tactile) Allodynia. Mechanical allodynia is assessed by applying a series of von Frey filaments (2-20 g) (Stoelting, Wood Dale, Ill.) to the mid-plantar surface of the hindpaw. In the test, rats are individually housed in Plexiglas chambers, which are placed on top of a metal mesh floor. Animals are allowed to habituate in the chambers for at least 30 min before the experiment. When the intensity of a tactile stimulus reaches to a level that the animal cannot tolerant for the pain, it moves its paw away from the stimulus. This is registered as paw withdrawal threshold (PWT). The intensity of this particular filament that evokes PWT is recorded as a positive withdrawal. A positive response is at least 3 positive paw-withdrawal responses out of 5 probing trials. Probing is performed only when the paw is in contact with the mesh floor. Each probe is applied to the paw until the filament is bent and kept in such position for 6-8 sec. An up-and-down method is used. In brief, the test starts with a filament in the middle of the series (usually the 8-gm filament), then changes to a higher or lower filament, depending on positive or negative response from the preceding trial. All experiments are conducted in a blinded fashion. TA, positive control, or vehicle are prepared and coded. The coding are blinded to the experimenter.

Plantar Test (Hargreaves Method) for Thermal Hyperalgesia. Amplified responses to thermal painful stimulation (thermal hyperalgesia) is assessed in unrestrained rats. Rats are individually housed in Plexiglas chambers, which are placed on top of a glass surface. Animals are habituated in the chambers for at least 30 min before the testing. Under the glass surface, a small radiant heating device (Ugo Basile, Comerio, Italy) with a stable halogen heating lamp and a timer will be adjusted below the plantar surface of the hindpaw. Turning the lamp on starts to heat the glass under the paw and activates the timer at the same time. When the glass temperature reaches to a level that the animal cannot tolerant, the animal moves its paw aside. This movement is picked up by a photocell built in the device and concurrently the timer is stopped and the lamp is turned off. The time spent, i.e. the paw withdrawal latency (PWL) is recorded. To avoid tissue damage, a cut-off time of 22 sec is preset, regardless of the paw movement. Tests are done on each hindpaw.

Cancer Tests. Cancer Cell lines are from American Type Culture Collection (ATCC, Manassas, Va.) and cultured in MEM supplemented with 5% fetal bovine serum (FBS) and 1% penicillin/streptomycin. WST-1 Proliferation Assay: Cancer cell lines are used for in vitro evaluation of cytotoxicity of TA. Cells are seeded in 96-well flat bottom cell culture plates at a density of $3-4\times10^3$ cells/well with compounds and incubated for 4 days. The rate of cell growth inhibition after treatment with increasing concentrations of the TA is determined by tetrazolium salt (WST-1). WST-1 is added at a final concentration of 10% to each well, and then the plates are incubated at 37° C. for 2-3 hrs. The absorbance of the samples is measured at 450 nm by a spectrophotometer. Concentration of the compounds that inhibited cell growth by 50% ($IC_{50}$) is calculated by comparing absorbance in the vehicle treated cells and the cells treated with the compounds. Cell invasion is determined as described from the cell invasion assay kit (Chemicon International, Temecula, Calif.). Cells are harvested and resuspended in serum-free medium. An aliquot ($1\times10^5$ cells) of the prepared cell suspension is added into the chamber and incubated for 48 hours at 37° C. in a 10% $CO_2$ tissue culture incubator. Noninvading cells are gently removed from the interior of the inserts with a cotton-tipped swab. Invasive cells are stained and quantified by colorimetric reading at 560 nm. Random cell motility is determined as described from the motility assay kit (Cellomics, Pittsburgh, Pa.). Cells are harvested, suspended in serum-free medium, and plated on top of a field of microscopic fluorescent beads. After a 48-hour incubation period, cells are fixed and areas of clearing in the fluorescent bead field corresponding to phagokinetic cell tracks are quantified using NIH ScionImager.

Xenograft tumor models. Mice are housed in microisolator cages and maintained on sterilized chow and water ad libitum in a barrier facility for 1-3 weeks before use. All mice are handled in accordance with the Guide to the Care and Use of Laboratory Animals (National Research Council, 1996). Body weights and tumor size are measured twice weekly and clinical observations are made twice daily. The in vivo human breast cancer xenograft model is established according to published methods (Pan et al., *Cancer Research* 2005, 65, 8366-8371). Mice with well-established tumors (~100 $mm^3$) are then randomly assigned into the vehicle, TA, positive control (PC) and TA plus PC treatment groups and the drug treatment start on day 0. The vehicle group is treated daily with 0.5% CMC-Na and 0.1% Tween 80 (vehicle) and TA group is treated with TA suspended in the vehicle at 25 mg/kg (low dose) or 50 mg/kg (high dose), by oral gavage. PC is given intraperitoneally (i.p.). The tumors are measured for the maximum width (X) and length (Y) and the tumor volumes (V) are calculated using the formula: $V=(X^2Y)/2$.

Therapeutic Uses

In accordance with the present invention, a compound of the present invention, or a salt, prodrug or softdrug, salt of prodrug or softdrug, solvate or hydrate, or physiologically functional derivative thereof, can be used as therapeutics. For example, the compound of the present invention can be formulated into a pharmaceutical composition containing the compound of the present invention, or a salt, prodrug or softdrug, salt of prodrug or softdrug, solvate or hydrate, or physiologically functional derivative thereof and one or more pharmaceutically acceptable vehicle. A therapeutically effective amount of the present compound or a pharmaceutical composition thereof can administered to a patient, preferably a human, suffering from a disease, disorder, symptom or condition associated with irregular activity of PKCε for medical treatment purpose. The disease, disorder, symptom or condition is selected from the group consisting of: acute pain, chronic pain, inflammatory pain, neuropathic pain, diabetic neuropathy, alcoholic polyneuropathy, cancer- or chemotherapy-induced pain, a generalized pain disorder, tonic pain, persistent pain, postoperative pain, chemical-induced pain, drug-induced pain, migraine, anxiety, skeletal muscle spasms, convulsive seizures, alcohol abuse and alcoholism associated diseases, insomnia, pain associated with alcohol-induced hyperalgesia, type 1 and type 2 diabetes, diabetic complications, hepatic steatosis or liver cirrhosis, bipolar disorder, mania, epilepsy, sleeping disorder, burn, posttraumatic stress disorder, cardiac disorder, smoking, inflammation and immune-mediated disorders (including microbial infection and organ transplantation), insomnia, postoperative pain, cancer (including breast, head and neck, prostate and lung cancer), maladaptive substance use, substance dependence, alcohol use or abuse, substance use or abuse, drug use or abuse, drug-related effect and a combination thereof.

In other embodiments, a compound of the present invention, or a salt, prodrug or softdrug, salt of prodrug or softdrug, solvate or hydrate, or physiologically functional derivative thereof, or a pharmaceutical composition containing the compound of the present invention, or a salt, prodrug or softdrug, salt of prodrug or softdrug, solvate or hydrate, or physiologically functional derivative thereof, is used in the preparation or manufacture of a medicament for use in the treatment of a disease, disorder, symptom or condition mediated by irregular PKCε activity.

In other embodiments, the compound of the present invention having structural formula (Ia), (Ic), (Ii), (Ih), (II), (IIa) or (IIb) inhibits PKCε with an $IC_{50}$ value of less than 1 μM.

In other embodiments, the compound of the present invention having structural formula (Ia), (Ic), (Ii), (Ih), (II), (IIa) or (IIb) inhibits PKCε selectively.

In other embodiments, the compound of the present invention having structural formula (Ia), (Ic), (Ii), (Ih), (II), (IIa) or (IIb) inhibits PKCε reversibly.

In other embodiments, the compound of the present invention having structural formula (Ia), (Ic), (Ii), (Ih), (II), (IIa) or (IIb) inhibits PKCε non-competitively with ATP.

In other embodiments, the compound of the present invention having structural formula (Ia), (Ic), (Ii), (Ih), (II), (IIa) or (IIb) increases sensitivity of $GABA_A$ receptors to positive allosteric modulators.

In other embodiments, the compound of the present invention having structural formula (Ia), (Ic), (Ii), (Ih), (II), (IIa) or (IIb) reduces alcohol self-administration.

In other embodiments, the compound of the present invention having structural formula (Ia), (Ic), (Ii), (Ih), (II), (IIa) or (IIb) reduces PKCε-dependent nociceptor sensitization.

In other embodiments, the compound of the present invention having structural formula (Ia), (Ic), (Ii), (II), (IIa) or (IIb) reduces hyperalgesia in alcoholic polyneuropathy.

In other embodiments, the present invention provides a kit comprising (a) a compound of the present invention having a structural formula (Ia), (Ic), (II), (Ih), (II), (IIa) or (IIb), and (b) instructions for treating carrying out the disease, disorder; symptom or condition, examples of which are selected from the group consisting of: acute pain, chronic pain, inflammatory pain, neuropathic pain, diabetic neuropathy, alcoholic polyneuropathy, cancer- or chemotherapy-induced pain, a generalized pain disorder, tonic pain, persistent pain, postoperative pain, chemical-induced pain, drug-induced pain, migraine, anxiety, skeletal muscle spasms, convulsive seizures, epilepsy, alcohol abuse and alcoholism associated disease, insomnia, pain associated with alcohol-induced hyperalgesia, type 1 and type 2 diabetes, hepatic steatosis or liver cirrhosis, bipolar disorder, mania, sleeping disorder, burn, posttraumatic stress disorder, cardiac disorder, smoking, inflammation and immune-mediated disorders, cancer, maladaptive substance use, substance dependence, alcohol use or abuse, substance use or abuse, drug use or abuse, drug-related effect and a combination thereof.

Therapeutic/Prophylactic Administration

The present compounds, or salts, prodrugs or softdrugs, salts of prodrugs or softdrugs, solvates or hydrates, or physiologically functional derivatives thereof, or pharmaceutical compositions containing the present compounds, or salts, prodrugs or softdrugs, salts of prodrugs or softdrugs, solvates or hydrates, or physiologically functional derivatives thereof, may be advantageously used in human medicine. As previously described in Section 6.5 above, the present compounds are useful for the treatment or prevention of various diseases.

When used to treat or prevent the above-mentioned diseases or disorders, the present compounds may be administered or applied solely, or in combination with other active agents (e.g., other pain agents, or other anticancer drugs).

The present invention provides methods of treatment and prophylaxis by administration to a patient in need of such treatment a therapeutically effective amount of one or more compounds of the present invention, or salts, prodrugs or softdrugs, salts of prodrugs or softdrugs, solvates or hydrates, or physiologically functional derivatives thereof. The patient may be an animal, more preferably, a mammal and most preferably, a human.

The present compounds, or salts, prodrugs or softdrugs, salts of prodrugs or softdrugs, solvates or hydrates, or physiologically functional derivatives thereof, may be administered orally. The present compounds, or salts, prodrugs or softdrugs, salts of prodrugs or softdrugs, solvates or hydrates, or physiologically functional derivatives thereof, may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or pharmaceutical composition thereof. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner and will depend in-part upon the site of the medical condition. In most instances, administration will result in the release of the present compounds, or salts, prodrugs or softdrugs, salts of prodrugs or softdrugs, solvates or hydrates, or physiologically functional derivatives thereof, into the bloodstream of a patient.

In specific embodiments, it may be desirable to administer one or more of the present compounds, or salts, prodrugs or softdrugs, salts of prodrugs or softdrugs, solvates or hydrates, or physiologically functional derivatives thereof, locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In some embodiments, administration can be accomplished by direct injection at the site (or former site) of cancer or arthritis.

In certain embodiments, it may be desirable to introduce one or more of the present compounds, or salts, prodrugs or softdrugs, salts of prodrugs or softdrugs, solvates or hydrates, or physiologically functional derivatives thereof, into the central nervous system of a patient by any suitable route, including intraventricular, intrathecal and epidural injection. Intraventricular injection may be facilitated by an intraventricular catheter, for example, attached to a reservoir, such as an Ommaya reservoir.

The present compounds, or salts, prodrugs or softdrugs, salts of prodrugs or softdrugs, solvates or hydrates, or physiologically functional derivatives thereof, may also be administered directly to the lung by inhalation. For administration by inhalation, the present compounds, or salts, prodrugs or softdrugs, salts of prodrugs or softdrugs, solvates or hydrates, or physiologically functional derivatives thereof, may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide or any other suitable gas), may be used to deliver compounds of the invention directly to the lung.

Alternatively, a Dry Powder Inhaler ("DPI") device may be used to administer the present compounds, or salts, prodrugs or softdrugs, salts of prodrugs or softdrugs, solvates or hydrates, or physiologically functional derivatives thereof, to the lung. DPI devices typically use a mechanism such as a burst of gas to create a cloud of dry powder inside a container, which may then be inhaled by the patient. DPI devices are also well known in the art. A popular variation is the multiple dose DPI ("MDDPI") system, which allows for the delivery of more than one therapeutic dose. For example, capsules and cartridges of gelatin for use in an inhaler or insufflator may be formulated containing a powder mix of a compound of the invention and a suitable powder base such as lactose or starch for these systems.

Another type of device that may be used to deliver the present compounds, or salts, prodrugs or softdrugs, salts of prodrugs or softdrugs, solvates or hydrates, or physiologically functional derivatives thereof, to the lung is a liquid spray device supplied, for example, by Aradigm Corporation, Hayward, Calif. Liquid spray systems use extremely small nozzle holes to aerosolize liquid drug formulations that may then be directly inhaled into the lung.

In some embodiments, a nebulizer is used to deliver the present compounds, or salts, prodrugs or softdrugs, salts of prodrugs or softdrugs, solvates or hydrates, or physiologically functional derivatives thereof, to the lung. Nebulizers create aerosols from liquid drug formulations by using, for example, ultrasonic energy to form fine particles that may be readily inhaled (see e.g., Verschoyle et al.; *British J. Cancer,* 1999, 80, Suppl. 2, 96. Nebulizers are available from a number of commercial sources such as Sheffield/Systemic Pulmonary Delivery Ltd. Aventis and Batelle Pulmonary Therapeutics.

In other embodiments, an electrohydrodynamic ("EHD") aerosol device is used to deliver the present compounds, or salts, prodrugs or softdrugs, salts of prodrugs or softdrugs, solvates or hydrates, or physiologically functional derivatives thereof, to the lung. EHD aerosol devices use electrical energy to aerosolize liquid drug solutions or suspensions (see e.g., Noakes et al., U.S. Pat. No. 4,765,539). The electrochemical properties of the formulation may be important parameters to optimize when delivering the present compounds, or salts, prodrugs or softdrugs, salts of prodrugs or softdrugs, solvates or hydrates, or physiologically functional derivatives thereof, to the lung with an EHD aerosol device and such optimization is routinely performed by one of skill in the art. EHD aerosol devices may more efficiently deliver drugs to the lung than existing pulmonary delivery technologies.

In other embodiments, the present compounds, or salts, prodrugs or softdrugs, salts of prodrugs or softdrugs, solvates or hydrates, or physiologically functional derivatives thereof, can be delivered in a vesicle, in particular a liposome (See, Langer, 1990, *Science,* 249:1527-1533; Treat et al., in "Liposomes in the Therapy of Infectious Disease and Cancer," Lopez-Berestein and Fidler (eds.), Liss, New York, pp. 353-365 (1989); see generally "Liposomes in the Therapy of Infectious Disease and Cancer," Lopez-Berestein and Fidler (eds.), Liss, New York, pp. 353-365 (1989)).

In other embodiments, the present compounds, or salts, prodrugs or softdrugs, salts of prodrugs or softdrugs, solvates or hydrates, or physiologically functional derivatives thereof, can be delivered via sustained release systems. In still other embodiments, the sustained release system is an oral sustained release systems. In still other embodiments, a pump may be used (See, Langer, supra; Sefton, 1987, *CRC Crit Ref Biomed Eng.* 14:201; Saudek et al., 1989, *N. Engl. J. Med.* 321:574).

In still other embodiments, polymeric materials can be used in the pharmaceutical compositions containing the present compounds, or salts, prodrugs or softdrugs, salts of prodrugs or softdrugs, solvates or hydrates, or physiologically functional derivatives thereof. (for exemplary polymeric materials, see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Ranger and Peppas, 1983, *J Macromol. Sci. Rev. Macromol Chem.* 23:61; see also Levy et al., 1985, *Science* 228: 190; During et al., 1989, *Ann. Neurol.* 25:351; Howard et al., 1989, *J. Neurosurg.* 71:105). In still other embodiments, polymeric materials are used for sustained release delivery of oral pharmaceutical compositions. Exemplary polymers include, but are not limited to, sodium carboxymethylcellulose, hydroxypropylcellulose, hydroxypropylmethylcellulose and hydroxyethylcellulose (most preferred, hydroxypropyl methylcellulose). Other cellulose ethers have been described (Alderman, *Int. J. Pharm. Tech. & Prod. Mfr.,* 1984, 5(3) 1-9). Factors affecting drug release are well known to the skilled artisan and have been described in the art (Bamba et al., *Int. J. Pharm.,* 1979, 2, 307).

In other embodiments, enteric-coated preparations can be used for oral sustained release administration. Coating materials include, but are not limited to, polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still other embodiments, osmotic delivery systems are used for oral sustained release administration (Verma et al., *Drug Dev. Ind. Pharm.,* 2000, 26:695-708). In still other embodiments, OROS™ osmotic devices are used for oral sustained release delivery devices (Theeuwes et al., U.S. Pat. No. 3,845,770; Theeuwes et al., U.S. Pat. No. 3,916,899).

In still other embodiments, a controlled-release system can be placed in proximity of the target of the present compounds, or salts, prodrugs or softdrugs, salts of prodrugs or softdrugs, solvates or hydrates, or physiologically functional derivatives thereof, thus requiring only a fraction of the systemic dose (See, e.g., Goodson, in "Medical Applications of Controlled Release," supra, vol. 2, pp. 115-138 (1984)). Other controlled-release systems discussed in Langer, 1990, *Science* 249:1527-1533 may also be used.

Pharmaceutical Compositions of the Invention

In one aspect, the present invention provides pharmaceutical compositions comprising one or more compounds of the present invention including the compound having structural formula (Ia), (Ic), (Ii), (Ih), or (II) and any of their subgeneric groups and specific embodiments described above in Section 6.2.

The present pharmaceutical compositions contain a therapeutically effective amount of one or more compounds of the present invention, or salts, prodrugs or softdrugs, salts of prodrugs or softdrugs, solvates or hydrates, or physiologically functional derivatives thereof, preferably in purified form, together with a suitable amount of a pharmaceutically acceptable vehicle, so as to provide a form for proper administration to a patient. When administered to a patient, the present compounds and the pharmaceutically acceptable vehicles are preferably sterile. Water is a preferred vehicle when a compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations that can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington: The Science and Practice of Pharmacy, Philadelphia College of Pharmacy and Science, $20^{th}$ Edition, 2000).

For topical administration a compound may be formulated as solutions, gels, ointments, creams, suspensions, etc. as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent such as another anticancer agent.

In some embodiments, the present compounds, or salts, prodrugs or softdrugs, salts of prodrugs or softdrugs, solvates or hydrates, or physiologically functional derivatives thereof, are formulated in accordance with routine procedures as a pharmaceutical composition adapted for intravenous administration to human beings. Typically, compounds for intravenous administration are solutions in sterile isotonic aqueous buffer. For injection, the present compounds, or salts, prodrugs or softdrugs, salts of prodrugs or softdrugs, solvates or hydrates, or physiologically functional derivatives thereof, may be formulated in aqueous solutions, preferably, in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent. Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent.

When the present compounds, or salts, prodrugs or softdrugs, salts of prodrugs or softdrugs, solvates or hydrates, or physiologically functional derivatives thereof, are administered by infusion, it can be dispensed, for example, with an infusion bottle containing sterile pharmaceutical grade water or saline. When the present compounds, or salts, prodrugs or softdrugs, salts of prodrugs or softdrugs, solvates or hydrates, or physiologically functional derivatives thereof, are administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin; flavoring agents such as peppermint, oil of wintergreen, or cherry coloring agents and preserving agents, to provide a pharmaceutically palatable preparation. Moreover, in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM) etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of the invention with a pharmaceutically acceptable vehicle. In some embodiments, the pharmaceutically acceptable vehicle is a liquid such as alcohol, water, polyethylene glycol or a perfluorocarbon. Optionally, another material may be added to alter the aerosol properties of the solution or suspension of compounds disclosed herein. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

The present compounds, or salts, prodrugs or softdrugs, salts of prodrugs or softdrugs, solvates or hydrates, or physiologically functional derivatives thereof, may also be formulated in rectal or vaginal pharmaceutical compositions such as suppositories or retention enemas, e.g., containing conventional suppository bases such as cocoa butter or other glycerides.

In addition to the formulations described previously, the present compounds, or salts, prodrugs or softdrugs, salts of prodrugs or softdrugs, solvates or hydrates, or physiologically functional derivatives thereof, may also be formulated as a depot preparation. Such long acting formulations may be administered by implantation (for example, subcutaneously or intramuscularly) or by intramuscular injection. Thus, for example, the present compounds, or salts, prodrugs or softdrugs, salts of prodrugs or softdrugs, solvates or hydrates, or physiologically functional derivatives thereof, may be formulated with suitable polymeric or hydrophobic materials (for example, as an emulsion in an acceptable oil) or ion exchange resins, or as sparingly soluble derivatives, for example, as a sparingly soluble salt.

Therapeutic Doses

The present compounds, or a salt, prodrug or softdrug, salt of prodrug or softdrug, solvate or hydrate, or physiologically functional derivative thereof and a pharmaceutically acceptable vehicle provided, will generally be used in an amount effective to achieve the intended purpose. For use to treat or prevent diseases or disorders the compounds and/or pharmaceutical compositions thereof, are administered or applied in a therapeutically effective amount.

The amount of the present compounds, or salts, prodrugs or softdrugs, salts of prodrugs or softdrugs, solvates or hydrates, or physiologically functional derivatives thereof, that will be effective in the treatment of a particular disorder or condition disclosed herein will depend on the nature of the disorder or condition, and can be determined by standard clinical techniques known in the art. In addition, in vitro or in vivo assays may optionally be employed to help identify optimal dosage ranges. The amount of the present compounds, or salts, prodrugs or softdrugs, salts of prodrugs or softdrugs, solvates or hydrates, or physiologically functional derivatives thereof, administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In some embodiment, the present compounds, or salts, prodrugs or softdrugs, salts of prodrugs or softdrugs, solvates or hydrates, or physiologically functional derivatives thereof, are delivered by oral sustained release administration. Dosing may be repeated intermittently, may be provided alone or in combination with other drugs and may continue as long as required for effective treatment of the disease state or disorder.

Suitable dosage ranges for oral administration depend on the potency of the present compounds, but are generally between about 0.001 mg to about 200 mg of a compound of the invention per kilogram body weight. Dosage ranges may be readily determined by methods known to the artisan of ordinary skill.

Suitable dosage ranges for intravenous (i.v.) administration are about 0.01 mg to about 100 mg per kilogram body weight. Suitable dosage ranges for intranasal administration are generally about 0.01 mg/kg body weight to about 1 mg/kg body weight. Suppositories generally contain about 0.01 milligram to about 50 milligrams of a compound of the invention per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems. Such animal models and systems are well-known in the art.

The present compounds, or salts, prodrugs or softdrugs, salts of prodrugs or softdrugs, solvates or hydrates, or physiologically functional derivatives thereof, are preferably assayed in vitro and in vivo, for the desired therapeutic or prophylactic activity, prior to use in humans. The present compounds, or salts, prodrugs or softdrugs, salts of prodrugs or softdrugs, solvates or hydrates, or physiologically functional derivatives thereof, may also be demonstrated to be effective and safe using animal model systems.

Preferably, a therapeutically effective dose of the present compounds, or salts, prodrugs or softdrugs, salts of prodrugs or softdrugs, solvates or hydrates, or physiologically functional derivatives thereof, will provide therapeutic benefit without causing substantial toxicity. Toxicity of the present compounds, or salts, prodrugs or softdrugs, salts of prodrugs or softdrugs, solvates or hydrates, or physiologically functional derivatives thereof, may be determined using standard pharmaceutical procedures and may be readily ascertained by the skilled artisan. The dose ratio between toxic and therapeutic effect is the therapeutic index. The present compounds, or salts, prodrugs or softdrugs, salts of prodrugs or softdrugs, solvates or hydrates, or physiologically functional derivatives thereof, generally exhibit particularly high therapeutic indices in treating disease and disorders. The dosage of the present compounds, or salts, prodrugs or softdrugs, salts of prodrugs or softdrugs, solvates or hydrates, or physiologically functional derivatives thereof, will preferably be within a range of circulating concentrations that include an effective dose with little or no toxicity.

Combination Therapy

In certain embodiments of the present invention, the present compounds, or salts, prodrugs or softdrugs, salts of prodrugs or softdrugs, solvates or hydrates, or physiologically functional derivatives thereof, can be used in combination therapy with at least one additional active or therapeutic agent. The present compounds, or salts, prodrugs or softdrugs, salts of prodrugs or softdrugs, solvates or hydrates, or physiologically functional derivatives thereof, and the at least one additional active or therapeutic agent can act additively or, more preferably, synergistically. In some embodiments, the present compounds, or salts, prodrugs or softdrugs, salts of prodrugs or softdrugs, solvates or hydrates, or physiologically functional derivatives thereof are administered concurrently, sequentially, or separately with the administration of another therapeutic agent. Exemplary active agents include, but are not limited to, aceglatone, aclarubicin, altretamine, aminoglutethimide; 5-aminogleavulinic acid, amsacrine, anastrozole, ancitabine hydrochloride, 17-1a antibody, anti-lymphocyte immunoglobulins, antineoplaston a10, asparaginase, pegaspargase, azacitidine, azathioprine, batimastat, benzoporphyrin derivative, bicalutamide, bisantrene hydrochloride, bleomycin sulphate, brequinar sodium, broxuridine, busulphan, campath-ih, caracemide, carbetimer, carboplatin, carboquone, carmofur, carmustine, chlorambucil, chlorozotocin, chromomyein, cisplatin, cladribine, *corynebacterium parvum*, cyclophosphamide, cyclosporin, cytarabine, dacarbazine, dactinomycin, daunorubicin hydrochloride, decitabine, diaziquone, dichlorodiethylsulphide, didemnin b, docetaxel, doxifluridine, doxorubicin hychloride, droloxifene, echinomycin, edatrexate, elliptinium, elmustine, enloplatin, enocitabine, epirubicin hydrochloride, estrainustine sodium phosphate, etanidazole, ethoglucid, etoposide, fadrozole hydrochloride, fazarabine, fenretinide, floxuridine, iludarabine phosphate, fluorouracil, flutamide, formestane, fotemustine, gallium nitrate, gencitabine, gusperimus, homoharringtonine, hydroxyurea, idarubicin hydrochloride, ifosfamide, ilmofosine, improsulfan tosylate, inolimomab, interleukin-2; irinotecan, jm-216, letrozole, lithium gamolenate, lobaplatin, lomustine, lonidamine, mafosfamide, merphalan, menogaril, mercaptopurine, methotrexate, methotrexate sodium, miboplatin, miltefosine, misonidazole, mitobronitol, mitoguazone dihydrochloride, mitolactol, mitomycin, mitotane, mitozanetronc hydrochloride, mizoribine, mopidamol, muitlaichilpeptide, muromonab-cd3, mustine hydrochloride, mycophenolic acid, mycophenolate mofetil, nedaplatin, nilutamide, nimustine hydrochloride, oxaliplatin, paclitaxel, pcnu, penostatin, peplomycin sulphate, pipobroman, pirarubicin, piritrexim isethionate, piroxantrone hydrochloride, plicamycin, porfimer sodium, prednimustine, procarbazine hydrochloride, raltitrexed, ranimustine, razoxane, rogletimide, roquinimex, sebriplatin, semustine, sirolimus, sizofuran, sobuzoxane, sodium bromebrate, sparfosic acid, sparfosate sodium, sreptozocin, sulofenur, tacrolimus, tamoxifen, tegafur, teloxantrone hydrochloride, temozolomide, teniposide, testolactone, tetrasodium mesotetraphenylporphine-sulphonate, thioguanine, thioinosine, thiotepa, topotecan, toremifene, treosulfan, trimetrexate, trofosfamide, tumor necrosis factor, ubeniinex, uramustine, vinblastine sulphate, vincristine sulphate, vindesine sulphate, vinorelbine tartrate, vorozole, zinostatin, zolimomab aritox, and zorubicin hydrochloride, and the like, either individually or in any combination, an inhibitor of protein kinase A (PKA), an inhibitor of cAMP signaling, a nonsteroidal anti-inflammatory drug, a prostaglandin synthesis inhibitor, a local anesthetic, an anticonvulsant, an antidepressant, an opioid receptor agonist, and a neuroleptic, an agonist of $GABA_A$ receptor (e.g. alprazolam, chlordiazepoxide, chlordiazepoxide hydrochloride, chlormezanone, clobazam, clonazepam, clorazepate clipotassium, diazepam, droperidol, estazolam, fentanyl citrate, flurazepam hydrochloride, halazepam, lorazepam, midazolam hydrochloride, oxazepam, prazepam, quazepam, temazepam, triazolam, amobarbital, amobarbital sodium, aprobarbital, butabarbital sodium, hexobarbital sodium, mephobarbital, metharbital, methohexital sodium, pentobarbital, pentobarbital sodium, phenobarbital, phenobarbital sodium, secobarbital, secobarbital sodium, talbutal, thiamylal sodium, thiopental sodium, ganaxalone, alphaxalone and isoflurane), a benzodiazepine, a barbiturate, a neurosteroid and a inhalation anesthetic, a anesthetic, an anti-cancer drug, and another pain killer.

All publications and patent applications herein are incorporated by reference to the same extent as if each individual publication or patent application was specifically and individually indicated to be incorporated by reference. The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

I claim:
1. A compound having a structural formula (IIa):

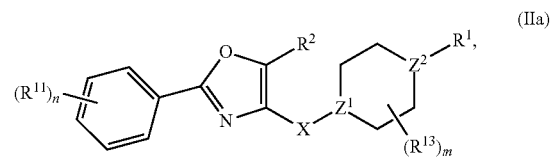

or a salt, solvate, ester or prodrug thereof,
wherein:
$R^1$ is $-C(O)NR^5R^6$;
$R^2$ is hydrogen, $C_{1-6}$alkyl, or substituted $C_{1-6}$ alkyl;
$-NR^5R^6$ is derived from a group consisted of 3-(Azepan-1-yl)propan-1-amine (Cpd A),

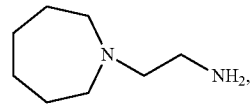
A1

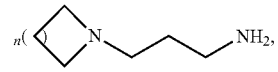
A3

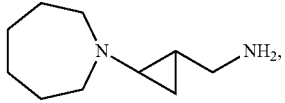
A4

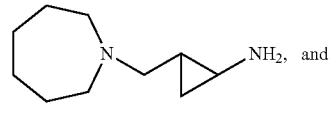
A5

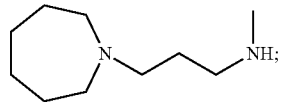
A5

(n is 1, 2, or 3)

X is $-CH_2-$;
$Z^1$ is N;
$Z^2$ is $CR^{12}$ or N;
$R^{12}$ is hydrogen, alkyl, or substituted alkyl;
n is an integer from 0 to 2;
m is 0; and
each $R^{11}$ is independently selected from the group consisting of halogen, $C_{1-6}$ acyl, substituted $C_{1-6}$ acyl, $C_{1-6}$ alkoxycarbonyl, substituted $C_{1-6}$ alkoxycarbonyl, $C_{6-10}$ aryloxycarbonyl, substituted $C_{6-10}$ aryloxycarbonyl, $-C(O)NR^5R^6$, $C_{2-6}$ alkyl, substituted $C_{2-6}$ alkyl, $C_{6-10}$ aryl, substituted $C_{6-10}$ aryl, $C_{6-20}$ arylalkyl, substituted $C_{6-20}$ arylalkyl, $C_{3-7}$ cycloheteroalkyl, substituted $C_{3-7}$ cycloheteroalkyl, $C_{6-10}$ heteroaryl, substituted $C_{6-10}$ heteroaryl, $C_{6-20}$ heteroarylalkyl, substituted $C_{6-20}$ heteroarylalkyl, $C_{1-6}$ heteroalkyl, and substituted $C_{1-6}$ heteroalkyl; wherein $R^5$ and $R^6$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl, or alternatively, $R^5$ and $R^6$, taken together with the nitrogen atom to which they are attached, form a 4-, 5-, 6-, or 7-membered cycloheteroalkyl ring.

2. The compound of claim 1, which is selected from the group consisting of

| ID  | IUPAC Name |
|-----|------------|
| 949 | N-[3-(azepan-1-yl)propyl]-1-{[2-(1,3-benzodioxol-5-yl)-5-methyl-1,3-oxazol-4-yl]methyl}piperidine-4-carboxamide; |
| 951 | N-[3-(azepan-1-yl)propyl]-1-{[2-(2,4-dimethoxyphenyl)-5-methyl-1,3-oxazol-4-yl]methyl}piperidine-4-carboxamide; |
| 953 | N-[3-(azepan-1-yl)propyl]-1-{[2-(4-benzylphenyl)-5-methyl-1,3-oxazol-4-yl]methyl}piperidine-4-carboxamide; |
| 955 | N-[3-(azepan-1-yl)propyl]-1-({2-[4-(dimethylcarbamoyl)phenyl]-5-methyl-1,3-oxazol-4-yl}methyl)piperidine-4-carboxamide; |
| 957 | N-[3-(azepan-1-yl)propyl]-1-({5-methyl-2-[4-(piperidin-1-yl)phenyl]-1,3-oxazol-4-yl}methyl)piperidine-4-carboxamide; and |
| 959 | N-[3-(azepan-1-yl)propyl]-1-{[5-methyl-2-(naphthalen-1-yl)-1,3-oxazol-4-yl]methyl}piperidine-4-carboxamide; | or a salt, solvate, ester or prodrug thereof.

3. A pharmaceutical composition comprising a therapeutically effective amount of a compound, or a salt, solvate, ester or prodrug thereof; and at least one pharmaceutically acceptable vehicle; wherein the compound is selected from the group consisting of

| ID  | IUPAC Name |
|-----|------------|
| 505 | 1-{[2-(4-chlorophenyl)-5-methyl-1,3-oxazol-4-yl]methyl}-N-[3-(3-methylpiperidin-1-yl)propyl]piperidine-4-carboxamide; |
| 507 | 1-{[2-(4-chlorophenyl)-5-methy-1,3-oxazol-4-yl]methyl}-N-[3-(2-ethylpiperidin-1-yl)propyl]piperidine-4-carboxamide; |
| 509 | 1-{[2-(4-chlorophenyl)-5-methyl-1,3-oxazol-4-yl]methyl}-N-[2-(2-methylpiperidin-1-yl)ethyl]piperidine-4-carboxamide; |
| 511 | 1-{[2-(4-chlorophenyl)-5-methyl-1,3-oxazol-4-yl]methyl}-N-{2-[ethyl(phenyl)amino]ethyl}piperidine-4-carboxamide; |
| 513 | 1-{[2-(4-chlorophenyl)-5-methyl-1,3-oxazol-4-yl]methyl}-N-{3-[methyl(phenyl)amino]propyl}piperidine-4-carboxamide; |
| 515 | 1-{[2-(3-chlorophenyl)-5-methyl-1,3-oxazol-4-yl]methyl}-N-{2-[ethyl(phenyl)amino]ethyl}piperidine-4-carboxamide; |
| 517 | 1-{[2-(4-chlorophenyl)-5-methyl-1,3-oxazol-4-yl]methyl}-N-{2-[ethyl(phenyl)amino]ethyl}piperidine-3-carboxamide; |
| 519 | 1-{[2-(3-chlorophenyl)-5-methyl-1,3-oxazol-4-yl]methyl}-N-{2-[ethyl(phenyl)amino]ethyl}piperidine-3-carboxamide; |
| 521 | 1-{[2-(3-chlorophenyl)-5-methyl-1,3-oxazol-4-yl]methyl}-N-{3-[methyl(phenyl)amino]propyl}piperidine-3-carboxamide; |
| 523 | 4-{5-methyl-4-[(phenylsulfanyl)methyl]-1,3-oxazol-2-yl}-N-[3-(4-methylpiperazin-1-yl)propyl]benzamide; |
| 525 | N-{3-[benzyl(methyl)amino]propyl}-1-{[2-(4-chlorophenyl)-5-methyl-1,3-oxazol-4-yl]methyl}piperidine-4-carboxamide; |
| 527 | 1-{[2-(4-chlorophenyl)-5-methyl-1,3-oxazol-4-yl]methyl}-N-[3-(3,5-dimethylpiperidin-1-yl)propyl]piperidine-4-carboxamide; |
| 529 | 1-{[2-(4-chlorophenyl)-5-methyl-1,3-oxazol-4-yl]methyl}-N-{2-[methyl(2-phenylethyl)amino]ethyl}piperidine-4-carboxamide; |
| 531 | 1-{[5-methyl-2-(2-methylphenyl)-1,3-oxazol-4-yl]methyl}-N-[3-(3-methylpiperidin-1-yl)propyl]piperidine-4-carboxamide; |
| 533 | 1-{[2-(3-chlorophenyl)-5-methyl-1,3-oxazol-4-yl]methyl}-N-[3-(3,5-dimethylpiperidin-1-yl)propyl]piperidine-4-carboxamide; |
| 535 | 1-{[2-(3-chlorophenyl)-5-methyl-1,3-oxazol-4-yl]methyl}-N-[3-(cyclohexylsulfanyl)propyl]piperidine-4-carboxamide; |
| 537 | N-{2-[ethyl(phenyl)amino]ethyl}-1-{[2-(2-fluorophenyl)-5-methyl-1,3-oxazol-4-yl]methyl}piperidine-4-carboxamide; |
| 539 | 1-{[2-(3-chlorophenyl)-5-methyl-1,3-oxazol-4-yl]methyl}-N-{2-[methyl(2-phenylethyl)amino]ethyl}piperidine-3-carboxamide; |
| 541 | 1-{[5-methyl-2-(3-methylphenyl)-1,3-oxazol-4-yl]methyl}-N-[2-(4-methylpiperidin-1-yl)ethyl]piperidine-4-carboxamide; |
| 543 | N-[2-(4-ethylpiperazin-1-yl)ethyl]-4-{5-methyl-4-[(phenylsulfanyl)methyl]-1,3-oxazol-2-yl}benzamide; |

-continued

| ID | IUPAC Name |
|---|---|
| 545 | 1-{[2-(4-chlorophenyl)-5-methyl-1,3-oxazol-4-yl]methyl}-N-[2-(4-ethylpiperazin-1-yl)ethyl]piperidine-4-carboxamide; |
| 547 | 1-{[2-(3-chlorophenyl)-5-methyl-1,3-oxazol-4-yl]methyl}-N-[3-(4-methylpiperazin-1-yl)propyl]piperidine-4-carboxamide; |
| 549 | 1-{[2-(4-chlorophenyl)-5-methyl-1,3-oxazol-4-yl]methyl}-N-[3-(4-methylpiperazin-1-yl)propyl]piperidine-3-carboxamide; |
| 551 | 1-{[2-(3-chlorophenyl)-5-methyl-1,3-oxazol-4-yl]methyl}-N-[2-(4-ethylpiperazin-1-yl)ethyl]piperidine-3-carboxamide; |
| 553 | 1-{[2-(4-chlorophenyl)-5-methyl-1,3-oxazol-4-yl]methyl}-N-(3-pyrrolidin-1-ylpropyl)piperidine-4-carboxamide; |
| 555 | 1-{[2-(3-chlorophenyl)-5-methyl-1,3-oxazol-4-yl]methyl}-N-(3-pyrrolidin-1-ylpropyl)piperidine-4-carboxamide; |
| 557 | 1-{[2-(3-chlorophenyl)-5-methyl-1,3-oxazol-4-yl]methyl}-N-(3-pyrrolidin-1-ylpropyl)piperidine-3-carboxamide; |
| 559 | 1-{[5-methyl-2-(2-methylphenyl)-1,3-oxazol-4-yl]methyl}-N-{3-[methyl(phenyl)amino]propyl}piperidine-4-carboxamide; |
| 561 | 1-{[2-(3-bromophenyl)-5-methyl-1,3-oxazol-4-yl]methyl}-N-[3-(cyclohexylsulfanyl)propyl]piperidine-4-carboxamide; |
| 563 | 4-(5-methyl-4-{[(4-methylphenyl)sulfanyl]methyl}-1,3-oxazol-2-yl)-N-[3-(4-methylpiperazin-1-yl)propyl]benzamide; |
| 565 | 4-{5-methyl-4-[(phenylsulfanyl)methyl]-1,3-oxazol-2-yl}-N-[3-(4-propylpiperazin-1-yl)propyl]benzamide; |
| 567 | 1-{[5-methyl-2-(4-propoxyphenyl)-1,3-oxazol-4-yl]methyl}-N-(pyridin-3-ylmethyl)piperidine-4-carboxamide; |
| 569 | N-(2-azepan-1-ylethyl)-4-(5-methyl-4-{[(4-methylphenyl)sulfanyl]methyl}-1,3-oxazol-2-yl)benzamide; |
| 571 | 4-(5-methyl-4-{[(4-methylphenyl)sulfanyl]methyl}-1,3-oxazol-2-yl)-N-[2-(4-methylpiperazin-1-yl)ethyl]benzamide; |
| 573 | N-(2-azepan-1-ylethyl)-4-{5-methyl-4-[(phenylsulfanyl)methyl]-1,3-oxazol-2-yl}benzamide |
| 575 | 1-{[2-(4-chlorophenyl)-5-methyl-1,3-oxazol-4-yl]methyl}-N-{3-[ethyl(3-methylphenyl)amino]propyl}piperidine-4-carboxamide; |
| 577 | 1-{[5-methyl-2-(4-propoxyphenyl)-1,3-oxazol-4-yl]methyl}-N-(pyridin-2-ylmethyl)piperidine-4-carboxamide; |
| 579 | N-{3-[cyclohexyl(methyl)amino]propyl}-1-{[5-methyl-2-(2-methylphenyl)-1,3-oxazol-4-yl]methyl}piperidine-4-carboxamide; |
| 581 | N-[2-(4-chlorophenyl)ethyl]-1-{[2-(4-ethylphenyl)-5-methyl-1,3-oxazol-4-yl]methyl}piperidine-4-carboxamide; |
| 583 | N-{2-[ethyl(phenyl)amino]ethyl}-1-{[2-(4-ethylphenyl)-5-methyl-1,3-oxazol-4-yl]methyl}piperidine-4-carboxamide; |
| 585 | N-[3-(cyclohexylsulfanyl)propyl]-1-{[5-methyl-2-(2-methylphenyl)-1,3-oxazol-4-yl]methyl}piperidine-3-carboxamide; |
| 587 | N-[2-(4-chlorophenyl)ethyl]-1-{[2-(4-ethylphenyl)-5-methyl-1,3-oxazol-4-yl]methyl}piperidine-3-carboxamide; |
| 589 | N-[2-(4-benzylpiperazin-1-yl)ethyl]-2-({[5-methyl-2-(4-methylphenyl)-1,3-oxazol-4-yl]methyl}sulfanyl)acetamide; |
| 591 | 4-[5-methyl-4-(phenoxymethyl)-1,3-oxazol-2-yl]-N-[3-(4-methylpiperazin-1-yl)propyl]benzamide; |
| 593 | N-[2-(4-ethylpiperazin-1-yl)ethyl]-4-(5-methyl-4-{[(4-methylphenyl)sulfanyl]methyl}-1,3-oxazol-2-yl)benzamide; |
| 595 | 1-{[2-(4-chlorophenyl)-5-methyl-1,3-oxazol-4-yl]methyl}-N-(pyridin-3-ylmethyl)piperidine-4-carboxamide; |
| 597 | 1-{[2-(4-chlorophenyl)-5-methyl-1,3-oxazol-4-yl]methyl}-N-(2-pyrrolidin-1-ylethyl)piperidine-4-carboxamide; and |
| 599 | 1-{[2-(3-chlorophenyl)-5-methyl-1,3-oxazol-4-yl]methyl}-N-(2-pyrrolidin-1-ylethyl)piperidine-4-carboxamide. |

4. A method of treating a disease, disorder, symptom, or condition associated with irregular PKCε activity in a patient, comprising administering to the patient a therapeutically effective amount of a compound of claim 1, or a salt, solvate, ester or prodrug thereof; wherein the disease, disorder, symptom or condition is selected from the group consisting of acute pain, chronic pain, inflammatory pain, neuropathic pain, diabetic neuropathy, alcoholic polyneuropathy, cancer- or chemotherapy-induced pain, a generalized pain disorder, tonic pain, persistent pain, postoperative pain, chemical-induced pain, drug-induced pain, migraine, anxiety, skeletal muscle spasms, convulsive seizures, epilepsy, alcohol abuse and alcoholism, insomnia, pain associated with alcohol-induced hyperalgesia, type 1 and type 2 diabetes, hepatic steatosis or liver cirrhosis, bipolar disorder, mania, sleeping disorder, burn, posttraumatic stress disorder, cardiac disorder, smoking, or inflammation associated with microbial infection and organ transplantation, immune disorders, cancer or cancer-induced pain wherein the cancer is breast cancer, head and neck cancer, oral cancer, prostate cancer, lung cancer, liver cancer, brain cancer, squamous cell carcinoma, gastrointestinal cancer, gastric cancer, pancreatic cancer, thyroid cancer, neuroblastoma, multiple myeloma, myeloid leukemia, squamous cell carcinoma, glioma, renal cancer, ovarian cancer, colorectal cancer, endometrial cancer, kidney cancer, thyroid cancer, neuroblastoma, stomach cancer, bladder cancer, hepatoma, colon carcinoma, germ cell tumor, sarcoma, acute myelogenous leukemia, lymphocytic leukemia, or a combination thereof, or a disease, disorder, symptom or condition associated with maladaptive substance use, substance dependence, alcohol use or abuse, substance use or abuse, drug use or abuse, or drug-related effect, or a combination thereof.

5. A pharmaceutical composition comprising a therapeutically effective amount of a compound of Formula (IIa):

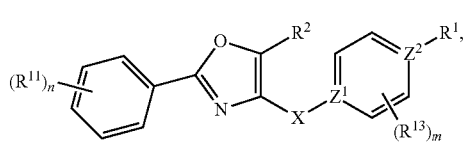

(IIa)

or a salt, solvate, ester or prodrug thereof; and at least one pharmaceutically acceptable vehicle; wherein:
$R^1$ is —C(O)NR$^5$R$^6$;
$R^2$ is hydrogen, $C_{1-6}$ alkyl, or substituted $C_{1-6}$ alkyl;
—NR$^5$R$^6$ is derived from a group consisted of 3-(Azepan-1-yl)propan-1-amine (Cpd A),

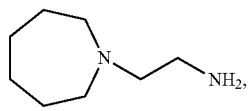 A1

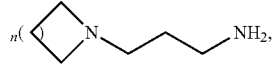 A3

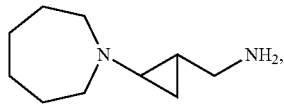 A4

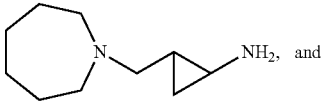 A5

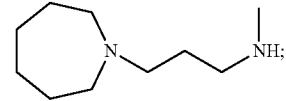 A5

(n is 1, 2, or 3)

X is —CH$_2$—;
Z$^1$ is N;
Z$^2$ is CR$^{12}$ or N;

R$^{12}$ is hydrogen, alkyl, or substituted alkyl;
n is an integer from 0 to 2;
m is 0; and
each R$^{11}$ is independently selected from the group consisting of halogen, $C_{1-6}$ acyl, substituted $C_{1-6}$ acyl, $C_{1-6}$ alkoxycarbonyl, substituted $C_{1-6}$ alkoxycarbonyl, $C_{6-10}$ aryloxycarbonyl, substituted $C_{6-10}$ aryloxycarbonyl, —C(O)NR$^5$R$^6$, $C_{1-6}$ alkyl, substituted $C_{1-6}$ alkyl, $C_{6-10}$ aryl, substituted $C_{6-10}$ aryl, $C_{6-20}$ arylalkyl, substituted $C_{6-20}$ arylalkyl, $C_{3-7}$ cycloheteroalkyl, substituted $C_{3-7}$ cycloheteroalkyl, $C_{6-10}$ heteroaryl, substituted $C_{6-10}$ heteroaryl, $C_{6-20}$ heteroarylalkyl, substituted $C_{6-20}$ heteroarylalkyl, $C_{1-6}$ heteroalkyl, and substituted $C_{1-6}$ heteroalkyl; wherein R$^5$ and R$^6$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl, or alternatively, R$^5$ and R$^6$, taken together with the nitrogen atom to which they are attached, form a 4-, 5-, 6-, or 7-membered cycloheteroalkyl ring.

6. The compound of claim 5, which is selected from the group consisting of

| ID | IUPAC Name |
|---|---|
| 901 | N-[3-(azepan-1-yl)propyl]-1-{[2-(4-chlorophenyl)-5-methyl-1,3-oxazol-4-yl]methyl}piperidine-4-carboxamide; |
| 929 | N-[3-(azepan-1-yl)propyl]-1-{[2-(4-chlorophenyl)-5-methyl-1,3-oxazol-4-yl]methyl}-N-methylpiperidine-4-carboxamide; |
| 933 | N-{[2-(azepan-1-yl)cyclopropyl]methyl}-1-{[2-(4-chlorophenyl)-5-methyl-1,3-oxazol-4-yl]methyl}piperidine-4-carboxamide; |
| 943 | N-[3-(azepan-1-yl)propyl]-1-({5-methyl-2-[4-(trifluoromethyl)phenyl]-1,3-oxazol-4-yl}methyl)piperidine-4-carboxamide; |
| 947 | N-[3-(azepan-1-yl)propyl]-1-{[2-(2,4-difluorophenyl)-5-methyl-1,3-oxazol-4-yl]methyl}piperidine-4-carboxamide; and |
| 503 | N-(2-azepan-1-ylethyl)-1-{[2-(4-chlorophenyl)-5-methyl-1,3-oxazol-4-yl]methyl}piperidine-4-carboxamide. |

7. A pharmaceutical composition of a therapeutically effective amount of a compound which is selected from the group consisting of

| ID | IUPAC Name |
|---|---|
| 903 | 1-{[2-(4-chlorophenyl)-5-methyl-1,3-oxazol-4-yl]methyl}-N-[3-(3,5-dimethylpiperidin-1-yl)propyl]piperidine-4-carboxamide; |
| 905 | 1-{[2-(4-chlorophenyl)-5-methyl-1,3-oxazol-4-yl]methyl}-N-[2-(2-methylpiperidin-1-yl)ethyl]piperidine-4-carboxamide; |
| 907 | N-[3-(4-benzylpiperidin-1-yl)propyl]-1-{[2-(4-chlorophenyl)-5-methyl-1,3-oxazol-4-yl]methyl}piperidine-4-carboxamide; |
| 909 | N-{2-[4-(3-chlorophenyl)piperazin-1-yl]ethyl}-1-{[2-(4-ethylphenyl)-5-methyl-1,3-oxazol-4-yl]methyl}piperidine-4-carboxamide; |
| 911 | N-{3-[4-(3-chlorobenzyl)piperidin-1-yl]propyl}-1-{[2-(3-chlorophenyl)-5-methyl-1,3-oxazol-4-yl]methyl}piperidine-4-carboxamide; |
| 913 | 1-{[2-(3-chlorophenyl)-5-methyl-1,3-oxazol-4-yl]methyl}-N-{3-[4-(4-fluorophenyl)piperazin-1-yl]propyl}piperidine-4-carboxamide; |
| 915 | 1-{[2-(4-chlorophenyl)-5-methyl-1,3-oxazol-4-yl]methyl}-N-{3-[4-(2-fluorophenyl)piperazin-1-yl]propyl}piperidine-3-carboxamide; |
| 919 | N-(2,4-difluorophenyl)-4-{5-methyl-4-[(4-phenylpiperazin-1-yl)methyl]-1,3-oxazol-2-yl}benzamide; |
| 931 | 1-{[2-(4-chlorophenyl)-5-methyl-1,3-oxazol-4-yl]methyl}-N-{3-[4-(pyridin-4-yl)piperidin-1-yl]propyl}piperidine-4-carboxamide; |
| 935 | 1-{[2-(4-chlorophenyl)-5-methyl-1,3-oxazol-4-yl]methyl}-N-[3-(morpholin-4-yl)propyl]piperidine-4-carboxamide; |
| 937 | 1-{[2-(4-chlorophenyl)-5-methyl-1,3-oxazol-4-yl]methyl}-N-[3-(4-cyclohexylpiperazin-1-yl)propyl]piperidine-4-carboxamide; |

-continued

| ID | IUPAC Name |
|---|---|
| 939 | 1-{[2-(4-chlorophenyl)-5-methyl-1,3-oxazol-4-yl]methyl}-N-[3-(piperidin-1-yl)-2-(piperidin-1-ylmethyl)propyl]piperidine-4-carboxamide; |
| 941 | 1-{[2-(4-chlorophenyl)-5-methyl-1,3-oxazol-4-ylmethyl}-N-[3-(1,4-dioxa-8-azaspiro[4.5]dec-8-yl)propyl]piperidine-4-carboxamide; |
| 945 | N-[3-(azepan-1-yl)propyl]-1-{[5-methyl-2-(pyridin-4-yl)-1,3-oxazol-4-yl]methyl}piperidine-4-carboxamide; |
| 961 | 1-{[2-(4-chlorophenyl)-5-methyl-1,3-oxazol-4-yl]methyl}-N-(3-{methyl[4-(morpholin-4-yl)benzyl]amino}propyl)piperidine-4-carboxamide; |
| 963 | 1-{[2-(4-chlorophenyl)-5-methyl-1,3-oxazol-4-yl]methyl}-N-(3-{[(4-methoxyphenyl)carbonyl]amino}propyl)piperidine-4-carboxamide; |
| 965 | 1-{[2-(4-chlorophenyl)-5-methyl-1,3-oxazol-4-yl]methyl}-N-[4-(4-methylpiperazin-1-yl)phenyl]piperidine-4-carboxamide; |
| 967 | N-(1-{[2-(4-chlorophenyl)-5-methyl-1,3-oxazol-4-yl]methyl}piperidine-4-yl)-5-(piperidin-1-yl)pyridin-2-amine; and |
| 969 | 1-{[2-(4-chlorophenyl)-5-methyl-1,3-oxazol-4-yl]methyl}-4-[4-(piperidin-1-yl)phenyl]piperazine. |

8. An oral unit dosage form comprising a therapeutically effective amount of a compound of Formula (IIa):

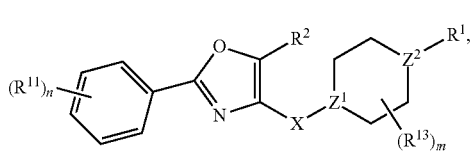

or a salt, solvate, ester or prodrug thereof; and at least one pharmaceutically acceptable vehicle; wherein:

$R^1$ is —C(O)NR$^5$R$^6$;

$R^2$ is hydrogen, $C_{1-6}$ alkyl, or substituted $C_{1-6}$ alkyl;

—NR$^5$R$^6$ is derived from a group consisted of 3-(Azepan-1-yl)propan-1-amine (Cpd A), A1
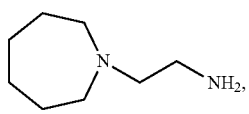

A3
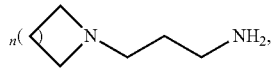

A4
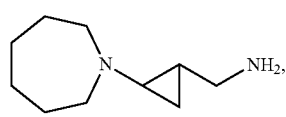

A5
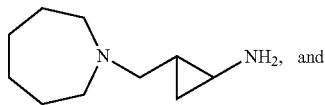 and

A5
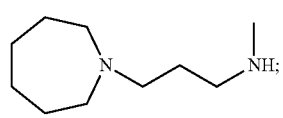

(n is 1, 2, or 3)

X is —CH$_2$—;

$Z^1$ is N;

$Z^2$ is CR$^{12}$ or N;

$R^{12}$ is hydrogen, alkyl, or substituted alkyl;

n is an integer from 0 to 2;

m is 0; and each R$^{11}$ is independently selected from the group consisting of halogen, $C_{1-6}$ acyl, substituted $C_{1-6}$ acyl, $C_{1-6}$ alkoxycarbonyl, substituted $C_{1-6}$ alkoxycarbonyl, $C_{6-10}$ aryloxycarbonyl, substituted $C_{6-10}$ aryloxycarbonyl, —C(O)NR$^5$R$^6$, $C_{1-6}$ alkyl, substituted $C_{1-6}$ alkyl, $C_{6-10}$ aryl, substituted $C_{6-10}$ aryl, $C_{6-20}$ arylalkyl, substituted $C_{6-20}$ arylalkyl, $C_{3-7}$ cycloheteroalkyl, substituted $C_{3-7}$ cycloheteroalkyl, $C_{6-10}$ heteroaryl, substituted $C_{6-10}$ heteroaryl, $C_{6-20}$ heteroarylalkyl, substituted $C_{6-20}$ heteroarylalkyl, $C_{1-6}$ heteroalkyl, and substituted $C_{1-6}$ heteroalkyl; wherein R$^5$ and R$^6$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl, or alternatively, R$^5$ and R$^6$, taken together with the nitrogen atom to which they are attached, form a 4-, 5-, 6-, or 7-membered cycloheteroalkyl ring;

wherein the oral unit dosage form is suitable for administration to a patient in need of about 0.001 mg to about 200 mg of the compound per kilogram body weight; and the patient is an animal; more preferably, a mammal; and most preferably, a human.

9. The oral unit dosage form of claim 8, which is in a form selected from tablets, pills, pellets, capsules, powders, lozenges, granules, solutions, suspensions, emulsion, syrups, elixirs, sustained-release formulations, aerosols, and sprays.

10. The oral unit dosage form of claim 8, which is an oral liquid preparation.

11. The oral unit dosage form of claim 8, which further comprises one or more optional agents selected from sweetening agents, flavoring agents, coloring agents, preserving agents, time delay or delay disintegration materials, standard oral vehicles, suitable carriers, excipients or diluents.

12. The oral unit dosage form of claim 8, wherein the compound is selected from the group consisting of

| ID | IUPAC Name |
|---|---|
| 901 | N-[3-(azepan-1-yl)propyl]-1-{[2-(4-chlorophenyl)-5-methyl-1,3-oxazol-4-yl]methyl}piperidine-4-carboxamide; |
| 929 | N-[3-(azepan-1-yl)propyl]-1-{[2-(4-chlorophenyl)-5-methyl-1,3-oxazol-4-yl]methyl}-N-methylpiperidine-4-carboxamide; |
| 933 | N-{[2-(azepan-1-yl)cyclopropyl]methyl}-1-{[2-(4-chlorophenyl)-5-methyl-1,3-oxazol-4-yl]methyl}piperidine-4-carboxamide; |
| 943 | N-[3-(azepan-1-yl)propyl]-1-({5-methyl-2-[4-(trifluoromethyl)phenyl]-1,3-oxazol-4-yl}methyl)piperidine-4-carboxamide; |
| 947 | N-[3-(azepan-1-yl)propyl]-1-{[2-(2,4-difluorophenyl)-5-methyl-1,3-oxazol-4-yl]methyl}piperidine-4-carboxamide; |
| 949 | N-[3-(azepan-1-yl)propyl]-1-{[2-(1,3-benzodioxol-5-methyl-1,3-oxazol-4-yl]methyl}piperidine-4-carboxamide; |
| 951 | N-[3-(azepan-1-yl)propyl]-1-{[2-(2,4-dimethoxyphenyl)-5-methyl-1,3-oxazol-4-yl]methyl}piperidine-4-carboxamide; |
| 953 | N-[3-(azepan-1-yl)propyl]-1-{[2-(4-benzylphenyl)-5-methyl-1,3-oxazol-4-yl]methyl}piperidine-4-carboxamide; |
| 955 | N-[3-(azepan-1-yl)propyl]-1-({2-4-(dimethylcarbamoyl)phenyl]-5-methyl-1,3-oxazol-4-yl}methyl)piperidine-4-carboxamide; |
| 957 | N-[3-(azepan-1-yl)propyl]-1-({5-methyl-2-[4-(piperidin-1-yl)phenyl]-1,3-oxazol-4-yl}methyl)piperidine-4-carboxamide; |
| 959 | N-[3-(azepan-1-yl)propyl]-1-{[5-methyl-2-(naphthalen-1-yl)-1,3-oxazol-4-yl]methyl}piperidine-4-carboxamide; |
| 503 | N-(2-azepan-1-ylethyl)-1-{[2-(4-chlorophenyl)-5-methyl-1,3-oxazol-4-yl]methyl}piperidine-4-carboxamide; |
| 505 | 1-{[2-(4-chlorophenyl)-5-methyl-1,3-oxazol-4-yl]methyl}-N-[3-(3-methylpiperidin-1-yl)propyl]piperidine-4-carboxamide; |
| 507 | 1-{[2-(4-chlorophenyl)-5-methyl-1,3-oxazol-4-yl]methyl}-N-[3-(2-ethylpiperidin-1-yl)propyl]piperidine-4-carboxamide; |
| 509 | 1-{[2-(4-chlorophenyl)-5-methyl-1,3-oxazol-4-yl]methyl}-N-[2-(2-methylpiperidin-1-yl)ethyl]piperidine-4-carboxamide; |
| 511 | 1-{[2-(4-chlorophenyl)-5-methyl-1,3-oxazol-4-yl]methyl}-N-{2-[ethyl(phenyl)amino]ethyl}piperidine-4-carboxamide; |
| 513 | 1-{[2-(4-chlorophenyl)-5-methyl-1,3-oxazol-4-yl]methyl}-N-{3-[methyl(phenyl)amino]propyl}piperidine-4-carboxamide; |
| 515 | 1-{[2-(3-chlorophenyl)-5-methyl-1,3-oxazol-4-yl]methyl}-N-{2-[ethyl(phenyl)amino]ethyl}piperidine-4-carboxamide; |
| 517 | 1-{[2-(4-chlorophenyl)-5-methyl-1,3-oxazol-4-yl]methyl}-N-{2-[ethyl(phenyl)amino]ethyl}piperidine-3-carboxamide; |
| 519 | 1-{[2-(3-chlorophenyl)-5-methyl-1,3-oxazol-4-yl]methyl}-N-{2-[ethyl(phenyl)amino]ethyl}piperidine-3-carboxamide; |
| 521 | 1-{[2-(3-chlorophenyl)-5-methyl-1,3-oxazol-4-yl]methyl}-N-{3-[methyl(phenyl)amino]propyl}piperidine-3-carboxamide; |
| 523 | 4-{5-methyl-4-[(phenylsulfanyl)methyl]-1,3-oxazol-2-yl}-N-[3-(4-methylpiperazin-1-yl)propyl]benzamide; |
| 525 | N-{3-[benzyl(methyl)amino]propyl}-1-{[2-(4-chlorophenyl)-5-methyl-1,3-oxazol-4-yl]methyl}piperidine-4-carboxamide; |
| 527 | 1-{[2-(4-chlorophenyl)-5-methyl-1,3-oxazol-4-yl]methyl}-N-[3-(3,5-dimethylpiperidin-1-yl)propyl]piperidine-4-carboxamide; |
| 529 | 1-{[2-(4-chlorophenyl)-5-methyl-1,3-oxazol-4-yl]methyl}-N-{2-[methyl(2-phenylethyl)amino]ethyl}piperidine-4-carboxamide; |
| 531 | 1-{[5-methyl-2-(2-methylphenyl)-1,3-oxazol-4-yl]methyl}-N-[3-(3-methylpiperidin-1-yl)propyl]piperidine-4-carboxamide; |
| 533 | 1-{[2-(3-chlorophenyl)-5-methyl-1,3-oxazol-4-yl]methyl}-N-[3-(3,5-dimethylpiperidin-1-yl)propyl]piperidine-4-carboxamide; |
| 535 | 1-{[2-(3-chlorophenyl)-5-methyl-1,3-oxazol-4-yl]methyl}-N-[3-(cyclohexylsulfanyl)propyl]piperidine-4-carboxamide; |
| 537 | N-{2-[ethyl(phenyl)amino]ethyl}-1-{[2-(2-fluorophenyl)-5-methyl-1,3-oxazol-4-yl]methyl}piperidine-4-carboxamide; |
| 539 | 1-{[2-(3-chlorophenyl)-5-methyl-1,3-oxazol-4-yl]methyl}-N-{2-[methyl(2-phenylethyl)amino]ethyl}piperidine-3-carboxamide; |
| 541 | 1-{[5-methyl-2-(3-methylphenyl)-1,3-oxazol-4-yl]methyl}-N-[2-(4-methylpiperidin-1-yl)ethyl]piperidine-4-carboxamide; |
| 543 | N-[2-(4-ethylpiperazin-1-yl)ethyl]-4-{5-methyl-4-[(phenylsulfanyl)methyl]-1,3-oxazol-2-yl}benzamide; |
| 545 | 1-{[2-(4-chlorophenyl)-5-methyl-1,3-oxazol-4-yl]methyl}-N-[2-(4-ethylpiperazin-1-yl)ethyl]piperidine-4-carboxamide; |
| 547 | 1-{[2-(3-chlorophenyl)-5-methyl-1,3-oxazol-4-yl]methyl}-N-[3-(4-methylpiperazin-1-yl)propyl]piperidine-4-carboxamide; |
| 549 | 1-{[2-(4-chlorophenyl)-5-methyl-1,3-oxazol-4-yl]methyl}-N-[3-(4-methylpiperazin-1-yl)propyl]piperidine-3-carboxamide; |
| 551 | 1-{[2-(3-chlorophenyl)-5-methyl-1,3-oxazol-4-yl]methyl}-N-[2-(4-ethylpiperazin-1-yl)ethyl]piperidine-3-carboxamide; |
| 553 | 1-{[2-(4-chlorophenyl)-5-methyl-1,3-oxazol-4-yl]methyl}-N-(3-pyrrolidin-1-ylpropyl)piperidine-4-carboxamide; |
| 555 | 1-{[2-(3-chlorophenyl)-5-methyl-1,3-oxazol-4-yl]methyl}-N-(3-pyrrolidin-1-ylpropyl)piperidine-4-carboxamide; |
| 557 | 1-{[2-(3-chlorophenyl)-5-methyl-1,3-oxazol-4-yl]methyl}-N-(3-pyrrolidin-1-ylpropyl)piperidine-3-carboxamide; |

| ID | IUPAC Name |
|---|---|
| 559 | 1-{[5-methyl-2-(2-methylphenyl)-1,3-oxazol-4-yl]methyl}-N-{3-[methyl(phenyl)amino]propyl}piperidine-4-carboxamide; |
| 561 | 1-{[2-(3-bromophenyl)-5-methyl-1,3-oxazol-4-yl]methyl}-N-[3-(cyclohexylsulfanyl)propyl]piperidine-4-carboxamide; |
| 563 | 4-(5-methyl-4-{[(4-methylphenyl)sulfanyl]methyl}-1,3-oxazol-2-yl)-N-[3-(4-methylpiperazin-1-yl)propyl]benzamide; |
| 565 | 4-{5-methyl-4-[(phenylsulfanyl)methyl]-1,3-oxazol-2-yl}-N-[3-(4-propylpiperazin-1-yl)propyl]benzamide; |
| 567 | 1-{[5-methyl-2-(4-propoxyphenyl)-1,3-oxazol-4-yl]methyl}-N-(pyridin-3-ylmethyl)piperidine-4-carboxamide; |
| 569 | N-(2-azepan-1-ylethyl)-4-(5-methyl-4-{[(4-methylphenyl)sulfanyl]methyl}-1,3-oxazol-2-yl)benzamide; |
| 571 | 4-(5-methyl-4-{[(4-methylphenyl)sulfanyl]methyl}-1,3-oxazol-2-yl)-N-[2-(4-methylpiperazin-1-yl)ethyl]benzamide; |
| 573 | N-(2-azepan-1-ylethyl)-4-{5-methyl-4-[(phenylsulfanyl)methyl]-1,3-oxazol-2-yl}benzamide |
| 575 | 1-{[2-(4-chlorophenyl)-5-methyl-1,3-oxazol-4-yl]methyl}-N-{3-[ethyl(3-methylphenyl)amino]propyl}piperidine-4-carboxamide; |
| 577 | 1-{[5-methyl-2-(4-propoxyphenyl)-1,3-oxazol-4-yl]methyl}-N-(pyridin-2-ylmethyl)piperidine-4-carboxamide; |
| 579 | N-{3-[cyclohexyl{methyl}amino]propyl}-1-{[5-methyl-2-(2-methylphenyl)-1,3-oxazol-4-yl]methyl}piperidine-4-carboxamide; |
| 581 | N-[2-(4-chlorophenyl)ethyl]-1-{[2-(4-ethylphenyl)-5-methyl-1,3-oxazol-4-yl]methyl}piperidine-4-carboxamide; |
| 583 | N-{2-[ethyl(phenyl)amino]ethyl}-1-{[2-(4-ethylphenyl)-5-methyl-1,3-oxazol-4-yl]methyl}piperidine-4-carboxamide; |
| 585 | N-[3-(cyclohexylsulfanyl)propyl]-1-{[5-methyl-2-(2-methylphenyl)-1,3-oxazol-4-yl]methyl}piperidine-3-carboxamide; |
| 587 | N-[2-(4-chlorophenyl)ethyl]-1-{[2-(4-ethylphenyl)-5-methyl-1,3-oxazol-4-yl]methyl}piperidine-3-carboxamide; |
| 589 | N-[2-(4-benzylpiperazin-1-yl)ethyl]-2-({[5-methyl-2-(4-methylphenyl)-1,3-oxazol-4-yl]methyl}sulfanyl)acetamide; |
| 591 | 4-[5-methyl-4-(phenoxymethyl)-1,3-oxazol-2-yl]-N-[3-(4-methylpiperazin-1-yl)propyl]benzamide; |
| 593 | N-[2-(4-ethylpiperazin-1-yl)ethyl]-4-(5-methyl-4-{[(4-methylphenyl)sulfanyl]methyl}-1,3-oxazol-2-yl)benzamide; |
| 595 | 1-{[2-(4-chlorophenyl)-5-methyl-1,3-oxazol-4-yl]methyl}-N-(pyridin-3-ylmethyl)piperidine-4-carboxamide; |
| 597 | 1-{[2-(4-chlorophenyl)-5-methyl-1,3-oxazol-4-yl]methyl}-N-(2-pyrrolidin-1-ylethyl)piperidine-4-carboxamide; and |
| 599 | 1-{[2-(3-chlorophenyl)-5-methyl-1,3-oxazol-4-yl]methyl}-N-(2-pyrrolidin-1-ylethyl)piperidine-4-carboxamide; | or a salt, solvate, ester or prodrug thereof.

13. An intravenous unit dosage form comprising a therapeutically effective amount of a compound of Formula (IIa):

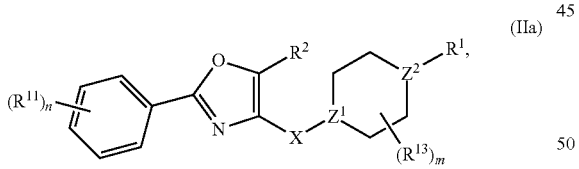

(IIa)

or a salt, solvate, ester or prodrug thereof and at least one pharmaceutically acceptable vehicle; wherein:

$R^1$ is —C(O)NR$^5$R$^6$;

$R^2$ is hydrogen, $C_{1-6}$ alkyl, or substituted $C_{1-6}$ alkyl;

—NR$^5$R$^6$ is derived from a group consisted of 3-(Azepan-1-yl)propan-1-amine (Cpd A),

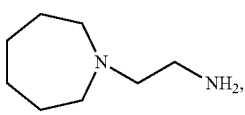

A1

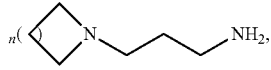

A3

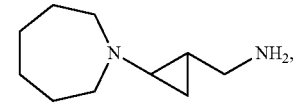

A4

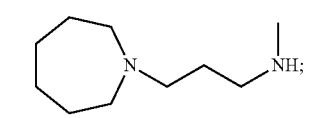

A5

(n is 1, 2, or 3)

X is —CH$_2$—;

$Z^1$ is N;

$Z^2$ is CR$^{12}$ or N;

$R^{12}$ is hydrogen, alkyl, or substituted alkyl;

n is an integer from 0 to 2;

m is 0; and each $R^{11}$ is independently selected from the group consisting of halogen, $C_{1-6}$ acyl, substituted $C_{1-6}$ acyl, $C_{1-6}$ alkoxycarbonyl, substituted $C_{1-6}$ alkoxycarbonyl, $C_{6-10}$ aryloxycarbonyl, substituted $C_{6-10}$ aryloxycarbonyl, —C(O)NR$^5$R$^6$, $C_{1-6}$ alkyl, substituted $C_{1-6}$ alkyl, $C_{6-10}$ aryl, substituted $C_{6-10}$ aryl, $C_{6-20}$ arylalkyl, substituted $C_{6-20}$ arylalkyl, $C_{3-7}$ cycloheteroalkyl, substituted $C_{3-7}$ cycloheteroalkyl, $C_{6-10}$ heteroaryl, substituted $C_{6-10}$ heteroaryl, $C_{6-20}$ heteroarylalkyl, substituted $C_{6-20}$ heteroarylalkyl, $C_{1-6}$ heteroalkyl, and substituted $C_{1-6}$ heteroalkyl; wherein $R^5$ and $R^6$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl, or alternatively, $R^5$ and $R^6$, taken together with the nitrogen atom to which they are attached, form a 4-, 5-, 6-, or 7-membered cycloheteroalkyl ring;

wherein the intravenous unit dosage form is suitable for administration of about 0.01 mg to about 100 mg of the compound per kilogram of body weight.

14. The intravenous unit dosage form of claim 13, which is in form of an aqueous solution.

15. The intravenous unit dosage form of claim 13, wherein the compound is selected the group consisting of

| ID | IUPAC Name |
|---|---|
| 901 | N-[3-(azepan-1-yl)propyl]-1-{[2-(4-chlorophenyl)-5-methyl-1,3-oxazol-4-yl]methyl}piperidine-4-carboxamide; |
| 929 | N-[3-(azepan-1-yl)propyl]-1-{[2-(4-chlorophenyl)-5-methyl-1,3-oxazol-4-yl]methyl}-N-methylpiperidine-4-carboxamide; |
| 933 | N-{[2-(azepan-1-yl)cyclopropyl]methyl}-1-{[2-(4-chlorophenyl)-5-methyl-1,3-oxazol-4-yl]methyl}piperidine-4-carboxamide; |
| 943 | N-[3-(azepan-1-yl)propyl]-1-([{5-methyl-2-[4-(trifluoromethyl)phenyl]-1,3-oxazol-4-yl}methyl)piperidine-4-carboxamide; |
| 947 | N-[3-(azepan-1-yl)propyl]-1-{[2-(2,4-difluorophenyl)-5-methyl-1,3-oxazol-4-yl]methyl}piperidine-4-carboxamide; |
| 949 | N-[3-(azepan-1-yl)propyl]-1-{[2-(1,3-benzodioxol-5-yl)-5-methyl-1,3-oxazol-4-yl]methyl}piperidine-4-carboxamide; |
| 951 | N-[3-(azepan-1-yl)propyl]-1-{[2-(2,4-dimethoxyphenyl)-5-methyl-1,3-oxazol-4-yl]methyl}piperidine-4-carboxamide; |
| 953 | N-[3-(azepan-1-yl)propyl]-1-{[2-(4-benzylphenyl)-5-methyl-1,3-oxazol-4-yl]methyl}piperidine-4-carboxamide; |
| 955 | N-[3-(azepan-1-yl)propyl]-1-({2-[4-(dimethylcarbanoyl)phenyl]-5-methyl-1,3-oxazol-4-yl}methyl)piperidine-4-carboxamide; |
| 957 | N-[3-(azepan-1-yl)propyl]-1-([{5-methyl-2-[4-(piperidin-1-yl)phenyl]-1,3-oxazol-4-yl}methyl)piperidine-4-carboxamide; |
| 959 | N-[3-(azepan-1-yl)propyl]-1-{[5-methyl-2-(naphthalen-1-yl)-1,3-oxazol-4-yl]methyl}piperidine-4-carboxamide; |
| 503 | N-(2-azepan-1-ylethyl)-1-{[2-(4-chlorophenyl)-5-methyl-1,3-oxazol-4-yl]methyl}piperidine-4-carboxamide; |
| 505 | 1-{[2-(4-chlorophenyl)-5-methyl-1,3-oxazol-4-yl]methyl}-N-[3-(3-methylpiperidin-1-yl)propyl]piperidine-4-carboxamide; |
| 507 | 1-{[2-(4-chlorophenyl)-5-methyl-1,3-oxazol-4-yl]methyl}-N-[3-(2-ethylpiperidin-1-yl)propyl]piperidine-4-carboxamide; |
| 509 | 1-{[2-(4-chlorophenyl)-5-methyl-1,3-oxazol-4-yl]methyl}-N-[2-(2-methylpiperidin-1-yl)ethyl]piperidine-4-carboxamide; |
| 511 | 1-{[2-(4-chlorophenyl)-5-methyl-1,3-oxazol-4-yl]methyl}-N-{2-[ethyl(phenyl)amino]ethyl}piperidine-4-carboxamide; |
| 513 | 1-{[2-(4-chlorophenyl)-5-methyl-1,3-oxazol-4-yl]methyl}-N-{3-[methyl(phenyl)amino]propyl}piperidine-4-carboxamide; |
| 515 | 1-{[2-(3-chlorophenyl)-5-methyl-1,3-oxazol-4-yl]methyl}-N-{2-[ethyl(phenyl)amino]ethyl}piperidine-4-carboxamide; |
| 517 | 1-{[2-(4-chlorophenyl)-5-methyl-1,3-oxazol-4-yl]methyl}-N-{2-[ethyl(phenyl)amino]ethyl}piperidine-3-carboxamide; |
| 519 | 1-{[2-(3-chlorophenyl)-5-methyl-1,3-oxazol-4-yl]methyl}-N-{2-[ethyl(phenyl)amino]ethyl}piperidine-3-carboxamide; |
| 521 | 1-{[2-(3-chlorophenyl)-5-methyl-1,3-oxazol-4-yl]methyl}-N-{3-[methyl(phenyl)amino]propyl}piperidine-3-carboxamide; |
| 523 | 4-{5-methyl-4-[(phenylsulfanyl)methyl]-1,3-oxazol-2-yl}-N-[3-(4-methylpiperazin-1-yl)propyl]benzamide; |
| 525 | N-{3-[benzyl(methyl)amino]propyl}-1-{[2-(4-chlorophenyl)-5-methyl-1,3-oxazol-4-yl]methyl}piperidine-4-carboxamide; |
| 527 | 1-{[2-(4-chlorophenyl)-5-methyl-1,3-oxazol-4-yl]methyl}-N-[3-(3,5-dimethylpiperidin-1-yl)propyl]piperidine-4-carboxamide; |
| 529 | 1-{[2-(4-chlorophenyl)-5-methyl-1,3-oxazol-4-yl]methyl}-N-{2-[methyl(2-phenylethyl)amino]ethyl}piperidine-4-carboxamide; |
| 531 | 1-{[5-methyl-2-(2-methylphenyl)-1,3-oxazol-4-yl]methyl}-N-[3-(3-methylpiperidin-1-yl)propyl]piperidine-4-carboxamide; |
| 533 | 1-{[2-(3-chlorophenyl)-5-methyl-1,3-oxazol-4-yl]methyl}-N-[3-(3,5-dimethylpiperidin-1-yl)propyl]piperidine-4-carboxamide; |
| 535 | 1-{[2-(3-chlorophenyl)-5-methyl-1,3-oxazol-4-yl]methyl}-N-[3-(cyclohexylsulfanyl)propyl]piperidine-4-carboxamide; |
| 537 | N-{2-[ethyl(phenyl)amino]ethyl}-1-{[2-(2-fluorophenyl)-5-methyl-1,3-oxazol-4-yl]methyl}piperidine-4-carboxamide; |
| 539 | 1-{[2-(3-chlorophenyl)-5-methyl-1,3-oxazol-4-yl]methyl}-N-{2-[methyl(2-phenylethyl)amino]ethyl}piperidine-3-carboxamide; |

| ID | IUPAC Name |
|---|---|
| 541 | 1-{[5-methyl-2-(3-methylphenyl)-1,3-oxazol-4-yl]methyl}-N-[2-(4-methylpiperidin-1-yl)ethyl]piperidine-4-carboxamide; |
| 543 | N-[2-(4-ethylpiperazin-1-yl)ethyl]-4-{5-methyl-4-[(phenylsulfanyl)methyl]-1,3-oxazol-2-yl}benzamide; |
| 545 | 1-{[2-(4-chlorophenyl)-5-methyl-1,3-oxazol-4-yl]methyl}-N-[2-(4-ethylpiperazin-1-yl)ethyl]piperidine-4-carboxamide; |
| 547 | 1-{[2-(3-chlorophenyl)-5-methyl-1,3-oxazol-4-yl]methyl}-N-[3-(4-methylpiperazin-1-yl)propyl]piperidine-4-carboxamide; |
| 549 | 1-{[2-(4-chlorophenyl)-5-methyl-1,3-oxazol-4-yl]methyl}-N-[3-(4-methylpiperazin-1-yl)propyl]piperidine-3-carboxamide; |
| 551 | 1-{[2-(3-chlorophenyl)-5-methyl-1,3-oxazol-4-yl]methyl}-N-[2-(4-ethylpiperazin-1-yl)ethyl]piperidine-3-carboxamide; |
| 553 | 1-{[2-(4-chlorophenyl)-5-methyl-1,3-oxazol-4-yl]methyl}-N-(3-pyrrolidin-1-ylpropyl)piperidine-4-carboxamide; |
| 555 | 1-{[2-(3-chlorophenyl)-5-methyl-1,3-oxazol-4-yl]methyl}-N-(3-pyrrolidin-1-ylpropyl)piperidine-4-carboxamide; |
| 557 | 1-{[2-(3-chlorophenyl)-5-methyl-1,3-oxazol-4-yl]methyl}-N-(3-pyrrolidin-1-ylpropyl)piperidine-3-carboxamide; |
| 559 | 1-{[5-methyl-2-(2-methylphenyl)-1,3-oxazol-4-yl]methyl}-N-{3-[methyl(phenyl)amino]propyl}piperidine-4-carboxamide; |
| 561 | 1-{[2-(3-bromophenyl)-5-methyl-1,3-oxazol-4-yl]methyl}-N-[3-(cyclohexylsulfanyl)propyl]piperidine-4-carboxamide; |
| 563 | 4-(5-methyl-4-{[(4-methylphenyl)sulfanyl]methyl}-1,3-oxazol-2-yl)-N-[3-(4-methylpiperazin-1-yl)propyl]benzamide; |
| 565 | 4-{5-methyl-4-[(phenylsulfanyl)methyl]-1,3-oxazol-2-yl}-N-[3-(4-propylpiperazin-1-yl)propyl]benzamide; |
| 567 | 1-{[5-methyl-2-(4-propoxyphenyl)-1,3-oxazol-4-yl]methyl}-N-(pyridin-3-ylmethyl)piperidine-4-carboxamide; |
| 569 | N-(2-azepan-1-ylethyl)-4-(5-methyl-4-{[(4-methylphenyl)sulfanyl]methyl}-1,3-oxazol-2-yl)benzamide; |
| 571 | 4-(5-methyl-4-{[(4-methylphenyl)sulfanyl]methyl}-1,3-oxazol-2-yl)-N-[2-(4-methylpiperazin-1-yl)ethyl]benzamide; |
| 573 | N-(2-azepan-1-ylethyl)-4-{5-methyl-4-[(phenylsulfanyl)methyl]-1,3-oxazol-2-yl}benzamide |
| 575 | 1-{[2-(4-chlorophenyl)-5-methyl-1,3-oxazol-4-yl]methyl}-N-{3-[ethyl(3-methylphenyl)amino]propyl}piperidine-4-carboxamide; |
| 577 | 1-{[5-methyl-2-(4-propoxyphenyl)-1,3-oxazol-4-yl]methyl}-N-(pyridin-2-ylmethyl)piperidine-4-carboxamide; |
| 579 | N-{3-[cyclohexyl(methyl)amino]propyl{-1-{[5-methyl-2-(2-methylphenyl)-1,3-oxazol-4-yl]methyl}piperidine-4-carboxamide; |
| 581 | N-[2-(4-chlorophenyl)ethyl]-1-{[2-(4-ethylphenyl)-5-methyl-1,3-oxazol-4-yl]methyl}piperidine-4-carboxamide; |
| 583 | N-{2-[ethyl(phenyl)amino]ethyl}-1-{[2-(4-ethylphenyl)-5-methyl-1,3-oxazol-4-yl]methyl}piperidine-4-carboxamide; |
| 585 | N-[3-(cyclohexylsulfanyl)propyl]-1-{[5-methyl-2-(2-methylphenyl)-1,3-oxazol-4-yl]methyl}piperidine-3-carboxamide; |
| 587 | N-[2-(4-chlorophenyl)ethyl]-1-{[2-(4-ethylphenyl)-5-methyl-1,3-oxazol-4-yl]methyl}piperidine-3-carboxamide; |
| 589 | N-[2-(4-benzylpiperazin-1-yl)ethyl]-2-({[5-methyl-2-(4-methylphenyl)-1,3-oxazol-4-yl]methyl}sulfanyl)acetamide; |
| 591 | 4-[5-methyl-4-(phenoxymethyl)-1,3-oxazol-2-yl]-N-[3-(4-methylpiperazin-1-yl)propyl]benzamide; |
| 593 | N-[2-(4-ethylpiperazin-1-yl)ethyl]-4-(5-methyl-4-{[(4-methylphenyl)sulfanyl]methyl}-1,3-oxazol-2-yl)benzamide; |
| 595 | 1-{[2-(4-chlorophenyl)-5-methyl-1,3-oxazol-4-yl]methyl}-N-(pyridin-3-ylmethyl)piperidine-4-carboxamide; |
| 597 | 1-{[2-(4-chlorophenyl)-5-methyl-1,3-oxazol-4-yl]methyl}-N-(2-pyrrolidin-1-ylethyl)piperidine-4-carboxamide; and |
| 599 | 1-{[2-(3-chlorophenyl)-5-methyl-1,3-oxazol-4-yl]methyl}-N-(2-pyrrolidin-1-ylethyl)piperidine-4-carboxamide; | or a salt, solvate, ester or prodrug thereof.

16. An intranasal unit dosage form comprising a therapeutically effective amount of a compound of Formula (IIa):

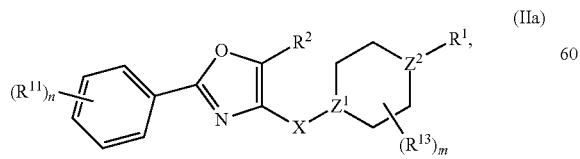
(IIa)

or a salt, solvate, ester or prodrug thereof; and at least one pharmaceutically acceptable vehicle; wherein:

$R^1$ is —C(O)NR$^5$R$^6$;

$R^2$ is hydrogen, $C_{1-6}$ alkyl, or substituted $C_{1-6}$ alkyl;

—NR$^5$R$^6$ is derived from a group consisted of 3-(Azepan-1-yl)propan-1-amine (Cpd A),

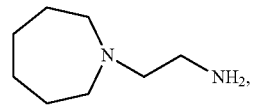
A1

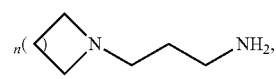
A3

-continued

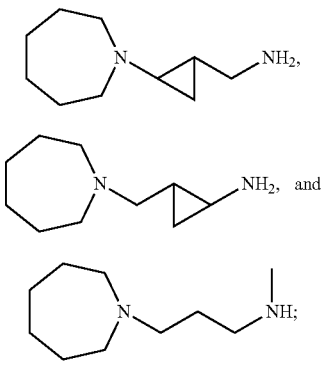

(n is 1, 2, or 3)

X is —CH$_2$—;
Z$^1$ is N;
Z$^2$ is CR$^{12}$ or N;
R$^{12}$ is hydrogen, alkyl, or substituted alkyl;
n is an integer from 0 to 2;
m is 0; and each R$^{11}$ is independently selected from the group consisting of halogen, C$_{1-6}$ acyl, substituted C$_{1-6}$ acyl, C$_{1-6}$ alkoxycarbonyl, substituted C$_{1-6}$ alkoxycarbonyl, C$_{6-10}$ aryloxycarbonyl, substituted C$_{6-10}$ aryloxycarbonyl, —C(O)NR$^5$R$^6$, C$_{1-6}$ alkyl, substituted C$_{1-6}$ alkyl, C$_{6-10}$ aryl, substituted C$_{6-10}$ aryl, C$_{6-20}$ arylalkyl, substituted C$_{6-20}$ arylalkyl, C$_{3-7}$ cycloheteroalkyl, substituted C$_{3-7}$ cycloheteroalkyl, C$_{6-10}$ heteroaryl, substituted C$_{6-10}$ heteroaryl, C$_{6-20}$ heteroarylalkyl, substituted C$_{6-20}$ heteroarylalkyl, C$_{1-6}$ heteroalkyl, and substituted C$_{1-6}$ heteroalkyl; wherein R$^5$ and R$^6$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl, or alternatively, R$^5$ and R$^6$, taken together with the nitrogen atom to which they are attached, form a 4-, 5-, 6-, or 7-membered cycloheteroalkyl ring;

wherein the intranasal unit dosage form is suitable for administration of about 0.01 mg to about 1 mg of the compound per kilogram of body weight.

17. The intranasal unit dosage form of claim 16, which is in form of an aqueous solution.

18. The intranasal unit dosage form of claim 16, wherein the compound is selected from the group consisting of

| ID | IUPAC Name |
|---|---|
| 901 | N-[3-(azepan-1-yl)propyl]-1-{[2-(4-chlorophenyl)-5-methyl-1,3-oxazol-4-yl]methyl}piperidine-4-carboxamide; |
| 929 | N-[3-(azepan-1-yl)propyl]-1-{[2-(4-chlorophenyl)-5-methyl-1,3-oxazol-4-yl]methyl}-N-methylpiperidine-4-carboxamide; |
| 933 | N-{[2-(azepan-1-yl)cyclopropyl]methyl}-1-{[2-(4-chlorophenyl)-5-methyl-1,3-oxazol-4-yl]methyl}piperidine-4-carboxamide; |
| 943 | N-[3-(azepan-1-yl)propyl]-1-({5-methyl-2-[4-(trifluoromethyl)phenyl]-1,3-oxazol-4-yl}methyl)piperidine-4-carboxamide; |
| 947 | N-[-(azepan-1-yl)propyl]-1-{[2-(2,4-difluorophenyl)-5-methyl-1,3-oxazol-4-yl]methyl}piperidine-4-carboxamide; |
| 949 | N-[3-(azepan-1-yl)propyl]-1-{[2-(1,3-benzodioxol-5-yl)-5-methyl-1,3-oxazol-4-yl]methyl}piperidine-4-carboxamide; |
| 951 | N-[3-(azepan-1-yl)propyl]-1-{[2-(2,4-dimethoxyphenyl)-5-methyl-1,3-oxazol-4-yl]methyl}piperidine-4-carboxamide; |
| 953 | N-[3-(azepan-1-yl)propyl]-1-{[2-(4-benzylphenyl)-5-methyl-1,3-oxazol-4-yl]methyl}piperidine-4-carboxamide; |
| 955 | N-[3-(azepan-1-yl)propyl]-1-({2-[4-(dimethylcarbamoyl)phenyl]-5-methyl-1,3-oxazol-4-yl}methyl)piperidine-4-carboxamide; |
| 957 | N-[3-(azepan-1-yl)propyl]-1-({5-methyl-2-[4-(piperidin-1-yl)phenyl]-1,3-oxazol-4-yl}methyl)piperidine-4-carboxamide; |
| 959 | N-[3-(azepan-1-yl)propyl]-1-{[5-methyl-2-(naphthalen-1-yl)-1,3-oxazol-4-yl]methyl}piperidine-4-carboxamide; |
| 503 | N-(2-azepan-1-ylethyl)-1-{[2-(4-chlorophenyl)-5-methyl-1,3-oxazol-4-yl]methyl}piperidine-4-carboxamide; |
| 505 | 1-{[2-(4-chlorophenyl)-5-methyl-1,3-oxazol-4-yl]methyl}-N-[3-(3-methylpiperidin-1-yl)propyl]piperidine-4-carboxamide; |
| 507 | 1-{[2-(4-chlorophenyl)-5-methyl-1,3-oxazol-4-yl]methyl}-N-[3-(2-ethylpiperidin-1-yl)propyl]piperidine-4-carboxamide; |
| 509 | 1-{[2-(4-chlorophenyl)-5-methyl-1,3-oxazol-4-yl]methyl}-N-[2-(2-methylpiperidin-1-yl)ethyl]piperidine-4-carboxamide; |
| 511 | 1-{[2-(4-chlorophenyl)-5-methyl-1,3-oxazol-4-yl]methyl}-N-{2-[ethyl(phenyl)amino]ethyl}piperidine-4-carboxamide; |
| 513 | 1-{[2-(4-chlorophenyl)-5-methyl-1,3-oxazol-4-yl]methyl}-N-{3-[methyl(phenyl)amino]propyl}piperidine-4-carboxamide; |
| 515 | 1-{[2-(3-chlorophenyl)-5-methyl-1,3-oxazol-4-yl]methyl}-N-{2-[ethyl(phenyl)amino]ethyl}piperidine-4-carboxamide; |
| 517 | 1-{[2-(4-chlorophenyl)-5-methyl-1,3-oxazol-4-yl]methyl}-N-{2-[ethyl(phenyl)amino]ethyl}piperidine-3-carboxamide; |
| 519 | 1-{[2-(3-chlorophenyl)-5-methyl-1,3-oxazol-4-yl]methyl}-N-{2-[ethyl(phenyl)amino]ethyl}piperidine-3-carboxamide; |
| 521 | 1-{[2-(3-chlorophenyl)-5-methyl-1,3-oxazol-4-yl]methyl}-N-{3-[methyl(phenyl)amino]propyl}piperidine-3-carboxamide; |
| 523 | 4-{5-methyl-4-[(phenylsulfanyl)methyl]-1,3-oxazol-2-yl}-N-[3-(4-methylpiperazin-1-yl)propyl]benzamide; |

-continued

| ID | IUPAC Name |
|---|---|
| 525 | N-{3-[benzyl(methyl)amino]propyl}-1-{[2-(4-chlorophenyl)-5-methyl-1,3-oxazol-4-yl]methyl}piperidine-4-carboxamide; |
| 527 | 1-{[2-(4-chlorophenyl)-5-methyl-1,3-oxazol-4-yl]methyl}-N-[3-(3,5-dimethylpiperidin-1-yl)propyl]piperidine-4-carboxamide; |
| 529 | 1-{[2-(4-chlorophenyl)-5-methyl-1,3-oxazol-4-yl]methyl}-N-{2-[methyl(2-phenylethyl)amino]ethyl}piperidine-4-carboxamide; |
| 531 | 1-{[5-methyl-2-(2-methylphenyl)-1,3-oxazol-4-yl]methyl}-N-[3-(3-methylpiperidin-1-yl)propyl]piperidine-4-carboxamide; |
| 533 | 1-{[2-(3-chlorophenyl)-5-methyl-1,3-oxazol-4-yl]methyl}-N-[3-(3,5-dimethylpiperidin-1-yl)propyl]piperidine-4-carboxamide; |
| 535 | 1-{[2-(3-chlorophenyl)-5-methyl-1,3-oxazol-4-yl]methyl}-N-[3-(cyclohexylsulfanyl)propyl]piperidine-4-carboxamide; |
| 537 | N-{2-[ethyl(phenyl)amino]ethyl}-1-{[2-(2-fluorophenyl)-5-methyl-1,3-oxazol-4-yl]methyl}piperidine-4-carboxamide; |
| 539 | 1-{[2-(3-chlorophenyl)-5-methyl-1,3-oxazol-4-yl]methyl}-N-{2-[methyl(2-phenylethyl)amino]ethyl}piperidine-3-carboxamide; |
| 541 | 1-{[5-methyl-2-(3-methylphenyl)-1,3-oxazol-4-yl]methyl}-N-[2-(4-methylpiperidin-1-yl)ethyl]piperidine-4-carboxamide; |
| 543 | N-[2-(4-ethylpiperazin-1-yl)ethyl]-4-{5-methyl-4-[(phenylsulfanyl)methyl]-1,3-oxazol-2-yl}benzamide; |
| 545 | 1-{[2-(4-chlorophenyl)-5-methyl-1,3-oxazol-4-yl]methyl}-N-[2-(4-ethylpiperazin-1-yl)ethyl]piperidine-4-carboxamide; |
| 547 | 1-{[2-(3-chlorophenyl)-5-methyl-1,3-oxazol-4-yl]methyl}-N-[3-(4-methylpiperazin-1-yl)propyl]piperidine-4-carboxamide; |
| 549 | 1-{[2-(4-chlorophenyl)-5-methyl-1,3-oxazol-4-yl]methyl}-N-[3-(4-methylpiperazin-1-yl)propyl]piperidine-3-carboxamide; |
| 551 | 1-{[2-(3-chlorophenyl)-5-methyl-1,3-oxazol-4-yl]methyl}-N-[2-(4-ethylpiperazin-1-yl)ethyl]piperidine-3-carboxamide; |
| 553 | 1-{[2-(4-chlorophenyl)-5-methyl-1,3-oxazol-4-yl]methyl}-N-(3-pyrrolidin-1-ylpropyl)piperidine-4-carboxamide; |
| 555 | 1-{[2-(3-chlorophenyl)-5-methyl-1,3-oxazol-4-yl]methyl}-N-(3-pyrrolidin-1-ylpropyl)piperidine-4-carboxamide; |
| 557 | 1-{[2-(3-chlorophenyl)-5-methyl-1,3-oxazol-4-yl]methyl}-N-(3-pyrrolidin-1-ylpropyl)piperidine-3-carboxamide; |
| 559 | 1-{[5-methyl-2-(2-methylphenyl)-1,3-oxazol-4-yl]methyl}-N-{3-[methyl(phenyl)amino]propyl}piperidine-4-carboxamide; |
| 561 | 1-{[2-(3-bromophenyl)-5-methyl-1,3-oxazol-4-yl]methyl}-N-[3-(cyclohexylsulfanyl)propyl]piperidine-4-carboxamide; |
| 563 | 4-(5-methyl-4-{[(4-methylphenyl)sulfanyl]methyl}-1,3-oxazol-2-yl)-N-[3-(4-methylpiperazin-1-yl)propyl]benzamide; |
| 565 | 4-{5-methyl-4-[(phenylsulfanyl)methyl]-1,3-oxazol-2-yl}-N-[3-(4-propylpiperazin-1-yl)propyl]benzamide; |
| 567 | 1-{[5-methyl-2-(4-propoxyphenyl)-1,3-oxazol-4-yl]methyl}-N-(pyridin-3-ylmethyl)piperidine-4-carboxamide; |
| 569 | N-(2-azepan-1-ylethyl)-4-(5-methyl-4-{[(4-methylphenyl)sulfanyl]methyl}-1,3-oxazol-2-yl)benzamide; |
| 571 | 4-(5-methyl-4-{[(4-methylphenyl)sulfanyl]methyl}-1,3-oxazol-2-yl)-N-[2-(4-methylpiperazin-1-yl)ethyl]benzamide; |
| 573 | N-(2-azepan-1-ylethyl)-4-{5-methyl-4-[(phenylsulfanyl)methyl]-1,3-oxazol-2-yl}benzamide |
| 575 | 1-{[2-(4-chlorophenyl)-5-methyl-1,3-oxazol-4-yl]methyl}-N-{3-[ethyl(3-methylphenyl)amino]propyl}piperidine-4-carboxamide; |
| 577 | 1-{[5-methyl-2-(4-propoxyphenyl)-1,3-oxazol-4-yl]methyl}-N-(pyridin-2-ylmethyl)piperidine-4-carboxamide; |
| 579 | N-{3-[cyclohexyl(methyl)amino]propyl}-1-{[5-methyl-2-(2-methylphenyl)-1,3-oxazol-4-yl]methyl}piperidine-4-carboxamide; |
| 581 | N-[2-(4-chlorophenyl)ethyl]-1-{[2-(4-ethylphenyl)-5-methyl-1,3-oxazol-4-yl]methyl}piperidine-4-carboxamide; |
| 583 | N-{2-[ethyl(phenyl)amino[ethyl}-1-{[2-(4-ethylphenyl)-5-methyl-1,3-oxazol-4-yl]methyl}piperidine-4-carboxamide; |
| 585 | N-[3-(cyclohexylsulfanyl)propyl]-1-{[5-methyl-2-(2-methylphenyl)-1,3-oxazol-4-yl]methyl}piperidine-3-carboxamide; |
| 587 | N-[2-(4-chlorophenyl)ethyl]-1-{[2-(4-ethylphenyl)-5-methyl-1,3-oxazol-4-yl]methyl}piperidine-3-carboxamide; |
| 589 | N-[2-(4-benzylpiperazin-1-yl)ethyl]-2-({[5-methyl-2-(4-methylphenyl)-1,3-oxazol-4-yl]methyl}sulfanyl)acetamide; |
| 591 | 4-[5-methyl-4-(phenoxymethyl)-1,3-oxazol-2-yl]-N-[3-(4-methylpiperazin-1-yl)propyl]benzamide; |
| 593 | N-[2-(4-ethylpiperazin-1-yl)ethyl]-4-(5-methyl-4-{[(4-methylphenyl)sulfanyl]methyl}-1,3-oxazol-2-yl)benzamide; |
| 595 | 1-{[2-(4-chlorophenyl)-5-methyl-1,3-oxazol-4-yl]methyl}-N-(pyridin-3-ylmethyl)piperidine-4-carboxamide; |
| 597 | 1-{[2-(4-chlorophenyl)-5-methyl-1,3-oxazol-4-yl]methyl}-N-(2-pyrrolidin-1-ylethyl)piperidine-4-carboxamide; and |
| 599 | 1-{[2-(3-chlorophenyl)-5-methyl-1,3-oxazol-4-yl]methyl}-N-(2-pyrrolidin-1-ylethyl)piperidine-4-carboxamide; | or a salt, solvate, ester or prodrug thereof.

19. A suppository unit dosage form comprising a therapeutically effective amount of a compound of Formula (IIa):

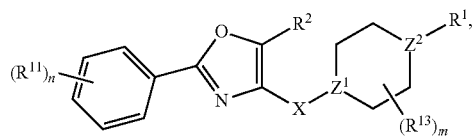
(IIa)

or a salt, solvate, ester or prodrug thereof; and at least one pharmaceutically acceptable vehicle; wherein:

$R^1$ is —C(O)NR$^5$R$^6$;

$R^2$ is hydrogen, $C_{1-6}$ alkyl, or substituted $C_{1-6}$ alkyl;

—NR$^5$R$^6$ is derived from a group consisted of 3-(Azepan-1-yl)propan-1-amine (Cpd A),

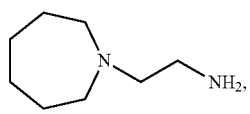
A1

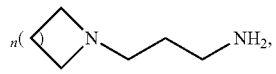
A3

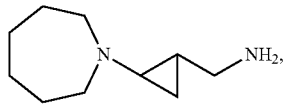
A4

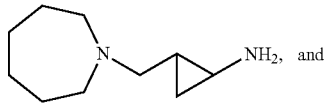
A5, and

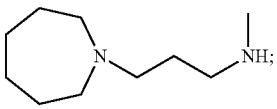
A5

(n is 1, 2, or 3)

X is —CH$_2$—;

$Z^1$ is N;

$Z^2$ is CR$^{12}$ or N;

$R^{12}$ is hydrogen, alkyl, or substituted alkyl;

n is an integer from 0 to 2;

m is 0; and each $R^{11}$ is independently selected from the group consisting of halogen, $C_{1-6}$ acyl, substituted $C_{1-6}$ acyl, $C_{1-6}$ alkoxycarbonyl, substituted $C_{1-6}$ alkoxycarbonyl, $C_{6-10}$ aryloxycarbonyl, substituted $C_{6-10}$ aryloxycarbonyl, —C(O)NR$^5$R$^6$, $C_{1-6}$ alkyl, substituted $C_{1-6}$ alkyl, $C_{6-10}$ aryl, substituted $C_{6-10}$ aryl, $C_{6-20}$ arylalkyl, substituted $C_{6-20}$ arylalkyl, $C_{3-7}$ cycloheteroalkyl, substituted $C_{3-7}$ cycloheteroalkyl, $C_{6-10}$ heteroaryl, substituted $C_{6-10}$ heteroaryl, $C_{6-20}$ heteroarylalkyl, substituted $C_{6-20}$ heteroarylalkyl, $C_{1-6}$ heteroalkyl, and substituted $C_{1-6}$ heteroalkyl; wherein $R^5$ and $R^6$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl, or alternatively, $R^5$ and $R^6$, taken together with the nitrogen atom to which they are attached, form a 4-, 5-, 6-, or 7-membered cycloheteroalkyl ring;

wherein the suppository unit dosage form is suitable for administration of about 0.01 mg to about 50 mg of the compound per kilogram of body weight and comprise active ingredient in the range of about 0.5% to about 10% by weight.

20. The suppository unit dosage form of any one of claim 19, wherein the compound is selected from the group consisting of

| ID | IUPAC Name |
|---|---|
| 901 | N-[3-(azepan-1-yl)propyl]-1-{[2-(4-chlorophenyl)-5-methyl-1,3-oxazol-4-yl]methyl}piperidine-4-carboxamide; |
| 929 | N-[3-(azepan-1-yl)propyl]-1-{[2-(4-chlorophenyl)-5-methyl-1,3-oxazol-4-yl]methyl}-N-methylpiperidine-4-carboxamide; |
| 933 | N-{[2-(azepan-1-yl)cyclopropyl]methyl}-1-{[2-(4-chlorophenyl)-5-methyl-1,3-oxazol-4-yl]methyl}piperidine-4-carboxamide; |
| 943 | N-[3-(azepan-1-yl)propyl]-1-({5-methyl-2-[4-(trifluoromethyl)phenyl]-1,3-oxazol-4-yl}methyl)piperidine-4-carboxamide; |
| 947 | N-[3-(azepan-1-yl)propyl]-1-{[2-(2,4-difluorophenyl)-5-methyl-1,3-oxazol-4-yl]methyl}piperidine-4-carboxamide; |
| 949 | N-[3-(azepan-1-yl)propyl]-1-{[2-(1,3-benzodioxol-5-yl)-5-methyl-1,3-oxazol-4-yl]methyl}piperidine-4-carboxamide; |
| 951 | N-[3-(azepan-1-yl)propyl]-1-{[2-(2,4-dimethoxyphenyl)-5-methyl-1,3-oxazol-4-yl]methyl}piperidine-4-carboxamide; |
| 953 | N-[3-(azepan-1-yl)propyl]-1-{[2-(4-benzylphenyl)-5-methyl-1,3-oxazol-4-yl]methyl}piperidine-4-carboxamide; |
| 955 | N-[3-(azepan-1-yl)propyl]-1-({2-[4-(dimethylcarbamoyl)phenyl]-5-methyl-1,3-oxazol-4-yl}methyl)piperidine-4-carboxamide; |
| 957 | N-[3-(azepan-1-yl)propyl]-1-({5-methyl-2-[4-(piperidin-1-yl)phenyl]-1,3-oxazol-4-yl}methyl)piperidine-4-carboxamide; |
| 959 | N-[3-(azepan-1-yl)propyl]-1-{[5-methyl-2-(naphthalen-1-yl)-1,3-oxazol-4-yl]methyl}piperidine-4-carboxamide; |
| 503 | N-(2-azepan-1-ylethyl)-1-{[2-(4-chlorophenyl)-5-methyl-1,3-oxazol-4-yl]methyl}piperidine-4-carboxamide; |
| 505 | 1-{[2-(4-chlorophenyl)-5-methyl-1,3-oxazol-4-yl]methyl}-N-[3-(3-methylpiperidin-1-yl)propyl]piperidine-4-carboxamide; |
| 507 | 1-{[2-(4-chlorophenyl)-5-methyl-1,3-oxazol-4-yl]methyl}-N-[3-(2-ethylpiperidin-1-yl)propyl]piperidine-4-carboxamide; |

-continued

| ID | IUPAC Name |
|---|---|
| 509 | 1-{[2-(4-chlorophenyl)-5-methyl-1,3-oxazol-4-yl]methyl}-N-[2-(2-methylpiperidin-1-yl)ethyl]piperidine-4-carboxamide; |
| 511 | 1-{[2-(4-chlorophenyl)-5-methyl-1,3-oxazol-4-yl]methyl}-N-{2-[ethyl(phenyl)amino]ethyl}piperidine-4-carboxamide; |
| 513 | 1-{[2-(4-chlorophenyl)-5-methyl-1,3-oxazol-4-yl]methyl}-N-{3-[methyl(phenyl)amino]propyl}piperidine-4-carboxamide; |
| 515 | 1-{[2-(3-chlorophenyl)-5-methyl-1,3-oxazol-4-yl]methyl}-N-{2-[ethyl(phenyl)amino]ethyl}piperidine-4-carboxamide; |
| 517 | 1-{[2-(4-chlorophenyl)-5-methyl-1,3-oxazol-4-yl]methyl}-N-{2-[ethyl(phenyl)amino]ethyl}piperidine-3-carboxamide; |
| 519 | 1-{[2-(3-chlorophenyl)-5-methyl-1,3-oxazol-4-yl]methyl}-N-{2-[ethyl(phenyl)amino]ethyl}piperidine-3-carboxamide; |
| 521 | 1-{[2-(3-chlorophenyl)-5-methyl-1,3-oxazol-4-yl]methyl}-N-{3-[methyl(phenyl)amino]propyl}piperidine-3-carboxamide; |
| 523 | 4-{5-methyl-4-[(phenylsulfanyl)methyl]-1,3-oxazol-2-yl}-N-[3-(4-methylpiperazin-1-yl)propyl]benzamide; |
| 525 | N-{3-[benzyl(methyl)amino]propyl}-1-{[2-(4-chlorophenyl)-5-methyl-1,3-oxazol-4-yl]methyl}piperidine-4-carboxamide; |
| 527 | 1-{[2-(4-chlorophenyl)-5-methyl-1,3-oxazol-4-yl]methyl}-N-[3-(3,5-dimethylpiperidin-1-yl)propyl]piperidine-4-carboxamide; |
| 529 | 1-{[2-(4-chlorophenyl)-5-methyl-1,3-oxazol-4-yl]methyl}-N-{2-[methyl(2-phenylethyl)amino]ethyl}piperidine-4-carboxamide; |
| 531 | 1-{[5-methyl-2-(2-methylphenyl)-1,3-oxazol-4-yl]methyl}-N-[3-(3-methylpiperidin-1-yl)propyl]piperidine-4-carboxamide; |
| 533 | 1-{[2-(3-chlorophenyl)-5-methyl-1,3-oxazol-4-yl]methyl}-N-[3-(3,5-dimethylpiperidin-1-yl)propyl]piperidine-4-carboxamide; |
| 535 | 1-{[2-(3-chlorophenyl)-5-methyl-1,3-oxazol-4-yl]methyl}-N-[3-(cyclohexylsulfanyl)propyl]piperidine-4-carboxamide; |
| 537 | N-{2-[ethyl(phenyl)amino]ethyl}-1-{[2-(2-fluorophenyl)-5-methyl-1,3-oxazol-4-yl]methyl}piperidine-4-carboxamide; |
| 539 | 1-{[2-(3-chlorophenyl)-5-methyl-1,3-oxazol-4-yl]methyl}-N-{2-[methyl(2-phenylethyl)amino]ethyl}piperidine-3-carboxamide; |
| 541 | 1-{[5-methyl-2-(3-methylphenyl)-1,3-oxazol-4-yl]methyl}-N-[2-(4-methylpiperidin-1-yl)ethyl]piperidine-4-carboxamide; |
| 543 | N-[2-(4-ethylpiperazin-1-yl)ethyl]-4-{5-methyl-4-[(phenylsulfanyl)methyl]-1,3-oxazol-2-yl}benzamide; |
| 545 | 1-{[2-(4-chlorophenyl)-5-methyl-1,3-oxazol-4-yl]methyl}-N-[2-(4-ethylpiperazin-1-yl)ethyl]piperidine-4-carboxamide; |
| 547 | 1-{[2-(3-chlorophenyl)-5-methyl-1,3-oxazol-4-yl]methyl}-N-[3-(4-methylpiperazin-1-yl)propyl]piperidine-4-carboxamide; |
| 549 | 1-{[2-(4-chlorophenyl)-5-methyl-1,3-oxazol-4-yl]methyl}-N-[3-(4-methylpiperazin-1-yl)propyl]piperidine-3-carboxamide; |
| 551 | 1-{[2-(3-chlorophenyl)-5-methyl-1,3-oxazol-4-yl]methyl}-N-[2-(4-ethylpiperazin-1-yl)ethyl]piperidine-3-carboxamide; |
| 553 | 1-{[2-(4-chlorophenyl)-5-methyl-1,3-oxazol-4-yl]methyl}-N-(3-pyrrolidin-1-ylpropyl)piperidine-4-carboxamide; |
| 555 | 1-{[2-(3-chlorophenyl)-5-methyl-1,3-oxazol-4-yl]methyl}-N-(3-pyrrolidin-1-ylpropyl)piperidine-4-carboxamide; |
| 557 | 1-{[2-(3-chlorophenyl)-5-methyl-1,3-oxazol-4-yl]methyl}-N-(3-pyrrolidin-1-ylpropyl)piperidine-3-carboxamide; |
| 559 | 1-{[5-methyl-2-(2-methylphenyl)-1,3-oxazol-4-yl]methyl}-N-{3-[methyl(phenyl)amino]propyl}piperidine-4-carboxamide; |
| 561 | 1-{[2-(3-bromophenyl)-5-methyl-1,3-oxazol-4-yl]methyl}-N-[3-(cyclohexylsulfanyl)propyl]piperidine-4-carboxamide; |
| 563 | 4-(5-methyl-4-{[(4-methylphenyl)sulfanyl]methyl}-1,3-oxazol-2-yl)-N-[3-(4-methylpiperazin-1-yl)propyl]benzamide; |
| 565 | 4-{5-methyl-4-[(phenylsulfanyl)methyl]-1,3-oxazol-2-yl}-N-[3-(4-propylpiperazin-1-yl)propyl]benzamide; |
| 567 | 1-{[5-methyl-2-(4-propoxyphenyl)-1,3-oxazol-4-yl]methyl}-N-(pyridin-3-ylmethyl)piperidine-4-carboxamide; |
| 569 | N-(2-azepan-1-ylethyl)-4-(5-methyl-4-{[(4-methylphenyl)sulfanyl]methyl}-1,3-oxazol-2-yl)benzamide; |
| 571 | 4-(5-methyl-4-{[(4-methylphenyl)sulfanyl]methyl}-1,3-oxazol-2-yl)-N-[2-(4-methylpiperazin-1-yl)ethyl]benzamide; |
| 573 | N-(2-azepan-1-ylethyl)-4-{5-methyl-4-[(phenylsulfanyl)methyl]-1,3-oxazol-2-yl}benzamide |
| 575 | 1-{[2-(4-chlorophenyl)-5-methyl-1,3-oxazol-4-yl]methyl}-N-{3-[ethyl(3-methylphenyl)amino]propyl}piperidine-4-carboxamide; |
| 577 | 1-{[5-methyl-2-(4-propoxyphenyl)-1,3-oxazol-4-yl]methyl}-N-(pyridin-2-ylmethyl)piperidine-4-carboxamide; |
| 579 | N-{3-[cyclohexyl(methyl)amino]propyl}-1-{[5-methyl-2-(2-methylphenyl)-1,3-oxazol-4-yl]methyl}piperidine-4-carboxamide; |
| 581 | N-[2-(4-chlorophenyl)ethyl]-1-{[2-(4-ethylphenyl)-5-methyl-1,3-oxazol-4-yl]methyl}piperidine-4-carboxamide; |
| 583 | N-{2-[ethyl(phenyl)amino]ethyl}-1-{[2-(4-ethylphenyl)-5-methyl-1,3-oxazol-4-yl]methyl}piperidine-4-carboxamide; |
| 585 | N-[3-(cyclohexylsulfanyl)propyl]-1-{[5-methyl-2-(2-methylphenyl)-1,3-oxazol-4-yl]methyl}piperidine-3-carboxamide; |

| ID | IUPAC Name |
|---|---|
| 587 | N-[2-(4-chlorophenyl)ethyl]-1-{[2-(4-ethylphenyl)-5-methyl-1,3-oxazol-4-yl]methyl}piperidine-3-carboxamide; |
| 589 | N-[2-(4-benzylpiperazin-1-yl)ethyl]-2-({[5-methyl-2-(4-methylphenyl)-1,3-oxazol-4-yl]methyl}sulfanyl)acetamide; |
| 591 | 4-[5-methyl-4-(phenoxymethyl)-1,3-oxazol-2-yl]-N-[3-(4-methylpiperazin-1-yl)propyl]benzamide; |
| 593 | N-[2-(4-ethylpiperazin-1-yl)ethyl]-4-(5-methyl-4-{[(4-methylphenyl)sulfanyl]methyl}-1,3-oxazol-2-yl)benzamide; |
| 595 | 1-{[2-(4-chlorophenyl)-5-methyl-1,3-oxazol-4-yl]methyl}-N-(pyridin-3-ylmethyl)piperidine-4-carboxamide; |
| 597 | 1-{[2-(4-chlorophenyl)-5-methyl-1,3-oxazol-4-yl]methyl}-N-(2-pyrrolidin-1-ylethyl)piperidine-4-carboxamide; and |
| 599 | 1-{[2-(3-chlorophenyl)-5-methyl-1,3-oxazol-4-yl]methyl}-N-(2-pyrrolidin-1-ylethyl)piperidine-4-carboxamide; | or a salt, solvate, ester or prodrug thereof.

21. An intradermal, intramuscular, intraperitoneal, subcutaneous, epidural, sublingual or intracerebral unit dosage form comprising a therapeutically effective amount of a compound of Formula (IIa):

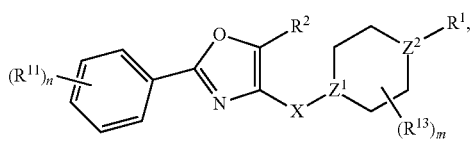
(IIa)

or a salt, solvate, ester or prodrug thereof; and at least one pharmaceutically acceptable vehicle; wherein:

$R^1$ is —C(O)NR$^5$R$^6$;
$R^2$ is hydrogen, $C_{1-6}$ alkyl, or substituted $C_{1-6}$ alkyl;
—NR$^5$R$^6$ is derived from a group consisted of 3-(Azepan-1-yl)propan-1-amine (Cpd A),

A1

A3

A4

A5
and

-continued

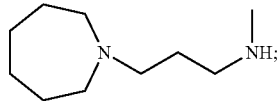
A5

(n is 1, 2, or 3)

X is —CH$_2$—;
$Z^1$ is N;
$Z^2$ is CR$^{12}$ or N;
$R^{12}$ is hydrogen, alkyl, or substituted alkyl;
n is an integer from 0 to 2;
m is 0; and
each $R^{11}$ is independently selected from the group consisting of halogen, $C_{1-6}$ acyl, substituted $C_{1-6}$ acyl, $C_{1-6}$ alkoxycarbonyl, substituted $C_{1-6}$ alkoxycarbonyl, $C_{6-10}$ aryloxycarbonyl, substituted $C_{6-10}$ aryloxycarbonyl, —C(O)NR$^5$R$^6$, $C_{1-6}$ alkyl, substituted $C_{1-6}$ alkyl, $C_{6-10}$ aryl, substituted $C_{6-10}$ aryl, $C_{6-20}$ arylalkyl, substituted $C_{6-20}$ arylalkyl, $C_{3-7}$ cycloheteroalkyl, substituted $C_{3-7}$ cycloheteroalkyl, $C_{6-10}$ heteroaryl, substituted $C_{6-10}$ heteroaryl, $C_{6-20}$ heteroarylalkyl, substituted $C_{6-20}$ heteroarylalkyl, $C_{1-6}$ heteroalkyl, and substituted $C_{1-6}$ heteroalkyl; wherein $R^5$ and $R^6$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl, or alternatively, $R^5$ and $R^6$, taken together with the nitrogen atom to which they are attached, form a 4-, 5-, 6-, or 7-membered cycloheteroalkyl ring;
wherein the intradermal, intramuscular, intraperitoneal, subcutaneous, epidural, sublingual or intracerebral unit dosage form is suitable for administration of about 0.001 mg to about 200 mg of the compound per kilogram of body weight.

22. The intradermal, intramuscular, intraperitoneal, subcutaneous, epidural, sublingual or intracerebral unit dosage form of claim 21, wherein the compound is selected from the group consisting of

| ID | IUPAC Name |
|---|---|
| 901 | N-[3-(azepan-1-yl)propyl]-1-{[2-(4-chloropheny])-5-methyl-1,3-oxazol-4-yl]methyl}piperidine-4-carboxamide; |
| 929 | N-[3-(azepan-1-yl)propyl]-1-{[2-(4-chlorophenyl)-5-methyl-1,3-oxazol-4-yl]methyl}-N-methylpiperidine-4-carboxamide; |

-continued

| ID | IUPAC Name |
|---|---|
| 933 | N-{[2-(azepan-1-yl)cyclopropyl]methyl}-1-{[2-(4-chlorophenyl)-5-methyl-1,3-oxazol-4-yl]methyl}piperidine-4-carboxamide; |
| 943 | N-[3-(azepan-1-yl)propyl]-1-({5-methyl-2-[4-(trifluoromethyl)phenyl]-1,3-oxazol-4-yl}methyl)piperidine-4-carboxamide; |
| 947 | N-[3-(azepan-1-yl)propyl]-1-{[2-(2,4-difluorophenyl)-5-methyl-1,3-oxazol-4-yl]methyl}piperidine-4-carboxamide; |
| 949 | N-[3-(azepan-1-yl)propyl]-1-{[2-(1,3-benzodioxol-5-yl)-5-methyl-1,3-oxazol-4-yl]methyl}piperidine-4-carboxamide; |
| 951 | N-[3-(azepan-1-yl)propyl]-1-{[2-(2,4-dimethoxyphenyl)-5-methyl-1,3-oxazol-4-yl]methyl}piperidine-4-carboxamide; |
| 953 | N-[3-(azepan-1-yl)propyl]-1-{[2-(4-benzylphenyl)-5-methyl-1,3-oxazol-4-yl]methyl}piperidine-4-carboxamide; |
| 955 | N-[3-(azepan-1-yl)propyl]-1-({2-[4-(dimethylcarbamoyl)phenyl]-5-methyl-1,3-oxazol-4-yl}methyl)piperidine-4-carboxamide; |
| 957 | N-[3-(azepan-1-yl)propyl]-1-({5-methyl-2-[4-(piperidin-1-yl)phenyl]-1,3-oxazol-4-yl}methyl)piperidine-4-carboxamide; |
| 959 | N-[3-(azepan-1-yl)propyl]-1-{[5-methyl-2-(naphthalen-1-yl)-1,3-oxazol-4-yl]methyl}piperidine-4-carboxamide; |
| 503 | N-(2-azepan-1-ylethyl)-1-{[2-(4-chlorophenyl)-5-methyl-1,3-oxazol-4-yl]methyl}piperidine-4-carboxamide; |
| 505 | 1-{[2-(4-chlorophenyl)-5-methyl-1,3-oxazol-4-yl]methyl}-N-[3-(3-methylpiperidin-1-yl)propyl]piperidine-4-carboxamide; |
| 507 | 1-{[2-(4-chlorophenyl)-5-methyl-1,3-oxazol-4-yl]methyl}-N-[3-(2-ethylpiperidin-1-yl)propyl]piperidine-4-carboxamide; |
| 509 | 1-{[2-(4-chlorophenyl)-5-methyl-1,3-oxazol-4-yl]methyl}-N-[2-(2-methylpiperidin-1-yl)ethyl]piperidine-4-carboxamide; |
| 511 | 1-{[2-(4-chlorophenyl)-5-methyl-1,3-oxazol-4-yl]methyl}-N-{2-[ethyl(phenyl)amino]ethyl}piperidine-4-carboxamide; |
| 513 | 1-{[2-(4-chlorophenyl)-5-methyl-1,3-oxazol-4-yl]methyl}-N-{3-[methyl(phenyl)amino]propyl}piperidine-4-carboxamide; |
| 515 | 1-{[2-(3-chlorophenyl)-5-methyl-1,3-oxazol-4-yl]methyl}-N-{2-[ethyl(phenyl)amino]ethyl}piperidine-4-carboxamide; |
| 517 | 1-{[2-(4-chlorophenyl)-5-methyl-1,3-oxazol-4-yl]methyl}-N-{2-[ethyl(phenyl)amino]ethyl}piperidine-3-carboxamide; |
| 519 | 1-{[2-(3-chlorophenyl)-5-methyl-1,3-oxazol-4-yl]methyl}-N-{2-[ethyl(phenyl)amino]ethyl}piperidine-3-carboxamide; |
| 521 | 1-{[2-(3-chlorophenyl)-5-methyl-1,3-oxazol-4-yl]methyl}-N-{3-[methyl(phenyl)amino]propyl}piperidine-3-carboxamide; |
| 523 | 4-{5-methyl-4-[(phenylsulfanyl)methyl]-1,3-oxazol-2-yl}-N-[3-(4-methylpiperazin-1-yl)propyl]benzamide; |
| 525 | N-{3-[benzyl(methyl)amino]propyl}-1-{[2-(4-chlorophenyl)-5-methyl-1,3-oxazol-4-yl]methyl}piperidine-4-carboxamide; |
| 527 | 1-{[2-(4-chlorophenyl)-5-methyl-1,3-oxazol-4-yl]methyl}-N-[3-(3,5-dimethylpiperidin-1-yl)propyl]piperidine-4-carboxamide; |
| 529 | 1-{[2-(4-chlorophenyl)-5-methyl-1,3-oxazol-4-yl]methyl}-N-{2-[methyl(2-phenylethyl)amino]ethyl}piperidine-4-carboxamide; |
| 531 | 1-{[5-methyl-2-(2-methylphenyl)-1,3-oxazol-4-yl]methyl}-N-[3-(3-methylpiperidin-1-yl)propyl]piperidine-4-carboxamide; |
| 533 | 1-{[2-(3-chlorophenyl)-5-methyl-1,3-oxazol-4-yl]methyl}-N-[3-(3,5-dimethylpiperidin-1-yl)propyl]piperidine-4-carboxamide; |
| 535 | 1-{[2-(3-chlorophenyl)-5-methyl-1,3-oxazol-4-yl]methyl}-N-[3-(cyclohexylsulfanyl)propyl]piperidine-4-carboxamide; |
| 537 | N-{2-[ethyl(phenyl)amino]ethyl}-1-{[2-(2-fluorophenyl)-5-methyl-1,3-oxazol-4-yl]methyl}piperidine-4-carboxamide; |
| 539 | 1-{[2-(3-chlorophenyl)-5-methyl-1,3-oxazol-4-yl]methyl}-N-{2-[methyl(2-phenylethyl)amino]ethyl}piperidine-3-carboxamide; |
| 541 | 1-{[5-methyl-2-(3-methylphenyl)-1,3-oxazol-4-yl]methyl}-N-[2-(4-methylpiperidin-1-yl)ethyl]piperidine-4-carboxamide; |
| 543 | N-[2-(4-ethylpiperazin-1-yl)ethyl]-4-{5-methyl-4-[(phenylsulfanyl)methyl]-1,3-oxazol-2-yl}benzamide; |
| 545 | 1-{[2-(4-chlorophenyl)-5-methyl-1,3-oxazol-4-yl]methyl}-N-[2-(4-ethylpiperazin-1-yl)ethyl]piperidine-4-carboxamide; |
| 547 | 1-{[2-(3-chlorophenyl)-5-methyl-1,3-oxazol-4-yl]methyl}-N-[3-(4-methylpiperazin-1-yl)propyl]piperidine-4-carboxamide; |
| 549 | 1-{[2-(4-chlorophenyl)-5-methyl-1,3-oxazol-4-yl]methyl}-N-[3-(4-methylpiperazin-1-yl)propyl]piperidine-3-carboxamide; |
| 551 | 1-{[2-(3-chlorophenyl)-5-methyl-1,3-oxazol-4-yl]methyl}-N-[2-(4-ethylpiperazin-1-yl)ethyl]piperidine-3-carboxamide; |
| 553 | 1-{[2-(4-chlorophenyl)-5-methyl-1,3-oxazol-4-yl]methyl}-N-(3-pyrrolidin-1-ylpropyl)piperidine-4-carboxamide; |
| 555 | 1-{[2-(3-chlorophenyl)-5-methyl-1,3-oxazol-4-yl]methyl}-N-(3-pyrrolidin-1-ylpropyl)piperidine-4-carboxamide; |
| 557 | 1-{[2-(3-chlorophenyl)-5-methyl-1,3-oxazol-4-yl]methyl}-N-(3-pyrrolidin-1-ylpropyl)piperidine-3-carboxamide; |
| 559 | 1-{[5-methyl-2-(2-methylphenyl)-1,3-oxazol-4-yl]methyl}-N-{3-[methyl(phenyl)amino]propyl}piperidine-4-carboxamide; |
| 561 | 1-{[2-(3-bromophenyl)-5-methyl-1,3-oxazol-4-yl]methyl}-N-[3-(cyclohexylsulfanyl)propyl]piperidine-4-carboxamide; |

-continued

| ID | IUPAC Name |
|---|---|
| 563 | 4-(5-methyl-4-{[(4-methylphenyl)sulfanyl]methyl}-1,3-oxazol-2-yl)-N-[3-(4-methylpiperazin-1-yl)propyl]benzamide; |
| 565 | 4-{5-methyl-4-[(phenylsulfanyl)methyl]-1,3-oxazol-2-yl}-N-[3-(4-propylpiperazin-1-yl)propyl]benzamide; |
| 567 | 1-{[5-methyl-2-(4-propoxyphenyl)-1,3-oxazol-4-yl]methyl}-N-(pyridin-3-ylmethyl)piperidine-4-carboxamide; |
| 569 | N-(2-azepan-1-ylethyl)-4-(5-methyl-4-{[(4-methylphenyl)sulfanyl]methyl}-1,3-oxazol-2-yl)benzamide; |
| 571 | 4-(5-methyl-4-{[(4-methylphenyl)sulfanyl]methyl}-1,3-oxazol-2-yl)-N-[2-(4-methylpiperazin-1-yl)ethyl]benzamide; |
| 573 | N-(2-azepan-1-ylethyl)-4-{5-methyl-4-[(phenylsulfanyl)methyl]-1,3-oxazol-2-yl}benzamide |
| 575 | 1-{[2-(4-chlorophenyl)-5-methyl-1,3-oxazol-4-yl]methyl}-N-{3-[ethyl(3-methylphenyl)amino]propyl}piperidine-4-carboxamide; |
| 577 | 1-{[5-methyl-2-(4-propoxyphenyl)-1,3-oxazol-4-yl]methyl}-N-(pyridin-2-ylmethyl)piperidine-4-carboxamide; |
| 579 | N-{3-[cyclohexyl(methyl)amino]propyl}-1-{[5-methy1-2-(2-methylphenyl)-1,3-oxazol-4-yl]methyl}piperidine-4-carboxamide; |
| 581 | N-[2-(4-chlorophenyl)ethyl]-1-{[2-(4-ethylphenyl)-5-methyl-1,3-oxazol-4-yl]methyl}piperidine-4-carboxamide; |
| 583 | N-{2-[ethyl(phenyl)amino]ethyl}-1-{[2-(4-ethylphenyl)-5-methyl-1,3-oxazol-4-yl]methyl}piperidine-4-carboxamide; |
| 585 | N-[3-(cyclohexylsulfanyl)propyl]-1-{[5-methyl-2-(2-methylphenyl)-1,3-oxazol-4-yl]methyl}piperidine-3-carboxamide; |
| 587 | N-[2-(4-chlorophenyl)ethyl]-1-{[2-(4-ethylphenyl)-5-methyl-1,3-oxazol-4-yl]methyl}piperidine-3-carboxamide; |
| 589 | N-[2-(4-benzylpiperazin-1-yl)ethyl]-2-({[5-methyl-2-(4-methylphenyl)-1,3-oxazol-4-yl]methyl}sulfanyl)acetamide; |
| 591 | 4-[5-methyl-4-(phenoxymethyl)-1,3-oxazol-2-yl]-N-[3-(4-methylpiperazin-1-yl)propyl]benzamide; |
| 593 | N-[2-(4-ethylpiperazin-1-yl)ethyl]-4-(5-methyl-4-{[(4-methylphenyl)sulfanyl]methyl}-1,3-oxazol-2-yl)benzamide; |
| 595 | 1-{[2-(4-chlorophenyl)-5-methyl-1,3-oxazol-4-yl]methyl}-N-(pyridin-3-ylmethyl)piperidine-4-carboxamide; |
| 597 | 1-{[2-(4-chlorophenyl)-5-methyl-1,3-oxazol-4-yl]methyl}-N-(2-pyrrolidin-1-ylethyl)piperidine-4-carboxamide; and |
| 599 | 1-{[2-(3-chlorophenyl)-5-methyl-1,3-oxazol-4-yl]methyl}-N-(2-pyrrolidin-1-ylethyl)piperidine-4-carboxamide; | or a salt, solvate, ester or prodrug thereof.

23. A method of treating a disease, disorder, symptom, or condition associated with irregular PKCε activity in a patient, comprising administering to the patient a therapeutically effective amount of a pharmaceutical composition of claim 3, 5, or 7; wherein the disease, disorder, symptom or condition is selected from the group consisting of acute pain, chronic pain, inflammatory pain, neuropathic pain, diabetic neuropathy, alcoholic polyneuropathy, cancer- or chemotherapy-induced pain, a generalized pain disorder, tonic pain, persistent pain, postoperative pain, chemical-induced pain, drug-induced pain, migraine, anxiety, skeletal muscle spasms, convulsive seizures, epilepsy, alcohol abuse and alcoholism, insomnia, pain associated with alcohol-induced hyperalgesia, type 1 and type 2 diabetes, hepatic steatosis or liver cirrhosis, bipolar disorder, mania, sleeping disorder, burn, posttraumatic stress disorder, cardiac disorder, smoking, or inflammation associated with microbial infection and organ transplantation, immune disorders, cancer or cancer-induced pain wherein the cancer is breast cancer, head and neck cancer, oral cancer, prostate cancer, lung cancer, liver cancer, brain cancer, squamous cell carcinoma, gastrointestinal cancer, gastric cancer, pancreatic cancer, thyroid cancer, neuroblastoma, multiple myeloma, myeloid leukemia, squamous cell carcinoma, glioma, renal cancer, ovarian cancer, colorectal cancer, endometrial cancer, kidney cancer, thyroid cancer, neuroblastoma, stomach cancer, bladder cancer, hepatoma, colon carcinoma, germ cell tumor, sarcoma, acute myelogenous leukemia, lymphocytic leukemia, or a combination thereof, or a disease, disorder, symptom or condition associated with maladaptive substance use, substance dependence, alcohol use or abuse, substance use or abuse, drug use or abuse, or drug-related effect, or a combination thereof.

24. The pharmaceutical composition of claim 3, 5, or 7, wherein the compound inhibits PKCε reversibly with an $IC_{50}$ of less than about 1 μM.

25. The pharmaceutical composition of claim 3, 5, or 7, wherein the compound inhibits PKCε non-competitively with ATP.

26. The pharmaceutical composition of claim 3, 5, or 7, wherein the compound of is selective for PKCε.

* * * * *

UNITED STATES PATENT AND TRADEMARK OFFICE
CERTIFICATE OF CORRECTION

PATENT NO. : 8,729,081 B2
APPLICATION NO. : 13/123399
DATED : May 20, 2014
INVENTOR(S) : Jay Jie-Qiang Wu Page 1 of 1

It is certified that error appears in the above-identified patent and that said Letters Patent is hereby corrected as shown below:

In the Specification

At column 1, lines 21-23, the sentence is amended as follows:

This invention was made "partly" with the U.S. Federal Government support under grant no. R44AA014843 --awarded by the National Institutes of Health--. The U.S. Federal Government "may have" --has-- certain rights in the invention.

At column 3, line 18, delete "13" and replace with --beta--.

At column 20, lines 50-51, the sentence is amended as follows:

...that produces pleasurable effects, "a" --as-- opposed "than" --to-- a control substance...

At column 118, line 2, delete "(Jib)" and replace with --(IIb)--.

In the Claims

In column 149, line 5, of Claim 5, formula (IIa):

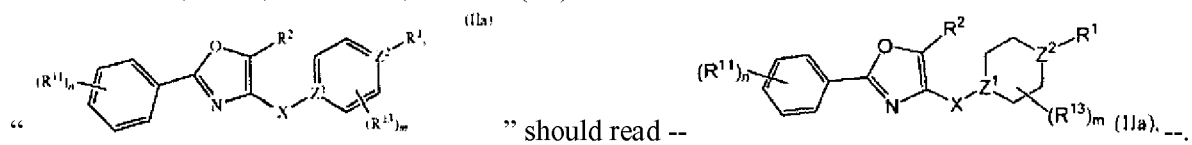

In column 162, ID 947, of Claim 18, insert --3-- before -(azepan-1-yl).

Signed and Sealed this
Twentieth Day of January, 2015

Michelle K. Lee
*Deputy Director of the United States Patent and Trademark Office*